US008951536B2

(12) United States Patent
Combs et al.

(10) Patent No.: US 8,951,536 B2
(45) Date of Patent: Feb. 10, 2015

(54) N-HYDROXYAMIDINOHETEROCYCLES AS MODULATORS OF INDOLEAMINE 2,3-DIOXYGENASE

(71) Applicant: Incyte Corporation, Wilmington, DE (US)

(72) Inventors: Andrew P. Combs, Kennett Square, PA (US); Amy Takvorian, Newnan, GA (US); Wenyu Zhu, Media, PA (US); Richard B. Sparks, Wilmington, DE (US)

(73) Assignee: Incyte Corporation, Wilmington, DE (US)

( * ) Notice: Subject to any disclaimer, the term of this patent is extended or adjusted under 35 U.S.C. 154(b) by 0 days.

(21) Appl. No.: 13/780,510

(22) Filed: Feb. 28, 2013

(65) Prior Publication Data
US 2013/0177590 A1 Jul. 11, 2013

Related U.S. Application Data

(62) Division of application No. 11/641,284, filed on Dec. 19, 2006, now Pat. No. 8,450,351.

(60) Provisional application No. 60/751,854, filed on Dec. 20, 2005, provisional application No. 60/801,337, filed on May 18, 2006, provisional application No. 60/857,558, filed on Nov. 8, 2006.

(51) Int. Cl.
| A61K 31/541 | (2006.01) |
| A61K 31/4245 | (2006.01) |
| A61K 31/454 | (2006.01) |
| A61K 31/496 | (2006.01) |
| A61K 31/06 | (2006.01) |
| A61K 31/4725 | (2006.01) |
| A61K 31/5377 | (2006.01) |
| A61K 31/433 | (2006.01) |
| A61K 31/427 | (2006.01) |
| A61K 31/4439 | (2006.01) |
| C07D 271/08 | (2006.01) |
| C07D 285/06 | (2006.01) |
| C07D 413/06 | (2006.01) |
| C07D 413/12 | (2006.01) |
| C07D 413/14 | (2006.01) |
| C07D 417/06 | (2006.01) |
| C07D 417/12 | (2006.01) |
| A61K 45/06 | (2006.01) |

(52) U.S. Cl.
CPC ............ *A61K 31/541* (2013.01); *C07D 271/08* (2013.01); *C07D 285/06* (2013.01); *C07D 413/06* (2013.01); *C07D 413/12* (2013.01); *C07D 413/14* (2013.01); *C07D 417/06* (2013.01); *C07D 417/12* (2013.01); *A61K 31/4245* (2013.01); *A61K 31/427* (2013.01); *A61K 31/433* (2013.01); *A61K 31/4439* (2013.01); *A61K 31/454* (2013.01); *A61K 31/4725* (2013.01); *A61K 31/496* (2013.01); *A61K 31/5377* (2013.01); *A61K 45/06* (2013.01)
USPC ........ 424/204.1; 546/208; 514/361; 514/364; 514/326; 514/254.03; 514/340; 514/307; 514/236.2; 514/227.8; 424/184.1

(58) Field of Classification Search
CPC ............ A61K 31/4245; A61K 31/433; A61K 31/454; C07D 271/08; C07D 417/02; C07D 413/02
USPC .............. 514/361; 546/208; 564/80; 548/125
See application file for complete search history.

(56) References Cited

U.S. PATENT DOCUMENTS

| 3,236,855 A | 2/1966 | Jones et al. |
| 3,553,228 A | 1/1971 | Freedman et al. |
| 3,948,928 A | 4/1976 | Nishimura et al. |
| 4,116,974 A | 9/1978 | Farge et al. |
| 4,323,681 A | 4/1982 | Wolf et al. |
| 4,699,916 A | 10/1987 | Sirrenberg et al. |
| 5,364,864 A | 11/1994 | Bigg et al. |
| 5,712,294 A | 1/1998 | Robert et al. |
| 6,482,416 B2 | 11/2002 | Munn et al. |
| 6,482,822 B1 | 11/2002 | Bigg et al. |
| 6,780,858 B2 | 8/2004 | Li et al. |
| 7,109,354 B2 * | 9/2006 | Subasinghe et al. ............ 549/29 |
| 7,144,902 B1 | 12/2006 | Baucke et al. |

(Continued)

FOREIGN PATENT DOCUMENTS

| BE | 659467 | 8/1965 |
| CA | 2500113 | 4/2004 |
| DE | 2040628 | 2/1972 |
| EP | 0352832 | 1/1990 |
| EP | 0516520 | 12/1992 |
| EP | 0536424 | 4/1993 |
| EP | 1038874 | 9/2000 |
| EP | 1188747 | 3/2002 |
| JP | 40020710 | 9/1965 |
| JP | 50-050369 | 5/1975 |

(Continued)

OTHER PUBLICATIONS

A.R. Katritzky et al., "Synthesis of mono and symmetrical di-N-hydroxy- and N-aminoguanidines", Journal of Organic Chemistry, 71(18):6753-8 (2006).

(Continued)

Primary Examiner — Yong Chu
(74) Attorney, Agent, or Firm — Fish & Richardson P.C.

(57) ABSTRACT

The present invention is directed to N-hydroxyamidino compounds which are modulators of indoleamine 2,3-dioxygenase (IDO), as well as pharmaceutical compositions thereof and methods of use thereof relating to the treatment of cancer and other diseases.

17 Claims, No Drawings

(56) References Cited

U.S. PATENT DOCUMENTS

| | | |
|---|---|---|
| 8,008,281 B2 | 8/2011 | Prendergast et al. |
| 8,034,953 B2 | 10/2011 | Combs et al. |
| 8,088,803 B2 | 1/2012 | Combs et al. |
| 8,372,870 B2 | 2/2013 | Combs et al. |
| 8,377,976 B2 | 2/2013 | Combs et al. |
| 8,450,351 B2 | 5/2013 | Combs et al. |
| 8,507,541 B2 | 8/2013 | Combs et al. |
| 2002/0155104 A1 | 10/2002 | Munn et al. |
| 2004/0234623 A1 | 11/2004 | Munn et al. |
| 2006/0194802 A1 | 8/2006 | Abdellaoui et al. |
| 2007/0037752 A1 | 2/2007 | Ansorge et al. |
| 2007/0037785 A1 | 2/2007 | Ansorge et al. |
| 2007/0038298 A1 | 2/2007 | Sulner et al. |
| 2007/0185165 A1 | 8/2007 | Combs et al. |
| 2007/0203140 A1 | 8/2007 | Combs et al. |
| 2007/0265257 A1 | 11/2007 | Tanaka et al. |
| 2008/0119491 A1 | 5/2008 | Combs |
| 2008/0125470 A1 | 5/2008 | Combs et al. |
| 2008/0146624 A1 | 6/2008 | Combs et al. |
| 2008/0182882 A1 | 7/2008 | Combs et al. |
| 2008/0214546 A1 | 9/2008 | Combs et al. |
| 2008/0214549 A1 | 9/2008 | Shaw et al. |
| 2009/0163545 A1 | 6/2009 | Goldfarb |
| 2009/0247586 A1 | 10/2009 | Dunkel et al. |
| 2011/0165188 A1 | 7/2011 | Combs et al. |
| 2011/0172279 A1 | 7/2011 | Combs et al. |
| 2012/0058079 A1 | 3/2012 | Combs et al. |
| 2013/0123246 A1 | 5/2013 | Combs et al. |

FOREIGN PATENT DOCUMENTS

| | | |
|---|---|---|
| JP | 58208275 | 12/1983 |
| JP | 60193968 | 10/1985 |
| JP | 62059283 | 3/1987 |
| JP | 02006453 | 1/1990 |
| JP | 4297449 | 10/1992 |
| JP | 06-065269 | 3/1994 |
| JP | 11171702 | 6/1999 |
| JP | 2000-505815 | 5/2000 |
| JP | 2001158785 | 6/2001 |
| JP | 2001158786 | 6/2001 |
| JP | 2001-233861 | 8/2001 |
| JP | 2002-542165 | 12/2002 |
| RU | 2230742 | 6/2004 |
| SU | 886740 | 12/1981 |
| WO | WO 97/14686 | 4/1997 |
| WO | WO 97/30047 | 8/1997 |
| WO | WO 97/42183 | 11/1997 |
| WO | WO 98/24784 | 6/1998 |
| WO | WO 99/29310 | 6/1999 |
| WO | WO 99/62903 | 12/1999 |
| WO | WO 00/52001 | 9/2000 |
| WO | WO 00/61609 | 10/2000 |
| WO | WO 01/51456 | 7/2001 |
| WO | WO 02/00196 | 1/2002 |
| WO | WO 02/079200 | 10/2002 |
| WO | WO 02/102799 | 12/2002 |
| WO | WO 03/045901 | 6/2003 |
| WO | WO 03/070236 | 8/2003 |
| WO | WO 03/087347 | 10/2003 |
| WO | WO 03/099805 | 12/2003 |
| WO | WO 2004/029031 | 4/2004 |
| WO | WO 2004/093871 | 11/2004 |
| WO | WO 2004/094409 | 11/2004 |
| WO | WO 2005/019190 | 3/2005 |
| WO | WO 2005/037257 | 4/2005 |
| WO | WO 2005/037779 | 4/2005 |
| WO | WO 2006/028284 | 3/2006 |
| WO | WO 2006/067532 | 6/2006 |
| WO | WO 2006/122150 | 11/2006 |
| WO | WO 2006/133417 | 12/2006 |
| WO | WO 2007/068377 | 6/2007 |
| WO | WO 2007/075598 | 7/2007 |
| WO | WO 2008/036642 | 3/2008 |
| WO | WO 2008/036643 | 3/2008 |
| WO | WO 2008/036652 | 3/2008 |
| WO | WO 2008/036653 | 3/2008 |
| WO | WO 2008/058178 | 5/2008 |
| WO | WO 2008/073825 | 6/2008 |

OTHER PUBLICATIONS

Ait-Mohand, Samia. and Dolbier, Jr. William R., "New and Convenient Method for Incorporation of pentafluorosulfanyl ($SF_5$) Substituents Into Aliphatic Organic Compounds", *Organic Letters*, 4(17), 3013-3015, 2002.

Andrianov et al. "Degenerate Rearrangement of 3-amino-1,2,5-oxadiazole-4-carboxamidoxime", *Khimiya Geterotsiklicheskikh Soedinenii*, (1988), (12), 1701 (and abstract Database Hcaplus, on STN, 1989:515108, No. 111:115108).

Andrianov et al., "4-aminofurazan-3-hydroximic halides", Institute of Organic Synthesis, 5:581-585 (1992) translation of "Acid halides of 4-aminofurazan-3-carbohydroximic acid", Khimiya Geterotsiklicheskikh Soedinenii, (1992), (5), 687-91 and abstract Database Hcaplus, on STN, 1993:212973, No. 118:212973.

Andrianov et al., "Acid halides of 4-aminofurazan-3-carbohydroxamic acids ", *Chemistry of Heterocyclic Compounds*, Latvian Institute of Organic Chemistry, vol. 30, 3:370-371 (1994) (English translation of *Khimiya Geterotsiklicheskikh Soedinenii*, (3), 420-21) and abstract Database Hcaplus STN File CA, 1995:376582; 123:198702.

Andrianov et al., "Rearrangements of 1-oxa-2-azoles. 2. Structure and isomerization of pentamethyleneamidoximes of 4-aminofurazan-3-carboxylic acid", *Khimiya Geterotsiklicheskikh Soedinenii*, (1991), (1), 122-3 (and abstract Database Hcaplus, STN, 1991:449555, No. 115:49555).

Andrianov et al., "Rearrangements of 5-trifluoromethyl-1,2,4-oxadiazoles by action of ammonia and amines", *Institute of Organic Synthesis*, Academy of Sciences of the Latvian SSR, p. 707 translation of "Ammonia- and amine-induced rearrangements of 5-(trifluoromethyl)-1,2,4-oxadiazoles", *Khimiya Geterotsiklicheskikh Soedinenii*, (1988), (6), 856-7 and abstract Database Hcaplus, on STN, 1989:212695, No. 110:212695).

Andrianov et al., "Ring formation reactions of 4-aminofurazan-3-carboxyamidoximes", *Chemistry of Heterocyclic Compounds*, 30(4):470-474 (1993) (English translation of Andrianov et al., "4-aminofurazan-3-carboxamidoxime cyclization", Khimiya Geterotsiklicheskikh Soedinenii (4):534-8 (1994) (and abstract Database Caplus No. 1995:393128; 122:290788); XP002526509 (1994).

Andrianov et al., "Synthesis and properties of derivatives of 4-aminofuroxan-3-carboxylic acid", *Chemistry of Heterocyclic Compounds*, 33(8), 973-976 (1997), translation of *Khimiya Geterotsiklicheskikh Soedinenii*, (1997) No. 8, pp. 1115-1119 and abstract Database Hcaplus, on STN, 1998:221958, No. 128:308445.

Andrianov et al., "Synthesis of furazans by rearrangement of 3-acyl-1-oxa-2-azole oximes", UDC 547.793.07(047) 2611(90):1199-1213 (1991), *Institute of Organic Synthesis*, Academy of Science of the Latvian SSR, (Translation of *Khimiya Geterotsiklicheskikh Soedinenii*, (1990) No. 11, pp. 1443-1459).

Andrianov et al., "Synthesis, structure, and rearrangement of 4-aminofurazan-3-carboxamide oximes", UDC 547.793.2, 29(5):877-880 (1994), (translation of *Zhurnal Organicheskoi Khimii*, (1993), 29(5), 1062-6) and abstract Database Hcaplus, on STN, 1994:270259, No. 120:270259; XP002526508 (1993).

Andrianov, et al., "Synthesis and properties of 4-amino-3-cyanofurazan", *Chemistry of Heterocyclic* Compounds, vol. 30, No. 5, pp. 608-611 (1994), translation of Khimiya Geterotsiklicheskikh Soedinenii, (5), 693-6 (1994) with abstract Database Hcaplus, on STN 1995:374071, No. 123:198701.

Andrianov et al., "4-Aminofurazan-3-carbohydroximic acid halides", *Khimiya Geterotsiklicheskikh Soedinenii*, (1994), (3), 420-5, and abstract.

Areschka et al., "Studies on the benzofuran series. LXI. 3-Benzofuranylacetamidoximes with antihypertenstive potential", *European Journal of Medicinal Chemistry*, (1977), 12(1), 87-91 (with English abstract).

(56) References Cited

OTHER PUBLICATIONS

Astigiano, et al., Neoplasia, 7(4):390-396 (2005).
Bagdasarov et al., "Extraction—photometric determination of copper and cobalt with oxime derivatives of benzimidazole", *Zavodskaya Laboratoriya* (1976), 42(2), 143-144 (Non-English Reference), (in Application No. 11/856,982 in Jan. 29, 2010 Office Action—copy provided with reference).
Beaudegnies et al., "Synthesis of furazan conjugated new heterocycles", *Heterocycles*, (2003), 60(11), 2417-2424 and abstract Database Hcaplus, on STN, 2003:865834, No. 140:59538.
Belik et al., "Descriptor v'cp-aided study of the rearrangement of 1-oxa-2-azoles", Zhurnal Organicheskoi Khimii, 30(5), 757-9 (1994) with abstract STN File CA, 122:238877; 1995:326366.
Belik, et al., "Theoretical investigation of rearrangements of 1-oxa-2-azole-3-carboxamidoximes", *Russian Journal of Organic Chemistry*, 34(4), 543-548 (1998) (Translation of Zhurnal Organicheskoi Khimii 34(4), 577-582) (with abstract STN File CA, 130:209340; 999:79495).
Berge, et al., "Pharmaceutical Salts", J. of Pharmaceutical Science, vol. 66 No. 1, pp. 1-19 (1977).
Bonda, et al., "Indoleamine 2,3-dioxygenase and 3-hydroxykynurenine modifications are found in the neuropathology of Alzheimer's disease", Redox Rep., 15(4):161-8 (2010).
Brandacher, et al., *Clin. Cancer Res.*, 12(4):1144-1151 (2006) (abstract).
Brown, et al., "Implications of Interferon-induced Tryptophan Catabolism in Cancer, Auto-immune Diseases and Aids", *Adv. Exp. Med. Biol.*, 294: 425-35 (1991).
Burger et al., "Janus kinase inhibitor INCB20 has antiproliferative and apoptotic effects on human myeloma cells in vitro and in vivo," Mol. Cancer Ther 2009;8(1) Jan. 2009, 26-35.
Chauhan et al., "Antifilarial profile of substituted pyrazoles: a new class of antifilarial agents," *Indian Journal of Chemistry*, Section B: Organic Chemistry Including Medicinal Chemistry (1993), 32B(8), 858-61 (with abstract Database Hcaplus STN File CA, 120:244819; 1994:244819).
Clercq, Journal of Clinical Virology, vol. 30, 2004, pp. 115-133.
'ClinicalTrials.gov' [online] "A Phase 2 Study of the IDO Inhibitor INCB024360 Versus Tamoxifen for Subjects with Biochemical-recurrent-only EOC, PPC or PTC Following Complete Remission with First-line Chemotherapy," [2013], [retrieved on Jul. 25, 2013] URL: <http://clinicaltrials.gov/ct2/show,NCT01685255?term=incyte&rank=4> 4 pages.
'ClinicalTrials.gov' [online] "A Phase 1/2 Randomized, Blinded, Placebo Controlled Study of Ipilimumab in Combination with INCB024360 or Placebo in Subjects with Unresectable or Metastatic Melanoma," [2012] [retrieved on Jul. 25, 2013] URL: http://clinicaltrials.gov/ct2/show/NCT01604889?term=incyte&rank=8 > 3 pages.
Corbett et al. In vivo methods for screening and preclinical testing. Cancer Drug Discovery and Development: Anticancer Drug Development Guide: Preclinical Screening, Clinical Trials, and Approval, 2nd Ed. Teicher, B.A. and Andrews, P.A., Gumana Press Inc., Totowa, NJ, 2004.
Current Protocols in Immunology, vol. 4, Coligan, J.E., et al; Immunotherapy of Cancer, Human Press, 2006, Disis, M.L.
Database CAPLUS, on STN, 1963: 73272, No. 83, 12528c-e, see RN 90585-88-9 CAPLUS, XP-002467962 dated May 2, 2008, (abstract of Sycheva, et al. "Compaunds with Potential Antitubercular Activity. VI. Amidoximes, amide Hydrazones, and S-Oxides of Thioamides of some Heterocyclic acids", (1962) 32, 3669-74) (1page).
Database CAPLUS, on STN, 1966: 35828, No. 64, 6633a-d, see RN 4698-75-3 CAPLUS, XP-002467245 dated May 2, 2008 (abstract of Sycheva, et al., "Compaunds with Potential Antitubercular Activity. X. Derivatives of Benzoxazole-2-carboxylic acid", (1965) 46-51 (1 page).
Database CAPLUS, on STN, 1975:606233, No. 83: 32463a, 32466a, see RN 55942-51-3 CAPLUS, XP-002467961 dated May 2, 2008 (abstract of Nishimura, Haruki et al., JP Patent No. 50050369, issued May 6, 1975 "Amidoxime Derivatives",) (1 page).
Database CAPLUS, on STN, 1992:6493, No. 116, 6493, XP-002467964, RN 137890-17-6 dated Jun. 2, 2008, (abstract of Andrianov, et al., "Rearrangements of 1-oxa-2-azoles. 4. synthesis and rearrangement of Amidoximes of soxazole-and 4,5-dihydrosoxazole-3-carboxylic acid", (1991) (6), 827-32) (1 page).
Daubener, et al., "IFN-γ Activated Indoleamine 2,3-Dioxygenase Activity in Human Cells is an Antiparasitic and an Antibacterial Effector Mechanism", Adv. Exp. Med. Biol., 467: 517-24 (1999).
Deeb et al., "Heterocyclic synthesis from 3-amino-4-cyanopyrazole," Collection of Czechoslovak Chemical Communications (1990), 55(3), 728-33 (with abstract Database Hcaplus STN File CA, 113:97502; 1990:497502).
Dranoff et al., "Vaccination with irradiated tumor cells engineered to secrete murine granulocyte-macrophage colony-stimulating factor stimulates potent, specific, and long-lasting anti-tumor immunity," *Proc. Natl. Acad. Sci, USA.* 90:3539-3543 (1993).
El-Mobayed et al., "Synthesis of heterocyclic compounds containing nitrogen and sulfur from 3- amino-4-cyanopyrazole," *Journal of the Chemical Society of Pakistan* (1989), 11(4), 287-90 (with abstract Database Hcaplus STN File CA, 113:231330; 1990:631330).
Expert Scientific Group on Phase One Clinical Trials Final Report, Nov. 30, 2006, pp. C1, C35-C38.
Feder-Mengus, et al., "High expression of indoleamine 2,3-dioxygenase gene in prostate cancer", *European J. Cancer*, 44 (2008) pp. 2266-2275.
Friberg, M., Jennings, R., et al. Indoleamine 2,3-dioxygenase contributes to tumor cell evasion of T cell-mediated rejection. Int. J. Cancer: 101:151-155, 2002.
Fujii et al., "Oxidation of N6-benzyladenine with m-chloroperoxybenzoic acid: formation of the N(1)-oxide," Heterocycles (1994), 37(1), 219-22 (with abstract Database Hcaplus STN File CA, 121:35143; 1994:435143).
Fujii et al., "Purines. III. Rearrangement of 1-alkoxy-9-alkyladenines to 6-alkoxyamino-9- alkylpurines through isolatable N'-alkoxy-1-alkyl-5-formamidoimidazole-4-carboxamidines ," Tetrahedron (1971), 27(12), 2415-23 (with abstract Database Hcaplus STN File CA, Abstract 75:76739; 1971:476739).
Fujii et al., "Purines. V. Dimroth rearrangement of 1-alkoxyadenines. Synthesis of N-alkoxyadenines," Chemical & Pharmaceutical Bulletin (1971), 19(8), 1731-4 (with abstract Database Hcaplus STN File CA, Abstract 75:110279; 1971:510279).
Fujii et al., "Purines. XLVIII. Syntheses and proton nuclear magnetic resonance study of 2- deuterioadenines substituted or unsubstituted at the 9-position and of their N-oxygenated derivatives," Chemical & Pharmaceutical Bulletin (1991), 39(2), 301-8 (with abstract Database Hcaplus STN File CA, 114:247645; 1991:247645).
Fujii et al., "Purines. XV. Conversion of N,9-dimethyladenine into the 1,9-dimethyl isomer. Reverse operation of the dimroth rearrangement," Chemical & Pharmaceutical Bulletin (1974), 22(10), 2211-16 (with abstract Database Hcaplus STN File CA, Abstract 82:43349; 1975:43349).
Fujii, et al., "Antitumor activities of some fifty compounds related to adenine derivatives," Yakugaku Zasshi (1977), 97(6), 689-91(with abstract Database Hcaplus STN File CA, 87:111278; 1977:511278).
Gasparri, et al., "Critical role of indoleamine 2,3-dioxygenase in tumor resistance to repeated treatments with targeted IFNγ", *Mol. Cancer Ther.*, 7(12) pp. 3859-3866 (2008).
Giron, D.J., "Applications of Thermal Analysis and Coupled Techniques in Pharmaceutical Industry", *J. Therm. Anal. Cal.* (2002), 68, pp. 335-357.
Giron, D.J., "Investigations of Polymorphism and Pseudo-Polymorphism in Pharmaceuticals by Combined Thermoanalytical Techniques", *J. Therm. Anal. Cal.* (2001), 64, pp. 37-60.
Graham, B.S., "Clinical trials of HIV vaccines." HIV Molecular Immunology Database 2000. Edited by: Korber BT, Brander C, Haynes BF, Koup R, Kuiken C, Moore JP, Walker BD, and Watkins D. Published by: Theoretical Biology and Biophysics Group, Los Alamos National Laboratory, Los Alamos, NM. pp. 1-20-38.
Greene, et al., Protective Groups in Organic Synthesis, 2d. Ed., Wiley & Sons, 1991.

(56) References Cited

OTHER PUBLICATIONS

Griesser, "The Importance of Solvates" in Polymorphism in the Pharmaceutical Industry, 211-233 (Rolf Hilfiker, ed., 2006).
Grohmann, et al., "Tolerance, DCs and tryptophan: much ado about IDO", Trends Immunol., 24: 242-8 (2003).
Gura, "Cancer Models: Systems for Identifying New Drugs are Often Faulty," Science, vol. 278, No. 5340, pp. 1041-1042 (1997).
Higuchi et al., "Pro-drugs as Novel Delivery Systems," vol. 14 of the A.C.S. Symposium Series Bioreversible Carriers in Drug Design, ed. Edward B. Roche, American Pharmaceutical Association and Pergamon Press, 1987.
Horig et al., "From bench to clinic and back: perspective on the 1st IQPC Translational Research Conference", *Journal of Translational Medicine*, 2:44 (2004) pp. 1-8.
Hoshi et al., "Indoleamine 2,3-dioxygenase is highly expressed in human adult T-cell leukemia/lymphoma and chemotherapy changes tryptophan catabolism in serum and reduced activity", *Leukemia Research*, 33 pp. 29-45 (2009).
Hou, et al., Cancer Res 67(2):792-801 (2007).
Hwu P, et al., "Indoleamine 2,3-dioxygenase production by human dendritic cells results in the inhibition of T cell proliferation", *J. Immunol.* 164(7):3596-9, (2000).
Ichikawa, T. et al., "A new synthesis of adenine and 4-aminoimidazole-5-carboxamide", J. Heterocycl. Chem., vol. 2 No. 3, pp. 253-255 (1965) (with STN File CA, abstract 68:78253).
Inaba et al., "Role of the immunosuppressive enzyme indoleamine 2,3-dioxygenase in the progression of ovarian cancer", Gyn. Oncol. 115, 185-92 (2009).
Ino, et al., *British Journal of Cancer*, 95:1555-1561 (2006).
Itaya et al., "Purines. XVIII. Kinetic studies of the Dimroth rearrangement of 1-alkoxy-9-methyladenines and 1-benzyloxyadenosine. Effect of 1-benzyloxy and 9-β-D-ribofuranosyl groups on the rates of the ring opening and the reclosure," *Chemical & Pharmaceutical Bulletin* (1975), 23(11), 2643-53 (with abstract Database Hcaplus STN File CA, Abstract 84:44592; 1976:44592) [prev. under Fuji but it's Itaya].
Itaya et al., "Purines. LXXII. Oxidation of N6-alkyladenines with m-chloroperoxybenzoic acid leading to N6-alkyladenine 1-oxides," *Chemical &Pharmaceutical Bulletin* (1996), 44(5), 967-971, (with abstract Database Hcaplus STN File CA, 125:86583; 1996:325165; CAS RN 155720-89-1).
Itaya et al., "Purines. LXXV. Dimroth rearrangement, hydrolytic deamination, and pyrimidine-ring breakdown of 7-alkylated 1-alkoxyadenines: N(1)-C(2) versus N(1)-C(6) bond fission," *Chemical & Pharmaceutical Bulletin* (1997), 45(5), 832-841(with abstract Database Hcaplus STN File CA, 127:65632, 1997:349657).
Ji, et al., "Provision of Granulocyte-Macrophage Colony-Stimulating Factor Converts an Autoimmune Response to a Self-Antigen into an Antitumor Response", *J. Immunol*, 2005, 175:1456-63.
Jordan, V. C. Nature Reviews: Drug Discovery, 2, 2003, p. 205.
Kamb, "What wrong with our cancer models?" Nature Reviews Drug Discovery 4, pp. 161-165 (2005).
Karanikas et al., "Indoleamine 2,3-Dioxygenase (IDO) Expression in Lung Cancer", *Cancer Biology & Therapy*, vol. 6, Issue 8 pp. 1258-1262, (2007).
Keith Guillory, "Generation of Polymorphs, Hydrates, Solvates, and Amorphous Solids", in Polymorphism in Pharmaceutical Solids, 183-226 (Harry G. Britain, ed., 1999).
Koblish, et al., "Hydroxyamidine Inhibitors of Indoleamine-2,3-dioxygenase Potently Suppress Systemic Tryptophan Catabolism and the Growth of IDO-Expressing Tumors", *Molecular Cancer Therapeutics*, 9(2):489-498 (Published Online Feb. 2, 2010 at 10.1158/11535-7163.MCT-09-0628).
Koblish, et al., "Potent, Orally Active Hydroxylamine Inhibitors of Indoleamine-2,3-dioxygenase Suppress Growth of IDO1-expressing Tumors through Systemic Inhibition of Tryptophan Catabolism", 24th Annual Meeting of the International Society for the Biological Therapy of Cancer (ISBTC) in National Harbor MD/Washington DC (Oct. 30, 2009) (poster—1 page) and abstract *J. Immunother.* vol. 32, No. 9 (2009) p. 1005.

Kocevar et al., "Neighboring group participation in formation of condensed azines. Formation of pyrazolo[3,4-b]pyrazines, isoxazolo[4,5-b]pyrazines and isothiazolo[5,4-b]pyridine. Heterocycles. CCX," Monatshefte fuer Chemie (1982), 113(6-7), 731-44 (with abstract Database Hcaplus STN File CA, 97:182276; 1982:582276).
Kocevar et al., "New synthetic approach for pyrazolo[3,4-b] pyrazines and isoxazolo[4,5-b] pyrazines," *Heterocycles* (1982), 19(2), 339-42 (with abstract Database Hcaplus STN File CA, 96:162655; 1982:162655).
Kocevar et al., "Simple Procedure for the Synthesis of Pyridinecarbohydroximoyl Chlorides and Bromides", Synth. Commun., 18(12), 1427-1432 (1988).
Kocevar et al., "Some new synthetic approaches for the preparation of pteridine 3-oxides and pteridines," *Heterocycles* (1981), 15(1), 293-6 (with abstract Database Hcaplus STN File CA, 94:121470; 1981:121470).
Kohl, et al., "IDO and clinical conditions associated with depressive symptoms", Curr. Drug Metab., 8:283-7 (2007).
Kola and Landis, "Can the pharmaceutical industry reduce attrition rates?" Nature Reviews Drug Discovery 3, pp. 711-715 (2004).
Leaf, Clifton, "Why are we losing the war on cancer (and how to win it)," Health Administrator vol. XVII, No. 1:172-183 (2005).
Liu et al., "Estimation and prediction on heats of formation for nitro furazan series compounds with new molecular subgraph", *Huaxue Wuli Xuebao*, (2002), 15(5), 351-356 and abstract Database Hcaplus, on STN, 2002:880171, No. 138:204550.
Liu, et al., "INCB024360, a Potent and Selective Inhibitor of Indoleamine 2,3-dioxygenase (IDO1) as a Novel Cancer Immunotherapeutic Agent", Mol Cancer Ther, 8(12 Suppl):Poster #C106 (2009).
Liu, et al., "Indoleamine 2,3-Dioxygenase, an Emerging Target for Anti-Cancer Therapy", Current Cancer Drug Targets, 9:938-952 (2009).
Liu et al., "Selective inhibition of IDO1 effectively regulates mediators of antitumor immunity," *Blood*, 2010, 115:3520-3530.
Lob, et al., "Inhibitors of indoleamine-2,3-dioxygenase for cancer therapy: can we see the wood for the trees?", Nature Reviews Cancer, 9:445-52 (2009).
Logan, et al., "HeLa cells cocultured with peripheral blood lymphocytes acquire an immuno-inhibitory phenotype through up-regulation of indoleamine 2,3-dioxygenase activity", Immunology, 105: 478-87 (2002).
Longo, G., "Dioximes. LXXVIII", *Gazzetta Chimica Italiana*, (1931), 61, 575-83 (and abstract Database Hcaplus, on STN, 1932:6117, No. 26:6117).
Luo et al. Cell, 2009, 136, pp. 823-837.
Mailankot, et al., "Cell Cycle Arrest by Kynurenine in Lens Epithelial Cells", IOVS, 49:5466-5475 at 5474 (2008).
Medawar, "Some immunological and endocrinological problems raised by the evolution of viviparity in vertebrates", Symp. Soc. Exp. Biol. 7: 320-38 (1953).
Mellman et al., "Cancer immunotherapy comes of age," *Nature*, 2011, 480:480-489.
Meyer, Kevin G., "Improved synthesis of 3-aminofurazan-4-carboxylic acid", Organic Preparations and Procedures INt. 36(4):361-362 (2004).
Milletti et al., "New and Original pKa Prediction Method Using Grid Molecular Interaction Fields", *Journal of Chemical Information and Modeling*, 2007, 47(6), 2172-2181 and abstract Database Hcaplus, on STN, 2007:1104249, No. 148:33199.
Mishnev et al., "Crystal and molecular structure of isomers of the oxime of 3-aminofurazanoyl piperidine", *Institute of Organic Synthesis, Latvian Academy of Sciences*, pp. 349-352 translation of Zhurnal Strukturnoi Khimii, 32(3):45-48 (1991).
Morissette, et al., "High-Throughput Crystallization: Polymorphs, Salts, Co-Crystals and Solvates", Adv. Drug Delivery Rev., 56:275-300 (2004).
Muller et al , "Inhibition of indoleamine 2,3-dioxygenase, an immunoregulatory target of the cancer suppression gene Bin1, potentiates cancer chemotherapy", Nature Med., 11:312-9 (2005).

(56) References Cited

OTHER PUBLICATIONS

Munn et al., "Expression of indoleamine 2,3-dioxygenase by plasmacytoid dendritic cells in tumor-draining lymph nodes", *J. Clin. Invest.*, 114(2): 280-90 (2004).
Munn et al., "Potential Regulatory Function of Human Dendritic Cells Expressing Indoleamine 2,3-Dioxygenase", *Science* 297: 1867-70 (2002).
Munn et al., "Prevention of Allogeneic Fetal Rejection by Tryptophan Catabolism", *Science* 281: 1191-3 (1998).
Munn, et al., *Journal of Clinical Investigation*, 117(5):1147-1154 (2007).
Neidle, Stephen, "Cancer Drug Design and Discovery," (Elsevier/Academic Press, 2008) pp. 427-431.
Nekrasov et al., "Effect of particular structural features of aminooximes on formation of final products in reactions with 5-aryl-2,3-dihydrofuran-2,3-diones", *Russian Journal of Organic Chemistry*, (2000), 36(2), 263-268, (*Translation of Zhurnal Organicheskoi Khimii*,vol. 36, No. 2 (2000) pp. 285-90) and abstract Database Hcaplus, on STN, 2000:643842, No. 133:321845.
Newton et al., "Pharmacodynamic assessment of INCB024360, an inhibitor of indoleamine 2,3- dioxygenase 1 (IDO1) in advanced cancer patients," *ASCO Annual Meeting*, 2012, 16 pages.
Nonaka et al., "Indoleamine 2,3-dioxygenase promotes peritoneal dissemination of ovarian cancer through inhibition of natural killercell function and angiogenesis promotion," *Int. J Oncology*, 2011, 38:113-120.
Okamoto, et al., Clin Cancer Res 11(16):6030-6039, at 6037-6038 (2005).
Pellegrin, et al., "Enhanced enzymatic degradation of tryptophan by indoleamine 2,3-dioxygenase contributes to the tryptophan deficient state seen after major trauma", Shock, 23:209-215 (2005).
Peterson et al., Evaluation of Functionalized Tryptophan Derivatives and related Compounds as Competitive Inhibitors of Indoleamine 2,3-Dioxygenase *Med. Chem. Res.* 3, 531-544, (1994).
Physicians' Desk Reference (PDR, e.g., 1996 edition, Medical Economics Company, Montvale, NJ) Zh. Org. Chim. (1993), 29, 1062-1066.
Pivina et al., "Comparative characteristic of energy content calculating methods for the furazan series as an example of energetic materials", *Propellants, Explosives, Pyrotechnics*, (1995), 20(1) 5-10 and abstract Database Hcaplus, on STN, 1995:464236, No. 122:217824.
Poluektova et al., "Generation of cytotoxic T cells against virus-infected human brain macrophages in a murine model of HIV-1 encephalitis", *J. Immunol.*, 168(8):3941-9 (2002).
Potula et al , "Inhibition of indoleamine 2,3-dioxygenase (IDO) enhances elimination of virus-infected macrophages in an animal model of HIV-1 encephalitis", *Blood*, 106:2382-90 (2005).
Quan, et al., Expert Opin. Biol. Ther., 8:1705 at 1714 (2008).
Rakitin et al., "Reaction of furoxannitrolic acids with nitrogen tetroxide", *Khimiya Geterotsiklicheskikh Soedinenii*, (1993), (9), 1283-7 (with abstract Database Hcaplus, on STN, 1994:244883, No. 120:244883).
Rakitin et al., "Synthesis of Furaxanenitrolic acids", N. D. Zelinskii Institute of Organic Chemistry, Russian Academy of Sciences, 117913 Moscow pp. 952-954 (1994), Translated from *Khimiya Geterotsiklicheskikh Soedinenii*,(1993), (8), 117-19 (with abstract Database Hcaplus, on STN, 1994:164073, No. 120:164073).
Ravin, Louis J., "Preformulation", *Remington's Pharmaceutical Sciences*, 17th ed., Mack Publishing Company, Easton, PA., Chapter 76, pp. 1409-1423 (1985).
Riesenberg et al., "Expression of Indoleamine 2,3-Dioxygenase inTumor Endothelial Cells Correlateswith Long-term Survival of Patients with Renal Cell Carcinoma", *Clin. Cancer Res.*, vol. 13 Issue 23 pp. 2993-3002 (2007).
Riffaud, et al., "Sur les propriétiés analgésiques at antiinflammatoires des benzofuryl-2 amidoximes", *European Journal of Medicinal Chemistry*, Editions Scientifique Elsevier, Paris, Fr., vol. 1796, pp. 577-580, (1982) (please see ISRPCTUS2007078759 regarding the relevance of this reference).

Roberts Jr. et al., "Trends in the Risks and Benefits to Patient with Cancer Participating in Phase 1 Clinical Trials,"JAMA 292(17):2130-2140 (2004).
Robev et al., "Pharmacological study of newly synthesized 2-phenyl-4-anilinopyrimidine-5-amidoxime," Doklady Bolgarskoi Akademii Nauk (1982), 35(10), 1451-4 (with abstract Database Hcaplus STN File CA, 98:191493; 1983:191493).
Roche, Edward B., Bioreversible Carriers in Drug Design, ed., American Pharmaceutical Association and Pergamon Press, 1987.
Rodriguez-Spong et al., "General principles of pharmaceutical solid polymorphism: a supramolecular perspective", *Advanced Drug Delivery Review*, (2004), 56, pp. 241-274.
Romanova et al., "Synthesis and reactivity of azidomes: III 1-Azido (4-amino-1,2,5-oxadiazol-3-yl) aldoxime in the Cycloaddtion Reaction," *Russian J. of Org. Chem.*, 39(4), 574-578 (translation of *Zhurnal Organicheskoi Khimii*, vol. 39 No. 4, pp. 610-615 (2002)).
Rozhov et al., "Synthesis of 1,2,4-oxadiazole-, pyrrole- and 1,2,3-triazole-substituted (1,2,3-triazol-1-yl)furazans", *Mendeleev Communications*, 2008, 18(3), 161-163 and abstract Database Hcaplus, on STN, 2008:880463, No. 150:352019.
Sako, "Product class 19: pyridopyrimidines," *Science of Synthesis* (2004), 16, 1155-1267 (and abstract Database Hcaplus STN File CA, 142:197902; 2004:205975).
Sambrook, J, Russel, D. Molecular Cloning: A laboratory Manual (3rd edition). Cold Spring Harbor Laboratory Press. Cold Spring Harbor, NY, USA. 2001.
Schafer et al., "Failure is an option: learning from unsuccessful proof of concept trials", *Drug Discovery Today*, vol. 13, Nos. 21/22, pp. 913-916 (2008).
Scherle, P., "Characterization of Novel and Potent Inhibitors of the Immunoregulatory Enzyme Indoleamine 2,3-Dioxygenase (IDO) for Use as Cancer Therapy" presented on Mar. 5, 2009 at the Translational Research Cancer Center Consortium annual meeting in Philadelphia, PA.
Search Run Jul. 13, 2010/Scifinder, 10 pages.
Search Run Jul. 28, 2009 / HCAPLUS, 95 pgs.
Search Run Jul. 28, 2009/Registry File Compounds, 107 pgs.
Search Run STN International "11641284" dated Jan. 16, 2009 (93 pages).
Shaposhnikov et al., "New Heterocycles with a 3-Aminofurazanyl Substituent", *Russian Journal of Organic Chemistry*, (2002), 38(9), 1351-1355, (*Translation of Zhurnal Organicheskoi Khimii*, (2002), 38(9), 1405-8, and abstract Database Hcaplus, on STN, 2002:953422, No. 138:368816.
Sheremetev et al., "Hydroxylammonium salts of Furazan family", *International Annual Conference of ICT* (2003), 34th, 101/1-101/10 and abstract Database Hcaplus, on STN, 2003:641413, No. 139:383553.
Sheremetev et al., "Synthesis of secondary and tertiary aminofurazans", Russian Chemical Bulletin 53(3), 596-614 (2004), translation from Izvestiya Akademii Nauk, Seriya Khimicheskaya, 53(3), pp. 569-586 (Mar. 2004) (and abstract Database Caplus No. 2004:589877; 142:219211); XP002526510 (2004).
Sherif et al., "Syntheses with heterocyclic β-enaminonitriles. An expeditious synthetic approach to polyfunctionally substituted 5-phenyl-sulfonylthiophenes and their fused derivatives," *Monatshefte fuer Chemie* (1997), 128(6/7), 687-696 (with abstract Database Hcaplus STN File CA, 127:331458; 1997:619483).
Shih et al., Medicinal Research Reviews, vol. 24, 2004, pp. 449-474.
Sinditskii et al., "Study on combustion of new energetic furazans", *29th International Annual Conference of ICT* (Jun. 30-Jul. 3, 1998) (*Energetic Materials*), 170.1-170.11 and abstract Database Hcaplus, on STN, 1998:498929, No. 129:163569.
Soliman et al., "Indoleamine 2,3-Dioxygenase: Is it an Immune Suppressor", Cancer J., 16, 354-59 (2010).
Soliman et al., "A phase I study of 1-methyl-D-tryptophan in patients with advanced malignancies," *J Clin Oncol.*, 2012, suppl; abstr 2501.
Sono, et al., "Indoleamine 2,3-Dioxygenase", J. Biol. Chem. 255(4), 1339-1345 (1980).
Souillac, et al., Characterization of Delivery Systems, Differential Scanning Calorimetry, pp. 217- 218 in Encyclopedia of Controlled Drug Delivery, (1999), John Wiley & Sons, pp. 212-227.

(56) References Cited

OTHER PUBLICATIONS

Spasova et al., "Certain derivatives of pyrazole as potential antimetabolites of 4(5)-amino-imidazole-5(4)-carboxamide," Progress in Chemotherapy, (Antibacterial, Antiviral, Antineoplast.), Proceedings of the 8th International Congress of Chemotherapy Athens 1973, vol. 3, 841-4 (with abstract Database Hcaplus STN File CA 84:54765; 1976:54765).

Spasova et al., "Inhibition of the growth of *L. casei* by some pyrazole analogues of 5(4)- aminoimidazole-4(5)-carboxamide," Doklady Bolgarskoi Akademii Nauk (1975), 28(11), 1517-20 (with abstract Database Hcaplus STN File CA Abstract 84:99208; 1976:99208).

Speeckaert et al., "Indoleamine 2,3-dioxygenase, a new prognostic marker in sentinel lymph nodes of melanoma patients", European Journal of Cancer, (2012), 48, 2004-2011.

STN File CA, Abstract 145:457146 (abstract of Wang et al, "Experimental study on synthesis of 3-amino-4-chloroximinofurazan" Hanneng Cailiao (2005), 13 (Suppl.), 1-3) (1 page) (also filed under Wang Aug. 5, 2010).

Storey, et al., "Automation of Solid Form Screening Procedures in the Pharmaceutical Industry-How to Avoid the Bottlenecks", Crystallography Reviews, 10(1):45-46 (2004).

Takikawa et al., "Mechanism of Interferon-γ Action," *J. Biol. Chem.* 263(4):2041-8 (1988).

Tan, et al., "Manipulation of indoleamine 2,3 dioxygenase; a novel therapeutic target for treatment of diseases", Expert Opin. Ther. Targets, 13:987-1012 (2009).

Tang, et al., Zhongguo Shi Yan Xue Ye Xue Za Zhi. 14(3):539-42 (2006) (Abstract).

Taneja et al., "MMTV mouse models and the diagnostic values of MMTV-like sequences in human breast cancer," *Expert Rev Mol Diagn.*, 2009, 9(5):423-440.

Taylor, et al., "Relationship between Interferon-γ, indoleamine 2,3-dioxygenase, and tryptophan catabolism", FASEB J., 5:2516-22 (1991).

Terness, et al , "Inhibition of Allogenieic T cell Proliferation by Indoleamine 3,3-Dioxygenase-expressing Dendritic Cells: Mediation of Suppression by Tryptophan Metabolites", *J.Exp. med.*, 196,(4),447-457, (2002).

Trinh and Hwu, "Ipilimumab in the treatment of melanoma," *Expert. Opin, Biol. Ther.*, 2012, 12(6):773-782.

Tselinskii et al., "Synthesis and reactivity of carbohydroximoyl azides: II. 4-substituted 1,2,5- oxadiazole-3-carbohydroximoylazides and 1-hydroxy-5-(4-R-1,2,5-oxadiazol-3-yl)tetrazoles", *Russian Journal of Organic Chemistry*, (2001), 37(11), 1638-1642, translation of *Zhurnal Organicheskoi Khimii* (2001), 37(11), 1708-1712 (with abstract Database Hcaplus, on STN, 2002:200728, No. 137:20337).

Uyttenhove, et al., "Evidence for a tumoral immune resistance mechanism based on tryptophan degradation by indoleamine 2,3-dioxygenase", *Nat. Med.*, 9(10):1269-1274, (2003).

Vippagunta, et al., "Crystalline Forms", Adv. Drug Delivery Rev., 48:3-26 (2001).

Wang et al., "Synthesis of 3-amino-4-aminoximidofurazan and its crystal structure", *Hecheng Huaxue*, (2006), 14(3), 234-239 (with abstract Database Hcaplus, on STN, 2006:616681, No. 146:206250.

Wang et al., "500 Gram-grade synthesis of 3-amino-4-aminoximinofurazan," *Hanneng Cailiao* (2006), 14(1), 27-28 (3 pages); (with Database Hcaplus STN File CA, 145:191465; 2006:477562) (1 page).

Wang et al., "Crystal structure of 3-amino-4-acylaminoximinofurazan", Chinese Journal of Energetic Materials, translation of *Hanneng Cailiao*, 14(6), 441-445 (2006) with abstract Database Hcaplus, on STN, 2007:380035, No. 148:382415.

Wang et al., "Furazan-functionalized tetrazolate-based salts: a new family of insensitive energetic materials", *Chemistry—A European Journal*, 2009, 15(11), 2625-2634 and abstract Database Hcaplus, on STN, 2009:347940, No. 150:518273.

Wang et al.,, "Synthesis and crystal structure of 3,6-bis(3'-aminofurazan-4-yl)-1,4-dioxa-2,5-diazacyclohexane-2,5-diene",

*Huaxue Yanjiu Yu Yingyong* (2006), 18(12), 1398-1402 (with abstract Database Hcaplus, on STN, 2007:633470, No. 148:561814).

WebMD entry for Parkinson's Disease Prevention, obtained from http://www.webmd.com/parkinsons-disease/guide/parkinsonsdisease-prevention on Jul. 19, 2012 (2 pages).

Wichers et al., "The role of indoleamine 2,3-dioxygenase (IDO) in the pathophysiology of interferon-α-induced depression", *J. Psychiatry Neurosci.*, 29(1): 11-17 (2004).

Wieland et al, "Zur Konstitution der polymeren Knallsauren. Pericyanilsaure, Epicyanilsaure und Metacyanilsaure", Eingelaufen am 25 pp. 54-78 (1929).

Wieland et al., "Zur Konstitution der polymeren Knallsauren. X", Aus dem Chem. Laboratorium der Bayr. Akademie der Wissenschaften zu Munchen, Eingelaufen am 23, pp. 43-53 (1929).

Wikipedia, "indoleamine 2,3-dioxygenase"; downloaded on Jan. 16, 2009 http://en.wikipedia.org/wiki/Indoleamine_2,3-dioxygenase (3 pages).

Wiley-VCH Verlag GmbH & Co. KGaA, Weinheim, "Organic Synthesis: General Remarks", pp. 1-16 (2005).

Wirleitner, et al., "Interferon-γ-Induced Conversion of Tryptophan: Immunologic and Neuropsychiatric Aspects", Curr. Med. Chem., 10: 1581-91 (2003).

Witkiewicz et al., "Expression of Indoleamine 2,3-Dioxygenase in Metastatic Pancreatic Ductal Adenocarcinoma Recruits Regulatory T Cells to Avoid Immune Detection", *J. Am. Coll. Surg.*, vol. 206, No. 5, pp. 849-856 (May 2008).

Witkiewicz et al., "IDO2 Genotyping and Expression in Pancreatic Cancer", *J. Am. Coll. Surg.*, vol. 208, No. 5 pp. 781-789 (May 2008).

Yarovenko et al., "A convenient synthesis of 3-substituted 5-guanidino-1,2,4-oxadiazoles", Russian Chem. Bulletin, vol. 43, No. 1 pp. 114-117 (1994) translation of *Izvestiya Akademii Nauk, Seriya Khimicheskaya*, (1994), (1), 118-21 and abstract Database Hcaplus, on STN, 1995:542485, No. 123:55777.

Yarovenko et al., "New method for the preparation of 5-amino-1,2,4-oxadiazoles", *Bulletin of the Academy of Sciences of the USSR*, p. 1924, translation of *Izvestiya Akademii Nauk SSSR, Seriya Khimicheskaya*, (1991), (9), 2166-7 (3 pages); (with abstract Database Hcaplus, on STN, 1992:21001, No. 116:21001) (1 page).

Yarovenko et al., "New synthesis of nitriles enriched with 15N isotope", Russian Chem. Bulletin, vol. 43, No. 3 pp. 402-404 (1994) translation of *Izvestiya Akademii Nauk, Seriya Khimicheskaya*, (1994), (3), 444-6 and abstract Database Hcaplus, on STN, 1995:542864, No. 123:111224.

Yarovenko et al., Tetrahedron, 1990, 46 (11), pp. 3941-3952.

Youngdale, Gilbert A. et al., "Synthesis and antifertility activity of 5-(phenoxymethyl)-2- oxazolidinethiones", Journal of Medicinal Chemistry, 9(1), 155-7, 1966 XP002467245 (1965).

Yue et al., "Discovery of Potent Competitive Inhibitors of Indoleamine 2,3-Dioxygenase with in Vivo Pharmacodynamic Activity and Efficacy in a Mouse Melanoma Model," J. Med. Chem. vol. 52, No. 23, pp. 7364-7367 (2009).

Zhou, et al., "Synthesis and properties of 3,4-Bis (4'-aminofurazano-3')furoxan", Huozhayao Xuebao, 30(1), 54-56 (2007) and abstract.

Zidarova et al., "Certain derivatives of 3-aminopyrazole-4-carboxylic acid as potential antimetabolites of 4(5)-aminoimidazole-5(4)-carboxamide in microorganisms," *Doklady Bolgarskoi Akademii Nauk* (1973), 26(3), 419-22 (with abstract Database Hcaplus STN File CA, Abstract 79:74187; 1973:474187).

Notification on the Result of Substantive Examination, National Office of Intellectual Property, No. 60636/SHTT-SC2, Vietnamese Application No. 1-2007-02634, dated Oct. 7, 2009 (3 pages).

Office Action (non-final) mailed Aug. 3, 2009, U.S. Appl. No. 11/430,441 (15 Pages).

Office Action (final) for U.S. Appl. No. 11/641,284 mailed Oct. 21, 2009 (8 pages).

Office Action (final) mailed Jun. 7, 2010, U.S. Appl. No. 11/430,441 (20 Pages).

International Preliminary Report on Patentability for PCT/US2006/17983 dated Nov. 13, 2007 (6 pages).

International Preliminary Report on Patentability for PCT/US2006/048290 dated Jun. 24, 2008 (9 pages).

International Preliminary Report on Patentability for PCT/US2007/078758 dated Mar. 24, 2009 (8 pages).

(56) References Cited

OTHER PUBLICATIONS

International Preliminary Report on Patentability for PCT/US2007/003364 dated Aug. 12, 2008 (9 pages).
International Preliminary Report on Patentability for PCT/US2007/078745 dated Mar. 24, 2009 (13 pages).
International Preliminary Report on Patentability for PCT/US2007/078759 dated Mar. 24, 2009 (15 pages).
International Preliminary Report on Patentability for PCT/US2009/049794 issued Jan. 11, 2011 (12 pages).
International Search Report and Written Opinion PCT/US2006/17983 dated Aug. 28, 2006, completed on Aug. 2, 2006) (12 Pages).
International Search Report and Written Opinion for PCT/US2006/048290 dated Sep. 17, 2007 (15 pages).
International Search Report and Written Opinion for PCT/US2007/003364 mailed Sep. 20, 2007 and completed on Sep. 12, 2007 (16 pages).
International Search Report and Written Opinion for PCT/US2007/078745 completed Feb. 8, 2008 and mailed Jun. 16, 2008 (21 pages).
International Search Report and Written Opinion for PCT/US2007/078759 completed Feb. 6, 2008 and mailed Jun. 16, 2008 (23 pages).
International Search Report and Written Opinion for PCT/US2007/078758 completed Apr. 28, 2008 and mailed May 9, 2008 (12 pages).
International Search Report and Written Opinion PCT/US2009/049794 dated Apr. 26, 2010 (May 6, 2010) (27 Pages).
Eurasia—Search Report for Application No. 200702455 dated Apr. 28, 2008 (1 page).
Extended European Search Report for European Application No. 06759438.2 dated Jun. 5, 2009 (10 pages).
Search Report dated Nov. 12, 2008 and Written Opinion dated Feb. 6, 2009—Singapore Application No. 200717302-4 (18 pages).
Singapore—Final Examination Report, Singapore Patent Application No. 2007/17302-4 dated Sep. 23, 2009 (11 Pages).
Examination Report - EP Patent Application No. 06759438.2 dated Jul. 29, 2010 (4 pages).
Office Action (nonfinal) for U.S. Appl. No. 12/498,782 mailed Jan. 14, 2011 (14 pages).
Office Action (nonfinal) for U.S. Appl. No. 11/641,284 mailed Jan. 29, 2009 (13 pages).
Office Action (nonfinal) for U.S. Appl. No. 11/641,284 mailed May 7, 2010 (9 pages).
Office Action (final) for U.S. Appl. No. 11/641,284 mailed Dec. 15, 2010 (8 pages).
Office Action (nonfinal) for U.S. Appl. No. 11/856,967 mailed Jan. 19, 2010 (5 pages).
Office Action (final) for U.S. Appl. No. 11/856,967 mailed Sep. 24, 2010 (11 pages).
Office Action (nonfinal) for U.S. Appl. No. 11/856,982 mailed Jan. 29, 2010 (10 pages).
Office Action (final) for U.S. Appl. No. 11/856,982 mailed Sep. 17, 2010 (6 pages).
Office Action (nonfinal) for U.S. Appl. No. 11/430,441 mailed Dec. 9, 2010 (15 pages).
Office Action (nonfinal) for U.S. Appl. No. 13/294,711 mailed Jan. 30, 2013 (110 pages).
Office Action (nonfinal) for U.S. Appl. No. 13/294,711 mailed Jul. 25, 2012, (26 pages).
Chilean Patent Office, Application No. 1096-2006, Office Action, Apr. 22, 2007 (2 pages).
State Intellectual Property Office—PR China, Application No. 200680024326-1, Office Action, Jan. 19, 2011 (10 pages).
State Intellectual Property Office—PR China, Application No. 200680024326-1, Office Action, Oct. 23, 2009 (6 pages).
Eurasian Patent Office, Application No. 200702455, Office Action, Oct. 9, 2009 (English translation) (6 pages).
Georgian Patent Office, Application No. AP2006010418, Office Action, Jul. 14, 2009 (English translation) (2 pages).
Malaysian Patent Office, Application No. PI20062122, Office Action, Oct. 18, 2010 (2 pages).
Intellectual Property Office of New Zealand, Application No. 562919, Examination Report, Sep. 17, 2009 (4 pages).
Office Action (final) U.S. Appl. No. 12/498,782 mailed May 31, 2011 (35 pages).
Office Action dated Nov. 8, 2011 for Japanese Patent Appln. No. 2008-511287 with English translation (11 pgs.).
Office Action—JP Patent Appl. No. 2008-547407 mailed Aug. 21, 2012 (7 pages).
Search Report, Taiwan Application No. 117382 dated Mar. 7, 2012 (English Translation 1 page—Taiwan Search Report 4 pages).
Office Action (non-final) Mexico Application No. MX/1/2007/013977 as communicated to undersigned representative on Nov. 18, 2011 (2 pages).
Office Action—JP Patent Appl. No. 2009-529341 mailed Oct. 16, 2012 (3 pages).
Office Action—JP Patent Appl. No. 2009-529343 mailed Oct. 16, 2012 (4 pages).
Extended European Search Report in EP Application No. 12178315.3, dated Jan. 18, 2013, 8 pages.
Costa Rican Office Action in CR Application No. 9485, Feb. 11, 2013, 14 pages. (with English translation).
Robinson et al., "The Role of IFN-γ and Tnf-α-Responsive Regulatory Elements in the Synergistic Induction of Indoleamine Dioxygenase," J Interferon Cytokin Res., 2005, 25(1):20-30.
Wong et al., "Programmed death-1 blockage enhances expansion and functional capacity of human melanoma antigen-specific CTLs," International Immunology, 2007, 19:1223-1234.
Office Action in Chinese Application No. 201210562826.8, mailed Mar. 18, 2014, 12 pages.

\* cited by examiner

N-HYDROXYAMIDINOHETEROCYCLES AS MODULATORS OF INDOLEAMINE 2,3-DIOXYGENASE

CROSS REFERENCE TO RELATED APPLICATIONS

This application is a divisional of U.S. Ser. No. 11/641,284, now U.S. Pat. No. 8,450,351, filed Dec. 19, 2006, which claims the benefit of U.S. Ser. Nos. 60/751,854, filed Dec. 20, 2005; 60/801,337, filed May 18, 2006; and 60/857,558, filed Nov. 8, 2006, the disclosures of each of which are incorporated herein by reference in their entireties.

FIELD OF THE INVENTION

The present invention is directed to modulators of indoleamine 2,3-dioxygenase (IDO), as well as compositions and pharmaceutical methods thereof.

BACKGROUND OF THE INVENTION

Tryptophan (Trp) is an essential amino acid required for the biosynthesis of proteins, niacin and the neurotransmitter 5-hydroxytryptamine (serotonin). The enzyme indoleamine 2,3-dioxygenase (also known as INDO or IDO) catalyzes the first and rate limiting step in the degradation of L-tryptophan to N-formyl-kynurenine. In human cells, a depletion of Trp resulting from IDO activity is a prominent gamma interferon (IFN-γ) inducible antimicrobial effector mechanism. IFN-γ stimulation induces activation of IDO, which leads to a depletion of Trp, thereby arresting the growth of Trp-dependent intracellular pathogens such as *Toxoplasma gondii* and *Chlamydia trachomatis*. IDO activity also has an antiproliferative effect on many tumor cells, and IDO induction has been observed in vivo during rejection of allogeneic tumors, indicating a possible role for this enzyme in the tumor rejection process (Daubener, et al, 1999, *Adv. Exp. Med. Biol.*, 467: 517-24; Taylor, et al., 1991, *FASEB J.*, 5: 2516-22).

It has been observed that HeLa cells co-cultured with peripheral blood lymphocytes (PBLs) acquire an immunoinhibitory phenotype through up-regulation of IDO activity. A reduction in PBL proliferation upon treatment with interleukin-2 (IL2) was believed to result from IDO released by the tumor cells in response to IFNG secretion by the PBLs. This effect was reversed by treatment with 1-methyl-tryptophan (1MT), a specific IDO inhibitor. It was proposed that IDO activity in tumor cells may serve to impair antitumor responses (Logan, et al., 2002, *Immunology*, 105: 478-87).

Recently, an immunoregulatory role of Trp depletion has received much attention. Several lines of evidence suggest that IDO is involved in induction of immune tolerance. Studies of mammalian pregnancy, tumor resistance, chronic infections and autoimmune diseases have shown that cells expressing IDO can suppress T-cell responses and promote tolerance. Accelerated Trp catabolism has been observed in diseases and disorders associated with cellular immune activation, such as infection, malignancy, autoimmune diseases and AIDS, as well as during pregnancy. For example, increased levels of IFNs and elevated levels of urinary Trp metabolites have been observed in autoimmune diseases; it has been postulated that systemic or local depletion of Trp occurring in autoimmune diseases may relate to the degeneration and wasting symptoms of these diseases. In support of this hypothesis, high levels of IDO were observed in cells isolated from the synovia of arthritic joints. IFNs are also elevated in human immunodeficiency virus (HIV) patients and increasing IFN levels are associated with a worsening prognosis. Thus, it was proposed that IDO is induced chronically by HIV infection, and is further increased by opportunistic infections, and that the chronic loss of Trp initiates mechanisms responsible for cachexia, dementia and diarrhea and possibly immunosuppression of AIDS patients (Brown, et al., 1991, *Adv. Exp. Med. Biol.*, 294: 425-35). To this end, it has recently been shown that IDO inhibition can enhance the levels of virus-specific T cells and, concomitantly, reduce the number of virally-infected macrophages in a mouse model of HIV (Portula et al., 2005, *Blood*, 106:2382-90).

IDO is believed to play a role in the immunosuppressive processes that prevent fetal rejection in utero. More than 40 years ago, it was observed that, during pregnancy, the genetically disparate mammalian conceptus survives in spite of what would be predicted by tissue transplantation immunology (Medawar, 1953, *Symp. Soc. Exp. Biol.* 7: 320-38). Anatomic separation of mother and fetus and antigenic immaturity of the fetus cannot fully explain fetal allograft survival. Recent attention has focused on immunologic tolerance of the mother. Because IDO is expressed by human syncytiotrophoblast cells and systemic tryptophan concentration falls during normal pregnancy, it was hypothesized that IDO expression at the maternal-fetal interface is necessary to prevent immunologic rejection of the fetal allografts. To test this hypothesis, pregnant mice (carrying syngeneic or allogeneic fetuses) were exposed to 1MT, and a rapid, T cell-induced rejection of all allogeneic concept was observed. Thus, by catabolizing tryptophan, the mammalian conceptus appears to suppresses T-cell activity and defends itself against rejection, and blocking tryptophan catabolism during murine pregnancy allows maternal T cells to provoke fetal allograft rejection (Munn, et al., 1998, *Science* 281: 1191-3).

Further evidence for a tumoral immune resistance mechanism based on tryptophan degradation by IDO comes from the observation that most human tumors constitutively express IDO, and that expression of IDO by immunogenic mouse tumor cells prevents their rejection by preimmunized mice. This effect is accompanied by a lack of accumulation of specific T cells at the tumor site and can be partly reverted by systemic treatment of mice with an inhibitor of IDO, in the absence of noticeable toxicity. Thus, it was suggested that the efficacy of therapeutic vaccination of cancer patients might be improved by concomitant administration of an IDO inhibitor (Uyttenhove et al., 2003, *Nature Med.*, 9: 1269-74). It has also been shown that the IDO inhibitor, 1-MT, can synergize with chemotherapeutic agents to reduce tumor growth in mice, suggesting that IDO inhibition may also enhance the anti-tumor activity of conventional cytotoxic therapies (Muller et al., 2005, *Nature Med.*, 11:312-9).

One mechanism contributing to immunologic unresponsiveness toward tumors may be presentation of tumor antigens by tolerogenic host APCs. A subset of human IDO-expressing antigen-presenting cells (APCs) that coexpressed CD123 (IL3RA) and CCR6 and inhibited T-cell proliferation have also been described. Both mature and immature CD123-positive dendritic cells suppressed T-cell activity, and this IDO suppressive activity was blocked by 1MT (Munn, et al., 2002, *Science* 297: 1867-70). It has also been demonstrated that mouse tumor-draining lymph nodes (TDLNs) contain a subset of plasmacytoid dendritic cells (pDCs) that constitutively express immunosuppressive levels of IDO. Despite comprising only 0.5% of lymph node cells, in vitro, these pDCs potently suppressed T cell responses to antigens presented by the pDCs themselves and also, in a dominant fashion, suppressed T cell responses to third-party antigens presented by nonsuppressive APCs. Within the population of pDCs, the majority of the functional IDO-mediated suppressor activity segregated with a novel subset of pDCs coexpressing the B-lineage marker CD19. Thus, it was hypothesized that IDO-mediated suppression by pDCs in'TDLNs creates a local microenvironment that is potently suppressive of host antitumor T cell responses (Munn, et al., 2004, *J. Clin. Invest.*, 114(2): 280-90).

IDO degrades the indole moiety of tryptophan, serotonin and melatonin, and initiates the production of neuroactive and immunoregulatory metabolites, collectively known as kynurenines. By locally depleting tryptophan and increasing proapoptotic kynurenines, IDO expressed by dendritic cells (DCs) can greatly affect T-cell proliferation and survival. IDO induction in DCs could be a common mechanism of deletional tolerance driven by regulatory T cells. Because such tolerogenic responses can be expected to operate in a variety of physiopathological conditions, tryptophan metabolism and kynurenine production might represent a crucial interface between the immune and nervous systems (Grohmann, et al., 2003, *Trends Immunol.*, 24: 242-8). In states of persistent immune activation, availability of free serum Trp is diminished and, as a consequence of reduced serotonin production, serotonergic functions may also be affected (Wirleitner, et al., 2003, *Curr. Med. Chem.*, 10: 1581-91).

Interestingly, administration of interferon-α has been observed to induce neuropsychiatric side effects, such as depressive symptoms and changes in cognitive function. Direct influence on serotonergic neurotransmission may contribute to these side effects. In addition, because IDO activation leads to reduced levels of tryptophan, the precursor of serotonin (5-HT), IDO may play a role in these neuropsychiatric side effects by reducing central 5-HT synthesis. Furthermore, kynurenine metabolites such as 3-hydroxy-kynurenine (3-OH-KYN) and quinolinic acid (QUIN) have toxic effects on brain function. 3-OH-KYN is able to produce oxidative stress by increasing the production of reactive oxygen species (ROS), and QUIN may produce overstimulation of hippocampal N-methyl-D-aspartate (NMDA) receptors, which leads to apoptosis and hippocampal atrophy. Both ROS overproduction and hippocampal atrophy caused by NMDA overstimulation have been associated with depression (Wichers and Maes, 2004, *J. Psychiatry Neurosci.*, 29: 11-17). Thus, IDO activity may play a role in depression.

Small molecule inhibitors of IDO are being developed to treat or prevent IDO-related diseases such as those described above. For example, PCT Publication WO 99/29310 reports methods for altering T cell-mediated immunity comprising altering local extracellular concentrations of tryptophan and tryptophan metabolites, using an inhibitor of IDO such as 1-methyl-DL-tryptophan, p-(3-benzofuranyl)-DL-alanine, p-[3 benzo(b)thienyl]-DL-alanine, and 6-nitro-L-tryptophan) (Munn, 1999). Reported in WO 03/087347, also published as European Patent 1501918, are methods of making antigen-presenting cells for enhancing or reducing T cell tolerance (Munn, 2003). Compounds having indoleamine-2,3-dioxygenase (IDO) inhibitory activity are further reported in WO 2004/094409; and U.S. Patent Application Publication No. 2004/0234623 is directed to methods of treating a subject with a cancer or an infection by the administration of an inhibitor of indoleamine-2,3-dioxygenase in combination with other therapeutic modalities.

In light of the experimental data indicating a role for IDO in immunosuppression, tumor resistance and/or rejection, chronic infections, HIV-infection, AIDS (including its manifestations such as cachexia, dementia and diarrhea), autoimmune diseases or disorders (such as rheumatoid arthritis), and immunologic tolerance and prevention of fetal rejection in utero, therapeutic agents aimed at suppression of tryptophan degradation by inhibiting IDO activity are desirable. Inhibitors of IDO can be used to activate T cells and therefore enhance T cell activation when the T cells are suppressed by pregnancy, malignancy or a virus such as HIV. Inhibition of IDO may also be an important treatment strategy for patients with neurological or neuropsychiatric diseases or disorders such as depression. The compounds, compositions and methods herein help meet the current need for IDO modulators.

SUMMARY OF THE INVENTION

The present invention provides, inter alia, compounds of Formula Ia:

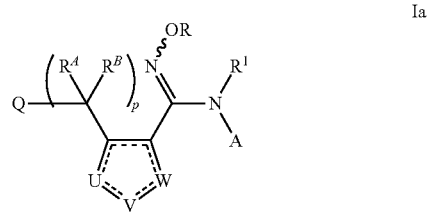

or pharmaceutically acceptable salts or prodrugs thereof, wherein constituent members are provided herein.

The present invention further provides compositions comprising a compound of Formula Ia, or pharmaceutically acceptable salt thereof, and at least one pharmaceutically acceptable carrier.

The present invention further provides methods of modulating enzyme activity of IDO comprising contacting a compound of Formula Ia, or pharmaceutically acceptable salt thereof, with IDO.

The present invention further provides methods of treating IDO-associated diseases, including cancer, viral infection and depression, comprising administering to a patient a therapeutically effective amount of a compound of Formula Ia, or pharmaceutically acceptable salt thereof.

The present invention further provides methods of altering extracellular tryptophan levels in a mammal comprising administering to the mammal an effective amount of a compound of Formula Ia, or pharmaceutically acceptable salt thereof.

The present invention further provides methods of inhibiting immunosuppression, such as IDO-mediated immunosuppression, in a patient comprising administering to the patient an effective amount of a compound of Formula Ia, or pharmaceutically acceptable salt thereof.

DETAILED DESCRIPTION

The present invention provides compounds which are modulators of IDO having Formula Ia:

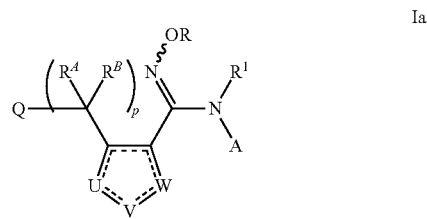

or pharmaceutically acceptable salts or prodrugs thereof, wherein:
U is N, O, S, CR', or NR";
V, and W are each, independently, N, O, S, $CR^2$, or $NR^3$, wherein the five-membered ring containing U, V, and W is an aromatic heterocycle;

A is aryl, cycloalkyl, heteroaryl, or heterocycloalkyl, each optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ cyanoalkyl, halosulfanyl, $Cy^1$, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^i)NR^cR^d$, $NR^cC(=NR^i)NR^cR^d$, $P(R^f)_2$, $P(OR^e)_2$, $P(O)R^eR^f$, $P(O)OR^eOR^f$, $S(O)R^b$, $S(O)NR^cR^d$, $S(O)_2R^b$, $NR^cS(O)_2R^b$, and $S(O)_2NR^cR^d$, wherein said $C_{1-6}$ alkyl, $C_{2-6}$ alkenyl, and $C_{2-6}$ alkynyl is optionally substituted with 1, 2, or 3 substituents independently selected from $Cy^1$, CN, $NO_2$, $OR^a$, $SR^a$, $C(O)R^b$, $C(O)NR^cR^d$, C(O)ORB, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^i)NR^cR^d$, $NR^cC(=NR^i)NR^cR^d$, $P(R^f)_2$, $P(OR^e)_2$, $P(O)R^eR^f$, $P(O)OR^eOR^f$, $S(O)R^b$, $S(O)NR^cR^d$, $S(O)_2R^b$, $NR^cS(O)_2R^b$, and $S(O)_2NR^cR^d$;

R is H, $C(O)R^5$, $C(O)OR^6$, or $C(O)NR^{6a}R^{6b}$;

$R^A$ and $R^B$ are independently selected from H, F, $C_{1-6}$ alkyl, $C_{2-6}$ alkenyl, $C_{2-6}$ alkynyl, $C_{1-6}$ haloalkyl, aryl, cycloalkyl, heteroaryl, heterocycloalkyl, arylalkyl, cycloalkylalkyl, heteroarylalkyl, heterocycloalkylalkyl, halosulfanyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $C(=NR^i)NR^{c1}R^{d1}$, $NR^{c1}C(=NR^i)NR^{c1}R^{d1}$, $P(R^{f1})_2$, $P(OR^{e1})_2$, $P(O)R^{e1}R^{f1}$, $P(O)OR^{e1}OR^{f1}$, $S(O)R^{b1}$, $S(O)NR^{c1}R^{d1}$, $S(O)_2R^{b1}$, $NR^{c1}S(O)_2R^{b1}$, and $S(O)_2NR^{c1}R^{d1}$; wherein said $C_{1-6}$ alkyl, $C_{2-6}$ alkenyl, $C_{2-6}$ alkynyl, aryl, cycloalkyl, heteroaryl, heterocycloalkyl, arylalkyl, cycloalkylalkyl, heteroarylalkyl, or heterocycloalkylalkyl is optionally substituted by 1, 2, 3, 4, or 5 substituents independently selected from halo, $C_{1-4}$ alkyl, $C_{2-4}$ alkenyl, $C_{2-4}$ alkynyl, $C_{1-4}$ haloalkyl, $C_{1-4}$ hydroxyalkyl, $C_{1-4}$ cyanoalkyl, halosulfanyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $C(=NR^i)NR^{c1}R^{d1}$, $NR^{c1}C(=NR^i)NR^{c1}R^{d1}$, $P(R^{f1})_2$, $P(OR^{e1})_2$, $P(O)R^{e1}R^{f1}$, $P(O)OR^{e1}OR^{f1}$, $S(O)R^{b1}$, $S(O)NR^{c1}R^{d1}$, $S(O)_2R^{b1}$, $NR^{c1}S(O)_2R^{b1}$, and $S(O)_2NR^{c1}R^{d1}$;

or $R^A$ and $R^B$ together with the carbon atom to which they are attached form a 3-, 4-, 5-, 6-, or 7-membered cycloalkyl group or 3-, 4-, 5-, 6-, or 7-membered heterocycloalkyl group, each optionally substituted with 1, 2, or 3 substituents independently selected from halo, $C_{1-4}$ alkyl, $C_{2-4}$ alkenyl, $C_{2-4}$ alkynyl, $C_{1-4}$ haloalkyl, $C_{1-4}$ hydroxyalkyl, $C_{1-4}$ cyanoalkyl, halosulfanyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $C(=NR^i)NR^{c1}R^{d1}$, $NR^{c1}C(=NR^i)NR^{c1}R^{d1}$, $P(R^{f1})_2$, $P(OR^{e1})_2$, $P(O)R^{e1}R^{f1}$, $P(O)OR^{e1}OR^{f1}$, $S(O)R^{b1}$, $S(O)NR^{c1}R^{d1}$, $S(O)_2R^{b1}$, $NR^{c1}S(O)_2R^{b1}$, and $S(O)_2NR^{c1}R^{d1}$;

or $R^A$ and $R^B$, together with the carbon atom to which they are attached, form a $C=CH_2$ group;

Q is $OR^Q$, $OC(O)R^Q$, $OC(O)NR^4R^Q$, $NR^4R^Q$, $NR^4C(O)R^Q$, $NR^4C(O)NR^4R^Q$, $NR^4C(O)OR^Q$, $NR^4S(O)R^Q$, $NR^4S(O)_2R^Q$, $NR^4C(=NR^i)NR^4R^Q$, $SR^Q$, $S(O)R^Q$, $S(O)NR^4R^Q$, $S(O)_2R^Q$, $S(O)_2NR^4R^Q$, $C(O)R^Q$, cope, $C(O)NR^4R^Q$, halo, cyano, azido, or nitro;

or Q is H, $C_{1-6}$ alkyl, $C_{2-6}$ alkenyl, $C_{2-6}$ alkynyl, aryl, heteroaryl, cycloalkyl, heterocycloalkyl, each optionally substituted by 1, 2, 3, 4, or 5 substituents independently selected from halo, $C_{1-4}$ alkyl, $C_{2-6}$ alkenyl, $C_{2-6}$ alkynyl, $C_{1-6}$ haloalkyl, $C_{1-6}$ hydroxyalkyl, $C_{1-6}$ cyanoalkyl, Cy, —($C_{1-4}$ alkyl)-Cy, halosulfanyl, CN, $NO_2$, $OR^{a2}$, —($C_{1-4}$ alkyl)-$OR^{a2}$, $SR^{a2}$, —($C_{1-4}$ alkyl)-$SR^{a2}$, $C(O)R^{b2}$, —($C_{1-4}$ alkyl)-$C(O)R^{b2}$, $C(O)NR^{c2}R^{d2}$, —($C_{1-4}$ alkyl)-$C(O)NR^{c2}R^{d2}$, $C(O)OR^{a2}$, —($C_{1-4}$ alkyl)-$C(O)OR^{a2}$, $OC(O)R^{b2}$, —($C_{1-4}$ alkyl)-$OC(O)R^{b2}$, $OC(O)NR^{c2}R^{d2}$, —($C_{1-4}$ alkyl)-$OC(O)NR^{c2}R^{d2}$, $NR^{c2}R^{d2}$, —($C_{1-4}$ alkyl)-$NR^{c2}R^{d2}$, $NR^{c2}C(O)R^{b2}$, —($C_{1-4}$ alkyl)-$NR^{c2}C(O)R^{b2}$, $NR^{c2}C(O)NR^{c2}R^{d2}$, —($C_{1-4}$ alkyl)-$NR^{c2}C(O)NR^{c2}R^{d2}$, $NR^{c2}C(O)OR^{a2}$, —($C_{1-4}$ alkyl)-$NR^{c2}C(O)OR^{a2}$, $C(=NR^i)NR^{c2}R^{d2}$, $NR^{c2}C(=NR^i)NR^{c2}R^{d2}$, $P(R^{f2})_2$, $P(OR^{e2})_2$, $P(O)R^{e2}R^{f2}$, $P(O)OR^{e2}OR^{f2}$, $S(O)R^{b2}$, —($C_{1-4}$ alkyl)-$S(O)R^{b2}$, $S(O)NR^{c2}R^{d2}$, —($C_{1-4}$ alkyl)-$S(O)NR^{c2}R^{d2}$, $S(O)_2R^{b2}$, —($C_{1-4}$ alkyl)-$S(O)_2R^{b2}$, $NR^{c2}S(O)_2R^{b2}$, —($C_{1-4}$ alkyl)-$NR^{c2}S(O)_2R^{b2}$, $S(O)_2NR^{c2}R^{d2}$, and —($C_{1-4}$ alkyl)-$S(O)_2NR^{c2}R^{d2}$;

$R^Q$ is H, $C_{1-6}$ alkyl, $C_{2-6}$ alkenyl, $C_{2-6}$ alkynyl, $C_{1-6}$ haloalkyl, aryl, cycloalkyl, heteroaryl, heterocycloalkyl, arylalkyl, cycloalkylalkyl, heteroarylalkyl, or heterocycloalkylalkyl, wherein said $C_{1-6}$ alkyl, $C_{2-6}$ alkenyl, $C_{2-6}$ alkynyl, aryl, cycloalkyl, heteroaryl, heterocycloalkyl, arylalkyl, cycloalkylalkyl, heteroarylalkyl, or heterocycloalkylalkyl is optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ cyanoalkyl, halosulfanyl, Cy, —($C_{1-4}$ alkyl)-Cy, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $C(=NR^i)NR^{c2}R^{d2}$, $NR^{c2}C(=NR^i)NR^{c2}R^{d2}$, $P(R^{f2})_2$, $P(OR^{e2})_2$, $P(O)R^{e2}R^{f2}$, $P(O)OR^{e2}OR^{f2}$, $S(O)R^{b2}$, $S(O)NR^{c2}R^{d2}$; $S(O)_2R^{b2}$, $NR^{c2}S(O)_2R^{b2}$, and $S(O)_2NR^{c2}R^{d2}$;

or $R^4$ and $R^Q$ together with the N atom to which they are attached form a 4-20 membered heterocycloalkyl group or 5-20 membered heteroaryl group, each optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ cyanoalkyl, halosulfanyl, Cy, —($C_{1-4}$ alkyl)-Cy, CN, $NO_2$, $OR^{a2}$, —($C_{1-4}$ alkyl)-$OR^{a2}$, $SR^{a2}$, —($C_{1-4}$ alkyl)-$SR^{a2}$, $C(O)R^{b2}$, —($C_{1-4}$ alkyl)-$C(O)R^{b2}$, $C(O)NR^{c2}R^{d2}$, —($C_{1-4}$ alkyl)-$C(O)NR^{c2}R^{d2}$, $C(O)OR^{a2}$, —($C_{1-4}$ alkyl)-$C(O)OR^{a2}$, $OC(O)R^{b2}$, —($C_{1-4}$ alkyl)-$OC(O)R^{b2}$, $OC(O)NR^{c2}R^{d2}$, —($C_{1-4}$ alkyl)-$OC(O)NR^{c2}R^{d2}$, $NR^{c2}R^{d2}$, —($C_{1-4}$ alkyl)-$NR^{c2}R^{d2}$, $NR^{c2}C(O)R^{b2}$, —($C_{1-4}$ alkyl)-$NR^{c2}C(O)R^{b2}$, $NR^{c2}C(O)NR^{c2}R^{d2}$, —($C_{1-4}$ alkyl)-$NR^{c2}C(O)NR^{c2}R^{d2}$, $NR^{c2}C(O)OR^{a2}$, —($C_{1-4}$ alkyl)-$NR^{c2}C(O)OR^{a2}$, $C(=NR^i)NR^{c2}R^{d2}$, $NR^{c2}C(=NR^i)NR^{c2}R^{d2}$, $P(R^{f2})_2$, $P(OR^{e2})_2$, $P(O)R^{e2}R^{f2}$, $P(O)OR^{e2}OR^{f2}$, $S(O)R^{b2}$, —($C_{1-4}$ alkyl)-$S(O)R^{b2}$, $S(O)NR^{c2}R^{d2}$, —($C_{1-4}$ alkyl)-$S(O)NR^{c2}R^{d2}$, $S(O)_2R^{b2}$, —($C_{1-4}$ alkyl)-$S(O)_2R^{b2}$, $NR^{c2}S(O)_2R^{b2}$, —($C_{1-4}$ alkyl)-$NR^{c2}S(O)_2R^{b2}$, $S(O)_2NR^{c2}R^{d2}$, and —($C_{1-4}$ alkyl)-$S(O)_2NR^{c2}R^{d2}$;

Cy, $Cy^1$, and $Cy^2$ are independently selected from aryl, heteroaryl, cycloalkyl, and heterocycloalkyl, each optionally substituted by 1, 2, 3, 4 or 5 substituents independently selected from halo, $C_{1-4}$ alkyl, $C_{2-4}$ alkenyl, $C_{2-4}$ alkynyl, $C_{1-4}$ haloalkyl, halosulfanyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $C(=NR^i)$—$NR^{c3}R^{d3}$; $NR^{c3}C(=NR^i)NR^{c3}R^{d3}$, $P(R^{f3})_2$, $P(OR^{e3})_2$, $P(O)R^{e3}R^{f3}$, $P(O)OR^{e3}OR^{f3}$, $S(O)R^{b3}$, $S(O)NR^{c3}R^{d3}$, $S(O)_2R^{b3}$, and $S(O)_2NR^{c3}R^{d3}$;

$R^1$ is H or $C_{1-4}$ alkyl;

$R^2$ is H, halo, $C_{1-4}$ alkyl, $C_{1-4}$ haloalkyl, $C_{2-4}$ alkenyl, $C_{2-4}$ alkynyl, CN, $NO_2$, OH, $C_{1-4}$ alkoxy, amino, $C_{1-4}$ alkylamino, or $C_{2-8}$ dialkylamino;

$R^3$ is H, $C_{1-4}$ alkyl, $C_{2-4}$ alkenyl, or $C_{2-4}$ alkynyl;

$R^4$ is H, $C_{1-4}$ alkyl, $C_{2-4}$ alkenyl, $C_{2-4}$ alkynyl, $C(O)$—$R^{4a}$, $SO_2$—$R^{4a}$, aryl, cycloalkyl, heteroaryl, heterocycloalkyl, arylalkyl, cycloalkylalkyl, heteroarylalkyl, or heterocycloalkylalkyl, wherein said $C_{1-4}$ alkyl, $C_{2-4}$ alkenyl, $C_{2-4}$ alkynyl, aryl, cycloalkyl, heteroaryl, heterocycloalkyl, arylalkyl, cycloalkylalkyl, heteroarylalkyl, or heterocycloalkylalkyl is optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ cyanoalkyl, aryl, heteroaryl, cycloalkyl, heterocycloalkyl, halosulfanyl, CN, $NO_2$, $OR^{a4}$, $SR^{a4}$, $C(O)R^{b4}$, $C(O)NR^{c4}R^{d4}$, $C(O)OR^{a4}$, $OR^{b4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)NR^{c4}R^{d4}$, $NR^{c4}C(O)OR^{a4}$, $C(=NR^i)NR^{c4}R_{d4}$, $NR^{c4}C(=NR^i)NR^{c4}R^{d4}$, $P(R^{f4})_2$, $P(OR^{e4})_2$, $P(O)R^{e4}R^{f4}$, $P(O)OR^{e4}OR^{f4}$, $S(O)R^{b4}$, $S(O)NR^{c4}R^{d4}$, $S(O)_2R^{b4}$, $NR^{c4}S(O)_2R^{b4}$, and $S(O)_2NR^{c4}R^{d4}$;

$R^{4a}$ is H, $C_{1-4}$ alkyl, $C_{2-4}$ alkenyl, $C_{2-4}$ alkynyl, aryl, cycloalkyl, heteroaryl, heterocycloalkyl, arylalkyl, cycloalkylalkyl, heteroarylalkyl, or heterocycloalkylalkyl;

$R^5$ and $R^6$ are independently selected from H, $C_{1-8}$ g alkyl, aryl, heteroaryl, cycloalkyl, heterocycloalkyl, arylalkyl, heteroarylalkyl, cycloalkylalkyl, and heterocycloalkylalkyl, each optionally substituted by one or more substituents independently selected from halo, CN, $NO_2$, OH, $C_{1-4}$ alkoxy, $C_{1-4}$ haloalkoxy, amino, $C_{1-4}$ alkylamino, $C_{2-8}$ dialkylamino, $C_{1-6}$ alkyl, $C_{1-6}$ alkenyl, and $C_{2-6}$ alkynyl;

$R^{6a}$ and $R^{6b}$ are independently selected from H, $C_{1-8}$ alkyl, aryl, heteroaryl, cycloalkyl, heterocycloalkyl, arylalkyl, heteroarylalkyl, cycloalkylalkyl, and heterocycloalkylalkyl, each optionally substituted by one or more substituents independently selected from halo, CN, $NO_2$, OH, $C_{1-4}$ alkoxy, $C_{1-4}$ haloalkoxy, amino, $C_{1-4}$ alkylamino, $C_{2-8}$ dialkylamino, $C_{1-6}$ alkyl, $C_{2-6}$ alkenyl, and $C_{2-6}$ alkynyl;

$R^a$, $R^{a1}$, $R^{a3}$, $R^{a4}$, and $R^{a5}$ are independently selected from H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein said $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with OH, amino, halo, $C_{1-6}$ alkyl, aryl, arylalkyl, heteroaryl, heteroarylalkyl, cycloalkyl or heterocycloalkyl;

$R^b$, $R^{b1}$, $R^{b3}$, $R^{b4}$, and $R^{b5}$ are independently selected from H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein said $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with OH, amino, halo, $C_{1-6}$ alkyl, $C_{1-6}$ haloalkyl, aryl, arylalkyl, heteroaryl, heteroarylalkyl, cycloalkyl, or heterocycloalkyl;

$R^{a2}$ is H, $C_{1-6}$ alkyl, $C_{1-6}$ haloalkyl, $C_{2-6}$ alkenyl, $C_{2-6}$ alkynyl, $Cy^2$, or $Cy^2$-($C_{1-6}$ alkyl)-, wherein said $C_{1-6}$ alkyl, $C_{1-6}$ haloalkyl, $C_{2-6}$ alkenyl, or $C_{2-6}$ alkynyl, is optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ cyanoalkyl, halosulfanyl, $Cy^2$, CN, $NO_2$, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^i)NR^{c5}R^{d5}$, $NR^{c5}C(=NR^i)NR^{c5}R^{d5}$, $P(R^{f5})_2$, $P(O)R^{e5}R^{f5}$, $P(O)OR^{e5}OR^{f5}$, $S(O)R^{b5}$, $S(O)NR^{c5}R^{d5}$, $R^{b2}$, $S(O)_2R^{b5}$, $NR^{c5}S(O)_2R^{b5}$, and $S(O)_2NR^{e5}R^{d5}$;

$R^{b2}$ is H, $C_{1-6}$ alkyl, $C_{1-6}$ haloalkyl, $C_{2-6}$ alkenyl, $C_{2-6}$ alkynyl, aryl, $Cy^2$, or $Cy^2$-($C_{1-6}$ alkyl)-, wherein said $C_{1-6}$ alkyl, $C_{1-6}$ haloalkyl, $C_{2-6}$ alkenyl, $C_{2-6}$ alkynyl, or aryl is optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, hydroxyalkyl, $C_{1-6}$ cyanoalkyl, halosulfanyl, $Cy^2$, CN, $NO_2$, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^i)NR^{c5}R^{d5}$, $NR^{c5}C(=NR^i)NR^{c5}R^{d5}$, $P(R^{f5})_2$, $P(OR^{e5})_2$, $P(O)R^{e5}R^{f5}$, $P(O)OR^{e5}OR^{f5}$, $S(O)R^{b5}$, $S(O)NR^{c5}R^{d5}$, $S(O)_2R^{b5}$, $NR^{c5}S(O)_2R^{b5}$, and $S(O)_2NR^{c5}R^{d5}$;

$R^c$ and $R^d$ are independently selected from H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl, and heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl, or heterocycloalkylalkyl is optionally substituted with OH, amino, halo, $C_{1-6}$ alkyl, $C_{1-6}$ haloalkyl, aryl, arylalkyl, heteroaryl, heteroarylalkyl, cycloalkyl or heterocycloalkyl;

or $R^c$ and $R^d$ together with the N atom to which they are attached form a 4-, 5-, 6- or 7-membered heterocycloalkyl group;

$R^{c1}$ and $R^{d1}$ are independently selected from H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl, and heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl, or heterocycloalkylalkyl is optionally substituted with OH, amino, halo, $C_{1-6}$ alkyl, $C_{1-6}$ haloalkyl, aryl, arylalkyl, heteroaryl, heteroarylalkyl, cycloalkyl or heterocycloalkyl;

or $R^{c1}$ and $R^{d1}$ together with the N atom to which they are attached form a 4-, 5-, 6- or 7-membered heterocycloalkyl group;

$R^{c2}$ and $R^{d2}$ are dependently selected from H, $C_{1-10}$ alkyl, $C_{1-6}$ haloalkyl, $C_{2-6}$ alkenyl, $C_{2-6}$ alkynyl, $Cy^2$ and $Cy^2$-($C_{1-6}$ alkyl)-, wherein said $C_{1-10}$ alkyl, $C_{1-6}$ haloalkyl, $C_{2-6}$ alkenyl, and $C_{2-6}$ alkynyl, is optionally substituted with 1, 2, or 3, substitutents independently selected from halo, $C_{1-4}$ alkyl, $C_{2-4}$ alkenyl, $C_{2-4}$ alkynyl, $C_{1-4}$ haloalkyl, halosulfanyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{d3}C(O)R^{b3}C(O)OR^{a3}$, $C(=NR^i)NR^{a3}R^{d3}$, $NR^{c3}C(=NR^i)NR^{c3}R^{d3}$, $P(R^{f3})_2$, $P(OR^{e3})_2$, $P(O)R^{e3}R^{f3}$, $P(O)OR^{e3}OR^{f3}$, $S(O)R^{b3}$, $S(O)NR^{c3}R^{d3}$, $S(O)_2R^{b3}$, and $S(O)_2NR^{a3}R^{d3}$;

or $R^{c2}$ and $R^{d2}$ together with the N atom to which they are attached form a 4-, 5-, 6- or 7-membered heterocycloalkyl group optionally substituted with 1, 2, or 3, substitutents independently selected from $Cy^2$, $Cy^2$-($C_{1-6}$ alkyl)-, halo, $C_{1-4}$ alkyl, $C_{2-4}$ alkenyl, $C_{2-4}$ alkynyl, $C_{1-4}$ haloalkyl, halosulfanyl, CN, $NO_2$, $OR^{a3}$, $SR^{a3}$, $C(O)R^{b3}$, $C(O)NR^{c3}R^{d3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $C(=NR^i)NR^{c3}R^{d3}$, $NR^{c3}C(=NR^i)NR^{c3}R^{d3}$, $P(R^{f3})_2$, $P(OR^{e3})_2$, $P(O)R^{e3}R^{f3}$, $P(O)OR^{e3}$, $OR^{f3}$, $S(O)R^{b3}$, $S(O)NR^{c3}R^{d3}$, $S(O)_2R^{b3}$, and $S(O)_2NR^{c3}R^{d3}$;

$R^{c3}$ and $R^{d3}$ are independently selected from H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl, and heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl, or heterocycloalkylalkyl is optionally substituted with OH, amino, halo, $C_{1-6}$ alkyl, $C_{1-6}$ haloalkyl, aryl, arylalkyl, heteroaryl, heteroarylalkyl, cycloalkyl, or heterocycloalkyl;

or $R^{c3}$ and $R^{d3}$ together with the N atom to which they are attached form a 4-, 5-, 6- or 7-membered heterocycloalkyl group;

$R^{c4}$ and $R^{d4}$ are independently selected from H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl, and heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl, or heterocycloalkylalkyl is optionally substituted with OH, amino, halo, $C_{1-6}$ alkyl, $C_{1-6}$ haloalkyl, aryl, arylalkyl, heteroaryl, heteroarylalkyl, cycloalkyl, or heterocycloalkyl;

or $R^{c4}$ and $R^{d4}$ together with the N atom to which they are attached form a 4-, 5-, 6- or 7-membered heterocycloalkyl group;

$R^{c5}$ and $R^{d5}$ are independently selected from H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl, and heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl, or heterocyclo-alkylalkyl is optionally substituted with OH, amino, halo, $C_{1-6}$ alkyl, $C_{1-6}$ haloalkyl, aryl, arylalkyl, heteroaryl, heteroarylalkyl, cycloalkyl, or heterocycloalkyl;

or $R^{c5}$ and $R^{d5}$ together with the N atom to which they are attached form a 4-, 5-, 6- or 7-membered heterocycloalkyl group;

$R^e$, $R^{e1}$, $R^{e2}$, $R^{e3}$, $R^{e4}$, and $R^{e5}$ are independently selected from H, $C_{1-6}$ alkyl, $C_{1-6}$ haloalkyl, $C_{2-6}$ alkenyl, $(C_{1-6}$ alkoxy)-$C_{1-6}$ alkyl, $C_{2-6}$ alkynyl, aryl, cycloalkyl, heteroaryl, heterocycloalkyl, arylalkyl, cycloalkylalkyl, heteroarylalkyl, and heterocycloalkylalkyl;

$R^f$, $R^{f1}$, $R^{f2}$, $R^{f3}$, $R^{f4}$, and $R^{f5}$ are independently selected from H, $C_{1-6}$ alkyl, $C_{1-6}$ haloalkyl, $C_{2-6}$ alkenyl, $C_{2-6}$ alkynyl, aryl, cycloalkyl, heteroaryl, and heterocycloalkyl;

$R^i$ is H, CN, $C(O)NH_2$, or $NO_2$;

R' is H, halo, $C_{1-10}$ alkyl, $C_{2-6}$ alkenyl, $C_{2-6}$ alkynyl, Cy, Cy-($C_{1-6}$ alkyl)-, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $S(O)R^{b3}$, $S(O)NR^{c3}R^{d3}$, $S(O)_2R^{b3}$, or $S(O)_2NR^{c3}R^{d3}$; wherein said $C_{1-10}$ alkyl, $C_{2-6}$ alkenyl, or $C_{2-6}$ alkynyl is optionally substituted with 1, 2, 3, 4, or 5 substituents independently selected from CN, $NO_2$, Cy, Cy-($C_{1-6}$ alkyl)-, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $C(=NR^i)NR^{c3}R^{d3}$, $NR^{c3}C(=NR^i)NR^{c3}R^{d3}$, $P(R^{f3})_2$, $P(OR^{e3})_2$, $P(O)R^{e3}R^{f3}$, $P(O)OR^{e3}OR^{f3}$, $S(O)R^{b3}$, $S(O)NR^{c3}R^{d3}$, $S(O)_2R^{b3}$, and $S(O)_2NR^{c3}R^{d3}$;

R" is H, $C_{1-10}$ alkyl, $C_{2-6}$ alkenyl, $C_{2-6}$ alkynyl, Cy, Cy-($C_{1-6}$ alkyl)-, $C(O)R^{b3}$, $C(O)NR^{c3}R^{d3}$, $C(O)OR^{a3}$, $S(O)R^{b3}$, $S(O)NR^{c3}R^{d3}$, $S(O)_2R^{b3}$, or $S(O)_2NR^{c3}R^{d3}$; wherein said $C_{1-10}$ alkyl, $C_{2-6}$ alkenyl, or $C_{2-6}$ alkynyl is optionally substituted with 1, 2, 3, 4, or 5 substituents independently selected from CN, $NO_2$, Cy, —($C_{1-6}$ alkyl)-Cy, $OR^{a3}$, $SR^{a3}$, $C(O)R^{b3}$, $C(O)NR^{e3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $C(=NR^i)NR^{c3}R^{d3}$, $C(=NR^i)NR^{c3}R^{d3}$, $P(R^{f3})_2$, $P(OR^{e3})_2$, $P(O)R^{e3}R^{f3}$, $P(O)OR^{e3}OR^{f3}$, $S(O)R^{b3}$, $S(O)NR^{c3}R^{d3}$, $S(O)_2R^{b3}$, and $S(O)_2NR^{c3}R^{d3}$; and p is 1, 2, 3, 4, 5, 6, 7, 8, 9 or 10.

In some embodiments, V is O.

In some embodiments, U is N.

In some embodiments, W is N.

In some embodiments, U and W are both N.

In some embodiments, U and W are both N and V is O.

In some embodiments, at least one of U, V and W is N.

In some embodiments, at least one of U, V, and W is N and another of U, V, and W is O or S.

In some embodiments, A is aryl, cycloalkyl, heteroaryl, or heterocycloalkyl, each optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ cyanoalkyl, $Cy^1$, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^i)$ $NR^cR^d$, $NR^cC(=NR^i)NR^cR^d$, $P(R^f)_2$, $P(OR^e)_2$, $P(O)R^eR^f$, $P(O)OR^e$-$OR^f$, $S(O)R^b$, $S(O)R^b$, $S(O)NR^cR^d$, $S(O)_2R^b$, $NR^cS(O)_2R^b$, and $S(O)_2NR^cR^d$, wherein said $C_{1-6}$ alkyl, $C_{2-6}$ alkenyl, and $C_{2-6}$ alkynyl is optionally substituted with 1, 2, or 3 substitutents independently selected from $Cy^1$, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^i)NR^cR^d$, $NR^cC(=NR^i)NR^cR^d$, $P(R^f)_2$, $P(OR^e)_2$, $P(O)R^eR^f$, $P(O)OR^eOR^f$, $S(O)R^b$, $S(O)NR^cR^d$, $S(O)_2R^b$, $NR^cS(O)_2R^b$, and $S(O)_2NR^cR^d$.

In some embodiments, A is aryl, cycloalkyl, heteroaryl, or heterocycloalkyl, each optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ cyanoalkyl, $Cy^1$, CN, $NO_2$, $OR^a$, $SR^a$, $C(O)R^b$, $C(O)NR^cR^d$, $C(O)OR^a$, $OC(O)R^b$, $OC(O)NR^cR^d$, $NRCR^d$, $NR^cC(O)R^b$, $NR^cC(O)NR^cR^d$, $NR^cC(O)OR^a$, $S(O)R^b$, $S(O)NR^cR^d$, $S(O)_2R^b$, $NR^cS(O)_2R^b$, and $S(O)_2NR^CR^d$.

In some embodiments, A is aryl or heteroaryl, each optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ cyanoalkyl, $Cy^1$, CN, $NO_2$, $OR^a$, $SR^a$, $C(O)R^b$, $C(O)NR^cR^d$, $C(O)OR^a$, $OC(O)R^b$, $OC(O)NR^eR^d$, $NR^eR^d$, $NR^eC(O)R^b$, $NR^eC(O)NR^eR^d$, $NR^eC(O)OR^a$, $C(=NR^i)NR^cR^d$, $NR^cC(=NR^i)NR^cR^d$, $P(R^f)_2$, $P(OR^e)_2$, $P(O)R^eR^f$, $P(O)OR^eOR^f$, $S(O)R^b$, $S(O)NR^eR^d$, $S(O)_2R^b$, $NR^cS(O)_2R^b$, and $S(O)_2NR^cR^d$, wherein said $C_{1-6}$ alkyl, $C_{2-6}$ alkenyl, and $C_{2-6}$ alkynyl is optionally substituted with 1, 2, or 3 substitutents independently selected from $Cy^1$, CN, $NO_2$, $OR^a$, $SR^a$, $C(O)R^b$, $C(O)NR^cR^d$, $C(O)OR^a$, $OC(O)$ $R^b$, $OC(O)NR^cR^d$, $NR^eR^d$, $NR^eC(O)R^b$, $NR^eC(O)NR^eR^d$, $NR^eC(O)OR^a$, $C(=NR^i)NR^cR^d$, $NR^cC(=NR^i)NR^cR^d$, $P(R^f)_2$, $P(OR^e)_2$, $P(O)R^eR^f$, $P(O)OR^eR^f$, $S(O)R^b$, $S(O)NR^cR^d$, $S(O)_2R^b$, $NR^cS(O)_2R^b$, and $S(O)_2NR^eR^d$.

In some embodiments, A is aryl or heteroaryl, each optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ cyanoalkyl, aryl, cycloalkyl, heteroaryl, heterocycloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $S(O)R^b$, $S(O)NR^cR^d$, $S(O)_2R^b$, $NR^cS(O)_2R^b$, and $S(O)_2NR^cR^d$.

In some embodiments, A is phenyl optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ cyanoalkyl, $Cy^1$, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^i)NR^cR^d$, $NR^cC(=NR^i)NR^cR^d$, $P(R^f)_2$, $P(OR^e)_2$, $P(O)R^eR^f$, $P(O)OR^eOR^f$, $S(O)R^b$, $S(O)NR^cR^d$, $S(O)_2R^b$, $NR^cS(O)_2R^b$, and $S(O)_2NR^cR^d$, wherein said $C_{1-6}$ alkyl, $C_{2-6}$ alkenyl, and $C_{2-6}$ alkynyl is optionally substituted with 1, 2, or 3 substitutents independently selected from $Cy^1$, CN, $NO_2$, $OR^a$, $SR^a$, $C(O)R^b$, $C(O)NR^cR^d$, $C(O)OR^a$, $OC(O)$ $R^b$, $OC(O)NR^cR^d$, $NR^eR^d$, $NR^eC(O)R^b$, $NR^eC(O)NR^eR^d$, $NR^cC(O)OR^a$, $C(=NR^i)NR^cR^d$, $NR^cC(=NR^i)NR^cR^d$, $P(R^f)_2$, $P(OR^e)_2$, $P(O)R^eR^f$, $P(O)OR^eOR^f$, $S(O)R^b$, $S(O)NR^cR^d$, $S(O)_2R^b$, $NR^cS(O)_2R^b$, and $S(O)_2NR^cR^d$.

In some embodiments, A is phenyl optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ cyanoalkyl, aryl, cycloalkyl, heteroaryl, heterocycloalkyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^b$, NR$^c$C(O)NR$^c$R$^d$, NR$^c$C(O)OR$^a$, S(O)R$^b$, S(O)NR$^c$R$^d$, S(O)$_2$R$^b$, NR$^c$S(O)$_2$R$^b$, and S(O)$_2$NR$^c$R$^d$.

In some embodiments, A is phenyl optionally substituted by 1, 2, 3, 4, or 5 substituents independently selected from halo, C$_{1-6}$ alkyl, C$_{1-6}$ haloalkyl, C$_{1-6}$ hydroxyalkyl, C$_{1-6}$ cyanoalkyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^b$, NR$^e$C(O)NR$^c$R$^d$, NR$^c$C(O)OR$^a$, S(O)R$^b$, S(O)NR$^c$R$^d$, S(O)$_2$R$^b$, NR$^e$S(O)$_2$R$^b$, and S(O)$_2$NR$^c$R$^d$.

In some embodiments, A is phenyl optionally substituted by 1, 2, 3, 4, or 5 substituents independently selected from halo, C$_{1-6}$ alkyl, and C$_{1-6}$ haloalkyl.

In some embodiments, Q is OR$^Q$, OC(O)R$^Q$, OC(O)NR$^4$R$^Q$, NR$^4$R$^Q$, NR$^4$C(O)R$^Q$, NR$^4$C(O)NR$^4$R$^Q$, NR$^4$C(O)OR$^Q$, NR$^4$S(O)R$^Q$, NR$^4$S(O)$_2$R$^Q$, SR$^Q$, S(O)R$^Q$, S(O)NR$^4$R$^Q$, S(O)$_2$R$^Q$, S(O)$_2$NR$^4$R$^Q$, C(O)R$^Q$, C(O)OR$^Q$, C(O)NR$^4$R$^Q$, halo, cyano, azido, or nitro;

In some embodiments, Q is H, CN, OR$^Q$, OC(O)NR$^4$R$^Q$, C(O)OR$^Q$, NR$^4$R$^Q$, NR$^4$C(O)R$^Q$, NR$^4$C(O)NR$^4$R$^Q$, NR$^4$C(O)OR$^Q$, NR$^4$S(O)$_2$R$^Q$, SR$^Q$, S(O)$_2$R$^Q$, or OC(O)NR$^4$R$^Q$.

In some embodiments, Q is H, CN, OR$^Q$, OC(O)NR$^4$R$^Q$, C(O)OR$^Q$, NR$^4$R$^Q$, NR$^4$C(O)R$^Q$, NR$^4$C(O)NR$^4$R$^Q$, NR$^4$C(O)OR$^Q$, NR$^4$S(O)$_2$R$^Q$, or OC(O)NR$^4$R$^Q$.

In some embodiments, Q is OR$^Q$, OC(O)NR$^4$R$^Q$, or NR$^4$R$^Q$.

In some embodiments, Q is OR$^Q$.

In some embodiments, Q is SR$^Q$.

In some embodiments, Q is S(O)$_2$R$^Q$.

In some embodiments, Q is NR$^4$R$^Q$.

In some embodiments, Q is NR$^4$R$^Q$, and R$^4$ and R$^Q$ together with the N atom to which they are attached form a 4-20 membered heterocycloalkyl group or 5-20 membered heteroaryl group, each optionally substituted by 1, 2, 3, 4, or 5 substituents independently selected from halo, C$_{1-6}$ alkyl, C$_{2-6}$ alkenyl, C$_{2-6}$ alkynyl, C$_{1-6}$ haloalkyl, C$_{1-6}$ hydroxyalkyl, C$_{1-6}$ cyanoalkyl, Cy, —(C$_{1-4}$ alkyl)-Cy, CN, NO$_2$, OR$^{a2}$, —(C$_{1-4}$ alkyl)-OR$^{a2}$, SR$^{a2}$, —(C$_{1-4}$ alkyl)-SR$^{a2}$, C(O)R$^{b2}$, —(C$_{1-4}$ alkyl)-C(O)R$^{b2}$, C(O)NR$^{c2}$R$^{d2}$, —(C$_{1-4}$ alkyl)-C(O)NR$^{c2}$R$^{d2}$, C(O)OR$^{a2}$, —(C$_{1-4}$ alkyl)-C(O)OR$^{a2}$, OC(O)R$^{b2}$, —(C$_{1-4}$ alkyl)-OC(O)R$^{b2}$, OC(O)NR$^{c2}$R$^{d2}$, —(C$_{1-4}$ alkyl)-OC(O)NR$^{c2}$R$^{d2}$, NR$^{c2}$R$^{d2}$, —(C$_{1-4}$ alkyl)-NR$^{c2}$R$^{d2}$, NR$^{c2}$C(O)R$^{b2}$, —(C$_{1-4}$ alkyl)-NR$^{c2}$C(O)R$^{b2}$, NR$^{c2}$C(O)NR$^{c2}$R$^{d2}$, —(C$_{1-4}$ alkyl)-NR$^{c2}$C(O)NR$^{c2}$R$^{d2}$, NR$^{c2}$C(O)OR$^{a2}$, —(C$_{1-4}$ alkyl)-NR$^{c2}$C(O)OR$^{a2}$, C(=NR$^i$)NR$^{c2}$R$^{d2}$, NR$^{c2}$C(=NR$^i$)NR$^{c2}$R$^{d2}$, P(R$^{f2}$)$_2$, P(OR$^{e2}$)$_2$, P(O)R$^{e2}$R$^{f2}$, P(O)OR$^{e2}$OR$^{f2}$, S(O)R$^{b2}$, —(C$_{1-4}$ alkyl)-S(O)R$^{b2}$, S(O)NR$^{c2}$R$^{d2}$, —(C$_{1-4}$ alkyl)-S(O)NR$^{c2}$R$^{d2}$, S(O)$_2$R$^{b2}$, —(C$_{1-4}$ alkyl)-S(O)$_2$R$^{b2}$, NR$^{c2}$S(O)$_2$R$^{b2}$, —(C$_{1-4}$ alkyl)-NR$^{c2}$S(O)$_2$R$^{b2}$, S(O)$_2$NR$^{c2}$R$^{d2}$ and —(C$_{1-4}$ alkyl)-S(O)$_2$NR$^{c2}$R$^{d2}$.

In some embodiments, Q is NR$^4$R$^Q$ and R$^4$ and R$^Q$ together with the N atom to which they are attached form a 5-20 membered heteroaryl group, optionally substituted by 1, 2, 3, 4, or 5 substituents independently selected from halo, C$_{1-6}$ alkyl, C$_{2-6}$ alkenyl, C$_{2-6}$ alkynyl, C$_{1-6}$ haloalkyl, C$_{1-6}$ hydroxy-alkyl, C$_{1-6}$ cyanoalkyl, Cy, —(C$_{1-4}$ alkyl)-Cy, CN, NO$_2$, OR$^{a2}$, —(C$_{1-4}$ alkyl)-OR$^{a2}$, SR$^{a2}$, —(C$_{1-4}$ alkyl)-SR$^{a2}$, C(O)R$^{b2}$, —(C$_{1-4}$ alkyl)-C(O)R$^{b2}$, C(O)NR$^{c2}$R$^{d2}$, —(C$_{1-4}$ alkyl)-C(O)NR$^{c2}$R$^{d2}$, C(O)OR$^{a2}$, —(C$_{1-4}$ alkyl)-C(O)OR$^{a2}$, OC(O)R$^{b2}$, —(C$_{1-4}$ alkyl)-OC(O)R$^{b2}$, OC(O)NR$^{c2}$R$^{d2}$, —(C$_{1-4}$ alkyl)-OC(O)NR$^{c2}$R$^{d2}$, NR$^{c2}$R$^{d2}$, —(C$_{1-4}$ alkyl)-NR$^{c2}$R$^{d2}$, NR$^{c2}$C(O)R$^{b2}$, —(C$_{1-4}$ alkyl)-NR$^{c2}$C(O)R$^{b2}$, NR$^{c2}$C(O)NR$^{c2}$R$^{d2}$, —(C$_{1-4}$ alkyl)-NR$^{c2}$C(O)NR$^{c2}$R$^{d2}$, NR$^{c2}$C(O)OR$^{a2}$, —(C$_{1-4}$ alkyl)-NR$^{c2}$C(O)OR$^{a2}$, C(=NR$^i$)NR$^{c2}$R$^{d2}$, NR$^{c2}$C(=NR$^i$)NR$^{c2}$R$^{d2}$, P(R$^{f2}$)$_2$, P(OR$^{e2}$)$_2$, P(O)R$^{e2}$R$^{f2}$, P(O)OR$^{e2}$OR$^{f2}$, S(O)R$^{b2}$, —(C$_{1-4}$ alkyl)-S(O)R$^{b2}$, S(O)NR$^{c2}$R$^{d2}$, —(C$_{1-4}$ alkyl)-S(O)NR$^{c2}$R$^{d2}$, S(O)$_2$R$^{b2}$, NR$^{c2}$S(O)$_2$R$^{b2}$, —(C$_{1-4}$ alkyl)-NR$^{c2}$S(O)$_2$R$^{b2}$, S(O)$_2$NR$^{c2}$R$^{d2}$, and —(C$_{1-4}$ alkyl)-S(O)$_2$NR$^{c2}$R$^{d2}$.

In some embodiments, Q is NR$^4$R$^Q$ and R$^4$ and R$^Q$ together with the N atom to which they are attached form a tetrazole group which is optionally substituted with halo, C$_{1-6}$ alkyl, C$_{1-6}$ haloalkyl, or NR$^{c2}$R$^{d2}$.

In some embodiments, Q is NR$^4$R$^Q$ and R$^4$ and R$^Q$ together with the N atom to which they are attached form a 5- or 6-membered heterocycloalkyl group optionally substituted by 1, 2, 3, 4, or 5 substituents independently selected from halo, C$_{1-6}$ alkyl, C$_{2-6}$ alkenyl, C$_{2-6}$ alkynyl, C$_{1-6}$ haloalkyl, C$_{1-6}$ hydroxyalkyl, C$_{1-6}$ cyanoalkyl, Cy, —(C$_{1-4}$ alkyl)-Cy, CN, NO$_2$, OR$^{a2}$, —(C$_{1-4}$ alkyl)-OR$^{a2}$, SR$^{a2}$, —(C$_{1-4}$ alkyl)-SR$^{a2}$, C(O)R$^{b2}$, —(C$_{1-4}$ alkyl)-C(O)R$^{b2}$, C(O)NR$^{c2}$R$^{d2}$, —(C$_{1-4}$ alkyl)-C(O)NR$^{c2}$R$^{d2}$, C(O)OR$^{a2}$, —(C$_{1-4}$ alkyl)-C(O)OR$^{a2}$, OC(O)R$^{b2}$, —(C$_{1-4}$ alkyl)-OC(O)R$^{b2}$, OC(O)NR$^{c2}$R$^{d2}$, —(C$_{1-4}$ alkyl)-OC(O)NR$^{c2}$R$^{d2}$, NR$^{c2}$R$^{d2}$, —(C$_{1-4}$ alkyl)-NR$^{c2}$R$^{d2}$, NR$^{c2}$C(O)R$^{b2}$, —(C$_{1-4}$ alkyl)-NR$^{c2}$C(O)R$^{b2}$, NR$^{c2}$C(O)NR$^{c2}$R$^{d2}$, —(C$_{1-4}$ alkyl)-NR$^{c2}$C(O)NR$^{c2}$R$^{d2}$, NR$^{c2}$C(O)OR$^{a2}$, —(C$_{1-4}$ alkyl)-NR$^{c2}$C(O)OR$^{a2}$, C(=NR$^i$)NR$^{c2}$R$^{d2}$, NR$^{c2}$C(=NR$^i$)NR$^{c2}$R$^{d2}$, P(R$^{f2}$)$_2$, P(OR$^{e2}$)$_2$, P(O)R$^{e2}$R$^{f2}$, P(O)OR$^{e2}$OR$^{f2}$, S(O)R$^{b2}$, —(C$_{1-4}$ alkyl)-S(O)R$^{b2}$, S(O)NR$^a$R$^{d2}$, —(C$_{1-4}$ alkyl)-S(O)NR$^a$R$^{d2}$, S(O)$_2$R$^{b2}$, —(C$_{1-4}$ alkyl)-S(O)$_2$R$^{b2}$, NR"S(O)$_2$R$^{b2}$, —(C$_{1-4}$ alkyl)-NR$^{e2}$S(O)$_2$R$^{b2}$, S(O)$_2$NR$^{c2}$R$^{d2}$, and —(C$_{1-4}$ alkyl)-S(O)$_2$NR$^{c2}$R$^{d2}$.

In some embodiments, Q is NR$^4$R$^Q$ and R$^4$ and R$^Q$ together with the N atom to which they are attached form piperidinyl, morpholino, piperazinyl, 2,3-dihydro-1H-isoindolyl, or 1,2,3,4-tetrahydro-isoquinoline, each optionally substituted by 1, 2, 3, 4, or 5 substituents independently selected from halo, C$_{1-6}$ alkyl, C$_{2-6}$ alkenyl, C$_{2-6}$ alkynyl, C$_{1-6}$ haloalkyl, C$_{1-6}$ hydroxyalkyl, C$_{1-6}$ cyanoalkyl, Cy, —(C$_{1-4}$ alkyl)-Cy, CN, NO$_2$, OR$^{a2}$, —(C$_{1-4}$ alkyl)-OR$^{a2}$, SR$^{a2}$, —(C$_{1-4}$ alkyl)-SR$^{a2}$, C(O)R$^{b2}$, —(C$_{1-4}$ alkyl)-C(O)R$^{b2}$, C(O)NR$^{c2}$R$^{d2}$, —(C$_{1-4}$ alkyl)-C(O)NR$^{c2}$R$^{d2}$, C(O)OR$^{a2}$, —(C$_{1-4}$ alkyl)-C(O)OR$^{a2}$, OC(O)R$^{b2}$, —(C$_{1-4}$ alkyl)-OC(O)R$^{b2}$, OC(O)NR$^{c2}$R$^{d2}$, —(C$_{1-4}$ alkyl)-OC(O)NR$^{c2}$R$^{d2}$, NR$^{c2}$R$^{d2}$, —(C$_{1-4}$ alkyl)-NR$^{c2}$R$^{d2}$, NR$^{c2}$C(O)R$^{b2}$, —(C$_{1-4}$ alkyl)-NR$^{c2}$C(O)R$^{b2}$, NR$^{c2}$C(O)NR$^{c2}$R$^{d2}$, —(C$_{1-4}$ alkyl)-NR$^{c2}$C(O)NR$^{c2}$R$^{d2}$, NR$^{c2}$C(O)OR$^{a2}$, —(C$_{1-4}$ alkyl)-NR$^{c2}$C(O)OR$^{a2}$, C(=NR$^i$)NR$^{c2}$R$^{d2}$, NR$^{c2}$C(=NR$^i$)NR$^{c2}$R$^{d2}$, P(R$^{f2}$)$_2$, P(OR$^{e2}$)$_2$, P(O)R$^{e2}$R$^{f2}$, P(O)OR$^{e2}$OR$^{f2}$, S(O)R$^{b2}$, —(C$_{1-4}$ alkyl)-S(O)R$^{b2}$, S(O)NR$^{c2}$R$^{d2}$, —(C$_{1-4}$ alkyl)-S(O)NR$^{c2}$R$^{d2}$, S(O)$_2$R$^{b2}$, —(C$_{1-4}$ alkyl)-S(O)$_2$R$^{b2}$, NR$^{c2}$S(O)$_2$R$^{b2}$, —(C$_{1-4}$ alkyl)-NR$^{c2}$S(O)$_2$R$^{b2}$, S(O)$_2$NR$^{c2}$R$^{d2}$, and —(C$_{1-4}$ alkyl)-S(O)$_2$NR$^{c2}$R$^{d2}$.

In some embodiments, Q is NR$^4$R$^Q$ and R$^4$ and R$^Q$ together with the N atom to which they are attached form a 4-20 membered heterocycloalkyl group optionally substituted by 1, 2, 3, 4, or 5 substituents independently selected from halo, C$_{1-6}$ alkyl, C$_{2-6}$ alkenyl, C$_{2-6}$ alkynyl, C$_{1-6}$ haloalkyl, C$_{1-6}$ hydroxyalkyl, C$_{1-6}$ cyanoalkyl, Cy, —(C$_{1-4}$ alkyl)-Cy, CN, NO$_2$, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, NR$^{c2}$R$^{d2}$, NR$^{c2}$C(O)R$^{b2}$, NR$^{c2}$C(O)NR$^{c2}$R$^{d2}$, NR$^{c2}$C(O)NR$^{c2}$R$^{d2}$, NR$^{c2}$C(O)OR$^{a2}$, S(O)R$^{b2}$, S(O)NR$^{c2}$R$^{d2}$, S(O)$_2$R$^{b2}$, NR$^{c2}$S(O)$_2$R$^{b2}$, and S(O)$_2$NR$^{c2}$R$^{d2}$.

In some embodiments, Q is NR$^4$R$^Q$ and R$^4$ and R$^Q$ together with the N atom to which they are attached form a 5- or 6-membered heterocycloalkyl group optionally substituted by 1, 2, 3, 4, or 5 substituents independently selected from halo, C$_{1-6}$ alkyl, C$_{2-6}$ alkenyl, C$_{2-6}$ alkynyl, C$_{1-6}$ haloalkyl, C$_{1-6}$ hydroxyalkyl, C$_{1-6}$ cyanoalkyl, Cy, —(C$_{1-4}$ alkyl)-Cy, CN, NO$_2$, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, NR$^{c2}$R$^{d2}$, NR$^{c2}$C(O)R$^{b2}$, $NR^{c2}C(O)NR^{c2}R^{d2}$, $NR^{c2}C(O)OR^{a2}$, $S(O)R^{b2}$, $S(O)NR^{c2}R^{d2}$, $S(O)_2R^{b2}$, $NR^{c2}S(O)_2R^{b2}$, and $S(O)_2NR^{c2}R^{d2}$.

In some embodiments, Q is $NR^4R^Q$ and $R^4$ and $R^Q$ together with the N atom to which they are attached form piperidinyl, morpholino, piperazinyl, 2,3-dihydro-1H-isoindolyl, or 1,2,3,4-tetrahydro-isoquinoline, each optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ cyanoalkyl, Cy, —($C_{1-4}$ alkyl)-Cy, CN, $NO_2$, $OR^{a2}$, $SR^{a2}$, $C(O)R^{b2}$, $C(O)NR^aR^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $S(O)R^{b2}$, $S(O)NR^{c2}R^{d2}$, $S(O)_2R^{b2}$, $NR^{c2}S(O)_2R^{b2}$, and $S(O)_2NR^{c2}R^{d2}$.

In some embodiments, or Q is H, $C_{1-6}$ alkyl, $C_{2-6}$ alkenyl, $C_{2-6}$ alkynyl, aryl, heteroaryl, cycloalkyl, heterocycloalkyl, each optionally substituted by 1, 2, 3, 4, or 5 substituents independently selected from halo, $C_{1-4}$ alkyl, $C_{2-6}$ alkenyl, $C_{2-6}$ alkynyl, $C_{1-6}$ haloalkyl, $C_{1-6}$ hydroxyalkyl, $C_{1-6}$ cyanoalkyl, Cy, —($C_{1-4}$ alkyl)-Cy, CN, $NO_2$, $OR^{a2}$, —($C_{1-4}$ alkyl)-$OR^{a2}$, $SR^{a2}$, —($C_{1-4}$ alkyl)-$SR^{a2}$, $C(O)R^{b2}$, —($C_{1-4}$ alkyl)-$C(O)R^{b2}$, $C(O)NR^{c2}R^{d2}$, —($C_{1-4}$ alkyl)-$C(O)NR^{c2}R^{d2}$, $C(O)OR^{a2}$, —($C_{1-4}$ alkyl)-$C(O)OR^{a2}$, $OC(O)R^{b2}$, —($C_{1-4}$ alkyl)-$OC(O)R^{b2}$, $OC(O)NR^{c2}R^{d2}$, —($C_{1-4}$ alkyl)-$C(O)NR^{c2}R^{d2}$, $NR^{c2}R^{d2}$, —($C_{1-4}$ alkyl)-$NR^{c2}R^{d2}$, $NR^{c2}C(O)R^{b2}$, —($C_{1-4}$ alkyl)-$NR^{c2}C(O)R^{b2}$, $NR^{c2}C(O)NR^{c2}R^{d2}$, —($C_{1-4}$ alkyl)-$NR^{c2}C(O)NR^{c2}R^{d2}$, $NR^{c2}C(O)OR^{a2}$, —($C_{1-4}$ alkyl)-$NR^{c2}C(O)OR^{a2}$, $C(=NR^i)NR^{c2}R^{d2}$, $NR^{c2}C(=NR^i)NR^{c2}R^{d2}$, $P(R^{f2})_2$, $P(OR^{e2})_2$, $P(O)R^{e2}R^{f2}$, $P(O)OR^{e2}OR^{f2}$, $S(O)R^{b2}$, —($C_{1-4}$ alkyl)-$S(O)R^{b2}$, $S(O)NR^{c2}R^{d2}$, —($C_{1-4}$ alkyl)-$S(O)NR^{c2}R^{d2}$, $S(O)_2R^{b2}$, —($C_{1-4}$ alkyl)-$S(O)_2R^{b2}$, $NR^{c2}S(O)_2R^{b2}$, —($C_{1-4}$ alkyl)-$NR^{c2}S(O)_2R^{b2}$, $S(O)_2NR^{c2}R^{d2}$, and —($C_{1-4}$ alkyl)-$S(O)_2NR^{c2}R^{d2}$.

In some embodiments, $R^Q$ is H, $C_{1-6}$ alkyl, $C_{2-6}$ alkenyl, $C_{2-6}$ alkynyl, $C_{1-6}$ haloalkyl, aryl, cycloalkyl, heteroaryl, heterocycloalkyl, arylalkyl, cycloalkylalkyl, heteroarylalkyl, or heterocycloalkylalkyl, wherein said $C_{1-6}$ alkyl, $C_{2-6}$ alkenyl, $C_{2-6}$ alkynyl, aryl, cycloalkyl, heteroaryl, heterocycloalkyl, arylalkyl, cycloalkylalkyl, heteroarylalkyl, or heterocycloalkylalkyl is optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ cyanoalkyl, Cy, —($C_{1-4}$ alkyl)-Cy, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $C(=NR^i)NR^{c2}R^{d2}$, $NR^{c2}C(=NR^i)NR^{c2}R^{d2}$, $P(R^{f2})_2$, $P(OR^{e2})_2$, $P(O)R^{e2}R^{f2}$, $P(O)OR^{e2}OR^{f2}$, $S(O)R^{b2}$, $S(O)NR^{c2}R^{d2}$, $S(O)_2R^{b2}$, and $S(O)_2NR^{c2}R^{d2}$.

In some embodiments, $R^Q$ is H, $C_{1-6}$ alkyl, aryl, cycloalkyl, heteroaryl, heterocycloalkyl, arylalkyl, cycloalkylalkyl, heteroarylalkyl, or heterocycloalkylalkyl, wherein said $C_{1-6}$ alkyl, aryl, cycloalkyl, heteroaryl, heterocycloalkyl, arylalkyl, cycloalkylalkyl, heteroarylalkyl, or heterocyclo-alkylalkyl is optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ cyanoalkyl, Cy, —($C_{1-4}$ alkyl)-Cy, CN, $NO_2$, $OR^{a2}$, $SR^{a2}$, $C(O)R^{b2}$, $C(O)NR^aR^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $C(=NR^i)NR^{c2}R^{d2}$, $NR^{c2}C(=NR^i)NR^{c2}R^{d2}$, $P(R^{f2})_2$, $P(OR^{e2})_2$, $P(O)R^{e2}R^{f2}$, $P(O)OR^{e2}OR^{f2}$, $S(O)R^{b2}$, $S(O)NR^{c2}R^{d2}$, $S(O)_2R^{b2}$, $NR^{c2}S(O)_2R^{b2}$, and $s(O)_2NR^{c2}R^{d2}$.

In some embodiments, $R^Q$ is H, $C_{1-6}$ alkyl, aryl, cycloalkyl, heteroaryl, heterocycloalkyl, arylalkyl, cycloalkylalkyl, heteroarylalkyl, or heterocycloalkylalkyl, wherein said $C_{1-6}$ alkyl, aryl, cycloalkyl, heteroaryl, heterocycloalkyl, arylalkyl, cycloalkylalkyl, heteroarylalkyl, or heterocyclo-alkylalkyl is optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ cyanoalkyl, Cy, —($C_{1-4}$ alkyl)-Cy, CN, $NO_2$, $OR^{a2}$, $SR^{a2}$, $C(O)R^{b2}$, $C(O)$—$NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $S(O)R^{b2}$, $S(O)R^{b2}$, $S(O)NR^{c2}R^{d2}$, $S(O)_2R^{b2}$, $NR^{c2}S(O)_2R^{b2}$, and $S(O)_2NR^{c2}R^{d2}$.

In some embodiments, $R^Q$ is $C_{1-6}$ alkyl optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, $C_{1-6}$ hydroxy-alkyl, $C_{1-6}$ cyanoalkyl, Cy, —($C_{1-4}$ alkyl)-Cy, CN, $NO_2$, $OR^{a2}$, $SR^{a2}$, $C(O)R^{b2}$, $C(O)NR^{a2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $C(=NR^i)NR^{c2}R^{d2}$, $NR^{c2}C(=NR^i)NR^{c2}R^{d2}$, $P(R^{f2})_2$, $P(OR^{e2})_2$, $P(O)R^{e2}R^{f2}$, $P(O)OR^{e2}OR^{f2}$, $S(O)R^{b2}$, $S(O)NR^{c2}R^{d2}$, $S(O)^2R^{b2}$, $NR^{c2}S(O)_2R^{b2}$, and $S(O)_2NR^{c2}R^{d2}$.

In some embodiments, $R^Q$ is $C_{1-6}$ alkyl optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, $C_{1-6}$ hydroxy-alkyl, $C_{1-6}$ cyanoalkyl, Cy, —($C_{1-4}$ alkyl)-Cy, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $S(O)R^{b2}$, $S(O)NR^{c2}R^{d2}$, $S(O)_2R^{b2}$, $NR^{c2}S(O)_2R^{b2}$, and $S(O)_2NR^{c2}R^{d2}$.

In some embodiments, $R^Q$ is aryl, heteroaryl, arylalkyl, or heteroarylalkyl, each optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ cyanoalkyl, Cy, —($C_{1-4}$ alkyl)-Cy, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $C(=NR^i)NR^{c2}R^{d2}$, $NR^{c2}C(=NR^i)NR^{c2}R^{d2}$, $P(R^{f2})_2$, $P(OR^{e2})_2$, $P(O)R^{e2}R^{f2}$, $P(O)OR^{e2}OR^{f2}$, $S(O)R^{b2}$, $S(O)NR^{c2}R^{d2}$, $S(O)_2R^{b2}$, $NR^{c2}S(O)_2R^{b2}$, and $S(O)_2NR^{e2}R^{d2}$.

In some embodiments, $R^4$ and $R^Q$ together with the N atom to which they are attached form a 4-20 membered heterocycloalkyl group or 5-20 membered heteroaryl group, each optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ cyanoalkyl, Cy, —($C_{1-4}$ alkyl)-Cy, CN, $NO_2$, $OR^{a2}$, —($C_{1-4}$ alkyl)-$OR^{a2}$, $SR^{a2}$, —($C_{1-4}$ alkyl)-$SR^{a2}$, $C(O)R^{b2}$, —($C_{1-4}$ alkyl)-$C(O)R^{b2}$, $C(O)NR^{c2}R^{d2}$, —($C_{1-4}$ alkyl)-$C(O)NR^{c2}R^{d2}$, $C(O)OR^{a2}$, —($C_{1-4}$ alkyl)-$C(O)OR^{a2}$, $OC(O)R^{b2}$, —($C_{1-4}$ alkyl)-$OC(O)R^{b2}$, $OC(O)NR^{c2}R^{d2}$, —($C_{1-4}$ alkyl)-$OC(O)NR^{c2}R^{d2}$, $NR^{c2}R^{d2}$, —($C_{1-4}$ alkyl)-$NR^{c2}R^{d2}$, $NR^{c2}C(O)R^{b2}$, —($C_{1-4}$ alkyl)-$NR^{c2}C(O)R^{b2}$, $NR^{c2}C(O)NR^{c2}R^{d2}$, —($C_{1-4}$ alkyl)-$NR^{c2}C(O)NR^{c2}R^{d2}$, $NR^{c2}C(O)OR^{a2}$, —($C_{1-4}$ alkyl)-$NR^{c2}C(O)OR^{a2}$, $C(=NR^i)NR^{c2}R^{d2}$, $NR^{c2}C(=NR^i)NR^{c2}R^{d2}$, $P(R^{f2})_2$, $P(OR^{e2})_2$, $P(O)R^{e2}R^{f2}$, $P(O)OR^{e2}OR^{f2}$, $S(O)R^{b2}$, —($C_{1-4}$ alkyl)-$S(O)R^{b2}$, $S(O)NR^{c2}R^{d2}$, —($C_{1-4}$ alkyl)-$S(O)NR^{c2}R^{d2}$, $S(O)_2R^{b2}$, —($C_{1-4}$ alkyl)-$S(O)_2R^{b2}$, $NR^{c2}S(O)_2R^{b2}$, —($C_{1-4}$ alkyl)-$NR^{c2}S(O)_2R^{b2}$, $S(O)_2NR^{c2}R^{d2}$, and —($C_{1-4}$ alkyl)-$S(O)_2NR^{c2}R^{d2}$.

In some embodiments, $R^4$ and $R^Q$ together with the N atom to which they are attached form a 4-20 membered heterocycloalkyl group optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, $C_{1-6}$ hydroxy-alkyl, $C_{1-6}$ cyanoalkyl, Cy, —($C_{1-4}$ alkyl)-Cy, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)$ $NR^{c2}R^{d2}$, $NR^{c2}C(O)OR^{a2}$, $S(O)R^{b2}$, $S(O)NR^{c2}R^{d2}$, $S(O)_2R^{b2}$, $NR^{c2}S(O)_2R^{b2}$, and $S(O)_2NR^{c2}R^{d2}$.

In some embodiments, $R^4$ is H, $C_{1-4}$ alkyl, $C_{2-4}$ alkenyl, $C_{2-4}$ alkynyl, $C(O)$—$R^{4a}$, $SO_2$—$R^{4a}$, aryl, cycloalkyl, heteroaryl, heterocycloalkyl, arylalkyl, cycloalkylalkyl, heteroarylalkyl, or heterocycloalkylalkyl, wherein said $C_{1-4}$ alkyl, $C_{2-4}$ alkenyl, $C_{2-4}$ alkynyl, aryl, cycloalkyl, heteroaryl, heterocycloalkyl, arylalkyl, cycloalkylalkyl, heteroarylalkyl, or heterocycloalkylalkyl is optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ cyanoalkyl, aryl, heteroaryl, cycloalkyl, heterocycloalkyl, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)NR^{c4}R^{d4}$, $NR^{c4}C(O)OR^{a4}$, $C(=NR^i)NR^{c4}R^{d4}$, $NR^{c4}C(=NR_i)NR^{c4}R^{d4}$, $P(R^{f4})_2$, $P(OR^{e4})_2$, $P(O)R^{e4}R^{f4}$, $P(O)OR^{e4}OR^{f4}$, $S(O)R^{b4}$, $S(O)NR^{c4}R^{d4}$, $S(O)_2R^{b4}$, $NR^{c4}S(O)_2R^{b4}$, and $S(O)_2NR^{c4}R^{d4}$.

In some embodiments, $R^4$ is H, $C_{1-4}$ alkyl, $C(O)$—$R^{4a}$, $SO_2$—$R^{4a}$, aryl, cycloalkyl, heteroaryl, heterocycloalkyl, arylalkyl, cycloalkylalkyl, heteroarylalkyl, or heterocycloalkylalkyl, wherein said $C_{1-4}$ alkyl, aryl, cycloalkyl, heteroaryl, heterocycloalkyl, arylalkyl, cycloalkylalkyl, heteroarylalkyl, or heterocycloalkylalkyl is optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ cyanoalkyl, aryl, heteroaryl, cycloalkyl, heterocycloalkyl, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)NR^{c4}R^{d4}$, $NR^{c4}C(O)OR^{a4}$, $C(=NR^i)NR^{c4}R^{d4}$, $NR^{c4}C(=NR^i)NR^{c4}R^{d4}$, $P(R^{f4})_2$, $P(OR^{e4})_2$, $P(O)R^{e4}R^{f4}$, $P(O)OR^{e4}OR^{f4}$, $S(O)R^{b4}$, $S(O)NR^{c4}R^{d4}$, $S(O)_2R^{b4}$, $NR^{c4}S(O)_2R^{b4}$, and $S(O)_2NR^{c4}R^{d4}$.

In some embodiments, $R^4$ is H.

In some embodiments, $R^A$ and $R^B$ are independently selected from H, F, $C_{1-6}$ alkyl, $C_{2-6}$ alkenyl, $C_{2-6}$ alkynyl, $C_{1-6}$ haloalkyl, aryl, cycloalkyl, heteroaryl, heterocycloalkyl, arylalkyl, cycloalkylalkyl, heteroarylalkyl, heterocycloalkylalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $C(=NR^i)NR^{c1}R^{d1}$, $NR^{c1}C(=NR^i)NR^{c1}R^{d1}$, $P(R^{f1})_2$, $P(OR^{e1})_2$, $P(O)R^{e1}R^{f1}$, $P(O)OR^{e1}OR^{f1}$, $S(O)R^{b1}$, $S(O)NR^{c1}R^{d1}$, $S(O)_2R^{b1}$, $NR^{c1}S(O)_2R^{b1}$, and $S(O)_2NR^{c1}R^{d1}$; wherein said $C_{1-6}$ alkyl, $C_{2-6}$ alkenyl, $C_{2-6}$ alkynyl, aryl, cycloalkyl, heteroaryl, heterocycloalkyl, arylalkyl, cycloalkylalkyl, heteroarylalkyl, or heterocycloalkylalkyl is optionally substituted by 1, 2, 3, 4, or 5 substituents independently selected from halo, $C_{1-4}$ alkyl, $C_{2-4}$ alkenyl, $C_{2-4}$ alkynyl, $C_{1-4}$ haloalkyl, $C_{1-4}$ hydroxyalkyl, $C_{1-4}$ cyanoalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $C(=NR^i)NR^{c1}R^{d1}$, $NR^{c1}C(=NR^i)NR^{c1}R^{d1}$, $P(R^{f1})_2$, $P(OR^{e1})_2$, $P(O)R^{e1}R^{f1}$, $P(O)OR^{e1}OR^{f1}$, $S(O)R^{b1}$, $S(O)NR^{c1}R^{d1}$, $S(O)_2R^{b1}$, $NR^{c1}S(O)_2R^{b1}$, and $S(O)_2NR^{c1}R^{d1}$.

In some embodiments, $R^A$ and $R^B$ are independently selected from H, $C_{1-6}$ alkyl, $C_{2-6}$ alkenyl, $C_{2-6}$ alkynyl, $C_{1-6}$ haloalkyl, aryl, cycloalkyl, heteroaryl, heterocycloalkyl, arylalkyl, cycloalkylalkyl, heteroarylalkyl, and heterocycloalkylalkyl, wherein said $C_{1-6}$ alkyl, $C_{2-6}$ alkenyl, $C_{2-6}$ alkynyl, aryl, cycloalkyl, heteroaryl, heterocycloalkyl, arylalkyl, cycloalkylalkyl, heteroarylalkyl, or heterocyclo-alkylalkyl is optionally substituted by 1, 2, 3, 4, or 5 substituents independently selected from halo, $C_{1-4}$ alkyl, $C_{2-4}$ alkenyl, $C_{2-4}$ alkynyl, $C_{1-4}$ haloalkyl, $C_{1-4}$ hydroxyalkyl, $C_{1-4}$ cyanoalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR_{c1}C(O)OR^{a1}$, $S(O)R^{b1}$, $S(O)NR^{c1}R^{d1}$, $S(O)_2R^{b1}$, $NR^{c1}S(O)_2R^{b1}$, and $S(O)_2NR^{c1}R^{d1}$.

In some embodiments, $R^A$ and $R^B$ are independently selected from H, F, and $C_{1-6}$ alkyl.

In some embodiments, $R^A$ and $R^B$ are, independently, H or $C_{1-6}$ alkyl.

In some embodiments, $R^A$ and $R^B$ are both H.

In some embodiments, $R^A$ and $R^B$ together with the carbon atom to which they are attached form a 3-, 4-, 5-, 6-, or 7-membered cycloalkyl group or 3-, 4-, 5-, 6-, or 7-membered heterocycloalkyl group, each optionally substituted with 1, 2, or 3 substituents independently selected from halo, $C_{1-4}$ alkyl, $C_{2-4}$ alkenyl, $C_{2-4}$ alkynyl, $C_{1-4}$ haloalkyl, $C_{1-4}$ hydroxyalkyl, $C_{1-4}$ cyanoalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $C(=NR^i)NR^{c1}R^{d1}$, $NR^{c1}C(=NR^i)NR^{c1}R^{d1}$, $P(R^{f1})_2$, $P(OR^{e1})_2$, $P(O)R^{e1}R^{f1}$, $P(O)OR^{e1}OR^{f1}$, $S(O)R^{b1}$, $S(O)NR^{c1}R^{d1}$, $S(O)_2R^{b1}$, $NR^{c1}S(O)_2R^{b1}$, and $S(O)_2NR^{c1}R^{d1}$.

In some embodiments, $R^i$ is H, CN, or $NO_2$.

In some embodiments, $R^{a2}$ is H, $C_{1-6}$ alkyl, $C_{1-6}$ haloalkyl, $C_{2-6}$ alkenyl, $C_{2-6}$ alkynyl, $Cy^2$, or $Cy^2$-($C_{1-6}$ alkyl)-, wherein said $C_{1-6}$ alkyl, $C_{1-6}$ haloalkyl, $C_{2-6}$ alkenyl, or $C_{2-6}$ alkynyl, is optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ hydroxyalkyl, $C_{1-6}$ cyanoalkyl, $Cy^2$, CN, $NO_2$, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^i)NR^{c5}R^{d5}$, $NR^{c5}C(=NR^i)NR^{c5}R^{d5}$, $P(R^{f5})_2$, $P(OR^{e5})_2$, $P(O)R^{e5}R^{f5}$, $P(O)OR^{e5}OR^{f5}$, $S(O)R^{b5}$, $S(O)NR^{c5}R^{d5}$, $R^{b2}$, $S(O)_2R^{b5}$, $NR^{c5}S(O)_2R^{b5}$, and $S(O)_2NR^{c5}R^{d5}$.

In some embodiments, $R^{b2}$ is H, $C_{1-6}$ alkyl, $C_{1-6}$ haloalkyl, $C_{2-6}$ alkenyl, $C_{2-6}$ alkynyl, aryl, $Cy^2$, or $Cy^2$-($C_{1-6}$ alkyl)-, wherein said $C_{1-6}$ alkyl, $C_{1-6}$ haloalkyl, $C_{2-6}$ alkenyl, $C_{2-6}$ alkynyl, or aryl is optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ cyanoalkyl, $Cy^2$, CN, $NO_2$, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR_{c5}R^{d5}$, $NR^{c5}C(O)OR^{a5}$, $C(=NR^i)NR^{c5}R^{d5}$, $NR^{c5}C(=NR^i)NR^{c5}R^{d5}$, $P(R^{f5})_2$, $P(OR^{e5})_2$, $P(O)R^{e5}R^{f5}$, $P(O)OR^{e5}OR^{f5}$, $S(O)R^{b5}$, $S(O)NR^{c5}R^{d5}$, $S(O)_2R^{b5}$, $NR^{c5}S(O)_2R^{b5}$, and $S(O)_2NR^{c5}R^{d5}$.

In some embodiments, $R^c$ and $R^d$ are independently selected from H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl, and heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl, or heterocycloalkylalkyl is optionally substituted with OH, amino, halo, $C_{1-6}$ alkyl, $C_{1-6}$ haloalkyl, aryl, arylalkyl, heteroaryl, heteroarylalkyl, cycloalkyl, or heterocycloalkyl.

In some embodiments, $R^c$ and $R^d$ together with the N atom to which they are attached form a 4-, 5-, 6- or 7-membered heterocycloalkyl group.

In some embodiments, Cy, $Cy^1$, and $Cy^2$ are independently selected from aryl, heteroaryl, cycloalkyl, and heterocycloalkyl, each optionally substituted by 1, 2, 3, 4 or 5 substituents independently selected from halo, $C_{1-4}$ alkyl, $C_{2-4}$ alkenyl, $C_{2-4}$ alkynyl, $C_{1-4}$ haloalkyl, CN, $NO_2$, $OR^{a3}$, $SR^{a3}$, $C(O)R^{b3}$, $C(O)NR^{c3}R^{d3}$, $C(O)OR^{a3}$, $C(O)OR^{a3}$, $OC(O)R^{b3}$, $OC(O)NR^{a3}R^{d3}$, $NR^{c3}C(O)R^{b3}$, $NR^{c3}C(O)OR^{a3}$, $C(=NR^i)$ $NR^{c3}R^{d3}$, $NR^{c3}C(=NR^i)NR^{c3}R^{d3}$, $P(R^{f3})_2$, $P(OR^{e3})_2$, $P(O)R^{e3}R^{f3}$, $P(O)OR^{e3}OR^{f3}$, $S(O)R^{b3}$, $S(O)NR^{c3}R^{d3}$, $S(O)_2R^{b3}$, and $S(O)_2NR^{c3}R^{d3}$.

In some embodiments, Cy is aryl, heteroaryl, cycloalkyl, or heterocycloalkyl, each optionally substituted by 1, 2, 3, 4 or 5 substituents independently selected from halo, $C_{1-4}$ alkyl, $C_{2-4}$ alkenyl, $C_{2-4}$ alkynyl, $C_{1-4}$ haloalkyl, CN, NO$_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $S(O)R^{b3}$, $S(O)NR^{c3}R^{d3}$, $S(O)_2R^{b3}$, and $S(O)_2NR^{c3}R^{d3}$.

In some embodiments, $R^1$ is H.
In some embodiments, R is H.
In some embodiments, $R^2$ is H.
In some embodiments, $R^3$ is H.
In some embodiments, p is 1, 2, 3, 4 or 5.
In some embodiments, p is 1 or 2.
In some embodiments, p is 1.
In some embodiments, the compounds of the invention have Formula I:

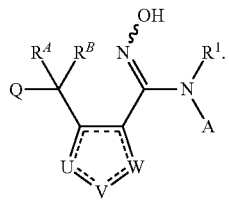

In some embodiments, the compounds of the invention have Formula IIa:

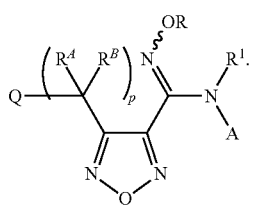

In some embodiments, the compounds of the invention have Formula II:

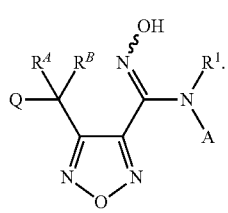

In some embodiments, the compound has Formula III:

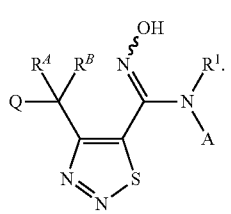

In some embodiments, the present invention provides compounds of Formula I:

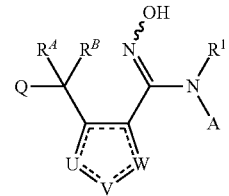

or pharmaceutically acceptable salts or prodrugs thereof, wherein:

U, V, and W are independently selected from N, O, S, $CR^2$, and $NR^3$, wherein the five-membered ring containing U, V, and W is an aromatic heterocycle;

A is aryl, cycloalkyl, heteroaryl, or heterocycloalkyl, each optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ halo-alkyl, $C_{1-6}$ hydroxyalkyl, $C_{1-6}$ cyanoalkyl, aryl, cycloalkyl, heteroaryl, heterocycloalkyl, CN, NO$_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^c(O)R^b$, $NR^cC(O)NR^cR^d$, $NR^c(O)OR^a$, $S(O)R^b$, $S(O)NR^cR^d$, $S(O)_2R^b$, $NR^cS(O)_2R^b$, and $S(O)_2NR^cR^d$;

In some embodiments, $R^A$ and $R^B$ are independently selected from H, $C_{1-6}$ alkyl, $C_{2-6}$ alkenyl, $C_{2-6}$ alkynyl, $C_{1-6}$ haloalkyl, aryl, cycloalkyl, heteroaryl, heterocycloalkyl, arylalkyl, cycloalkylalkyl, heteroarylalkyl, and heterocycloalkylalkyl, wherein said $C_{1-6}$ alkyl, $C_{2-6}$ alkenyl, $C_{2-6}$ alkynyl, aryl, cycloalkyl, heteroaryl, heterocycloalkyl, arylalkyl, cycloalkylalkyl, heteroarylalkyl, or heterocycloalkylalkyl is optionally substituted by 1, 2, 3, 4, or 5 substituents independently selected from halo, $C_{1-4}$ alkyl, $C_{2-4}$ alkenyl, $C_{2-4}$ alkynyl, $C_{1-4}$ haloalkyl, $C_{1-4}$ hydroxyalkyl, cyanoalkyl, CN, NO$_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $S(O)R^{b1}$, $S(O)NR^{c1}R^{d1}$, $S(O)_2R^{b1}$, $NR^{c1}S(O)_2R^{b1}$, and $S(O)_2NR^{c1}R^{d1}$.

or $R^A$ and $R^B$ together with the carbon atom to which they are attached form a 3-, 4-, 5-, 6-, or 7-membered cycloalkyl group or 3-, 4-, 5-, 6-, or 7-membered heterocycloalkyl group, each optionally substituted with 1, 2, or 3 substituents independently selected from halo, $C_{1-4}$ alkyl, $C_{2-4}$ alkenyl, $C_{2-4}$ alkynyl, $C_{1-4}$ haloalkyl, $C_{1-4}$ hydroxyalkyl, $C_{1-4}$ cyanoalkyl, CN, NO$_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $S(O)R^{b1}$, $S(O)NR^{c1}R^{d1}$, $S(O)_2R^{b1}$, $NR^{c1}S(O)_2R^{b1}$, and $S(O)_2NR^{c1}R^{d1}$;

Q is $OR^Q$, $OC(O)R^Q$, $OC(O)NR^4R^Q$, $NR^4R^Q$, $NR^4C(O)R^Q$, $NR^4C(O)NR^4R^Q$, $SR^Q$, $S(O)R^Q$, $S(O)NR^4R^Q$, $S(O)_2R^Q$, or $S(O)_2NR^4R^Q$;

$R^Q$ is H, $C_{1-6}$ alkyl, $C_{2-6}$ alkenyl, $C_{2-6}$ alkynyl, $C_{1-6}$ haloalkyl, aryl, cycloalkyl, heteroaryl, heterocycloalkyl, arylalkyl, cycloalkylalkyl, heteroarylalkyl, or heterocycloalkylalkyl, wherein said $C_{1-6}$ alkyl, $C_{2-6}$ alkenyl, $C_{2-6}$ alkynyl, aryl, cycloalkyl, heteroaryl, heterocycloalkyl, arylalkyl, cycloalkylalkyl, heteroarylalkyl, or heterocycloalkylalkyl is optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ cyanoalkyl, Cy, —($C_{1-4}$ alkyl)-Cy, CN, NO$_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $S(O)R^{b2}$, $S(O)NR^{c2}R^{d2}$, $S(O)_2R^{b2}$, $NR^{c2}S(O)_2R^{b2}$, and $S(O)_2NR^{c2}R^{d2}$;

or $R^4$ and $R^Q$ together with the N atom to which they are attached form a 4-20 membered heterocycloalkyl group optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ cyanoalkyl, Cy, —($C_{1-4}$ alkyl)-Cy, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $S(O)R^{b2}$, $S(O)NR^{c2}R^{d2}$, $S(O)_2R^{b2}$, $NR^{c2}S(O)_2R^{b2}$, and $S(O)_2NR^{c2}R^{d2}$;

Cy is aryl, heteroaryl, cycloalkyl, or heterocycloalkyl, each optionally substituted by 1, 2, 3, 4 or 5 substituents independently selected from halo, $C_{1-4}$ alkyl, $C_{2-4}$ alkenyl, $C_{2-4}$ alkynyl, $C_{1-4}$ halo-alkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $S(O)R^{b3}$, $S(O)NR^{c3}R^{d3}$, $S(O)_2R^{b3}$, and $S(O)_2NR^{c3}R^{d3}$;

$R^1$ is H or $C_{1-4}$ alkyl;

$R^2$ is H, halo, $C_{1-4}$ alkyl, $C_{1-4}$ haloalkyl, $C_{2-4}$ alkenyl, $C_{2-4}$ alkynyl, CN, $NO_2$, OH, $C_{1-4}$ alkoxy, amino, $C_{1-4}$ alkylamino, or $C_{2-8}$ dialkylamino;

$R^3$ is H, $C_{1-4}$ alkyl, $C_{2-4}$ alkenyl, or $C_{2-4}$ alkynyl;

$R^4$ is H, $C_{1-4}$ alkyl, $C_{2-4}$ alkenyl, $C_{2-4}$ alkynyl, or C(O)—($C_{1-4}$ alkyl);

$R^a$, $R^{a1}$, $R^{a2}$, and $R^{a3}$ are independently selected from H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl and heterocycloalkylalkyl, wherein said $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or heterocycloalkylalkyl is optionally substituted with OH, amino, halo, $C_{1-6}$ alkyl, aryl, arylalkyl, heteroaryl, heteroarylalkyl, cycloalkyl or heterocycloalkyl;

$R^b$, $R^{b1}$, $R^{b2}$, and $R^{b3}$ are independently selected from H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cyclo-alkylalkyl and heterocycloalkylalkyl, wherein said $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or hetero-cycloalkylalkyl is optionally substituted with OH, amino, halo, $C_{1-6}$ alkyl, $C_{1-6}$ haloalkyl, aryl, aryl-alkyl, heteroaryl, heteroarylalkyl, cycloalkyl or heterocycloalkyl;

$R^c$ and $R^d$ are independently selected from H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl and heterocycloalkylalkyl, wherein said $C_{1-10}$ alkyl, $C_{1-6}$ haloalkyl, $C_{2-6}$ alkenyl, $C_{2-6}$ alkynyl, aryl, hetero-aryl, cycloalkyl, heterocycloalkyl, arylalkyl, heteroarylalkyl, cycloalkylalkyl or heterocycloalkylalkyl is optionally substituted with OH, amino, halo, $C_{1-6}$ alkyl, $C_{1-6}$ haloalkyl, aryl, arylalkyl, heteroaryl, heteroarylalkyl, cycloalkyl or heterocycloalkyl;

or $R^c$ and $R^d$ together with the N atom to which they are attached form a 4-, 5-, 6- or 7-membered heterocycloalkyl group;

$R^{c1}$ and $R^{d1}$ are independently selected from H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl and heterocycloalkylalkyl, wherein said $C_{1-10}$ alkyl, $C_{1-6}$ haloalkyl, $C_{2-6}$ alkenyl, $C_{2-6}$ alkynyl, aryl, hetero-aryl, cycloalkyl, heterocycloalkyl, arylalkyl, heteroarylalkyl, cycloalkylalkyl or heterocycloalkylalkyl is optionally substituted with OH, amino, halo, $C_{1-6}$ alkyl, $C_{1-6}$ haloalkyl, aryl, arylalkyl, heteroaryl, heteroarylalkyl, cycloalkyl or heterocycloalkyl;

or $R^{c1}$ and $R^{d1}$ together with the N atom to which they are attached form a 4-, 5-, 6- or 7-membered heterocycloalkyl group;

$R^{c2}$ and $R^{d2}$ are independently selected from H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with OH, amino, halo, $C_{1-6}$ alkyl, $C_{1-6}$ haloalkyl, aryl, arylalkyl, heteroaryl, heteroarylalkyl, cycloalkyl or heterocycloalkyl;

or $R^{c2}$ and $R^{d2}$ together with the N atom to which they are attached form a 4-, 5-, 6- or 7-membered heterocycloalkyl group; and $R^{c3}$ and $R^{d3}$ are independently selected from H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with OH, amino, halo, $C_{1-6}$ alkyl, $C_{1-6}$ haloalkyl, aryl, arylalkyl, heteroaryl, heteroarylalkyl, cycloalkyl or heterocycloalkyl;

or $R^{c3}$ and $R^{d3}$ together with the N atom to which they are attached form a 4-, 5-, 6- or 7-membered heterocycloalkyl group.

At various places in the present specification, substituents of compounds of the invention are disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

It is further intended that the compounds of the invention are stable. As used herein "stable" refers to a compound that is sufficiently robust to survive isolation to a useful degree of purity from a reaction mixture, and preferably capable of formulation into an efficacious therapeutic agent.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

As used herein, the term "alkyl" is meant to refer to a saturated hydrocarbon group which is straight-chained or branched. Example alkyl groups include methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like. An alkyl group can contain from 1 to about 20, from 2 to about 20, from 1 to about 10, from 1 to about 8, from 1 to about 6, from 1 to about 4, or from 1 to about 3 carbon atoms.

As used herein, "alkenyl" refers to an alkyl group having one or more double carbon-carbon bonds. Example alkenyl groups include ethenyl, propenyl, and the like.

As used herein, "alkynyl" refers to an alkyl group having one or more triple carbon-carbon bonds. Example alkynyl groups include ethynyl, propynyl, and the like.

As used herein, "haloalkyl" refers to an alkyl group having one or more halogen substituents. Example haloalkyl groups include $CF_3$, $C_2F_5$, $CHF_2$, $CCl_3$, $CHCl_2$, $C_2Cl_5$, and the like.

As used herein, "halosulfanyl" refers to a sulfur group having one or more halogen substituents. Example halosulfanyl groups include pentahalosulfanyl groups such as $SF_5$.

As used herein, "aryl" refers to monocyclic or polycyclic (e.g., having 2, 3 or 4 fused rings) aromatic hydrocarbons such as, for example, phenyl, naphthyl, anthracenyl, phenanthrenyl, indanyl, indenyl, and the like. In some embodiments, aryl groups have from 6 to about 20 carbon atoms.

As used herein, "cycloalkyl" refers to non-aromatic carbocycles including cyclized alkyl, alkenyl, and alkynyl groups. Cycloalkyl groups can include mono- or polycyclic (e.g., having 2, 3 or 4 fused rings) ring systems, including spirocycles. In some embodiments, cycloalkyl groups can have from 3 to about 20 carbon atoms, 3 to about 14 carbon atoms, 3 to about 10 carbon atoms, or 3 to 7 carbon atoms. Cycloalkyl groups can further have 0, 1, 2, or 3 double bonds and/or 0, 1, or 2 triple bonds. Cycloalkyl groups can further be substituted by one or more oxo groups. Also included in the definition of cycloalkyl are moieties that have one or more aromatic rings fused (i.e., having a bond in common with) to the cycloalkyl ring, for example, benzo derivatives of cyclopentane, cyclopentene, cyclohexane, and the like. A cycloalkyl group having one or more fused aromatic rings can be attached though either the aromatic or non-aromatic portion. One or more ring-forming carbon atoms of a cycloalkyl group can be oxidized, for example, having an oxo or sulfido substituent. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, adamantyl, and the like.

As used herein, a "heteroaryl" group refers to an aromatic heterocycle having at least one heteroatom ring member such as sulfur, oxygen, or nitrogen. Heteroaryl groups include monocyclic and polycyclic (e.g., having 2, 3 or 4 fused rings) systems. Any ring-forming N atom in a heteroaryl group can also be oxidized to form an N-oxo moiety. Examples of heteroaryl groups include without limitation, pyridyl, N-oxopyridyl, pyrimidinyl, pyrazinyl, pyridazinyl, triazinyl, furyl, quinolyl, isoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,3-thiadiazolyl, 1,2,4-thiadiazolyl, isothiazolyl, benzothienyl, purinyl, carbazolyl, benzimidazolyl, indolinyl, xanthene, and the like. In some embodiments, the heteroaryl group has from 1 to about 20 carbon atoms, and in further embodiments from about 3 to about 20 carbon atoms. In some embodiments, the heteroaryl group contains 3 to about 14, 3 to about 7, or 5 to 6 ring-forming atoms. In some embodiments, the heteroaryl group has 1 to about 4, 1 to about 3, or 1 to 2 heteroatoms.

As used herein, "heterocycloalkyl" refers to a non-aromatic heterocycle where one or more of the ring-forming atoms is a heteroatom such as an O, N, or S atom. Heterocycloalkyl groups can include mono- or polycyclic (e.g., having 2, 3 or 4 fused rings) ring systems as well as spirocycles. Any ring-forming C, N or S atom in a heterocycloalkyl group can be substituted by 1 or 2 oxo groups to form a carbonyl, N-oxo, sulfinyl, or sulfonyl moiety. Example "heterocycloalkyl" groups include morpholino, thiomorpholino, piperazinyl, tetrahydrofuranyl, tetrahydrothienyl, 2,3-dihydrobenzofuryl, 1,3-benzodioxole, benzo-1,4-dioxane, piperidinyl, pyrrolidinyl, isoxazolidinyl, isothiazolidinyl, pyrazolidinyl, oxazolidinyl, thiazolidinyl, imidazolidinyl, and the like. Also included in the definition of heterocycloalkyl are moieties that have one or more aromatic rings fused (i.e., having a bond in common with) to the nonaromatic heterocyclic ring, for example phthalimidyl, naphthalimidyl, and benzo derivatives of heterocycles such as indolene, isoindoline, tetrahydroquinoline, and tetrahydroisoquinoline groups. A heterocycloalkyl group having one or more fused aromatic rings can be attached though either the aromatic or non-aromatic portion. In some embodiments, the heterocycloalkyl group has from 1 to about 20 carbon atoms, and in further embodiments from about 3 to about 20 carbon atoms. In some embodiments, the heterocycloalkyl group contains 3 to about 20, 3 to about 14, 3 to about 7, or 5 to 6 ring-forming atoms. In some embodiments, the heterocycloalkyl group has 1 to about 4, 1 to about 3, or 1 to 2 heteroatoms. In some embodiments, the heterocycloalkyl group contains 0 to 3 double bonds. In some embodiments, the heterocycloalkyl group contains 0 to 2 triple bonds.

As used herein, "halo" or "halogen" includes fluoro, chloro, bromo, and iodo.

As used herein, "hydroxyalkyl" refers to an alkyl group substituted with a hydroxyl group.

As used herein, "cyanoalkyl" refers to an alkyl group substituted with a cyano group.

As used herein, "alkoxy" refers to an O-alkyl group. Example alkoxy groups include methoxy, ethoxy, propoxy (e.g., n-propoxy and isopropoxy), t-butoxy, and the like.

As used herein, "arylalkyl" refers to alkyl substituted by aryl and "cycloalkylalkyl" refers to alkyl substituted by cycloalkyl. An example arylalkyl group is benzyl.

As used herein, "heteroarylalkyl" refers to alkyl substituted by heteroaryl and "heterocycloalkylalkyl" refers to alkyl substituted by heterocycloalkyl.

As used herein, "amino" refers to $NH_2$.

As used herein, "alkylamino" refers to an amino group substituted by an alkyl group.

As used herein, "dialkylamino" refers to an amino group substituted by two alkyl groups.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically active starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. A bond, in a structure diagram represented by a wavy line "〜" is intended to indicate that the structure represents the cis or the trans isomer, or a mixture of the cis and trans isomers in any proportion.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone—enol pairs, amide—imidic acid pairs, lactam—lactim pairs, amide—imidic acid pairs, enamine—imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds of the invention can also include all isotopes of atoms occurring in the intermediates or final compounds. Isotopes include those atoms having the same atomic number but different mass numbers. For example, isotopes of hydrogen include tritium and deuterium.

In some embodiments, the compounds of the invention, and salts thereof, are substantially isolated. By "substantially isolated" is meant that the compound is at least partially or substantially separated from the environment in which is was formed or detected. Partial separation can include, for example, a composition enriched in the compound of the invention. Substantial separation can include compositions containing at least about 50%, at least about 60%, at least about 70%, at least about 80%, at least about 90%, at least about 95%, at least about 97%, or at least about 99% by weight of the compound of the invention, or salt thereof. Methods for isolating compounds and their salts are routine in the art.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or ACN are preferred. Lists of suitable salts are found in *Remington's Pharmaceutical Sciences*, 17'" e a Mack Publishing Company, Easton, Pa., 1985, p. 1418 and *Journal of Pharmaceutical Science*, 66, 2 (1977), each of which is incorporated herein by reference in its entirety.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present invention also includes prodrugs of the compounds described herein. As used herein, "prodrugs" refer to any covalently bonded carriers which release the active parent drug when administered to a mammalian subject. Prodrugs can be prepared by modifying functional groups present in the compounds in such a way that the modifications are cleaved, either in routine manipulation or in vivo, to the parent compounds. Prodrugs include compounds wherein hydroxyl, amino, sulfhydryl, or carboxyl groups are bonded to any group that, when administered to a mammalian subject, cleaves to form a free hydroxyl, amino, sulfhydryl, or carboxyl group respectively. Examples of prodrugs include, but are not limited to, acetate, formate and benzoate derivatives of alcohol and amine functional groups in the compounds of the invention. Preparation and use of prodrugs is discussed in T. Higuchi and V. Stella, "Pro-drugs as Novel Delivery Systems," Vol. 14 of the A.C.S. Symposium Series, and in *Bioreversible Carriers in Drug Design*, ed. Edward B. Roche, American Pharmaceutical Association and Pergamon Press, 1987, both of which are hereby incorporated by reference in their entirety.

Synthesis

The novel compounds of the present invention can be prepared in a variety of ways known to one skilled in the art of organic synthesis. The compounds of the present invention can be synthesized using the methods as hereinafter described below, together with synthetic methods known in the art of synthetic organic chemistry or variations thereon as appreciated by those skilled in the art.

The compounds of this invention can be prepared from readily available starting materials using the following general methods and procedures. It will be appreciated that where typical or preferred process conditions (i.e., reaction temperatures, times, mole ratios of reactants, solvents, pressures, etc.) are given; other process conditions can also be used unless otherwise stated. Optimum reaction conditions may vary with the particular reactants or solvent used, but such conditions can be determined by one skilled in the art by routine optimization procedures.

The processes described herein can be monitored according to any suitable method known in the art. For example, product formation can be monitored by spectroscopic means, such as nuclear magnetic resonance spectroscopy (e.g., $^1$H or $^{13}$C) infrared spectroscopy, spectrophotometry (e.g., UV-visible), or mass spectrometry, or by chromatography such as high performance liquid chromatography (HPLC) or thin layer chromatography.

Preparation of compounds can involve the protection and deprotection of various chemical groups. The need for protection and deprotection, and the selection of appropriate protecting groups can be readily determined by one skilled in the art. The chemistry of protecting groups can be found, for example, in Greene, et al., *Protective Groups in Organic Synthesis*, 2d. Ed., Wiley & Sons, 1991, which is incorporated herein by reference in its entirety.

The reactions of the processes described herein can be carried out in suitable solvents which can be readily selected by one of skill in the art of organic synthesis. Suitable solvents can be substantially nonreactive with the starting materials (reactants), the intermediates, or products at the temperatures at which the reactions are carried out, i.e., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected.

Resolution of racemic mixtures of compounds can be carried out by any of numerous methods known in the art. An example method includes fractional recrystallization using a "chiral resolving acid" which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids. Resolution of racemic mixtures can also be carried out by elution on a column packed with an optically active resolving agent (e.g., dinitrobenzoyl-phenylglycine). Suitable elution solvent composition can be determined by one skilled in the art.

Compounds of the invention can be synthesized according to routine methods by those skilled in the art and as shown in the below Schemes.

According to Scheme 1, intermediates 1-5 (such as 6H-furo[3,4-c][1,2,5]oxadiazol-4-one) can be prepared starting with cleavage of bicyclic compounds I-1 with a primary amine to yield hydroxymethyl derivatives 1-2. The hydroxyl group can be protected in any suitable manner such as by alklysilylchloride, ester, ether or other suitable protecting group (see, e.g., Greene, et al., *Protective Groups in Organic Synthesis*, supra) to yield protected compounds 1-3. The protected compounds 1-3 can be converted to the corresponding N-hydroxyamidines 1-4 by thionation with an appropriate reagent such as $CS_2$ or Lawesson's reagent followed by S-alkylation (e.g., S-methylation) with an appropriate reagent such as methyl iodide or methyltriflate followed by treatment with $NH_2OH$. The N-hydroxyamidine group can be protected using, for example, phosgene, triphosgene, carbonyldiimidazole, etc., and the protected hydroxymethyl group can then be deprotected (such as by treatment with acid for alkylsilylethers) for further modification if desired.

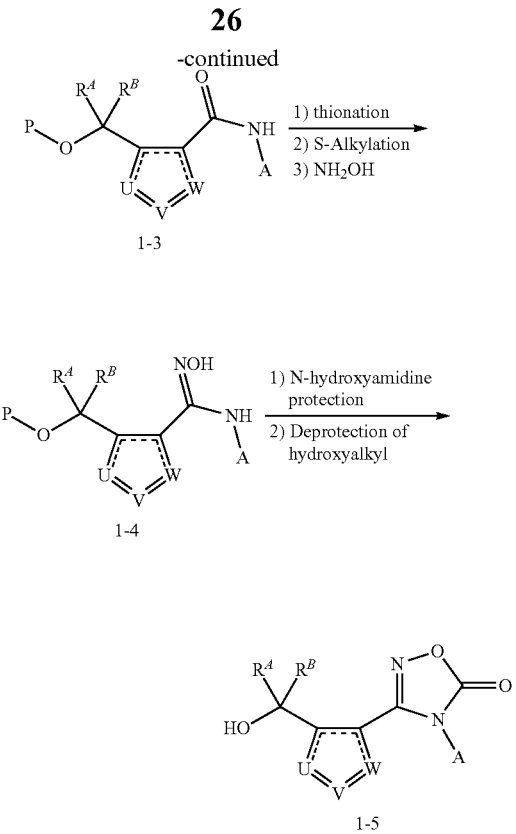

According to Scheme 2, compounds of the invention can be prepared starting with the intermediate 2-1 (which can be prepared according to Scheme 1) which can be oxidized at the hydroxymethyl group according to standard procedures for conversion of an alcohol to an aldehyde to yield intermediates 2-2. The aldehydes (2-2) can be further reacted with appropriate nucleophiles to yield hydroxyl (2-5) or amino (2-4) intermediates with optional substitution ($R^A$) on the methylene. These intermediates can be further modified by reaction of the hydroxyl groups with suitable electrophiles (e.g., alkylation, acylate, arylation) optionally in the presence of catalytic amounts of base or acid followed by deprotection to yield compounds of the invention 2-7 and 2-11. Additionally, intermediate 2-5 can be oxidized to afford ketone 2-3 which can be further reacted with appropriate nucleophiles to yield hydroxyl (2-9) or amino (2-8) intermediates with optional substitution ($R^A$ and $R^B$) on the methylene. Similarly, amines 2-4 and 2-8 can be directly deprotected to yield further compounds of the invention 2-6 and 2-10.

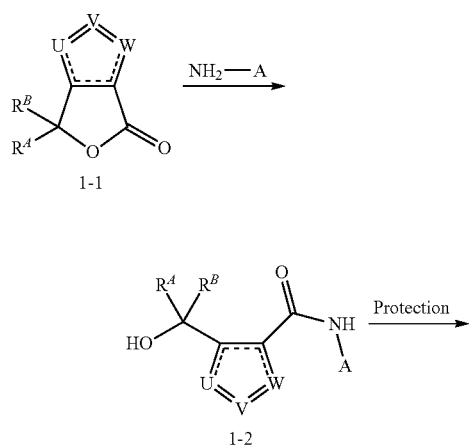

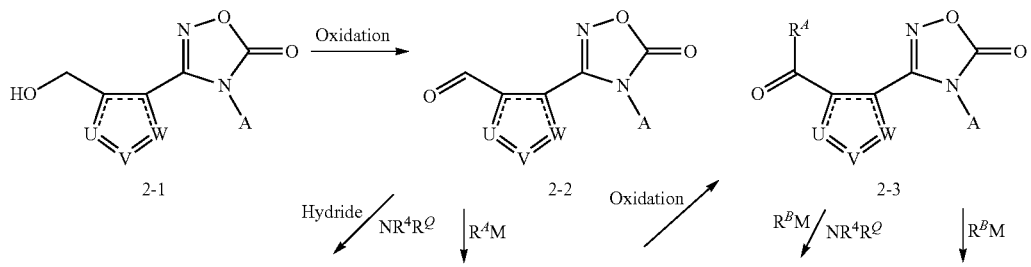

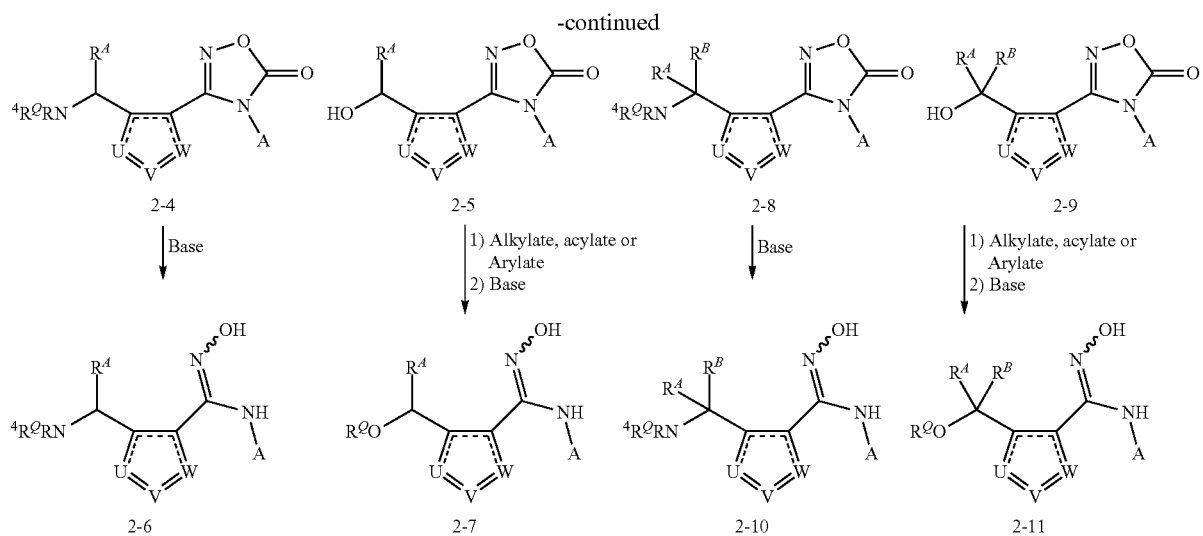

Various compounds of the invention can be prepared according to the method shown in Scheme 3 where protected N-hydroxyamidines 3-1 are modified by Mitsonubu reaction with various aryl or heteroaryl alcohols (e.g., phenol or substituted phenol) followed by treatment with a base such as hydroxide to give aryloxy and heteroaryloxy derivatives 3-2. Additionally, protected N-hydroxyamidines 3-1 can be reacted with suitable reagents $R^4R^QNC(O)X$ (where X is halo) or isocyanates $R^Q—N=C=O$ followed by treatment with base such as hydroxide to give compounds of the invention 3-3. In the case of reaction with the isocyanates, $R^4$ of 3-3 would typically be H.

Amino methyl compounds of the invention can be prepared according to the methods of Scheme 4 where the hydroxymethyl group of a protected N-hydroxyamidine intermediate 4-1 is treated with mesylchloride or other suitable reagent to produce a good leaving group such as mesylate as exemplified in intermediate 4-2. The intermediate 4-2 is then reacted with amine $NHR^4R^Q$ followed by treatment with base (such as hydroxide) to yield amino methyl compounds 4-3. The amino methyl compounds can be further derivatized to make various amides, ureas, sulfonamides, carbamates and the like by reaction of the amino moiety with $R^QC(O)—X$, $R^QS(O)_2—X$, $R^QOC(O)—X$ and the like (X is a leaving group).

Scheme 3

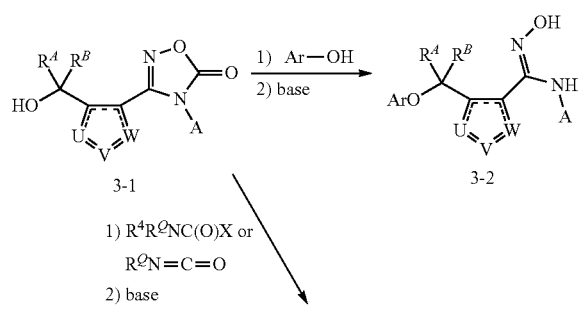

Scheme 4

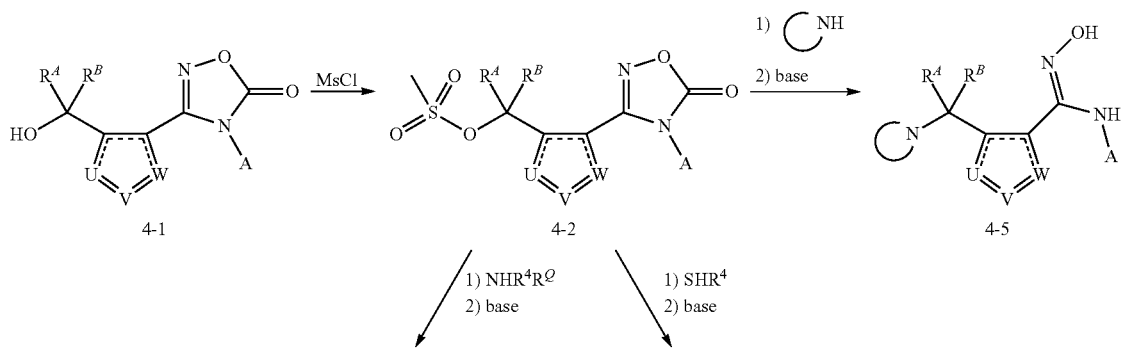

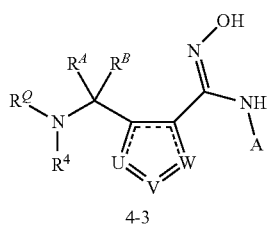

4-3

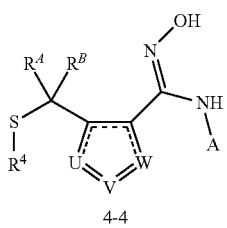

4-4

Additional amino methyl compounds of the invention can be prepared according to the methods of Scheme 5 where the intermediate 4-2 is reacted with sodium azide followed by reduction (such as hydrogen over palladium or triphenylphosphine) to yield amino methyl compounds 4-6. The amino methyl compounds 4-6 can be further derivatized to make various compounds 4-7, such as amides, ureas, sulfonamides, carbamates and the like, by reaction of the amino moiety with $R^Q C(O)$—X, $R^Q S(O)_2$—X, $R^Q OC(O)$—X and the like (X is a leaving group).

Scheme 5

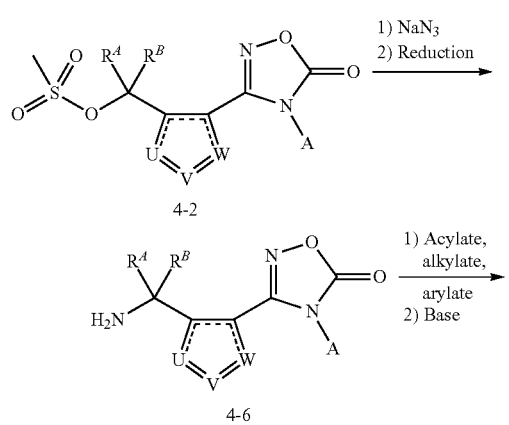

Alkoxy compounds 6-2 can be prepared, for example, according the route shown in Scheme 6. Here, hydroxyalkyl or related compounds 6-1 are reacted with various electrophiles such as alkyl halides ("alkyl-X," where X is halo) followed by reaction with base such as hydroxide to form alkylated and similar compounds of formula 6-2. The alkyl halides can be optionally substituted with other various functional groups.

Scheme 6

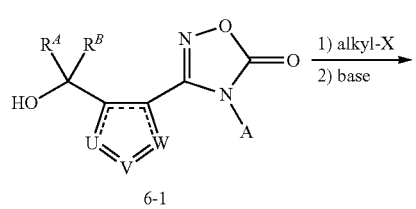

-continued

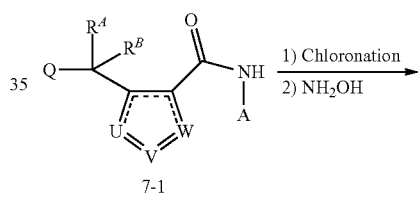

6-2

An alternative method for the synthesis of N-hydroxyamidines (e.g., Example 33) is shown in Scheme 7 where an amide 7-1 is chlorinated with suitable chlorination reagent (such as $PCl_5$, $POCl_3$, $SO_2Cl_2$, or alike) followed by addition of $NH_2OH$ to the crude reaction mixture to afford the desired products 7-2.

Scheme 7

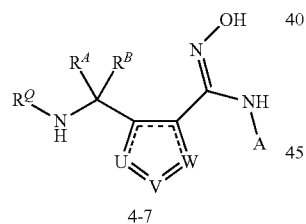

Methods of Use

Compounds of the invention can modulate activity of the enzyme indoleamine-2,3-dioxygenase (IDO). The term "modulate" is meant to refer to an ability to increase or decrease activity of an enzyme or receptor. Accordingly, compounds of the invention can be used in methods of modulating IDO by contacting the enzyme with any one or more of the compounds or compositions described herein. In some embodiments, compounds of the present invention can act as inhibitors of IDO. In further embodiments, the compounds of the invention can be used to modulate activity of IDO in cell or in an individual in need of modulation of the enzyme by administering a modulating (e.g., inhibiting) amount of a compound of the invention.

The present invention further provides methods of inhibiting the degradation of tryptophan in a system containing cells expressing IDO such as a tissue, living organism, or cell culture. In some embodiments, the present invention provides methods of altering (e.g., increasing) extracellular tryptophan levels in a mammal by administering an effective amount of a compound of composition provided herein. Methods of measuring tryptophan levels and tryptophan degradation are routine in the art.

The present invention further provides methods of inhibiting immunosuppression such as IDO-mediated immunosuppression in a patient by administering to the patient an effective amount of a compound or composition recited herein. IDO-mediated immunosuppression has been associated with, for example, cancers, tumor growth, metastasis, viral infection, viral replication, etc.

The present invention further provides methods of treating diseases associated with activity or expression, including abnormal activity and/or overexpression, of IDO in an individual (e.g., patient) by administering to the individual in need of such treatment a therapeutically effective amount or dose of a compound of the present invention or a pharmaceutical composition thereof. Example diseases can include any disease, disorder or condition that is directly or indirectly linked to expression or activity of the IDO enzyme, such as over expression or abnormal activity. An IDO-associated disease can also include any disease, disorder or condition that can be prevented, ameliorated, or cured by modulating enzyme activity. Examples of IDO-associated diseases include cancer, viral infection such as HIV infection, depression, neurodegenerative disorders such as Alzheimer's disease and Huntington's disease, trauma, age-related cataracts, organ transplantation (e.g., organ transplant rejection), and autoimmune diseases including asthma, rheumatoid arthritis, multiple sclerosis, inflammatory bowel disease, psoriasis and systemic lupus erythematosusor. Example cancers treatable by the methods herein include cancer of the colon, pancreas, breast, prostate, lung, brain, ovary, cervix, testes, renal, head and neck, lymphoma, leukemia, melanoma, and the like.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" the IDO enzyme with a compound of the invention includes the administration of a compound of the present invention to an individual or patient, such as a human, having IDO, as well as, for example, introducing a compound of the invention into a sample containing a cellular or purified preparation containing the IDO enzyme.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician, which includes one or more of the following:

(1) preventing the disease; for example, preventing a disease, condition or disorder in an individual who may be predisposed to the disease, condition or disorder but does not yet experience or display the pathology or symptomotology of the disease;

(2) inhibiting the disease; for example, inhibiting a disease, condition or disorder in an individual who is experiencing or displaying the pathology or symptomotology of the disease, condition or disorder; and (3) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

Combination Therapy

One or more additional pharmaceutical agents or treatment methods such as, for example, anti-viral agents, chemotherapeutics or other anti-cancer agents, immune enhancers, immunosuppressants, radiation, anti-tumor and anti-viral vaccines, cytokine therapy (e.g., IL2, GM-CSF, etc.), and/or tyrosine kinase inhibitors can be used in combination with the compounds of the present invention for treatment of IDO-associated diseases, disorders or conditions. The agents can be combined with the present compounds in a single dosage form, or the agents can be administered simultaneously or sequentially as separate dosage forms.

Suitable antiviral agents contemplated for use in combination with the compounds of the present invention can comprise nucleoside and nucleotide reverse transcriptase inhibitors (NRTIs), non-nucleoside reverse transcriptase inhibitors (NNRTIs), protease inhibitors and other antiviral drugs.

Example suitable NRTIs include zidovudine (AZT); didanosine (ddI); zalcitabine (ddC); stavudine (d4T); lamivudine (3TC); abacavir (1592U89); adefovir dipivoxil[bis (POM)-PMEA]; lobucavir (BMS-180194); BCH-10652; emitricitabine [(−)-FTC]; beta-L-FD4 (also called beta-L-D4C and named beta-L-2', 3'-dicleoxy-5-fluoro-cytidene); DA PD, ((−)-b eta-D-2,6,-diamino-purine dioxolane); and lodenosine (FddA). Typical suitable NNRTIs include nevirapine (BI-RG-587); delaviradine (BHAP, U-90152); efavirenz (DMP-266); PNU-142721; AG-1549; MKC-442 (1-(ethoxy-methyl)-5-(1-methylethyl)-6-(phenylmethyl)-(2, 4(1H,3H)-pyrimidinedione); and (+)-calanolide A (NSC-675451) and B. Typical suitable protease inhibitors include saquinavir (Ro 31-8959); ritonavir (ABT-538); indinavir (MK-639); nelfnavir (AG-1343); amprenavir (141W94); lasinavir (BMS-234475); DMP-450; BMS-2322623; ABT-378; and AG-1549. Other antiviral agents include hydroxyurea, ribavirin, IL-2, IL-12, pentafuside and Yissum Project No. 11607.

Suitable chemotherapeutic or other anti-cancer agents include, for example, alkylating agents (including, without limitation, nitrogen mustards, ethylenimine derivatives, alkyl sulfonates, nitrosoureas and triazenes) such as uracil mustard, chlormethine, cyclophosphamide (Cytoxan™) ifosfamide, melphalan, chlorambucil, pipobroman, triethylenemelamine, triethylenethio-phosphoramine, busulfan, carmustine, lomustine, streptozocin, dacarbazine, and temozolomide.

In the treatment of melanoma, suitable agents for use in combination with the compounds of the present invention include: dacarbazine (DTIC), optionally, along with other chemotherapy drugs such as carmustine (BCNU) and cisplatin; the "Dartmouth regimen," which consists of DTIC, BCNU, cisplatin and tamoxifen; a combination of cisplatin, vinblastine, and DTIC; or temozolomide. Compounds according to the invention may also be combined with immunotherapy drugs, including cytokines such as interferon alpha, interleukin 2, and tumor necrosis factor (TNF) in the treatment of melanoma.

Compounds of the invention may also be used in combination with vaccine therapy in the treatment of melanoma. Antimelanoma vaccines are, in some ways, similar to the anti-virus vaccines which are used to prevent diseases caused by viruses such as polio, measles, and mumps. Weakened melanoma cells or parts of melanoma cells called antigens may be injected into a patient to stimulate the body's immune system to destroy melanoma cells.

Melanomas that are confined to the arms or legs may also be treated with a combination of agents including one or more compounds of the invention, using a hypothermic isolated limb perfusion technique. This treatment protocol temporarily separates the circulation of the involved limb from the rest of the body and injects high doses of chemotherapy into the artery feeding the limb, thus providing high doses to the area of the tumor without exposing internal organs to these doses that might otherwise cause severe side effects. Usually the fluid is warmed to 102° to 104° F. Melphalan is the drug most often used in this chemotherapy procedure. This can be given with another agent called tumor necrosis factor (TNF) (see section on cytokines).

Suitable chemotherapeutic or other anti-cancer agents include, for example, antimetabolites (including, without limitation, folic acid antagonists, pyrimidine analogs, purine analogs and adenosine deaminase inhibitors) such as methotrexate, 5-fluorouracil, floxuridine, cytarabine, 6-mercaptopurine, 6-thioguanine, fludarabine phosphate, pentostatine, and gemcitabine.

Suitable chemotherapeutic or other anti-cancer agents further include, for example, certain natural products and their derivatives (for example, vinca alkaloids, antitumor antibiotics, enzymes, lymphokines and epipodophyllotoxins) such as vinblastine, vincristine, vindesine, bleomycin, dactino-mycin, daunorubicin, doxorubicin, epirubicin, idarubicin, ara-C, paclitaxel (TAXOL™), mithramycin, deoxycoformycin, mitomycin-C, L-asparaginase, interferons (especially IFN-a), etoposide, and teniposide.

Other cytotoxic agents include navelbene, CPT-11, anastrazole, tetrazole, capecitabine, reloxafine, cyclophosphamide, ifosamide, and droloxafine.

Also suitable are cytotoxic agents such as epidophyllotoxin; an antineoplastic enzyme; a topoisomerase inhibitor; procarbazine; mitoxantrone; platinum coordination complexes such as cis-platin and carboplatin; biological response modifiers; growth inhibitors; antihormonal therapeutic agents; leucovorin; tegafur; and haematopoietic growth factors.

Other anti-cancer agent(s) include antibody therapeutics such as trastuzumab (Herceptin), antibodies to costimulatory molecules such as CTLA-4, 4-1BB and PD-1, or antibodies to cytokines (IL-10, TGF-($\beta$, etc.).

Other anti-cancer agents also include those that block immune cell migration such as antagonists to chemokine receptors, including CCR2 and CCR4.

Other anti-cancer agents also include those that augment the immune system such as adjuvants or adoptive T cell transfer.

Anti-cancer vaccines include dendritic cells, synthetic peptides, DNA vaccines and recombinant viruses.

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR, e.g., 1996 edition, Medical Economics Company, Montvale, N.J.), the disclosure of which is incorporated herein by reference as if set forth in its entirety.

Pharmaceutical Formulations and Dosage Forms

When employed as pharmaceuticals, the compounds of the invention can be administered in the form of pharmaceutical compositions which is a combination of a compound of the invention and a pharmaceutically acceptable carrier. These compositions can be prepared in a manner well known in the pharmaceutical art, and can be administered by a variety of routes, depending upon whether local or systemic treatment is desired and upon the area to be treated. Administration may be topical (including ophthalmic and to mucous membranes including intranasal, vaginal and rectal delivery), pulmonary (e.g., by inhalation or insufflation of powders or aerosols, including by nebulizer; intratracheal, intranasal, epidermal and transdermal), ocular, oral or parenteral. Methods for ocular delivery can include topical administration (eye drops), subconjunctival, periocular or intravitreal injection or introduction by balloon catheter or ophthalmic inserts surgically placed in the conjunctival sac. Parenteral administration includes intravenous, intraarterial, subcutaneous, intraperitoneal or intramuscular injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This invention also includes pharmaceutical compositions which contain, as the active ingredient, one or more of the compounds of the invention above in combination with one or more pharmaceutically acceptable carriers. In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions can be formulated in a unit dosage form, each dosage containing from about 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, 0.1 to about 500 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the compounds of the present invention can vary according to, for example, the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compounds of the invention can also be formulated in combination with one or more additional active ingredients which can include any pharmaceutical agent such as antiviral agents, vaccines, antibodies, immune enhancers, immune suppressants, anti-inflammatory agents and the like.

Labeled Compounds and Assay Methods

Another aspect of the present invention relates to fluorescent dye, spin label, heavy metal or radio-labeled compounds of the invention that would be useful not only in imaging but also in assays, both in vitro and in vivo, for localizing and quantitating the IDO enzyme in tissue samples, including human, and for identifying IDO enzyme ligands by inhibition binding of a labeled compound. Accordingly, the present invention includes IDO enzyme assays that contain such labeled compounds.

The present invention further includes isotopically-labeled compounds of Formula I. An "isotopically" or "radio-labeled" compound is a compound of the invention where one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^{2}H$ (also written as D for deuterium), $^{3}H$ (also written as T for tritium), $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{82}Br$, $^{75}Br$, $^{76}Br$, $^{77}Br$, $^{123}I$, $^{124}I$, $^{125}I$ and $^{131}I$. The radionuclide that is incorporated in the instant radio-labeled compounds will depend on the specific application of that radio-labeled compound. For example, for in vitro IDO enzyme labeling and competition assays, compounds that incorporate $^{3}H$, $^{14}C$, $^{82}Br$, $^{125}I$, $^{131}I$, $^{35}S$ or will generally be most useful. For radio-imaging applications $^{11}C$, $^{18}F$, $^{125}I$, $^{123}I$, $^{124}I$, $^{131}I$, $^{75}Br$, $^{76}Br$ or $^{77}Br$ will generally be most useful.

It is understood that a "radio-labeled" or "labeled compound" is a compound that has incorporated at least one radionuclide. In some embodiments the radionuclide is selected from the group consisting of $^{3}H$, $^{14}C$, $^{125}I$, $^{35}S$ and $^{82}Br$.

Synthetic methods for incorporating radio-isotopes into organic compounds are applicable to compounds of the invention and are well known in the art.

A radio-labeled compound of the invention can be used in a screening assay to identify/evaluate compounds. In general terms, a newly synthesized or identified compound (i.e., test compound) can be evaluated for its ability to reduce binding of the radio-labeled compound of the invention to the IDO enzyme. Accordingly, the ability of a test compound to compete with the radio-labeled compound for binding to the IDO enzyme directly correlates to its binding affinity.

Kits

The present invention also includes pharmaceutical kits useful, for example, in the treatment or prevention of IDO-associated diseases or disorders, obesity, diabetes and other diseases referred to herein which include one or more containers containing a pharmaceutical composition comprising a therapeutically effective amount of a compound of the invention. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results. The compounds of the Examples were found to be inhibitors of IDO according to one or more of the assays provided herein. In some instances where the compounds of the examples were isolated by preparative HPLC in the presence of trifluoroacetic acid (TFA) or other acid, the compound may have been obtained as the corresponding salt.

EXAMPLES

Example 1

N-(3-Chloro-4-fluoro-phenyl)-N'-hydroxy-4-hydroxymethyl-furazan-3-carboxamidine

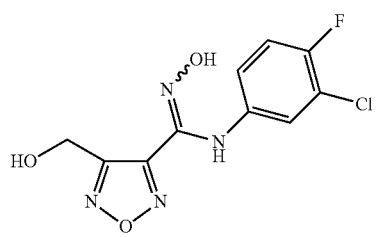 [SMILES: OCc1nonc1C(=NO)Nc1ccc(F)c(Cl)c1]

Step A: 4H,6H-Furo[3,4-c][1,2,5]oxadiazol-4-one

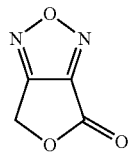

4H,6H-Furo[3,4-c][1,2,5]oxadiazol-4-one was synthesized according to literature procedures (Pollet, et al., *Synthesis Communications*, 1979, 977-979.) To a stirred solution of (3Z,4Z)-furan-2,3,4(5H)-trione 3,4-dioxime (3.0 g, 0.021 mol) in 1,4-dioxane (21 mL) under nitrogen, thionyl chloride (2.1 mL, 0.029 mol) was added dropwise. The resulting yellow solution was stirred overnight and then concentrated in vacuo. The resultant crystalline material was recrystallized once from a minimum amount of ethanol (EtOH) to give the desired compound as an off-white powder. The filtrate was concentrated down and recrystallized again. Combined solids yielded the desired product (2.0 g, 76%). $^{1}H$ NMR (400 MHz, DMSO-$d_{6}$) δ: 5.67 (s, 2H). MF=$C_{4}H_{2}N_{2}O_{3}$; LCMS calculated for $C_{4}H_{3}N_{2}O_{3}(M+H)^{+}$: m/z=127.014.

Step B. N-(3-Chloro-4-fluorophenyl)-4-(hydroxymethyl)-1,2,5-oxadiazole-3-carboxamide

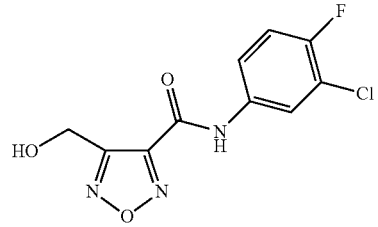 [SMILES: O=C(Nc1ccc(F)c(Cl)c1)c1nonc1CO]

4H,6H-Furo[3,4-c][1,2,5]oxadiazol-4-one (2.00 g, 0.0159 mol) was dissolved in EtOH (80 mL) and N,N-dimethylacetamide (10 mL) and then 3-chloro-4-fluoroaniline (2.5 g, 0.017 mol) was added as a solid. The reaction was heated at 80° C. overnight. The crude reaction mixture was concentrated in vacuo. The oil was extracted twice with EtOAc and washed with water. The organic was dried over $Na_{2}SO_{4}$ and concentrated. The crude residue was purified by flash column chromatography eluting with EtOAc:Hexane (1:1) to yield the desired product (3.2 g, 74%). $^{1}H$ NMR (400 MHz, DMSO-$d_{6}$) δ: 11.30 (s, 1H), 8.30 (dd, J=7.0, 2.7 Hz, 1H), 7.69 (ddd, J=9.1, 4.4, 2.6 Hz, 1H) 7.45 (dd, J=9.1, 9.1 Hz, 1H), 4.86 (d=5.8 Hz, 2H), 5.78 (t, 5.8 Hz, 1H); MF=$C_{10}H_{7}ClFN_{3}O_{3}$; LCMS calculated for $C_{10}H_{8}ClFN_{3}O_{3}$ (M+H)$^{+}$: m/z=272.024.

Step C: N-(3-Chloro-4-fluorophenyl)-4-[(triisopropylsilyl)oxy]methyl-1,2,5-oxadiazole-3-carboxamide

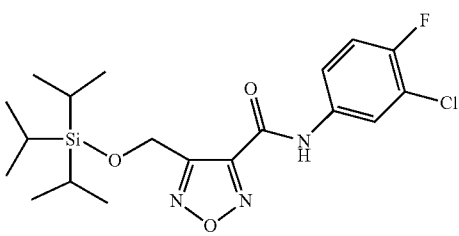 [SMILES: CC(C)[Si](OCc1nonc1C(=O)Nc1ccc(F)c(Cl)c1)(C(C)C)C(C)C]

To a stirred solution of N-(3-chloro-4-fluorophenyl)-4-(hydroxymethyl)-1,2,5-oxadiazole-3-carboxamide (3.2 g, 0.012 mol) in dichloromethane (DCM) (23 mL) at 0° C. was added 2,6-lutidine (3.4 mL, 0.029 mol) followed by triisopropylsilyl triflate (4.1 mL). The solution was stirred at 0° C. for 30 min and then the reaction was warmed to rt overnight. The reaction was concentrated and chromatographed on a silica column eluting with 15% ethyl acetate/hexane to yield a colorless oil (4.59 g, 91%). $^1$H NMR (400 MHz, DMSO-$d_6$) δ: 11.03 (s, 1H), 8.01 (dd, J=6.7, 2.6 Hz, 1H), 7.67 (ddd, J=9.1, 4.3, 2.6 Hz, 1H), 7.44 (dd, J=9.1, 9.1 Hz, 1H), 5.2 (s, 2H), 1.09 (m, 3H), 0.99 (d, J=7.1 Hz, 18H); MF=$C_{19}H_{27}ClFN_3O_3Si$; LCMS calculated for $C_{19}H_{28}ClFN_3O_3Si(M+H)^+$: m/z=428.157.

Step D: N-(3-Chloro-4-fluorophenyl)-4-[(triisopropylsilyl)oxy]methyl-1,2,5-oxadiazole-3-carbothioamide

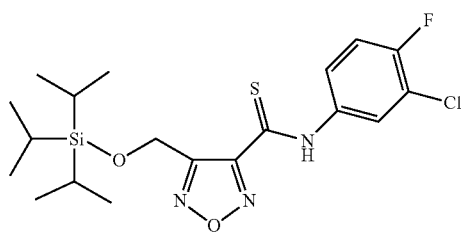 [SMILES: CC(C)[Si](OCc1nonc1C(=S)Nc1ccc(F)c(Cl)c1)(C(C)C)C(C)C]

Into a round bottom flask was placed a solution of N-(3-chloro-4-fluorophenyl)-4-[(triisopropylsilyl)oxy]methyl-1,2,5-oxadiazole-3-carboxamide (4.1 g, 9.5 mmol) in anhydrous toluene (79 mL) under $N_2$. 2,4-Bis(4-methoxyphenyl)-2,4-dithioxo-1,3,2,4-dithiadiphosphetane (7.7 g, 19 mmol) was added while stirring at ambient temperature. After addition, the resulting suspension was stirred and heated at 100° C. for 20 hrs. A considerable amount of solid precipitate was filtered off while the reaction was still hot, which was residual Lawesson's reagent. The liquid was then concentrated to give a yellow oil which was dissolved in chloroform and loaded onto a 330 g silica column eluting with 25% ethyl acetate/hexane to yield the desired product (3.31 g, 78%). $^1$H NMR (400 MHz, DMSO-$d_6$) δ: 12.87 (s, 1H), 7.8 (ddd, J=8.9, 4.3, 2.7 Hz, 1H), 8.21 (dd, J=6.8, 2.7 Hz, 1H) 7.55 (dd, J=9.0, 9.0 Hz, 1H), 5.14 (s, 2H), 1.07 (m, 3H), 0.97 (d, J=7.0, 18H); $(M+H)^+$: m/z=444.134.

Step E: Methyl N-(3-chloro-4-fluorophenyl)-4-[(triisopropylsilyl)oxy]methyl-1,2,5-oxadiazole-3-carbimidothioate

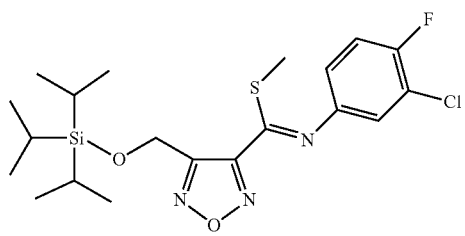 [SMILES: CS/C(=N\c1ccc(F)c(Cl)c1)c1nonc1CO[Si](C(C)C)(C(C)C)C(C)C]

To a solution of N-(3-chloro-4-fluorophenyl)-4-[(triisopropylsilyl)oxy]methyl-1,2,5-oxadiazole-3-carbothioamide (3.3 g, 7.4 mmol) in anhydrous DCM (148 mL) under $N_2$ was added N,N-diisopropylethylamine (DIPEA) (1.4 mL). Methyl trifluoromethanesulfonate (900 μL, 8.2 mmol) was then added dropwise and stirred for 2 hrs. The reaction was stripped to dryness and purified on a 330 g silica ISCO cartridge, eluting with 25% EtOAc/hexane to yield the desired product as a yellow oil that solidified upon standing. (2.97 g, 87%). $^1$H NMR (400 MHz, DMSO-$d_6$) δ: 11.32 (s, 1H), 8.01 (dd, J=7.1, 2.7 Hz, 1H), 7.45 (dd, J=9.5, 9.5 Hz, 1H), 7.67 (m, 1H), 4.4 (s=3H), 5.13 (s, 2H), 1.1 (m, 3H); 0.99 (m, 18H); MF=$C_{20}H_{29}ClFN_3O_2SSi$; LCMS calculated for $C_{20}H_{30}ClFN_3O_2SSi(M+H)^+$: m/z=458.150.

Step F: N-(3-Chloro-4-fluorophenyl)-N'-hydroxy-4-[(triisopropylsilyl)oxy]methyl-1,2,5-oxadiazole-3-carboximidamide

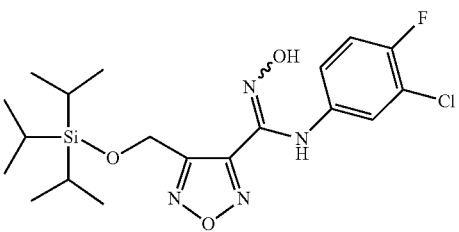 [SMILES: CC(C)[Si](OCc1nonc1C(=NO)Nc1ccc(F)c(Cl)c1)(C(C)C)C(C)C]

Methyl N-(3-chloro-4-fluorophenyl)-4-[(triisopropylsilyl)oxy]methyl-1,2,5-oxadiazole-3-carbimidothioate (3.0 g, 6.5 mmol) was dissolved in EtOH followed by addition of 4 mL hydroxylamine (99.9% in water solution). The reaction was stirred at 75° C. for 6 hrs and monitored by HPLC. The reaction was concentrated in vacuo to a yellow oil which was dissolved in chloroform and chromatographed on 120 g of silica gel eluting with (1:4), EtOAc/hexane. The product was concentrated to give the desired product as a white solid (2.57 g, 89%); MF=$C_{19}H_{28}ClFN_4O_3Si$; LCMS calculated for $C_{19}H_{29}ClFN_4O_3Si(M+H)^+$: m/z=443.168.

Step G: 4-(3-Chloro-4-fluorophenyl)-3-(4-[(triisopropylsilyl)oxy]methyl-1,2,5-oxadiazol-3-yl)-1,2,4-oxadiazol-5(4H)-one

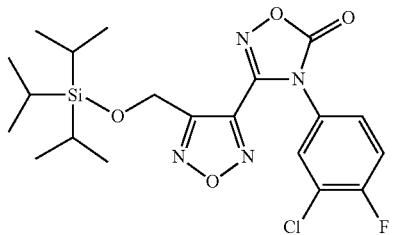 [SMILES: CC(C)[Si](OCc1nonc1-c1noc(=O)n1-c1ccc(F)c(Cl)c1)(C(C)C)C(C)C]

N-(3-chloro-4-fluorophenyl)-N-hydroxy-4-[(triisopropylsilyl)oxy]methyl-1,2,5-oxadiazole-3-carboximidamide (2.2 g, 5.0 mmol) was dissolved in anhydrous tetrahydrofuran (THF) (31 mL) followed by addition of N,N-carbonyldiimidazole (980 mg, 6 mmol). The reaction was heated to 70° C. and monitored by LCMS. Another 0.5 eq of N,N-carbonyldiimidazole was added and the reaction was stirred overnight at 70° C. The reaction was cooled and concentrated in vacuo. The crude oil was dissolved in chloroform and loaded onto a 120 g ISCO cartridge, eluted with 25% EtOAc/Hexane. The combined fractions were stripped to dryness to give the desired product as a white solid (1.74 g, 73%). $^1$H NMR (400 MHz, DMSO-$d_6$) δ: 7.95 (m, 1H), 7.65 (m, 1H), 7.64 (m, 1H), 5.12 (s, 2H), 1.14 (m, 3H), 1.04 (d, J=7.0 Hz, 18H);

MF=C$_{20}$H$_{26}$ClFN$_4$O$_4$Si; LCMS calculated for C$_{20}$H$_{27}$ClFN$_4$O$_4$Si(M+H)$^+$: m/z=469.147.

Step H: 4-(3-Chloro-4-fluorophenyl)-3-[4-(hydroxymethyl)-1,2,5-oxadiazol-3-yl]-1,2,4-oxadiazol-5(4H)-one

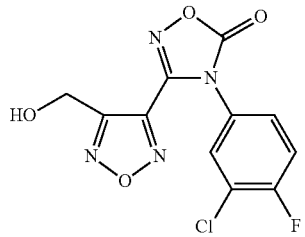 [SMILES: O=c1onc(-c2nonc2CO)n1-c1ccc(F)c(Cl)c1]

4-(3-Chloro-4-fluorophenyl)-3-(4-[(triisopropylsilyl)oxy]methyl-1,2,5-oxadiazol-3-yl)-1,2,4-oxadiazol-5(4H)-one (1.7 g, 3.7 mmol) was dissolved in anhydrous MeOH(MeOH) (110 mL) followed by addition of 2 M of hydrogen chloride in MeOH (9.2 mL). Reaction was stirred at 70° C. for 4 hrs. After concentration in vacuo the sample was loaded onto 120 g ISCO cartridge eluting with EtOAc/hexane. Fractions were combined and evaporated to yield desired product as an off-white powder. (1.12 g, 97%). $^1$H NMR (400 MHz, DMSO-d$_6$) δ: 7.96 (dd, J=6.8, 2.3 Hz, 1H), 7.66 (m, 1H), 7.64 (m, 1H), 5.95 (s, 1H), 4.85 (s, 2H); MF=C$_H$H$_6$ClFN$_4$O$_4$; LCMS calculated for C$_{11}$H$_7$ClFN$_4$O$_4$(M+H)$^+$: m/z=313.014.

Step I: N-(3-Chloro-4-fluoro-phenyl)-N'-hydroxy-4-hydroxymethyl-furazan-3-carboxamidine 4-(3-Chloro-4-fluorophenyl)-3-[4-(hydroxymethyl)-1,2,5-oxadiazol-3-yl]-1,2,4-oxadiazol-5(4H)-one (20 mg, 0.064 mmol) was dissolved in anhydrous EtOH (0.6 mL) followed by addition of 2 M of sodium hydroxide in water (60 µL). Reaction was stirred at 50° C. for 4 hrs. Consumption of starting material was monitored by TLC. The sample was quenched with acetic acid, diluted with MeOH and purified by preparative LCMS. The reaction was diluted with water and extracted with ethyl acetate three times, dried with sodium sulfate, filtered, and concentrated in vacuo. The crude residue was purified by flash silica column chromatography to yield the desired product (16 mg, 87%). $^1$1-1 NMR (400 MHz, DMSO-d$_6$) δ: 11.49 (s, 1H), 9.02 (s, 1H), 7.18 (dd, J=9.1, 9.1 Hz, 1H), 6.97 (dd, J=6.6, 2.7 Hz, 1H), 6.69 (m, 1H), 5.68 (t, J=6.2 Hz, 1H) 4.72 (d, J=5.8 Hz, 2H); MF=C$_{10}$H$_8$ClFN$_4$O$_3$; LCMS calculated for C$_{10}$H$_9$ClFN$_4$O$_3$ (M+H)$^+$: m/z=287.035.

Example 2

N-(3-Chloro-4-fluorophenyl)-N'-hydroxy-4-(phenoxymethyl)-1,2,5-oxadiazole-3-carboximidamide

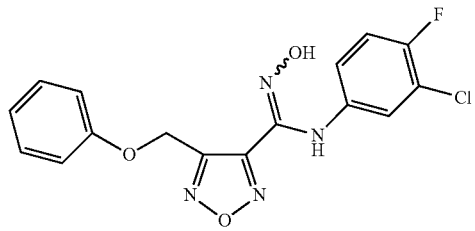 [SMILES: ON=C(Nc1ccc(F)c(Cl)c1)c1nonc1COc1ccccc1]

Step A: 4-(3-Chloro-4-fluorophenyl)-3-[4-(phenoxymethyl)-1,2,5-oxadiazol-3-yl]-1,2,4-oxadiazol-5(4H)-one

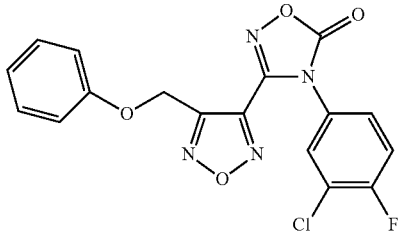 [SMILES: O=c1onc(-c2nonc2COc2ccccc2)n1-c1ccc(F)c(Cl)c1]

4-(3-Chloro-4-fluorophenyl)-3-[4-(hydroxymethyl)-1,2,5-oxadiazol-3-yl]-1,2,4-oxadiazol-5(4H)-one (15 mg, 0.0480 mmol), phenol (14 mg, 0.14 mmol) and triphenylphosphine (16 mg, 0.062 mmol) were dissolved in anhydrous THF (500 µL) then cooled to 0° C., followed by a dropwise addition of diethyl azodicarboxylate (9.8 µL, 0.062 mmol) in a solution of THF. Reaction was allowed to warm to rt then stirred 4 hrs. After concentration in vacuo, the sample was purified by reverse phase HPLC to yield a white powder (9 mg, 48%). MF=C$_{17}$H$_{10}$ClFN$_4$O$_4$; LCMS calculated for C$_{17}$H$_{11}$ClFN$_4$O$_4$(M+H)$^+$: m/z=389.045

Step C: N-(3-Chloro-4-fluorophenyl)-N'-hydroxy-4-(phenoxymethyl)-1,2,5-oxadiazole-3-carboximidamide Into a vial was added 4-(3-chloro-4-fluorophenyl)-3-[4-(phenoxymethyl)-1,2,5-oxadiazol-3-yl]-1,2,4-oxadiazol-5(4H)-one (9 mg, 23 mmol), EtOH (0.5 mL), and 2.0 M of sodium hydroxide in water (35 µL). Reaction was stirred for 2 hrs at rt. The reaction mixture was neutralized with acetic acid and then purified by preparative HPLC to yield the desired compound (7.6 mg, 90%). $^1$H NMR (400 MHz, DMSO-d$_6$) δ: 11.58 (s, 1H), 9.05 (s, 1H), 7.32 (t, J=7.8 Hz, 2H) 7.19 (dd, J=9.1, 9.1 Hz, 1H), 7.0 (m, 1H), 6.97 (m, 2 H) 6.96 (m, 1 H), 6.72 (ddd, J=8.8, 4.0, 2.8 Hz, 1H), 5.43 (s, 2H); MF=C$_{16}$H$_{12}$ClFN$_4$O$_3$; LCMS calculated for C$_{16}$H$_{13}$ClFN$_4$O$_3$(M+H)$^+$: m/z=363.066.

Example 3

4-[(E/Z)-[(3-Chloro-4-fluorophenyl)amino](hydroxyimino)methyl]-1,2,5-oxadiazol-3-ylmethyl phenylcarbamate

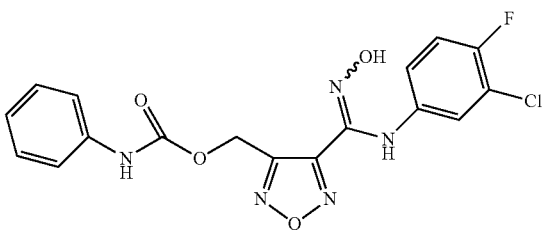 [SMILES: O=C(Nc1ccccc1)OCc1nonc1C(=NO)Nc1ccc(F)c(Cl)c1]

4-(3-Chloro-4-fluorophenyl)-3-[4-(hydroxymethyl)-1,2,5-oxadiazol-3-yl]-1,2,4-oxadiazol-5(4H)-one (20 mg, 0.064 mmol), was dissolved in anhydrous DCM (400 µL). 4-Dimethylamino-pyridine (DMAP) (4 mg, 0.03 mmol) was added followed by addition of phenyl isocyanate (7.6 µL, 0.07 mmol). Reaction was stirred at rt for 24 hrs and then concentrated in vacuo. The crude was purified by HPLC to yield a white powder. The intermediate was redissolved in EtOH (0.7 mL) and 2 M of sodium hydroxide in water (60 μL) was added. Reaction was stirred for 2 hr at rt. Reaction was quenched with acetic acid and diluted with MeOH and then purified by preparative LCMS to yield the desired compound as a white powder (16 mg, 62%). $^1$H NMR (400 MHz, DMSO-$d_6$) δ: 11.68 (s, 1H), 10.00 (s, 1 H), 9.04 (s, 1H), 7.47 (d, J=8.1 Hz, 2 H), 7.00 (m, 1H), 7.28 (dd, J=7.5, 8.0 Hz, 2 H), 7.19 (dd, J=9.1, 9.1 Hz, 1H), 7.0 (m, 1H), 6.79 (m, 1 H) 5.49 (s, 2H).; MF=$C_{16}H_{12}ClFN_4O_3$; LCMS calculated for $C_{16}H_{13}ClFN_4O_3$(M+H)$^+$: m/z=363.066.

Example 4

4-[(Benzylamino)methyl]-N-(3-chloro-4-fluorophenyl)-N-hydroxy-1,2,5-oxadiazole-3-carboximidamide

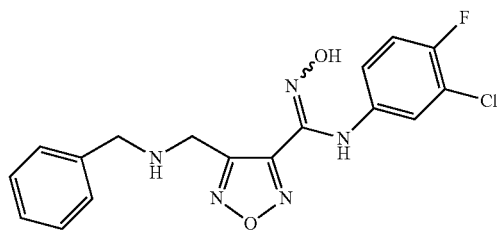 [SMILES: ON=C(Nc1ccc(F)c(Cl)c1)c1nonc1CNCc1ccccc1]

Step A: 4-[4-(3-Chloro-4-fluorophenyl)-5-oxo-4,5-dihydro-1,2,4-oxadiazol-3-yl]-1,2,5-oxadiazol-3-ylmethyl methanesulfonate

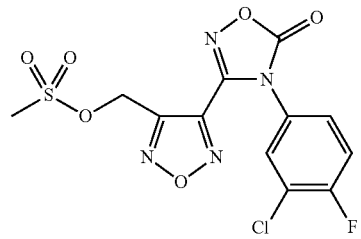 [SMILES: CS(=O)(=O)OCc1nonc1-c1noc(=O)n1-c1ccc(F)c(Cl)c1]

4-(3-Chloro-4-fluorophenyl)-3-[4-(hydroxymethyl)-1,2,5-oxadiazol-3-yl]-1,2,4-oxadiazol-5(4H)-one (250 mg, 0.7996 mmol) was dissolved in anhydrous DCM (8 mL) followed by addition of triethylamine (TEA) (134 μL, 0.96 mmol). Reaction was cooled to 0° C. and methanesulfonyl chloride (68 μL, 0.88 mmol) was added dropwise. The reaction was diluted with water and extracted with ethyl acetate three times, dried with sodium sulfate, filtered, and concentrated in vacuo. The crude residue was purified by flash column chromatography eluting with 25%-70% EtOAc to yield the desired product (259 mg, 83%). MF=$C_{12}H_8ClFN_4O_6S$; LCMS calculated for $C_{12}H_9ClFN_4O_6S$ (M+H)$^+$: m/z=390.992.

4-[4-(3-Chloro-4-fluorophenyl)-5-oxo-4,5-dihydro-1,2,4-oxadiazol-3-yl]-1,2,5-oxadiazol-3-ylmethyl methanesulfonate (0.020 g, 0.051 mmol) was dissolved in anhydrous acetonitrile (ACN) (500 μL) followed by addition of DIPEA (44 pt, 0.26 mmol) and benzylamine (8.4 μL, 0.077 mmol). The reaction was stirred and heated at 60° C. for 1 hr. The reaction was stripped to dryness, redissolved in EtOH (500 μL) and 2 M sodium hydroxide in water (0.1 mL) was added. The reaction was stirred and heated at 60° C. for 2 hrs, quenched with acetic acid, diluted with MeOH and purified by preparative LCMS to yield desired product as a pure white powder (15 mg, 78%). MF=$C_{17}H_{15}ClFN_5O_2$; LCMS calculated for $C_{17}H_{16}ClFN_5O_2$(M+H)$^+$: m/z=376.098.

Additional example compounds of the invention are provided below. Table 1 below (and Tables 2 and 3, infra) provide example compounds of the invention that show activity as IDO modulators according to one or more of the assays provided herein. The compounds were prepared according to synthetic procedure of the Example compound specified in the column marked "Prep. Ex." and were purified by the method in the column marked "Pur. Meth." In the "Pur. Meth." column, "A" refers to purification by LCMS (HPLC, pH=2, trifluoroacetic acid (TFA)); "B" refers to purification by LCMS (HPLC, pH=10, NH$_4$OH); "C" refers to silica gel chromatography (typically hexanes/ethyl acetate); "D" refers to routine crystallization or precipitation methods; and "E" refers to the purification method as provided in the synthetic procedure for preparing that compound. Certain compounds of the Tables were isolated in the free base form or as a salt (typically as a result of the purification procedure) as indicated in the column marked "Salt". The salt stoichiometry indicated in the below tables and preparation descriptions is typically based on theory and one skilled in the art would understand that the actual product might contain more or less acid. Actual stoichiometry can be determined by routine methods such as elemental analysis. ACN refers to acetonitrile. DCM refers to dichloromethane. DMF refers to dimethylformamide. TFA refers to trifluoroacetic acid. TEA refers to tetraethylamine. DMAP refers to dimethylaminopyridine. DIPEA refers to N,N-diethylisopropylamine.

TABLE 1

| Ex. No. | Structure | MS (M + 1) | Prep. Ex. | Pur. Meth | Salt | Name |
|---|---|---|---|---|---|---|
| 5 | 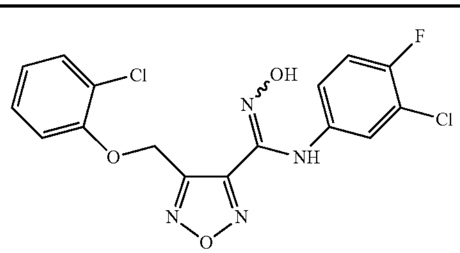 | 397.1 | Ex. 2 | A | Free Base | N-(3-chloro-4-fluorophenyl)-4-[(2-chlorophenoxy)methyl]-N'-hydroxy-1,2,5-oxadiazole-3-carboximidamide |

TABLE 1-continued

| Ex. No. | Structure | MS (M + 1) | Prep. Ex. | Pur. Meth | Salt | Name |
|---|---|---|---|---|---|---|
| 6 | 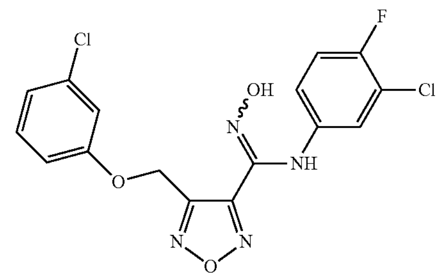 [SMILES: ON=C(Nc1ccc(F)c(Cl)c1)c1nonc1COc1cccc(Cl)c1] | 397.1 | Ex. 2 | A | Free Base | N-(3-chloro-4-fluorophenyl)-4-[(3-chlorophenoxy)methyl]-N'-hydroxy-1,2,5-oxadiazole-3-carboximidamide |
| 7 | 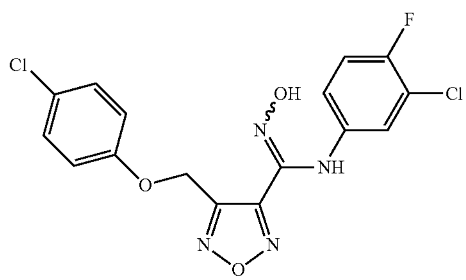 [SMILES: ON=C(Nc1ccc(F)c(Cl)c1)c1nonc1COc1ccc(Cl)cc1] | 397.1 | Ex. 2 | A | Free Base | N-(3-chloro-4-fluorophenyl)-4-[(4-chlorophenoxy)methyl]-N'-hydroxy-1,2,5-oxadiazole-3-carboximidamide |
| 8 | 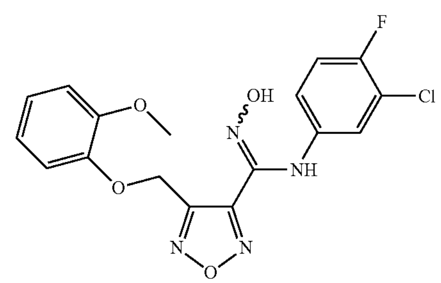 [SMILES: COc1ccccc1OCc1nonc1C(=NO)Nc1ccc(F)c(Cl)c1] | 393.1 | Ex. 2 | B | Free Base | N-(3-chloro-4-fluorophenyl)-N'-hydroxy-4-[(2-methoxyphenoxy)methyl]-1,2,5-oxadiazole-3-carboximidamide |
| 9 | 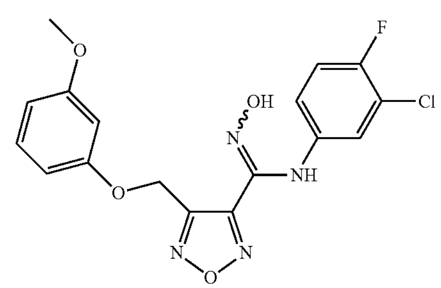 [SMILES: COc1cccc(OCc2nonc2C(=NO)Nc2ccc(F)c(Cl)c2)c1] | 393.1 | Ex. 2 | B | Free Base | N-(3-chloro-4-fluorophenyl)-N'-hydroxy-4-[(3-methoxyphenoxy)methyl]-1,2,5-oxadiazole-3-carboximidamide |
| 10 | 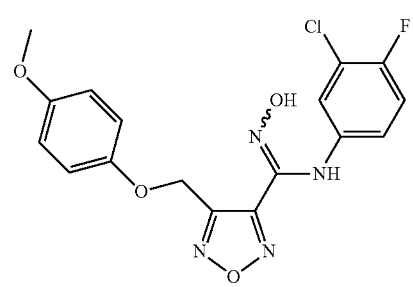 [SMILES: COc1ccc(OCc2nonc2C(=NO)Nc2ccc(F)c(Cl)c2)cc1] | 393.1 | Ex. 2 | B | Free Base | N-(3-chloro-4-fluorophenyl)-N'-hydroxy-4-[(4-methoxyphenoxy)methyl]-1,2,5-oxadiazole-3-carboximidamide |

TABLE 1-continued

| Ex. No. | Structure | MS (M + 1) | Prep. Ex. | Pur. Meth | Salt | Name |
|---|---|---|---|---|---|---|
| 11 | 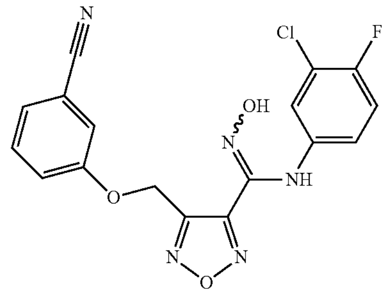 [SMILES: N#Cc1cccc(OCc2nonc2C(=NO)Nc2ccc(F)c(Cl)c2)c1] | 388.1 | Ex. 2 | B | Free Base | N-(3-chloro-4-fluorophenyl)-4-[(3-cyanophenoxy)methyl]-N'-hydroxy-1,2,5-oxadiazole-3-carboximidamide |
| 12 | 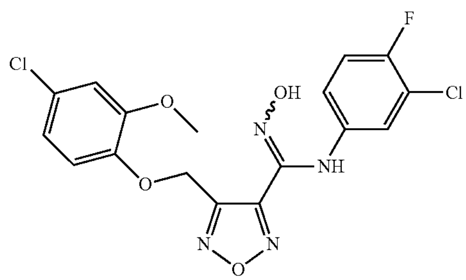 [SMILES: COc1cc(Cl)ccc1OCc1nonc1C(=NO)Nc1ccc(F)c(Cl)c1] | 427.1 | Ex. 2 | B | Free Base | N-(3-chloro-4-fluorophenyl)-4-[(4-chloro-2-methoxyphenoxy)methyl]-N'-hydroxy-1,2,5-oxadiazole-3-carboximidamide |
| 13 | 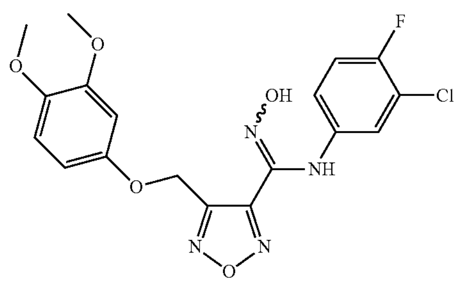 [SMILES: COc1ccc(OCc2nonc2C(=NO)Nc2ccc(F)c(Cl)c2)cc1OC] | 423.1 | Ex. 2 | B | Free Base | N-(3-chloro-4-fluorophenyl)-4-[(3,4-dimethoxyphenoxy)methyl]-N'-hydroxy-1,2,5-oxadiazole-3-carboximidamide |
| 14 | 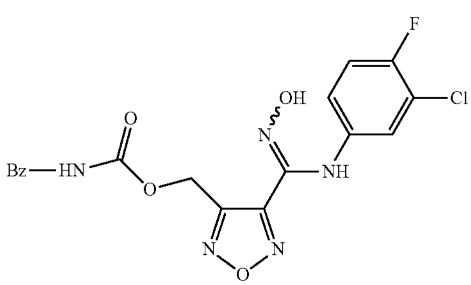 | 420.1 | Ex. 3 | A | Free Base | {4-[(E/Z)-[(3-chloro-4-fluorophenyl)amino](hydroxyimino)methyl]-1,2,5-oxadiazol-3-yl}methyl phenylcarbamate |
| 15 | 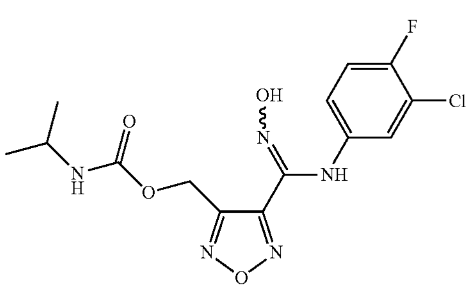 [SMILES: CC(C)NC(=O)OCc1nonc1C(=NO)Nc1ccc(F)c(Cl)c1] | 372.1 | Ex. 3 | A | Free Base | {4-[(E/Z)-[(3-chloro-4-fluorophenyl)amino](hydroxyimino)methyl]-1,2,5-oxadiazol-3-yl}methyl isopropylcarbamate |

TABLE 1-continued

| Ex. No. | Structure | MS (M + 1) | Prep. Ex. | Pur. Meth | Salt | Name |
|---|---|---|---|---|---|---|
| 16 | 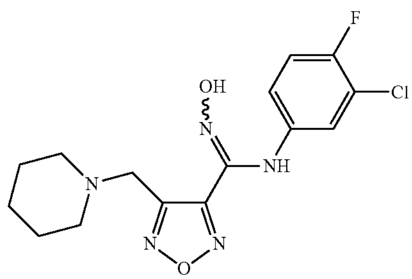 [SMILES: ON=C(Nc1ccc(F)c(Cl)c1)c1nonc1CN1CCCCC1] | 354.2 | Ex. 4 | B | Free Base | N-(3-chloro-4-fluorophenyl)-N'-hydroxy-4-(piperidin-1-ylmethyl)-1,2,5-oxadiazole-3-carboximidamide |
| 17 | 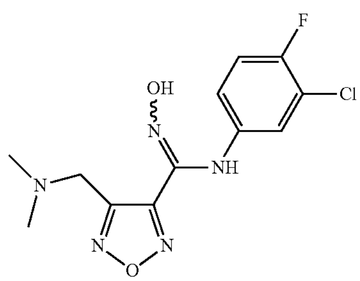 [SMILES: CN(C)Cc1nonc1C(=NO)Nc1ccc(F)c(Cl)c1] | 314.1 | Ex. 4 | B | Free Base | N-(3-chloro-4-fluorophenyl)-4-[(dimethylamino)-methyl]-N'-hydroxy-1,2,5-oxadiazole-3-carboximidamide |
| 18 | 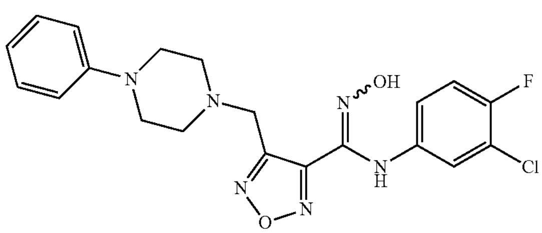 [SMILES: ON=C(Nc1ccc(F)c(Cl)c1)c1nonc1CN1CCN(c2ccccc2)CC1] | 431.1 | Ex. 4 | B | Free Base | N-(3-chloro-4-fluorophenyl)-N'-hydroxy-4-[(4-phenylpiperazin-1-yl)methyl]-1,2,5-oxadiazole-3-carboximidamide |
| 19 | 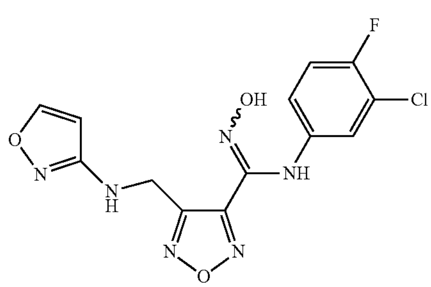 [SMILES: ON=C(Nc1ccc(F)c(Cl)c1)c1nonc1CNc1ccon1] | 353.1 | Ex. 4 | B | Free Base | N-(3-chloro-4-fluorophenyl)-N'-hydroxy-4-[(isoxazol-3-ylamino)methyl]-1,2,5-oxadiazole-3-carboximidamide |
| 20 | 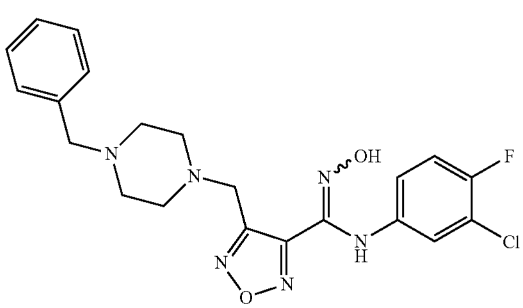 [SMILES: ON=C(Nc1ccc(F)c(Cl)c1)c1nonc1CN1CCN(Cc2ccccc2)CC1] | 459.2 | Ex. 4 | B | Free Base | 4-{[(1-benzylpiperidin-4-yl)amino]methyl}-N-(3-chloro-4-fluorophenyl)-N'-hydroxy-1,2,5-oxadiazole-3-carboximidamide |

TABLE 1-continued

| Ex. No. | Structure | MS (M + 1) | Prep. Ex. | Pur. Meth | Salt | Name |
| --- | --- | --- | --- | --- | --- | --- |
| 21 | 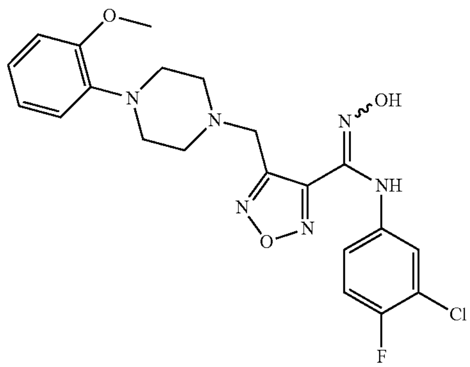 [SMILES: COc1ccccc1N1CCN(Cc2nonc2C(=NO)Nc2ccc(F)c(Cl)c2)CC1] | 461.1 | Ex. 4 | B | Free Base | N-(3-chloro-4-fluorophenyl)-N'-hydroxy-4-{[4-(2-methoxyphenyl)piperazin-1-yl]-methyl}-1,2,5-oxadiazole-3-carboximidamide |
| 22 | 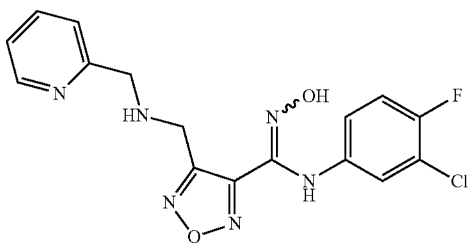 [SMILES: ON=C(Nc1ccc(F)c(Cl)c1)c1nonc1CNCc1ccccn1] | 377.1 | Ex. 4 | B | Free Base | N-(3-chloro-4-fluorophenyl)-N'-hydroxy-4-{[(pyridin-2-ylmethyl)amino]methyl}-1,2,5-oxadiazole-3-carboximidamide |
| 23 | 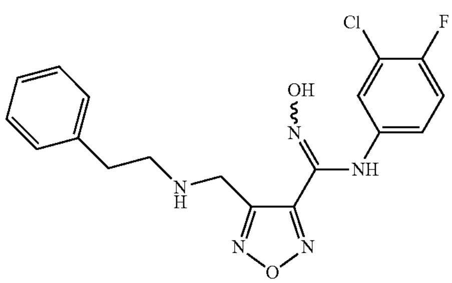 [SMILES: ON=C(Nc1ccc(F)c(Cl)c1)c1nonc1CNCCc1ccccc1] | 390.2 | Ex. 4 | A | TFA | N-(3-chloro-4-fluorophenyl)-N'-hydroxy-4-{[(2-phenylethyl)amino]-methyl}-1,2,5-oxadiazole-3-carboximidamide trifluoroacetate |
| 24 | 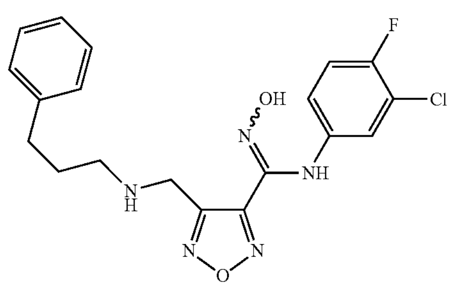 [SMILES: ON=C(Nc1ccc(F)c(Cl)c1)c1nonc1CNCCCc1ccccc1] | 404.1 | Ex. 4 | A | TFA | N-(3-chloro-4-fluorophenyl)-N'-hydroxy-4-{[(3-phenylpropyl)amino]-methyl}-1,2,5-oxadiazole-3-carboximidamide trifluoroacetate |
| 25 | 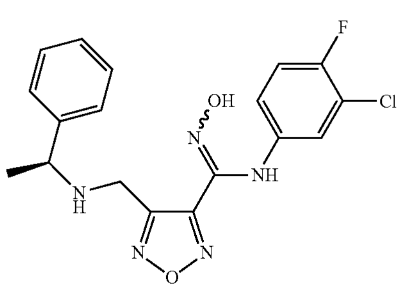 [SMILES: C[C@H](NCc1nonc1C(=NO)Nc1ccc(F)c(Cl)c1)c1ccccc1] | 390.1 | Ex. 4 | A | TFA | N-(3-chloro-4-fluorophenyl)-N'-hydroxy-4-({[(1R)-1-phenylethyl]-amino}methyl)-1,2,5-oxadiazole-3-carboximidamide trifluoroacetate |

TABLE 1-continued

| Ex. No. | Structure | MS (M + 1) | Prep. Ex. | Pur. Meth | Salt | Name |
|---|---|---|---|---|---|---|
| 26 | 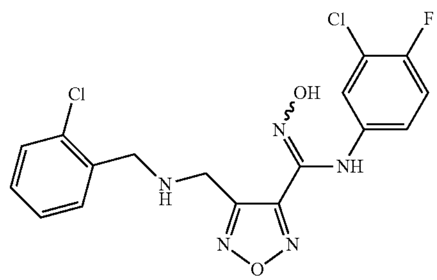 [SMILES: ON=C(Nc1ccc(F)c(Cl)c1)c1nonc1CNCc1ccccc1Cl] | 410.1 | Ex. 4 | A | TFA | 4-{[(2-chlorobenzyl)amino]-methyl}-N-(3-chloro-4-fluoro-phenyl)-N'-hydroxy-1,2,5-oxadiazole-3-carboximidamide trifluoroacetate |
| 27 | 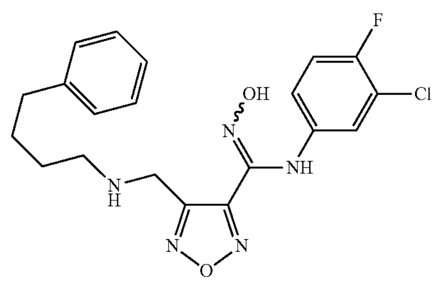 [SMILES: ON=C(Nc1ccc(F)c(Cl)c1)c1nonc1CNCCCCc1ccccc1] | 418.1 | Ex. 4 | A | TFA | N-(3-chloro-4-fluorophenyl)-N'-hydroxy-4-{[(4-phenylbutyl)amino]-methyl}-1,2,5-oxadiazole-3-carboximidamide trifluoroacetate |
| 28 | 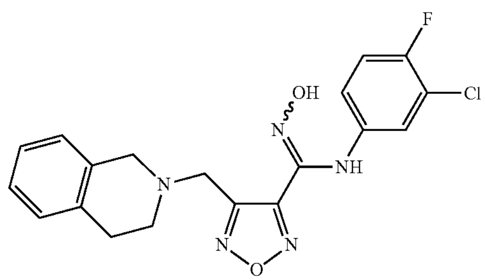 [SMILES: ON=C(Nc1ccc(F)c(Cl)c1)c1nonc1CN1CCc2ccccc2C1] | 402.1 | Ex. 4 | A | TFA | N-(3-chloro-4-fluorophenyl)-4-(3,4-dihydroiso-quinolin-2(1H)-ylmethyl)-N'-hydroxy-1,2,5-oxadiazole-3-carboximidamide trifluoroacetate |
| 29 | 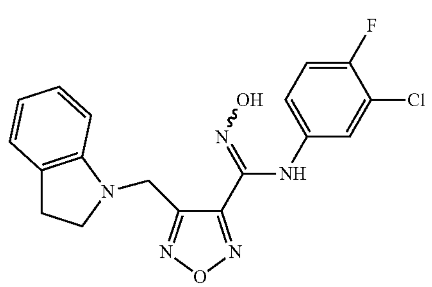 [SMILES: ON=C(Nc1ccc(F)c(Cl)c1)c1nonc1CN1CCc2ccccc21] | 388.1 | Ex. 4 | A | TFA | N-(3-chloro-4-fluorophenyl)-4-(2,3-dihydro-1H-indol-1-ylmethyl)-N'-hydroxy-1,2,5-oxadiazole-3-carboximidamide trifluoroacetate |
| 30 | 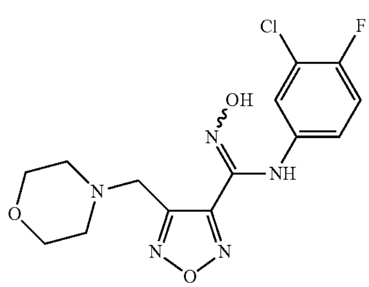 [SMILES: ON=C(Nc1ccc(F)c(Cl)c1)c1nonc1CN1CCOCC1] | 356.1 | Ex. 4 | A | TFA | N-(3-chloro-4-fluorophenyl)-N'-hydroxy-4-(morpholin-4-ylmethyl)-1,2,5-oxadiazole-3-carboximidamide trifluoroacetate |

Example 31

3-(4-[(2-Morpholin-4-ylethyl)amino]methyl-1,2,5-oxadiazol-3-yl)-4-[3-(trifluoromethyl)phenyl]-1,2,4-oxadiazol-5(4H)-one

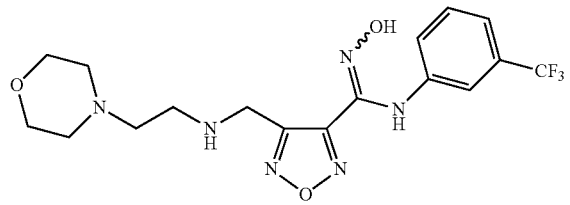 [SMILES: ON=C(Nc1cccc(C(F)(F)F)c1)c1nonc1CNCCN1CCOCC1]

Step A: 4-(3-(Trifluoromethyl)phenyl-3-(4-[(2-morpholin-4-ylethyl)amino]methyl-1,2,5-oxadiazol-3-yl)-1,2,4-oxadiazol-5(4H)-one

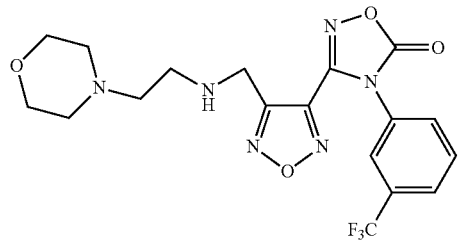 [SMILES: O=c1onc(-c2nonc2CNCCN2CCOCC2)n1-c1cccc(C(F)(F)F)c1]

4-5-oxo-4-[3-(trifluoromethyl)phenyl]-4,5-dihydro-1,2,4-oxadiazol-3-yl-1,2,5-oxadiazol-3-yl)methyl methanesulfonate (0.01 g, 0.025 mmol) was dissolved in anhydrous ACN (20 μL) followed by addition of DIPEA(21 μL, 0.12 mmol) and N-(2-aminoethyl)morpholine (0.05 mmol). The reaction was stirred at 40° C. for 2 hrs. The reaction was diluted with MeOH and purified by preparative LCMS to afford the desired product. MF=$C_{18}H_{19}F_3N_6O_4$; LCMS calculated for $C_{18}H_{20}F_3N_6O_4(M+H)^+$: m/z=441.1.

Step B: 3-(4-[(2-Morpholin-4-ylethyl)amino]methyl-1,2,5-oxadiazol-3-yl)-4-[3-(trifluoromethyl)-phenyl]-1,2,4-oxadiazol-5 (4H)-one The purified intermediate was evaporated to dryness and then redissolved in EtOH (200 μL) and 2 M of sodium hydroxide in water (60 μL) was added. The reaction was stirred at rt for 2 hrs, quenched with acetic acid, diluted with MeOH and purified by preparative LCMS to afford the desired product (3 mg) MF=$C_{17}H_{21}F_3N_6O_3$; LCMS calculated for $C_{17}H_{22}F_3N_6O_3(M+H)^+$: m/z=415.2.

Example 32

N-(3-Chloro-4-fluorophenyl)-N'-hydroxy-4-[(methylsulfonyl)(2-morpholin-4-yl-ethyl)amino]methyl-1,2,5-oxadiazole-3-carboximidamide

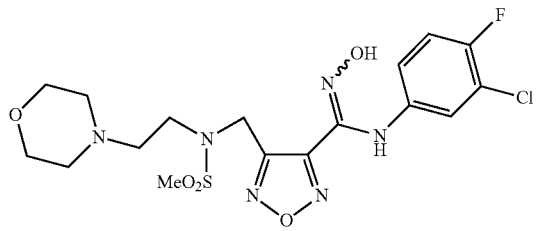 [SMILES: CS(=O)(=O)N(CCN1CCOCC1)Cc1nonc1C(=NO)Nc1ccc(F)c(Cl)c1]

Step A: 4-(3-Chloro-4-fluorophenyl)-3-(4-[(2-morpholin-4-ylethyl)amino]methyl-1,2,5-oxadiazol-3-yl)-1,2,4-oxadiazol-5(4H)-one

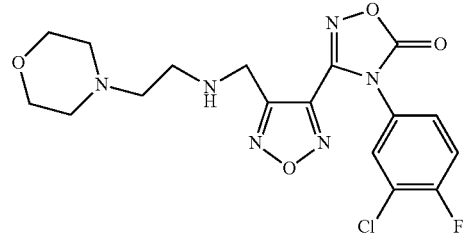 [SMILES: O=c1onc(-c2nonc2CNCCN2CCOCC2)n1-c1ccc(F)c(Cl)c1]

This intermediate was prepared by procedures analogous to those described for Example 31.

Step B. N-(3-Chloro-4-fluorophenyl)-N'-hydroxy-4-[(methylsulfonyl)(2-morpholin-4-ylethyl)amino]methyl-1,2,5-oxadiazole-3-carboximidamide 4-(3-Chloro-4-fluorophenyl)-3-(4-[(2-morpholin-4-ylethyl)amino]methyl-1,2,5-oxadiazol-3-yl)-1,2,4-oxadiazol-5(4H)-one (20 mg, 0.047 mmol) was dissolved in anhydrous ACN (200 μL) followed by addition of DIPEA (40 μL, 0.2 mmol) and methanesulfonyl chloride (4.0 μL, 0.052 mmol). The reaction was stirred at 40° C. for 2 hrs. The reactions was then diluted with MeOH and purified by HPLC. The purified fractions were concentrated to dryness, redissolved in EtOH (1 mL) and 2 M of sodium hydroxide in water (0.26 mL) was added. The reaction was stirred at rt for 2 hrs, quenched with acetic acid, diluted with MeOH and purified by preparative LCMS to afford the desired product (1.4 mg). MF=$C_{17}H_{22}ClFN_6O_5S$; LCMS calculated for $C_{17}H_{23}ClFN_6O_5S(M+H)^+$: m/z=477.1.

Example 33

N-{4-[N-(3-Chloro-4-fluoro-phenyl)-N'-hydroxy-carbamimidoyl]-furazan-3-yl-methyl}-benzamide

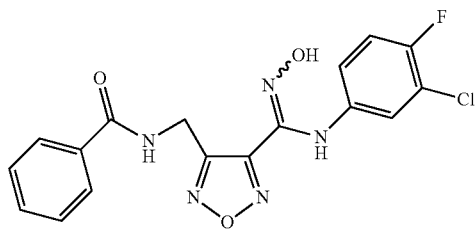 [SMILES: O=C(NCc1nonc1C(=NO)Nc1ccc(F)c(Cl)c1)c1ccccc1]

Step A: 3-[4-(azidomethyl)-1,2,5-oxadiazol-3-yl]-4-(3-chloro-4-fluorophenyl)-1,2,4-oxadiazol-5(4H)-one

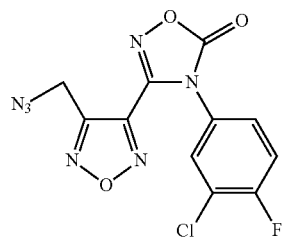 [SMILES: [N-]=[N+]=NCc1nonc1-c1noc(=O)n1-c1ccc(F)c(Cl)c1]

4-[4-(3-Chloro-4-fluorophenyl)-5-oxo-4,5-dihydro-1,2,4-oxadiazol-3-yl]-1,2,5-oxadiazol-3-ylmethyl methanesulfonate (400 mg, 1.02 mmol) was dissolved in anhydrous DMF (10 mL) followed by addition of sodium azide (133 mg, 2.04 mmol). Reaction was stirred for 3 hrs. Consumption of starting material was monitored by TLC and HPLC. The reaction mixture was added to a mixture of (400 μL) bromine/water and stirred for 10 min. DCM was added and the layers were separated. The combined organics were dried with sodium sulfate, filtered, and concentrated in vacuo. The crude residue was purified by flash column chromatography to yield the desired product (225 mg, 65%). MF=$C_{11}H_5ClFN_7O_3$; LCMS calculated for $C_{11}H_6ClFN_7O_3(M+H)^+$: m/z=338.020.

Step B: 3-[4-(Aminomethyl)-1,2,5-oxadiazol-3-yl]-4-(3-chloro-4-fluorophenyl)-1,2,4-oxadiazol-5 (4H)-one

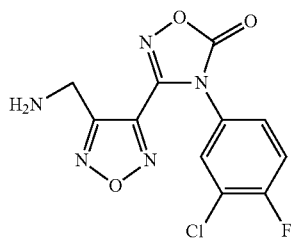 [SMILES: NCc1nonc1-c1noc(=O)n1-c1ccc(F)c(Cl)c1]

3-[4-(Azidomethyl)-1,2,5-oxadiazol-3-yl]-4-(3-chloro-4-fluorophenyl)-1,2,4-oxadiazol-5(4H)-one (225 mg, 0.66 mmol) was dissolved in anhydrous THF (5.6 mL) and water (5.6 mL). The reaction was cooled to 0° C. followed by addition of triphenylphosphine (192 mg, 0.73 mmol). The reaction was allowed to warm to rt and was stirred overnight. The reaction was stripped to dryness, azeotroped with toluene and redissolved in MeOH. The crude residue was purified by preparative LCMS to yield the desired product (200 mg, 96%). MF=$C_{11}H_7ClFN_5O_3$; LCMS calculated for $C_{11}H_8ClFN_5O_3(M+H)^+$: m/z=312.030.

Step C: 4-[(Benzylamino)methyl]-N-(3-chloro-4-fluorophenyl)-N'-hydroxy-1,2,5-oxadiazole-3-carboximidamide Benzoic acid (4.3 mg, 0.035 mmol) and 3-[4-(aminomethyl)-1,2,5-oxadiazol-3-yl]-4-(3-chloro-4-fluorophenyl)-1,2,4-oxadiazol-5(4H)-one (10 mg, 0.032 mmol) was dissolved in ACN (0.2 mL) and DCM (0.2 mL). To the mixture was added DMAP (2.4 mg, 0.02 mmol) and DIPEA (17 μL, 0.096 mmol). After the mixture became a clear solution, bromotris(pyrrolydino)phosphonium hexa-fluorophosphate (16 mg, 0.035 mmol) was added, followed by additional DIPEA(17 μL, 0.0962 mmol). The reaction mixture was stirred at rt for 6 hrs. LCMS indicated 70% ratio of product to starting amine. The reaction was then diluted with MeOH and crude residue was purified by preparative LCMS. The intermediate was stripped to dryness, redissolved in EtOH (1 mL) and 1 M of sodium hydroxide in water (0.06 mL). The reaction was stirred for 1 hr at rt. The reaction was quenched with acetic acid and then diluted with MeOH and crude residue was purified by preparative LCMS to afford the desired product (1.1 mg). MF=$C_{17}H_{13}ClFN_5O_3$; LCMS calculated for $C_{17}H_{14}ClFN_5O_3(M+H)^+$: m/z=390.077.

Example 34

N-(3-Chloro-4-fluoro-phenyl)-N'-hydroxy-4-[(3-phenyl-ureido)-methyl]-furazan-3-carboxamidine

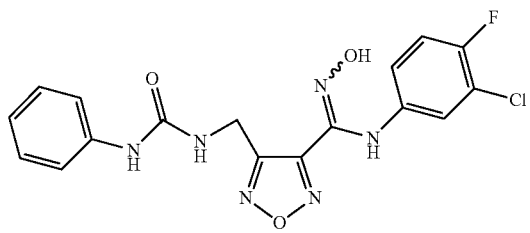 [SMILES: O=C(NCc1nonc1C(=NO)Nc1ccc(F)c(Cl)c1)Nc1ccccc1]

3-[4-(Aminomethyl)-1,2,5-oxadiazol-3-yl]-4-(3-chloro-4-fluorophenyl)-1,2,4-oxadiazol-5(4H)-one (10 mg, 0.003 mmol) was dissolved in ACN (0.2 mL) and DCM (0.2 mL). Phenyl isocyanate (7.6 mg, 0.064 mmol) DIPEA(0.012 mg, 0.096 mmol) and DMAP (0.4 mg, 0.03 mmol) were added and stirred at rt for 6 hrs. The reaction was then diluted with MeOH and purified by preparative LCMS. The intermediate was stripped to dryness, redissolved in EtOH (1 mL) and 1 M of sodium hydroxide in water (0.06 mL) was added. The reaction was stirred at rt for 1 hour, quenched with acetic acid and diluted with MeOH. The crude was purified by preparative LCMS to afford the desired product (2.0 mg). MF=$C_{17}H_{14}ClFN_6O_3$; LCMS calculated for $C_{17}H_{15}ClFN_6O_3(M+H)^+$: m/z=405.1.

Example 35

4-(Benzenesulfonylamino-methyl)-N-(3-chloro-4-fluoro-phenyl)-N'-hydroxy-furazan-3-carboxamidine

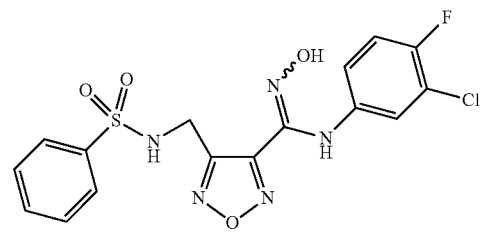 [SMILES: O=S(=O)(NCc1nonc1C(=NO)Nc1ccc(F)c(Cl)c1)c1ccccc1]

3-[4-(Aminomethyl)-1,2,5-oxadiazol-3-yl]-4-(3-chloro-4-fluorophenyl)-1,2,4-oxadiazol-5(4H)-one (10 mg, 0.003 mmol) was dissolved in ACN (0.2 mL) and DCM (0.2 mL). Benzenesulfonyl chloride (11 mg, 0.064 mmol) DIPEA (12 mg, 0.096 mmol) and DMAP (0.4 mg, 0.003 mmol) were dissolved in DMF (1 mL). The reaction was stirred at rt for 6 hrs. The reaction was then diluted with MeOH and purified by preparative LCMS. The intermediate was stripped to dryness, redissolved in EtOH (1 mL) and 1 M of sodium hydroxide in water (0.06 mL) was added. The reaction was stirred at rt for 1 hr, quenched with acetic acid, diluted with MeOH and the crude residue was purified by preparative LCMS to afford the desired product (2.4 mg). MF=$C_{16}H_{13}ClFN_5O_4S$; LCMS calculated for $C_{16}H_{14}ClFN_5O_4S(M+H)^+$: m/z=426.0.

Example 36

Benzyl({4-[(E/Z)-[(3-chloro-4-fluorophenyl)amino](hydroxyimino)methyl]-1,2,5-oxadiazol-3-yl}methyl)carbamate

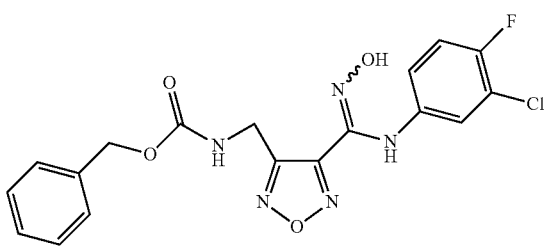 [SMILES: O=C(NCc1nonc1C(=NO)Nc1ccc(F)c(Cl)c1)OCc1ccccc1]

3-[4-(Aminomethyl)-1,2,5-oxadiazol-3-yl]-4-(3-chloro-4-fluorophenyl)-1,2,4-oxadiazol-5(4H)-one (10.0 mg, 0.032 mmol) was dissolved in ACN (0.2 mL) and DCM (0.3 mL). Benzyl chloroformate (4.6 µL, 0.03 mmol) and DIPEA (5.6 µL, 0.032 mmol) was added and stirred overnight at rt. The reaction was concentrated, redissolved in MeOH, then purified on the preparative HPLC to give the desired intermediate. The intermediate was dissolved in EtOH (1.0 mL) and 1.0 M of sodium hydroxide in water (0.1 mL) and stirred for 1 hr. The reaction was quenched with acetic acid, MeOH (1 mL) was added and the solution purified by preparative HPLC to afford the desired product (2.5 mg). MF=$C_{18}H_{15}ClFN_5O_4$; LCMS calculated for $C_{18}H_{16}ClFN_5O_4$ (M+H)$^+$: m/z=419.9.

Example 37

N-(3-Cyanophenyl)-N'-hydroxy-4-methyl-1,2,5-oxadiazole-3-carboximidamide

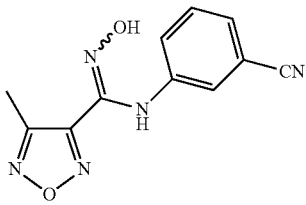 [SMILES: Cc1nonc1C(=NO)Nc1cccc(C#N)c1]

Step A: N-(3-Cyanophenyl)-4-methyl-1,2,5-oxadiazole-3-carboxamide

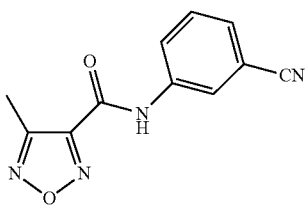 [SMILES: Cc1nonc1C(=O)Nc1cccc(C#N)c1]

4-Methyl-1,2,5-oxadiazole-3-carboxylic acid (200 mg, 1.6 mmol) and bromotris-(pyrrolydino)phosphonium hexafluorophosphate was dissolved in a 1/1 mixture of DMF/DCM. To the mixture was added DMAP (120 mg, 0.95 mmol) and 3-amino-benzonitrile (184 mg, 1.6 mol) followed by N,N-diisopropylethylamine. The reaction mixture was stirred at rt overnight. The volatiles were removed in vacuo and the residue dissolved with chloroform and loaded onto a 40 g Silica ISCO cartridge eluting with 25%-50% EtOAc/Hexane to afford a white powder (25 mg). MF=$C_{11}H_8N_4O_2$; LCMS calculated for $C_{11}H_9N_4O_2$(M+H)$^+$: m/z=229.1.

Step B: N-(3-Cyanophenyl)-N'-hydroxy-4-methyl-1,2,5-oxadiazole-3-carboximidamide N-(3-Cyanophenyl)-4-methyl-1,2,5-oxadiazole-3-carboxamide (25 mg, 0.11 mmol) was suspended in benzene (2 mL) under an atmosphere of nitrogen. Phosphorus pentachloride (25 mg, 0.12 mmol) was added and the solution was heated at reflux for 2.5 hrs. The reaction was then evaporated to dryness. The crude was dissolved in EtOH (1.6 mL) and hydroxylamine (200 µL, 3 mmol, 50% solution in water) was added to the reaction. The crude was purified by preparative LCMS to afford the desired product (2.9 mg). MF=$C_{11}H_9N_5O_2$; LCMS calculated for $C_{11}H_{10}N_5O_2$ (M+H)$^+$: m/z=244.1.

Example 38

N-(3-Chloro-4-fluorophenyl)-N'-hydroxy-4-methyl-1,2,3-thiadiazole-5-carboximidamide

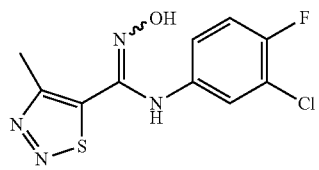 [SMILES: Cc1nnsc1C(=NO)Nc1ccc(F)c(Cl)c1]

Step A: 4-Methyl-[1,2,3]thiadiazole-5-carboxylic acid (3-chloro-4-fluoro-phenyl)-amide

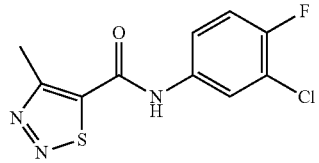 [SMILES: Cc1nnsc1C(=O)Nc1ccc(F)c(Cl)c1]

4-Methyl-1,2,3-thiadiazole-5-carboxylic acid (39.6 mg, 0.275 mmol) was suspended in DCM (2.0 mL). Bromotris (pyrrolydino)phosphonium hexafluorophosphate (128 mg, 0.27 mmol) and DIPEA (96 µL, 0.55 mmol) were added and premixed for 5 minutes. 3-Chloro-4-fluoroaniline (40 mg, 0.27 mmol) was added. The solution was stirred for 3 hrs, then purified by silica gel chromatography, (Hex/EA)-eluting at ~60% EA in hexane to afford the desired product (44 mg). MF=$C_{10}H_7ClFN_3OS$; LCMS calculated for $C_{10}H_8ClFN_3OS$ (M+H)$^+$: m/z=272.0.

Step B: N-(3-Chloro-4-fluorophenyl)-N'-hydroxy-4-methyl-1,2,3-thiadiazole-5-carboximidamide 4-Methyl-[1,2,3]thiadiazole-5-carboxylic acid (3-chloro-4-fluoro-phenyl)-amide (44 mg, 0.164 mmol) was dissolved in toluene (1 mL). Phosphorus pentachloride (41 mg, 0.20 mmol) was added and the vial was sealed and heated in an oil bath at 120° C. for 2 hrs. The solvent was removed in vacuo and the crude material was redissolved in EtOH (1.0 mL). 15.1 M of hydroxylamine in water (108 µL) was added and the solution was mixed for 0.5 hr. The compound was purified by preparative LCMS to afford the desired product (18 mg). MF=$C_{10}H_8ClFN_4OS$; LCMS calculated for $C_{10}H_9ClFN_4OS$ (M+H)$^+$: m/z=287.0.

Examples 39 and 40

4-[(5-Amino-1H-tetrazol-1-yl)methyl]-N-(3-chloro-4-fluorophenyl)-N'-hydroxy-1,2,5-oxadiazole-3-carboximidamide (39), and 4-[(5-Amino-2H-tetrazol-2-yl)methyl]-N-(3-chloro-4-fluorophenyl)-N'-hydroxy-1,2,5-oxadiazole-3-carboximidamide (40)

Ex. 39

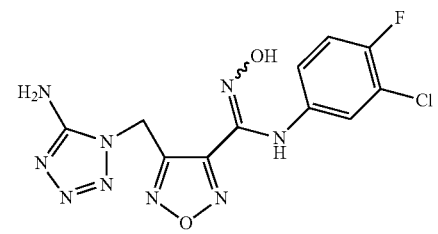

Ex. 40

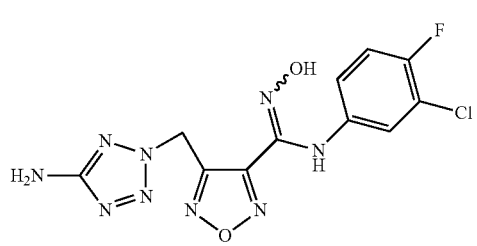

4-[4-(3-Chloro-4-fluorophenyl)-5-oxo-4,5-dihydro-1,2,4-oxadiazol-3-yl]-1,2,5-oxadiazol-3-ylmethyl methanesulfonate (45 mg, 0.012 mmol) was dissolved in anhydrous ACN (100 μL) followed by addition of DIPEA (100 μL, 0.6 mmol) and 1H-tetrazol-5-amine (15 mg, 0.017 mmol). The reaction was stirred and heated at 40° C. for 4 hr. The reaction was diluted with MeOH and purified by preparative LCMS to yield hydroxyamidine protected form of isomers A and B. The separated isomers were each stripped to dryness and redissolved in EtOH (500 μL) and 2 M sodium hydroxide in water (0.1 mL). The reactions were stirred at rt for 2 hrs. The reactions were quenched with acetic acid, diluted with MeOH and each purified by preparative LCMS to afford the desired products A and B as pure white powders (A, 18 mg, 44%; MF=$C_{11}H_9ClFN_9O_2$; LCMS calculated for $C_{11}H_9ClFN_9O_2$ (M+H)$^+$: m/z=354.2; $^1$H NMR (400 MHz, DMSO-$d_6$) δ: 11.70 (s, 1H), 8.98 (s, 1H), 7.22 (dd, 1H), 7.04 (dd, 1H), 6.89 (bs, 2H), 6.82 (dd, 1H), 5.71 (s, 2H); B, 25 mg, 61%, MF=$C_{11}H_9ClFN_9O_2$; LCMS calculated for $C_{11}H_9ClFN_9O_2$ (M+H)$^+$: m/z=354.2; NMR (500 MHz, DMSO-$d_6$) δ: 11.61 (s, 1H), 8.98 (s, 1H), 7.21 (dd, 1H), 6.98 (dd, 1H), 6.65 (dd, 1H), 6.1 (bs, 2H), 6.07 (s, 2H)).

Example 41

N-(3-Chloro-4-fluorophenyl)-N'-hydroxy-4-[(1H-tetrazol-5-ylamino)methyl]-1,2,5-oxadiazole-3-carboximidamide

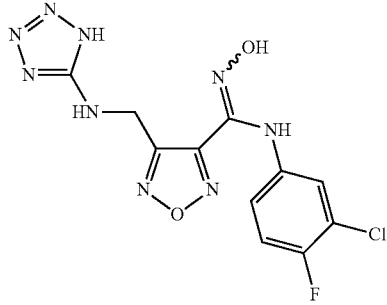 [SMILES: ON=C(Nc1ccc(F)c(Cl)c1)c1nonc1CNc1nnn[nH]1]

Step A: N-(3-Chloro-4-fluorophenyl)-4-[(1H-tetrazol-5-ylamino)methyl]-1,2,5-oxadiazole-3-carboxamide

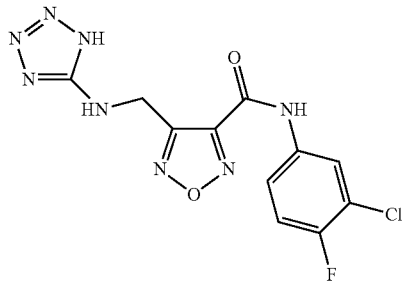 [SMILES: O=C(Nc1ccc(F)c(Cl)c1)c1nonc1CNc1nnn[nH]1]

To a solution of N-(3-chloro-4-fluorophenyl)-4-formyl-1,2,5-oxadiazole-3-carboxamide (4.5 g, 17 mmol) in THF (75 mL) was added 5-aminotetrazole (4.26 g, 50.1 mmol), sodium sulfate (1.0 g, 8.0 mmol) and acetic acid (50 μL, 0.80 mmol). The resulting mixture was stirred at 40° C. for 36 h, and then an additional 20 mL THF was added followed by sodium tetrahydroborate (947 mg, 25 mmol). After stirring for 3 h, lithium tetrahydroborate (545 mg, 25.0 mol) was added to the reaction solution and stirred overnight. The reaction solution was diluted with 1 N NaOH solution. The aqueous layer was separated and acidified with 6 N HCl to pH 1. A white solid precipitated out of solution and was filtered to afford the desired product (4.82 g, 85%). LCMS for $C_{11}H_9ClFN_8O_2$(M+H)$^+$: m/z=339.0.

Step B: N-(3-Chloro-4-fluorophenyl)-4-[(1-[2-(trimethylsilyl)ethoxy]methyl-1H-tetrazol-5-yl)amino]-methyl-1,2,5-oxadiazole-3-carboxamide, and N-(3-Chloro-4-fluorophenyl)-4-[(2-[2-(trimethyl-silyl)ethoxy]methyl-2H-tetrazol-5-yl)amino]methyl-1,2,5-oxadiazole-3-carboxamide

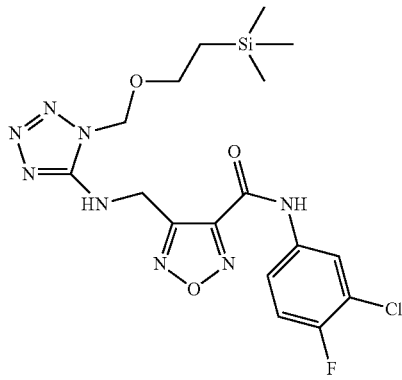

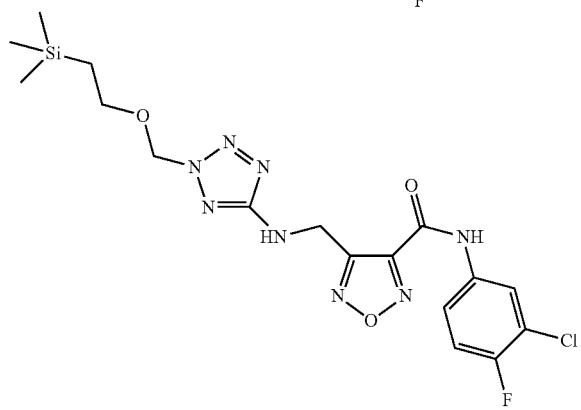

To a solution of N-(3-chloro-4-fluorophenyl)-4-[(1H-tetrazol-5-ylamino)methyl]-1,2,5-oxa-diazole-3-carboxamide (130 mg, 0.38 mmol) in DCM (4.0 mL) was added TEA (134 µL, 0.96 mmol) and [β-(trimethylsilyl)ethoxy]methyl chloride (143 µL, 0.806 mmol). The resulting mixture was stirred for 1 h. The reaction was concentrated and then purified by silica chromatography (20% ethyl acetate/hexanes) to afford the desired products as colorless oils (100 mg, 55%) and (70 mg, 39%). LCMS for $C_{17}H_{23}ClFN_8O_3Si(M+H)^+$: m/z=469.1.

Step C: N-(3-chloro-4-fluorophenyl)-N'-hydroxy-4-[(1-[2-(trimethylsilyl)ethoxy]methyl-1H-tetrazol-5-yl)amino]methyl-1,2,5-oxadiazole-3-carboximidamide

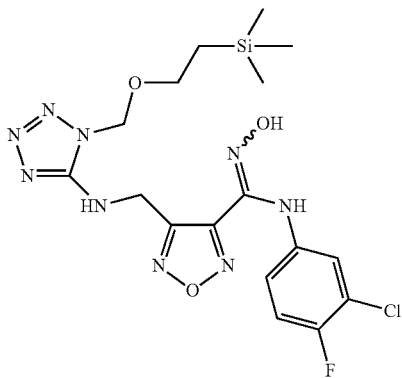 [SMILES: C[Si](C)(C)CCOCn1nnnc1NCc1nonc1C(=NO)Nc1ccc(F)c(Cl)c1]

N-(3-Chloro-4-fluorophenyl)-4-[(1-[2-(trimethylsilyl)ethoxy]methyl-1H-tetrazol-5-yl)amino]-methyl-1,2,5-oxadiazole-3-carboxamide (96 mg, 0.20 mmol) was suspended in benzene (1.0 mL) and pyridine (0.5 mL) under an atmosphere of nitrogen. Phosphorus pentachloride (46.9 mg, 0.225 mmol) was added and the solution was heated at reflux for 2 hrs. The reaction was then stripped to dryness in vacuo. The reaction was dissolved in EtOH (2.6 mL) and hydroxylamine (300 µL, 5 mmol, 50% solution in water) was added to the reaction. After stirring for 1 h, the reaction solution was diluted with MeOH and purified by preparative LCMS to afford the desired product as a white solid (32 mg, 32%). LCMS $C_{17}H_{24}ClFN_9O_3Si(M+H)^+$: m/z=484.144.

Step D: N-(3-chloro-4-fluorophenyl)-N'-hydroxy-4-[(1H-tetrazol-5-ylamino)methyl]-1,2,5-oxadiazole-3-carboximidamide To a solution of N-(3-chloro-4-fluorophenyl)-N'-hydroxy-4-[(1-[2-(trimethylsilyl)ethoxy]-methyl-1H-tetrazol-5-yl)-amino]-methyl-1,2,5-oxadiazole-3-carboximidamide (10.2 mg, 0.021 mmol) in DCM (0.5 mL) was added TFA (0.5 mL). The reaction solution was stirred at rt for 2 hrs. The reaction solution was concentrated in vacuo, and purified with LCMS to afford the desired product as a white powder (5.2 mg, 70%). LCMS for $C_{11}H_{10}ClFN_9O_2(M+H)^+$: m/z=354.1.

Further example compounds of the invention are provided in Table 2.

TABLE 2

| Ex. No. | Structure | MS (M + 1) | Prep. Ex. | Pur. Meth. | Salt | Name |
|---|---|---|---|---|---|---|
| 42 | 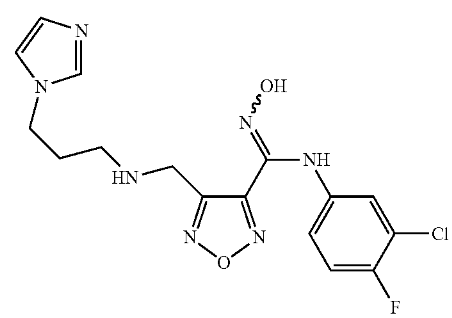 [SMILES: ON=C(Nc1ccc(F)c(Cl)c1)c1nonc1CNCCCn1ccnc1] | 394.1 | Ex. 4 | A | 2 TFA | N-(3-chloro-4-fluorophenyl)-N'-hydroxy-4-({[3-(1H-imidazol-1-yl)propyl]amino}methyl)-1,2,5-oxadiazole-3-carboximidamide bis(trifluoroacetate) |
| 43 | 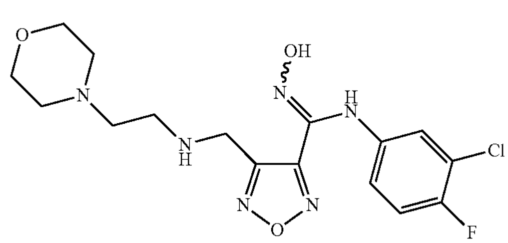 [SMILES: ON=C(Nc1ccc(F)c(Cl)c1)c1nonc1CNCCN1CCOCC1] | 399.2 | Ex. 4 | A | 2 TFA | N-(3-chloro-4-fluorophenyl)-N'-hydroxy-4-{[(2-morpholin-4-ylethyl)amino]methyl}-1,2,5-oxadiazole-3-carboximidamide bis(trifluoroacetate) |

TABLE 2-continued

| Ex. No. | Structure | MS (M + 1) | Prep. Ex. | Pur. Meth. | Salt | Name |
| --- | --- | --- | --- | --- | --- | --- |
| 44 | 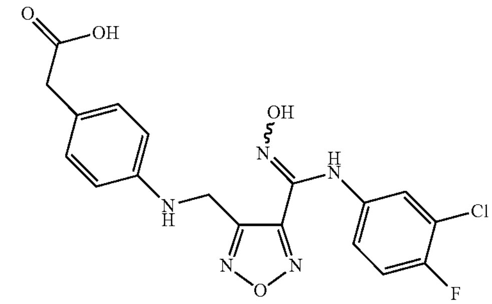 [SMILES: O=C(O)Cc1ccc(NCc2nonc2C(=NO)Nc2ccc(F)c(Cl)c2)cc1] | 420.2 | Ex. 4 | A | TFA | {4-{({4-[(E/Z)-[(3-chloro-4-fluoro-phenyl)amino]-(hydroxyimino)methyl]-1,2,5-oxadiazol-3-yl}methyl)amino]phenyl} acetic acid trifluoroacetate |
| 45 | 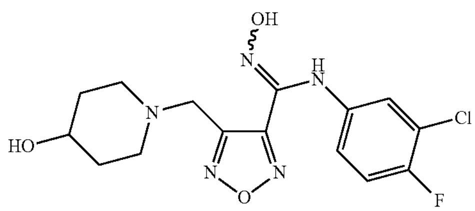 [SMILES: ON=C(Nc1ccc(F)c(Cl)c1)c1nonc1CN1CCC(O)CC1] | 370.2 | Ex. 4 | A | TFA | N-(3-chloro-4-fluoro-phenyl)-N'-hydroxy-4-[(4-hydroxypiperidin-1-yl)methyl]-1,2,5-oxadiazole-3-carboximidamide trifluoroacetate |
| 46 | 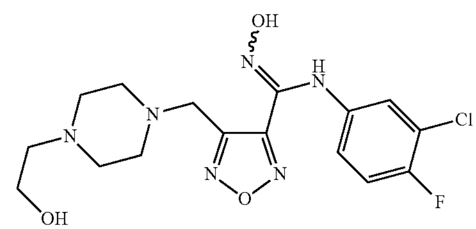 [SMILES: OCCN1CCN(Cc2nonc2C(=NO)Nc2ccc(F)c(Cl)c2)CC1] | 399.2 | Ex. 4 | A | 2 TFA | N-(3-chloro-4-fluoro-phenyl)-N'-hydroxy-4-{[4-(2-hydroxyethyl)-piperazin-1-yl]-methyl}-1,2,5-oxadiazole-3-carboximidamide bis(trifluoroacetate) |
| 47 | 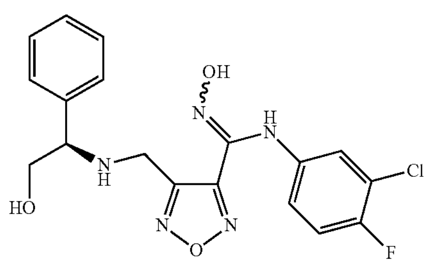 [SMILES: OC[C@H](NCc1nonc1C(=NO)Nc1ccc(F)c(Cl)c1)c1ccccc1] | 406.2 | Ex. 4 | A | TFA | N-(3-chloro-4-fluoro-phenyl)-N-hydroxy-4-({[(1R)-2-hydroxy-1-phenylethyl]amino}-methyl)-1,2,5-oxadiazole-3-carboximidamide trifluoroacetate |
| 48 | 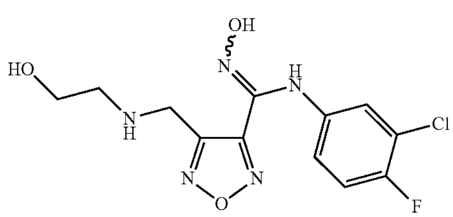 [SMILES: OCCNCc1nonc1C(=NO)Nc1ccc(F)c(Cl)c1] | 330.2 | Ex. 4 | A | TFA | N-(3-chloro-4-fluoro-phenyl)-N-hydroxy-4-{[(2-hydroxyethyl)-amino]methyl}-1,2,5-oxadiazole-3-carboximidamide trifluoroacetate |
| 49 | 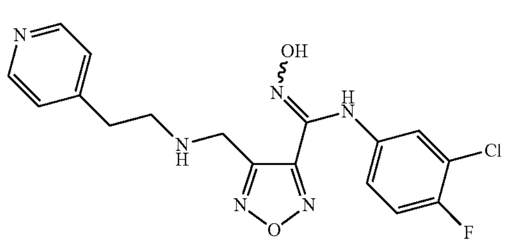 [SMILES: ON=C(Nc1ccc(F)c(Cl)c1)c1nonc1CNCCc1ccncc1] | 391.2 | Ex. 4 | A | 2 TFA | N-(3-chloro-4-fluoro-phenyl)-N'-hydroxy-4-{[(2-pyridin-4-ylethyl)amino]methyl}-1,2,5-oxadiazole-3-carboximidamide bis(trifluoroacetate) |

TABLE 2-continued

| Ex. No. | Structure | MS (M + 1) | Prep. Ex. | Pur. Meth. | Salt | Name |
|---|---|---|---|---|---|---|
| 50 | 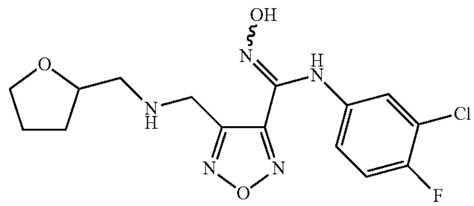 [SMILES: ON=C(Nc1ccc(F)c(Cl)c1)c1nonc1CNCC1CCCO1] | 370.2 | Ex. 4 | A | TFA | N-(3-chloro-4-fluorophenyl)-N'-hydroxy-4-{[[(tetrahydrofuran-2-ylmethyl)amino]methyl}-1,2,5-oxadiazole-3-carboximidamide trifluoroacetate |
| 51 | 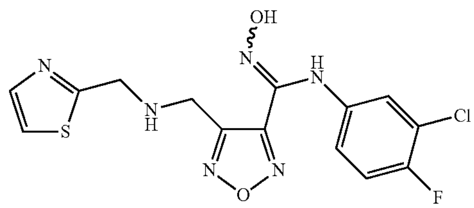 [SMILES: ON=C(Nc1ccc(F)c(Cl)c1)c1nonc1CNCc1nccs1] | 383.2 | Ex. 4 | A | TFA | N-(3-chloro-4-fluorophenyl)-N'-hydroxy-4-{[[(1,3-thiazol-2-ylmethyl)amino]methyl}-1,2,5-oxadiazole-3-carboximidamide trifluoroacetate |
| 52 | 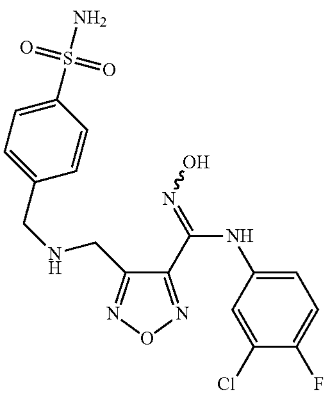 [SMILES: NS(=O)(=O)c1ccc(CNCc2nonc2C(=NO)Nc2ccc(F)c(Cl)c2)cc1] | 455.2 | Ex. 4 | A | TFA | 4-({[4-(aminosulfony)benzyl]amino}-methyl)-N-(3-chloro-4-fluorophenyl)-N'-hydroxy-1,2,5-oxadiazole-3-carboximidamide trifluoroacetate |
| 53 | 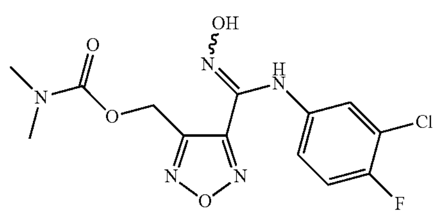 [SMILES: CN(C)C(=O)OCc1nonc1C(=NO)Nc1ccc(F)c(Cl)c1] | 358.2 | Ex. 3 | A | Free Base | {4-[(E/Z)-[(3-chloro-4-fluorophenyl)-amino](hydroxyimino)-methyl]-1,2,5-oxadiazol-3-yl}methyl dimethylcarbamate |
| 54 | 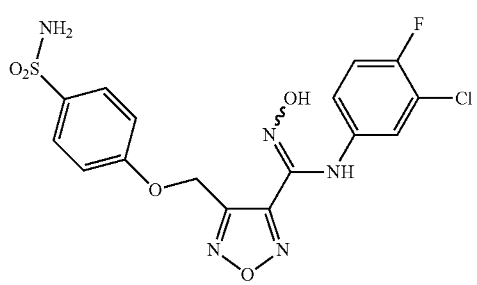 [SMILES: NS(=O)(=O)c1ccc(OCc2nonc2C(=NO)Nc2ccc(F)c(Cl)c2)cc1] | 442.2 | Ex. 2 | A | Free Base | 4-{[4-(aminosulfonyl)phenoxy]methyl}-N-(3-chloro-4-fluorophenyl)-N'-hydroxy-1,2,5-oxadiazole-3-carboximidamide |
| 55 | 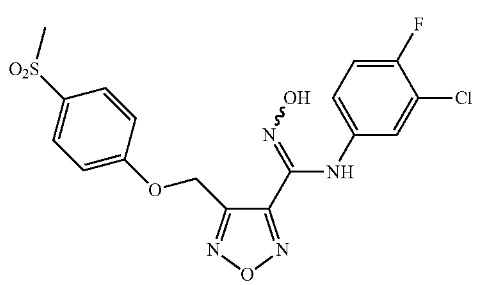 [SMILES: CS(=O)(=O)c1ccc(OCc2nonc2C(=NO)Nc2ccc(F)c(Cl)c2)cc1] | 441.2 | Ex. 2 | A | Free Base | N-(3-chloro-4-fluorophenyl)-N'-hydroxy-4-{[4-(methylsulfonyl)phenoxy]methyl}-1,2,5-oxadiazole-3-carboximidamide |

TABLE 2-continued

| Ex. No. | Structure | MS (M + 1) | Prep. Ex. | Pur. Meth. | Salt | Name |
|---|---|---|---|---|---|---|
| 56 | 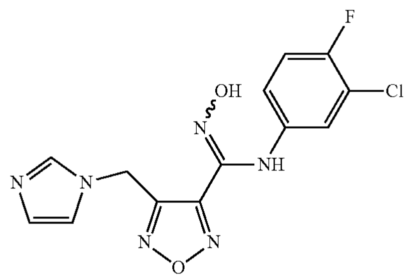 [SMILES: ON=C(Nc1ccc(F)c(Cl)c1)c1nonc1Cn1ccnc1] | 337.2 | Exs. 39 and 40 | A | TFA | N-(3-chloro-4-fluoro-phenyl)-N'-hydroxy-4-(1H-imidazol-1-yl-methyl)-1,2,5-oxadiazole-3-carboximidamide trifluoroacetate |
| 57 | 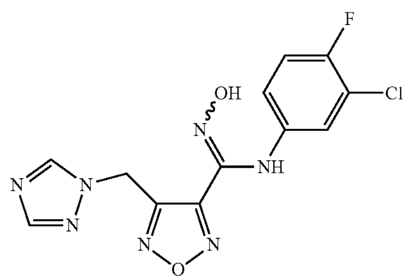 [SMILES: ON=C(Nc1ccc(F)c(Cl)c1)c1nonc1Cn1cncn1] | 338.2 | Exs. 39 and 40 | A | Free Base | N-(3-chloro-4-fluoro-phenyl)-N'-hydroxy-4-(1H-1,2,4-triazol-1-yl-methyl)-1,2,5-oxadiazole-3-carboximidamide |
| 58 | 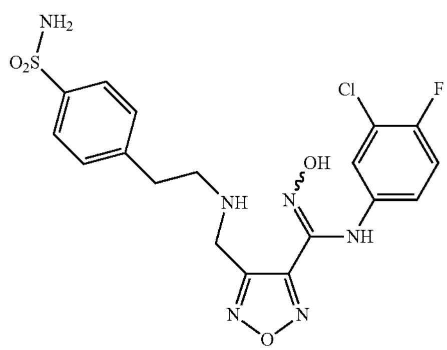 [SMILES: NS(=O)(=O)c1ccc(CCNCc2nonc2C(=NO)Nc2ccc(F)c(Cl)c2)cc1] | 469.2 | Ex. 4 | A | TFA | 4-[({2-[4-(amino-sulfonyl)phenyl]ethyl}-amino)methyl]-N-(3-chloro-4-fluoro-phenyl)-N'-hydroxy-1,2,5-oxadiazole-3-carboximidamide trifluoroacetate |
| 59 | 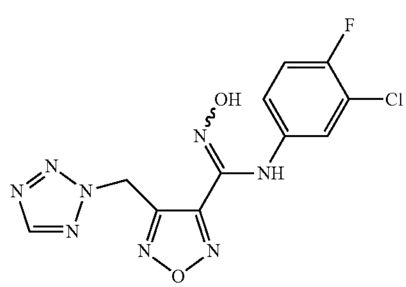 [SMILES: ON=C(Nc1ccc(F)c(Cl)c1)c1nonc1Cn1ncnn1] | 339.2 | Exs. 39 and 40 | A | Free Base | N-(3-chloro-4-fluoro-phenyl)-N'-hydroxy-4-(2H-tetrazol-2-ylmethyl)-1,2,5-oxadiazole-3-carboximidamide |
| 60 | 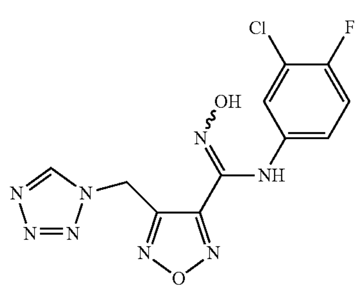 [SMILES: ON=C(Nc1ccc(F)c(Cl)c1)c1nonc1Cn1cnnn1] | 339.2 | Exs. 39 and 40 | B | Free Base | N-(3-chloro-4-fluorophenyl)-N'-hydroxy-4-(1H-tetrazol-1-ylmethyl)-1,2,5-oxadiazole-3-carboximidamide |

TABLE 2-continued

| Ex. No. | Structure | MS (M + 1) | Prep. Ex. | Pur. Meth. | Salt | Name |
|---|---|---|---|---|---|---|
| 61 | 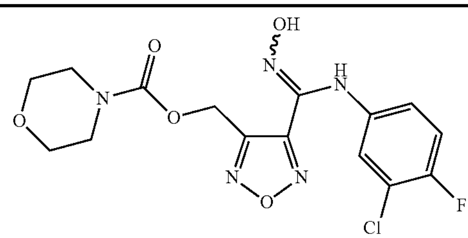 | 400.2 | Ex. 3 | A | Free Base | {4-[(E/Z)-[(3-chloro-4-fluorophenyl)-amino](hydroxyimino)-methyl]-1,2,5-oxadiazol-3-yl}methyl-morpholine-4-carboxylate |
| 62 | 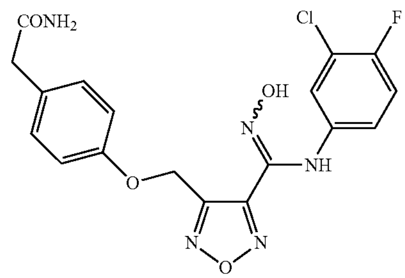 [SMILES: NC(=O)Cc1ccc(OCc2nonc2C(=NO)Nc2ccc(F)c(Cl)c2)cc1] | 420.2 | Ex. 2 | A | Free Base | 2-[4-({4-[(E/Z)-[(3-chloro-4-fluoro-phenyl)amino](hydroxy-imino)methyl]-oxadiazol-3-yl}-methoxy)phenyl]aceta-mide |
| 63 | 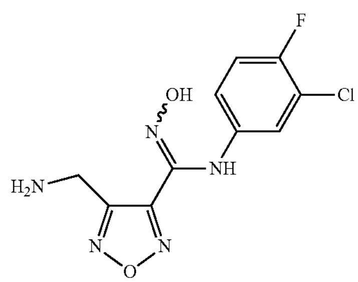 [SMILES: NCc1nonc1C(=NO)Nc1ccc(F)c(Cl)c1] | 286.2 | Ex. 33, Step B | A | TFA | 4-(aminomethyl)-N-(3-chloro-4-fluoro-phenyl)-N'-hydroxy-1,2,5-oxadiazole-3-carboximidamide trifluoroacetate |
| 64 | 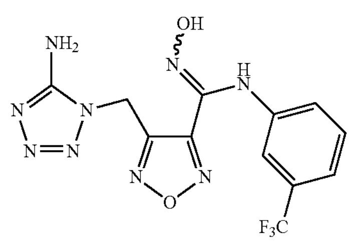 [SMILES: Nc1nnnn1Cc1nonc1C(=NO)Nc1cccc(C(F)(F)F)c1] | 370.1 | Exs. 39 and 40 | A | Free Base | 4-[(5-amino-1H-tetrazol-1-yl)methyl]-N-[3-(trifluoro-methyl)phenyl]-N'-hydroxy-1,2,5-oxadiazole-3-carboximidamide |
| 65 | 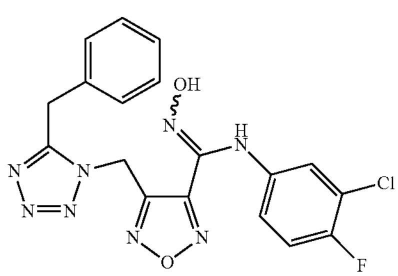 [SMILES: ON=C(Nc1ccc(F)c(Cl)c1)c1nonc1Cn1nnnc1Cc1ccccc1] | 429.2 | Exs. 39 and 40 | A | Free Base | 4-[(5-benzyl-1H-tetrazol-1-yl)methyl]-N-(3-chloro-4-fluoro-phenyl)-N'-hydroxy-1,2,5-oxadiazole-3-carboximidamide |
| 66 | 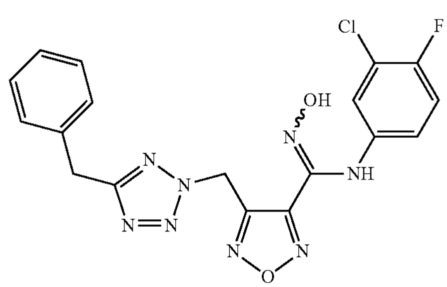 [SMILES: ON=C(Nc1ccc(F)c(Cl)c1)c1nonc1Cn1nnc(Cc2ccccc2)n1] | 429.2 | Exs. 39 and 40 | A | Free Base | 4-[(5-benzyl-2H-tetrazol-2-yl)methyl]-N-(3-chloro-4-fluoro-phenyl)-N'-hydroxy-1,2,5-oxadiazole-3-carboximidamide |

TABLE 2-continued

| Ex. No. | Structure | MS (M + 1) | Prep. Ex. | Pur. Meth. | Salt | Name |
|---|---|---|---|---|---|---|
| 67 | 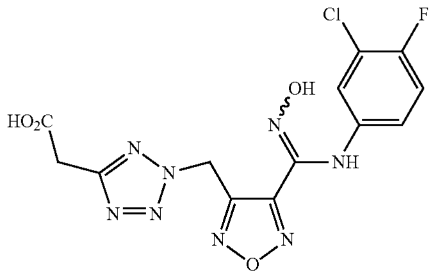 [SMILES: O=C(O)Cc1nnn(Cc2nonc2C(=NO)Nc2ccc(F)c(Cl)c2)n1] | 397.2 | Exs. 39 and 40 | B | Free base | [2-({4-[(E/Z)-[(3-chloro-4-fluoro-phenyl)amino](hydroxy-imino)methyl]-1,2,5-oxadiazol-3-yl}methyl)-2H-tetrazol-5-yl]acetic acid |
| 68 | 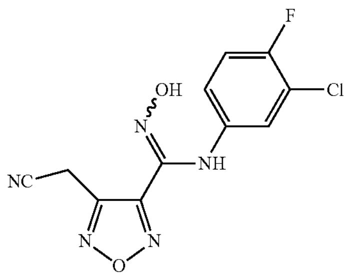 [SMILES: N#CCc1nonc1C(=NO)Nc1ccc(F)c(Cl)c1] | 296.2 | Exs. 39 and 40 | B | Free Base | N-(3-chloro-4-fluoro-phenyl)-4-(cyano-methyl)-N'-hydroxy-1,2,5-oxadiazole-3-carboximidamide |
| 69 | 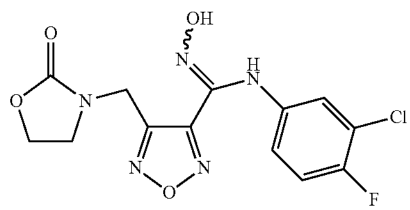 [SMILES: O=C1OCCN1Cc1nonc1C(=NO)Nc1ccc(F)c(Cl)c1] | 356.2 | Exs. 39 and 40 | B | Free Base | N-(3-chloro-4-fluoro-phenyl)-N'-hydroxy-4-[(2-oxo-1,3-oxazolidin-3-yl)-methyl]-1,2,5-oxadiazole-3-carboximidamide |
| 70 | 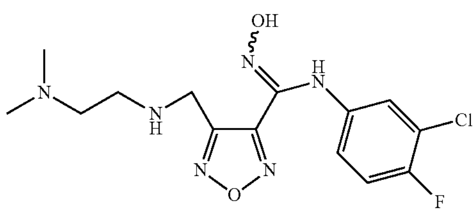 [SMILES: CN(C)CCNCc1nonc1C(=NO)Nc1ccc(F)c(Cl)c1] | 357.2 | Ex. 4 | B | Free Base | N-(3-chloro-4-fluoro-phenyl)-4-({[2-(dimethylamino)ethyl]-amino}methyl)-N'-hydroxy-1,2,5-oxadiazole-3-carboximidamide |
| 71 | 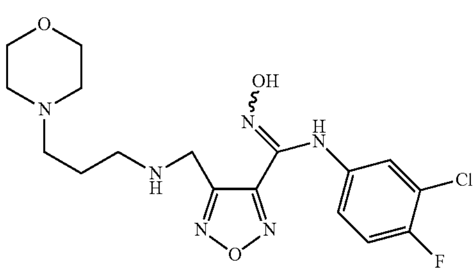 [SMILES: ON=C(Nc1ccc(F)c(Cl)c1)c1nonc1CNCCCN1CCOCC1] | 413.2 | Ex. 4 | B | Free Base | N-(3-chloro-4-fluoro-phenyl)-N'-hydroxy-4-{[(3-morpholin-4-ylpropyl)amino]meth-yl}-1,2,5-oxadiazole-3-carboximidamide |
| 72 | 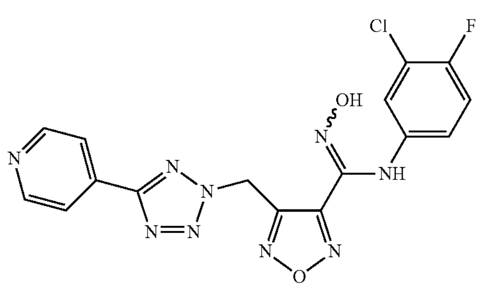 [SMILES: ON=C(Nc1ccc(F)c(Cl)c1)c1nonc1Cn1nnc(-c2ccncc2)n1] | 416.2 | Exs. 39 and 40 | B | Free Base | N-(3-chloro-4-fluoro-phenyl)-N'-hydroxy-4-[(5-pyridin-4-yl-2H-tetrazol-2-yl)methyl]-1,2,5-oxadiazole-3-carboximidamide |

TABLE 2-continued

| Ex. No. | Structure | MS (M + 1) | Prep. Ex. | Pur. Meth. | Salt | Name |
| --- | --- | --- | --- | --- | --- | --- |
| 73 | 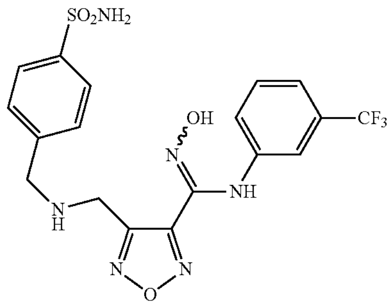 [SMILES: NS(=O)(=O)c1ccc(CNCc2nonc2C(=NO)Nc2cccc(C(F)(F)F)c2)cc1] | 471.2 | Ex. 4 | B | Free Base | 4-({[4-(amino-sulfonyl)benzyl]amino}-methyl)-N-[3-(trifluoromethyl)phenyl]-N'-hydroxy-1,2,5-oxadiazole-3-carboximidamide |
| 74 | 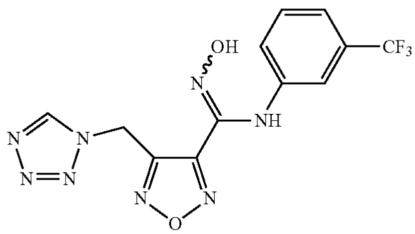 [SMILES: ON=C(Nc1cccc(C(F)(F)F)c1)c1nonc1Cn1cnnn1] | 355.2 | Exs. 39 and 40 | B | Free Base | N-[3-(trifluoro-methyl)phenyl]-N'-hydroxy-4-(1H-tetrazol-1-ylmethyl)-1,2,5-oxadiazole-3-carboximidamide |
| 75 | 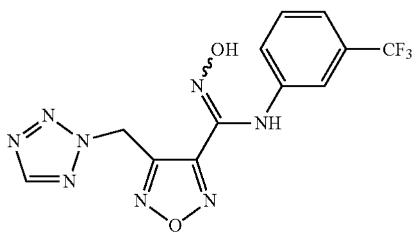 [SMILES: ON=C(Nc1cccc(C(F)(F)F)c1)c1nonc1Cn1ncnn1] | 355.2 | Exs. 39 and 40 | B | Free Base | N-[3-(trifluoro-methyl)phenyl]-N'-hydroxy-4-(2H-tetrazol-2-ylmethyl)-1,2,5-oxadiazole-3-carboximidamide |
| 76 | 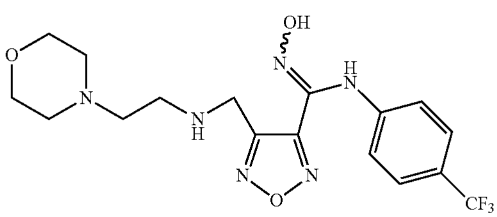 [SMILES: ON=C(Nc1ccc(C(F)(F)F)cc1)c1nonc1CNCCN1CCOCC1] | 415.2 | Ex. 4 | B | Free Base | N-[3-(trifluoro-methyl)phenyl]-N'-hydroxy-4-{[(2-morpholin-4-ylethyl)-amino]methyl}-1,2,5-oxadiazole-3-carboximidamide |
| 77 | 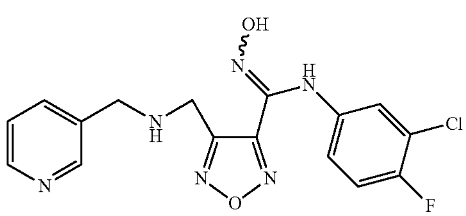 [SMILES: ON=C(Nc1ccc(F)c(Cl)c1)c1nonc1CNCc1cccnc1] | 377.2 | Ex. 4 | B | Free Base | N-(3-chloro-4-fluoro-phenyl)-N'-hydroxy-4-{[(pyridin-3-yl-methyl)amino]methyl}-1,2,5-oxadiazole-3-carboximidamide |
| 78 | 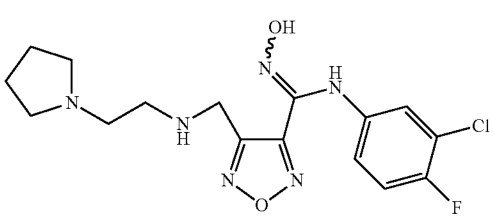 [SMILES: ON=C(Nc1ccc(F)c(Cl)c1)c1nonc1CNCCN1CCCC1] | 383.2 | Ex. 4 | B | Free Base | N-(3-chloro-4-fluoro-phenyl)-N'-hydroxy-4-{[(2-pyrrolidin-1-ylethyl)amino]methyl}-1,2,5-oxadiazole-3-carboximidamide |

TABLE 2-continued

| Ex. No. | Structure | MS (M + 1) | Prep. Ex. | Pur. Meth. | Salt | Name |
|---|---|---|---|---|---|---|
| 79 | 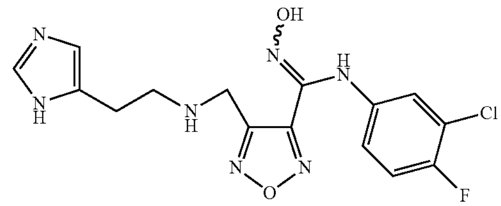 [SMILES: ON=C(Nc1ccc(F)c(Cl)c1)c1nonc1CNCCc1cnc[nH]1] | 380.2 | Ex. 4 | B | Free Base | N-(3-chloro-4-fluoro-phenyl)-N'-hydroxy-4-({[2-(1H-imidazol-4-yl)ethyl]amino}methyl)-1,2,5-oxadiazole-3-carboximidamide |
| 80 | 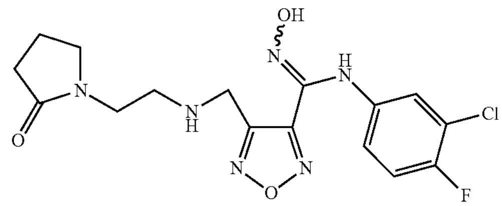 [SMILES: O=C1CCCN1CCNCc1nonc1C(=NO)Nc1ccc(F)c(Cl)c1] | 397.2 | Ex. 4 | B | Free Base | N-(3-chloro-4-fluoro-phenyl)-N'-hydroxy-4-({[2-(2-oxopyrrolidin-1-yl)ethyl]amino}-methyl)-1,2,5-oxadiazole-3-carboximidamide |
| 81 | 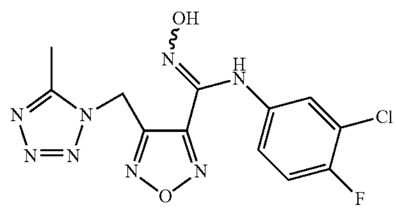 [SMILES: Cc1nnnn1Cc1nonc1C(=NO)Nc1ccc(F)c(Cl)c1] | 353.2 | Exs. 39 and 40 | B | Free Base | N-(3-chloro-4-fluoro-phenyl)-N'-hydroxy-4-[(5-methyl-1H-tetrazol-1-yl)methyl]-1,2,5-oxadiazole-3-carboximidamide |
| 82 | 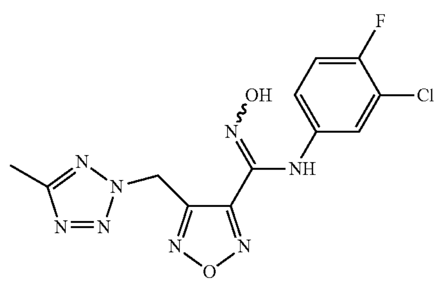 [SMILES: Cc1nnn(Cc2nonc2C(=NO)Nc2ccc(F)c(Cl)c2)n1] | 353.2 | Exs. 39 and 40 | B | Free Base | N-(3-chloro-4-fluoro-phenyl)-N'-hydroxy-4-[(5-methyl-2H-tetrazol-2-yl)methyl]-1,2,5-oxadiazole-3-carboximidamide |
| 83 | 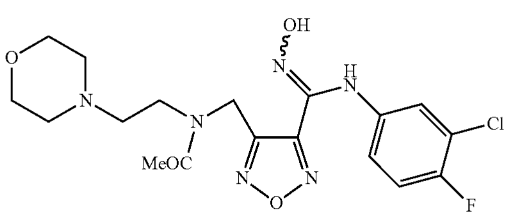 | 441.2 | Ex. 33 | B | Free Base | N-({4-[(E/Z)-[(3-chloro-4-fluoro-phenyl)amino](hydroxy-imino)methyl]-1,2,5-oxadiazol-3-yl}methyl)-N-(2-morpholin-4-ylethyl)acetamide |
| 84 | 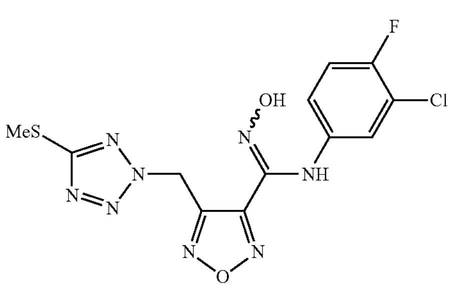 [SMILES: CSc1nnn(Cc2nonc2C(=NO)Nc2ccc(F)c(Cl)c2)n1] | 385.2 | Exs. 39 and 40 | B | Free Base | N-(3-chloro-4-fluorophenyl)-N'-hydroxy-4-{[5-(methylthio)-2H-tetrazol-2-yl]methyl}-1,2,5-oxadiazole-3-carboximidamide |

TABLE 2-continued

| Ex. No. | Structure | MS (M + 1) | Prep. Ex. | Pur. Meth. | Salt | Name |
|---|---|---|---|---|---|---|
| 85 | 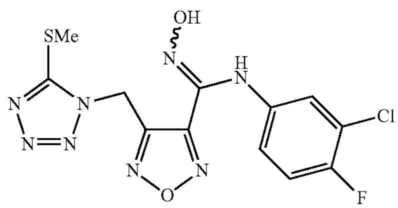 [SMILES: CSc1nnnn1Cc1nonc1C(=NO)Nc1ccc(F)c(Cl)c1] | 385.2 | Exs. 39 and 40 | B | Free Base | N-(3-chloro-4-fluoro-phenyl)-N'-hydroxy-4-{[5-(methylthio)-1H-tetrazol-1-yl]methyl}-1,2,5-oxadiazole-3-carboximidamide |
| 86 | 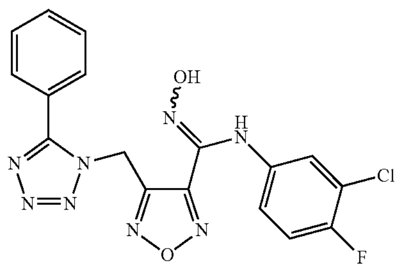 [SMILES: ON=C(Nc1ccc(F)c(Cl)c1)c1nonc1Cn1nnnc1-c1ccccc1] | 415.2 | Exs. 39 and 40 | B | Free Base | N-(3-chloro-4-fluoro-phenyl)-N'-hydroxy-4-[(5-phenyl-1H-tetrazol-1-yl)methyl]-1,2,5-oxadiazole-3-carboximidamide |
| 87 | 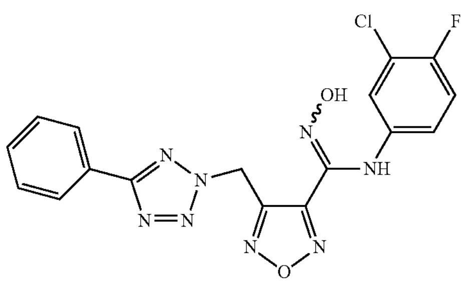 [SMILES: ON=C(Nc1ccc(F)c(Cl)c1)c1nonc1Cn1nnc(-c2ccccc2)n1] | 415.2 | Exs. 39 and 40 | B | Free Base | N-(3-chloro-4-fluoro-phenyl)-N'-hydroxy-4-[(5-phenyl-2H-tetrazol-2-yl)methyl]-1,2,5-oxadiazole-3-carboximidamide |
| 88 | 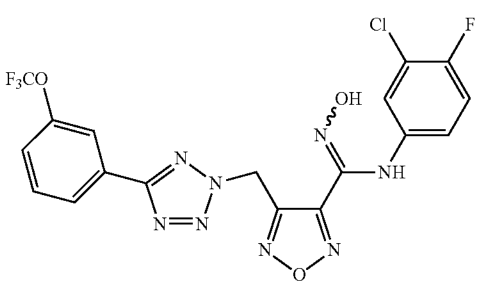 [SMILES: ON=C(Nc1ccc(F)c(Cl)c1)c1nonc1Cn1nnc(-c2cccc(OC(F)(F)F)c2)n1] | 499.2 | Exs. 39 and 40 | B | Free Base | N-(3-chloro-4-fluoro-phenyl)-N'-hydroxy-4-({5-[3-(trifluoro-methoxy)phenyl]-2H-tetrazol-2-yl}methyl)-1,2,5-oxadiazole-3-carboximidamide |
| 89 | 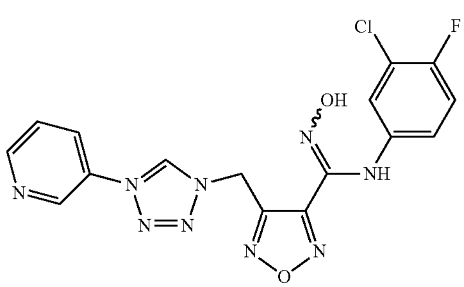 | 416.2 | Exs. 39 and 40 | B | Free Base | N-(3-chloro-4-fluoro-phenyl)-N'-hydroxy-4-[(5-pyridin-3-yl-2H-tetrazol-2-yl)methyl]-1,2,5-oxadiazole-3-carboximidamide |

TABLE 2-continued

| Ex. No. | Structure | MS (M + 1) | Prep. Ex. | Pur. Meth. | Salt | Name |
|---|---|---|---|---|---|---|
| 90 | 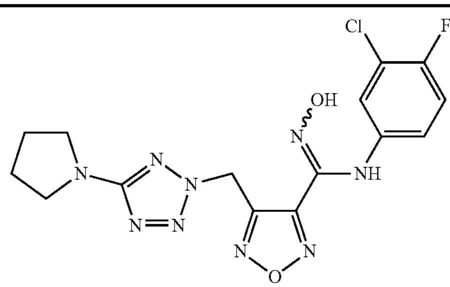 | 408.2 | Exs. 39 and 40 | B | Free Base | N-(3-chloro-4-fluorophenyl)-N'-hydroxy-4-[(5-pyrrolidin-1-yl-2H-tetrazol-2-yl)methyl]-1,2,5-oxadiazole-3-carboximidamide |
| 91 | 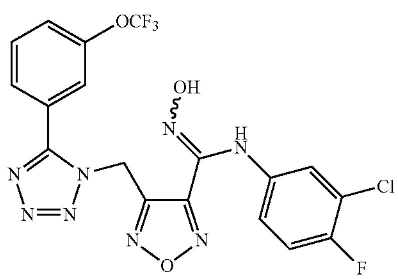 [SMILES: ON=C(Nc1ccc(F)c(Cl)c1)c1nonc1Cn1nnnc1-c1cccc(OC(F)(F)F)c1] | 499.2 | Exs. 39 and 40 | B | Free Base | N-(3-chloro-4-fluorophenyl)-N'-hydroxy-4-({5-[3-(trifluoromethoxy)phenyl]-1H-tetrazol-1-yl}methyl)-1,2,5-oxadiazole-3-carboximidamide |
| 92 | 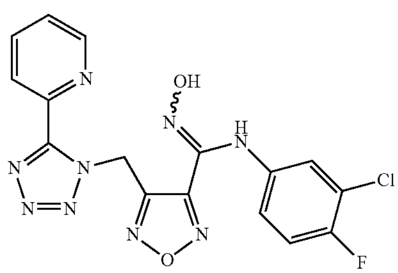 [SMILES: ON=C(Nc1ccc(F)c(Cl)c1)c1nonc1Cn1nnnc1-c1ccccn1] | 416.2 | Exs. 39 and 40 | B | Free Base | N-(3-chloro-4-fluorophenyl)-N'-hydroxy-4-[(5-pyridin-2-yl-1H-tetrazol-1-yl)methyl]-1,2,5-oxadiazole-3-carboximidamide |
| 93 | 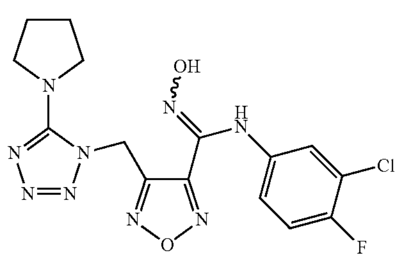 [SMILES: ON=C(Nc1ccc(F)c(Cl)c1)c1nonc1Cn1nnnc1N1CCCC1] | 408.2 | Exs. 39 and 40 | B | Free Base | N-(3-chloro-4-fluorophenyl)-N'-hydroxy-4-[(5-pyrrolidin-1-yl-1H-tetrazol-1-yl)methyl]-1,2,5-oxadiazole-3-carboximidamide |
| 94 | 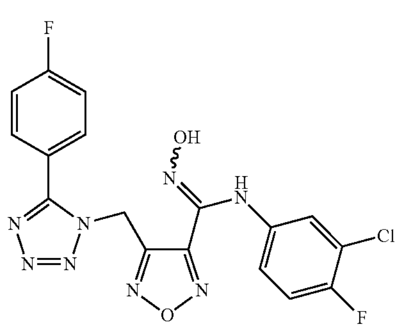 [SMILES: ON=C(Nc1ccc(F)c(Cl)c1)c1nonc1Cn1nnnc1-c1ccc(F)cc1] | 433.2 | Exs. 39 and 40 | B | Free Base | N-(3-chloro-4-fluorophenyl)-4-{[5-(4-fluorophenyl)-1H-tetrazol-1-yl]methyl}-N'-hydroxy-1,2,5-oxadiazole-3-carboximidamide |

TABLE 2-continued

| Ex. No. | Structure | MS (M + 1) | Prep. Ex. | Pur. Meth. | Salt | Name |
|---|---|---|---|---|---|---|
| 95 | 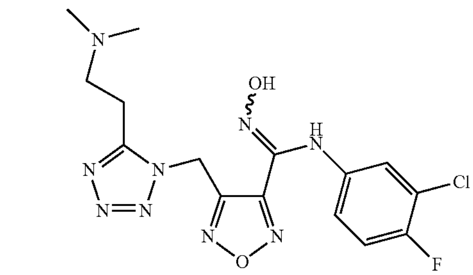 [SMILES: CN(C)CCc1nnnn1Cc1nonc1C(=NO)Nc1ccc(F)c(Cl)c1] | 410.2 | Exs. 39 and 40 | B | Free Base | N-(3-chloro-4-fluorophenyl)-4-({5-[2-(dimethylamino)-ethyl]-1H-tetrazol-1-yl}methyl)-N'-hydroxy-1,2,5-oxadiazole-3-carboximidamide |
| 96 | 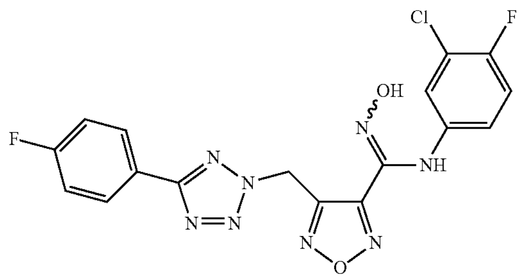 [SMILES: ON=C(Nc1ccc(F)c(Cl)c1)c1nonc1Cn1nnc(-c2ccc(F)cc2)n1] | 433.2 | Exs. 39 and 40 | B | Free Base | N-(3-chloro-4-fluoro-phenyl)-4-{[5-(4-fluorophenyl)-2H-tetrazol-2-yl]methyl}-N'-hydroxy-1,2,5-oxadiazole-3-carboximidamide |
| 97 | 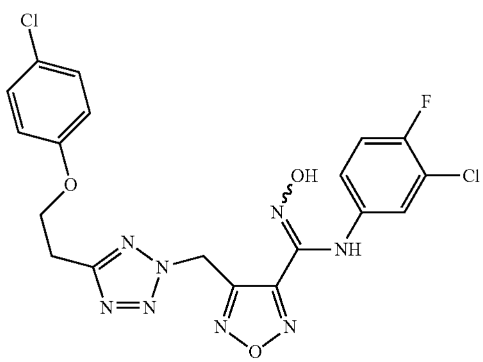 [SMILES: ON=C(Nc1ccc(F)c(Cl)c1)c1nonc1Cn1nnc(CCOc2ccc(Cl)cc2)n1] | 494.2 | Exs. 39 and 40 | B | Free Base | N-(3-chloro-4-fluoro-phenyl)-4-({5-[2-(4-chlorophenoxy)ethyl]-2H-tetrazol-2-yl}-methyl)-N'-hydroxy-1,2,5-oxadiazole-3-carboximidamide |
| 98 | 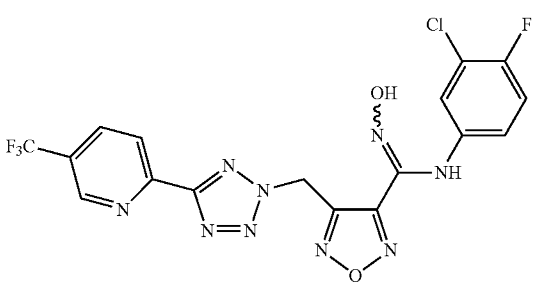 [SMILES: ON=C(Nc1ccc(F)c(Cl)c1)c1nonc1Cn1nnc(-c2ccc(C(F)(F)F)cn2)n1] | 484.2 | Exs. 39 and 40 | B | Free Base | N-(3-chloro-4-fluoro-phenyl)-N'-hydroxy-4-({5-[5-(trifluoro-methyl)pyridin-2-yl]-2H-tetrazol-2-yl}-methyl)-1,2,5-oxadiazole-3-carboximidamide |
| 99 | 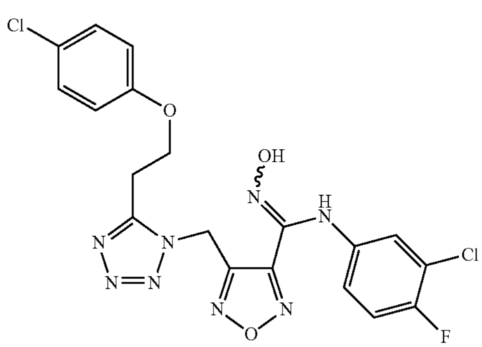 [SMILES: ON=C(Nc1ccc(F)c(Cl)c1)c1nonc1Cn1nnnc1CCOc1ccc(Cl)cc1] | 494.2 | Exs. 39 and 40 | B | Free Base | N-(3-chloro-4-fluoro-phenyl)-4-({5-[2-(4-chlorophenoxy)ethyl]-1H-tetrazol-1-yl}methyl)-N'-hydroxy-1,2,5-oxadiazole-3-carboximidamide |

TABLE 2-continued

| Ex. No. | Structure | MS (M + 1) | Prep. Ex. | Pur. Meth. | Salt | Name |
|---|---|---|---|---|---|---|
| 100 | 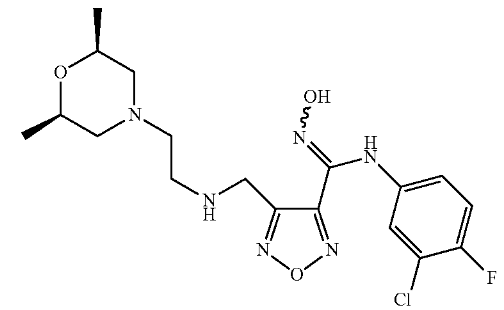 [SMILES: C[C@@H]1CN(CCNCc2nonc2C(=NO)Nc2ccc(F)c(Cl)c2)C[C@H](C)O1] | 427.2 | Ex. 4 | B | Free Base | N-(3-chloro-4-fluoro-phenyl)-4-[({2-[(2R,6S)-2,6-dimethylmorpholin-4-yl]ethyl}amino)methyl]-N'-hydroxy-1,2,5-oxadiazole-3-carboximidamide |
| 101 | 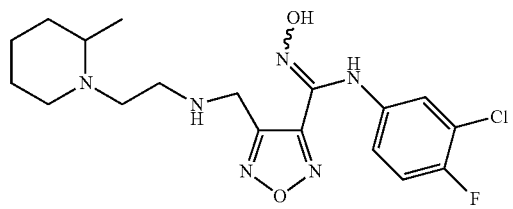 [SMILES: CC1CCCCN1CCNCc1nonc1C(=NO)Nc1ccc(F)c(Cl)c1] | 411.2 | Ex. 4 | B | Free Base | N-(3-chloro-4-fluoro-phenyl)-N'-hydroxy-4-({[2-(2-methylpiperidin-1-yl)ethyl]amino}methyl)-1,2,5-oxadiazole-3-carboximidamide |
| 102 | 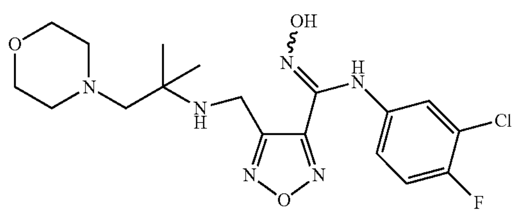 [SMILES: CC(C)(CN1CCOCC1)NCc1nonc1C(=NO)Nc1ccc(F)c(Cl)c1] | 427.2 | Ex. 4 | B | Free Base | N-(3-chloro-4-fluoro-phenyl)-4-{[(1,1-dimethyl-2-morpholin-4-ylethyl)amino]methyl}-N'-hydroxy-1,2,5-oxadiazole-3-carboximidamide |
| 103 | 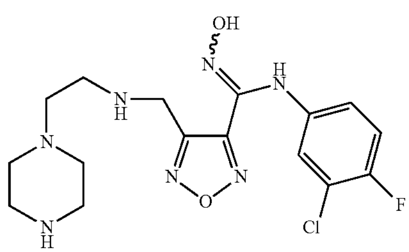 [SMILES: ON=C(Nc1ccc(F)c(Cl)c1)c1nonc1CNCCN1CCNCC1] | 398.2 | Ex. 4 | B | Free Base | N-(3-chloro-4-fluoro-phenyl)-N'-hydroxy-4-{[(2-piperazin-1-ylethyl)amino]methyl}-1,2,5-oxadiazole-3-carboximidamide |
| 104 | 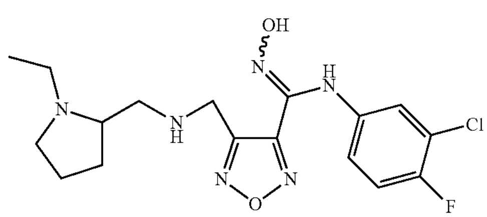 [SMILES: CCN1CCCC1CNCc1nonc1C(=NO)Nc1ccc(F)c(Cl)c1] | 397.2 | Ex. 4 | B | Free Base | N-(3-chloro-4-fluoro-phenyl)-4-({[(1-ethylpyrrolidin-2-yl)methyl]amino}-methyl)-N'-hydroxy-1,2,5-oxadiazole-3-carboximidamide |
| 105 | 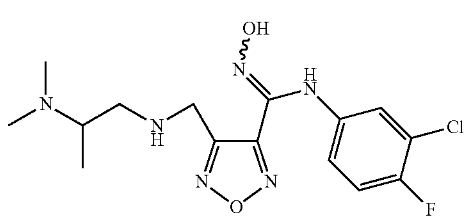 [SMILES: CC(CNCc1nonc1C(=NO)Nc1ccc(F)c(Cl)c1)N(C)C] | 371.2 | Ex. 4 | B | Free Base | N-(3-chloro-4-fluoro-phenyl)-4-({[2-(dimethylamino)propyl]-amino}methyl)-N'-hydroxy-1,2,5-oxadiazole-3-carboximidamide |

TABLE 2-continued

| Ex. No. | Structure | MS (M + 1) | Prep. Ex. | Pur. Meth. | Salt | Name |
|---|---|---|---|---|---|---|
| 106 | 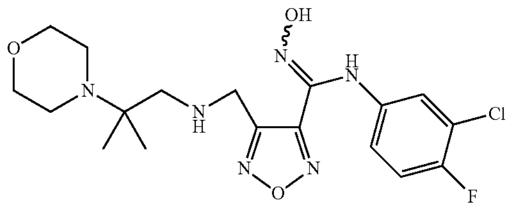 [SMILES: CC(C)(CNCc1nonc1C(=NO)Nc1ccc(F)c(Cl)c1)N1CCOCC1] | 427.2 | Ex. 4 | B | Free Base | N-(3-chloro-4-fluoro-phenyl)-N'-hydroxy-4-{[(2-methyl-2-morpholin-4-ylpropyl)amino]-methyl}-1,2,5-oxadiazole-3-carboximidamide |
| 107 | 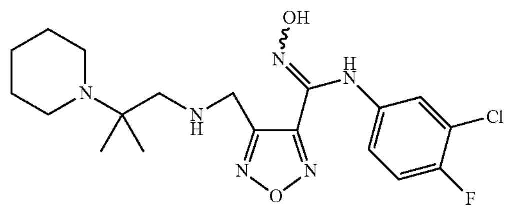 [SMILES: CC(C)(CNCc1nonc1C(=NO)Nc1ccc(F)c(Cl)c1)N1CCCCC1] | 425.1 | Ex. 4 | B | Free Base | N-(3-chloro-4-fluoro-phenyl)-N'-hydroxy-4-{[(2-methyl-2-piperidin-1-ylpropyl)-amino]methyl}-1,2,5-oxadiazole-3-carboximidamide |
| 108 | 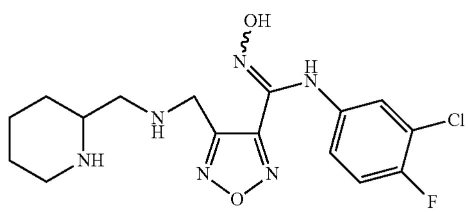 [SMILES: ON=C(Nc1ccc(F)c(Cl)c1)c1nonc1CNCC1CCCCN1] | 383.1 | Ex. 4 | B | Free Base | N-(3-chloro-4-fluorophenyl)-N'-hydroxy-4-{[(piperidin-2-ylmethyl)amino]methyl}-1,2,5-oxadiazole-3-carboximidamide |
| 109 | 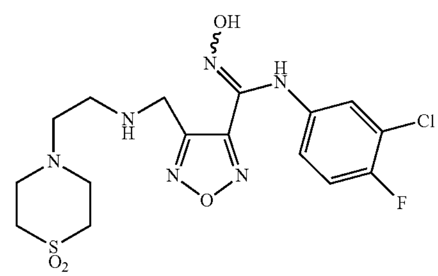 [SMILES: O=S1(=O)CCN(CCNCc2nonc2C(=NO)Nc2ccc(F)c(Cl)c2)CC1] | 447.1 | Ex. 4 | B | Free Base | N-(3-chloro-4-fluoro-phenyl)-4-({[2-(1,1-dioxidothiomorpholin-4-yl)ethyl]amino}-methyl)-N'-hydroxy-1,2,5-oxadiazole-3-carboximidamide |
| 110 | 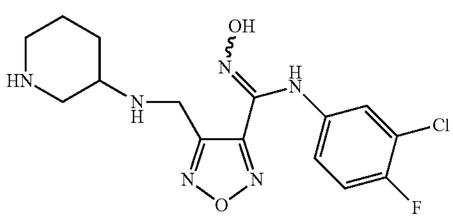 [SMILES: ON=C(Nc1ccc(F)c(Cl)c1)c1nonc1CNC1CCCNC1] | 369.2 | Ex. 4 | B | Free Base | N-(3-chloro-4-fluoro-phenyl)-N'-hydroxy-4-{[(piperidin-3-yl-amino)methyl]-1,2,5-oxadiazole-3-carboximidamide |
| 111 | 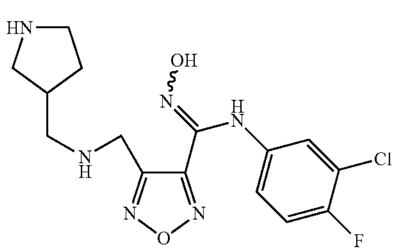 [SMILES: ON=C(Nc1ccc(F)c(Cl)c1)c1nonc1CNCC1CCNC1] | 369.2 | Ex. 4 | B | Free Base | N-(3-chloro-4-fluoro-phenyl)-N'-hydroxy-4-{[(pyrrolidin-3-yl-methyl)amino]methyl}-1,2,5-oxadiazole-3-carboximidamide |

| Ex. No. | Structure | MS (M + 1) | Prep. Ex. | Pur. Meth. | Salt | Name |
|---|---|---|---|---|---|---|
| 112 | 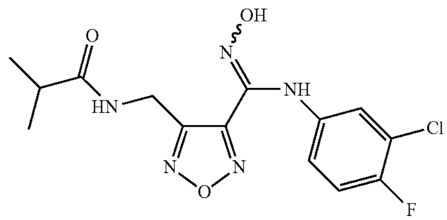 [SMILES: CC(C)C(=O)NCc1nonc1C(=NO)Nc1ccc(F)c(Cl)c1] | 355.1 | Ex. 33 | B | Free Base | N-({4-[(E/Z)-[(3-chloro-4-fluoro-phenyl)amino](hydroxy-imino)methyl]-1,2,5-oxadiazol-3-yl}-methyl)-2-methyl-propanide |
| 113 | 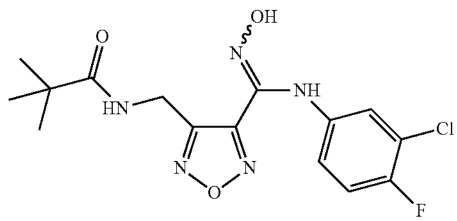 [SMILES: CC(C)(C)C(=O)NCc1nonc1C(=NO)Nc1ccc(F)c(Cl)c1] | 369.1 | Ex. 33 | B | Free Base | N-({4-[(E/Z)-[(3-chloro-4-fluoro-phenyl)amino]-(hydroxyimino)-methyl]-1,2,5-oxadiazol-3-yl}-methyl)-2,2-dimethylpropanamide |
| 114 | 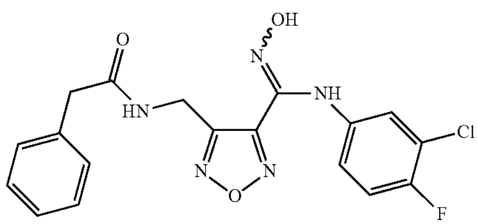 [SMILES: O=C(Cc1ccccc1)NCc1nonc1C(=NO)Nc1ccc(F)c(Cl)c1] | 403.1 | Ex. 33 | B | Free Base | N-({4-[(E/Z)-[(3-chloro-4-fluoro-phenyl)amino](hydroxy-imino)methyl]-1,2,5-oxadiazol-3-yl}methyl)-2-phenylacetamide |
| 115 | 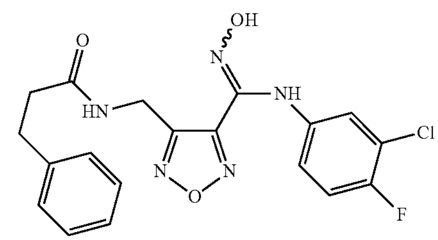 [SMILES: O=C(CCc1ccccc1)NCc1nonc1C(=NO)Nc1ccc(F)c(Cl)c1] | 417.1 | Ex. 33 | B | Free Base | N-({4-[(E/Z)-[(3-chloro-4-fluoro-phenyl)amino](hydroxy-imino)methyl]-1,2,5-oxadiazol-3-yl}-methyl)-3-phenyl-propanamide |
| 116 | 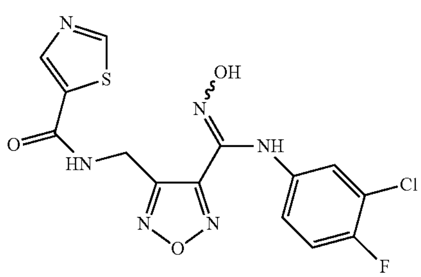 [SMILES: O=C(NCc1nonc1C(=NO)Nc1ccc(F)c(Cl)c1)c1cncs1] | 396.0 | Ex. 33 | B | Free Base | N-({4-[(E/Z)-[(3-chloro-4-fluoro-phenyl)amino](hydroxy-imino)methyl]-1,2,5-oxadiazol-3-yl}-methyl)-1,3-thiazole-5-carboxamide |
| 117 | 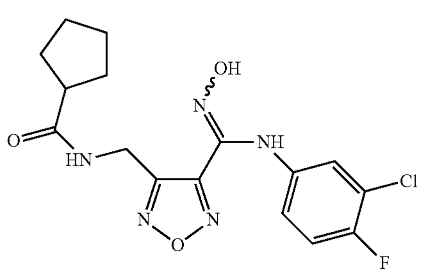 [SMILES: O=C(NCc1nonc1C(=NO)Nc1ccc(F)c(Cl)c1)C1CCCC1] | 381.1 | Ex. 33 | B | Free Base | N-({4-[(E/Z)-[(3-chloro-4-fluoro-phenyl)amino](hydroxy-imino)methyl]-1,2,5-oxadiazol-3-yl}-methyl)cyclopentane-carboxamide |

TABLE 2-continued

| Ex. No. | Structure | MS (M + 1) | Prep. Ex. | Pur. Meth. | Salt | Name |
|---|---|---|---|---|---|---|
| 118 | 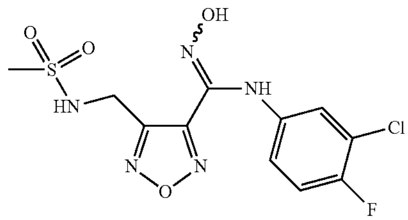 [SMILES: CS(=O)(=O)NCc1nonc1C(=NO)Nc1ccc(F)c(Cl)c1] | 363.0 | Ex. 35 | B | Free Base | N-(3-chloro-4-fluoro-phenyl)-N'-hydroxy-4-{[(methylsulfonyl)amino]-methyl}-1,2,5-oxadiazole-3-carboximidamide |
| 119 | 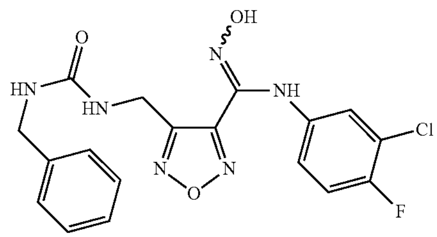 [SMILES: O=C(NCc1ccccc1)NCc1nonc1C(=NO)Nc1ccc(F)c(Cl)c1] | 418.1 | Ex. 34 | B | Free Base | 4-({[(benzylamino)-carbonyl]amino}-methyl)-N-(3-chloro-4-fluorophenyl)-N'-hydroxy-1,2,5-oxadiazole-3-carboximidamide |
| 120 | 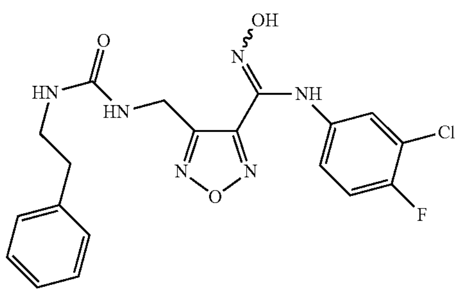 [SMILES: O=C(NCCc1ccccc1)NCc1nonc1C(=NO)Nc1ccc(F)c(Cl)c1] | 432.1 | Ex. 34 | B | Free Base | N-(3-chloro-4-fluoro-phenyl)-N'-hydroxy-4-[({[(2-phenylethyl)-amino]carbonyl}amino)-methyl]-1,2,5-oxadiazole-3-carboximidamide |
| 121 | 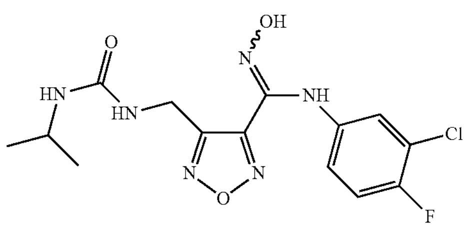 [SMILES: CC(C)NC(=O)NCc1nonc1C(=NO)Nc1ccc(F)c(Cl)c1] | 370.1 | Ex. 34 | B | Free Base | N-(3-chloro-4-fluoro-phenyl)-N'-hydroxy-4-({[(isopropylamino)-carbonyl]-amino}methyl)-1,2,5-oxadiazole-3-carboximidamide |
| 122 | 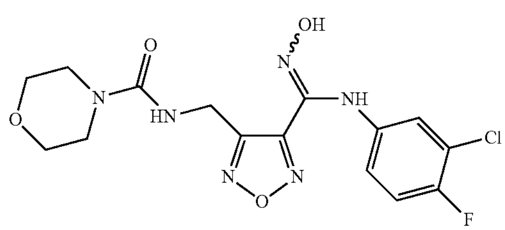 [SMILES: O=C(NCc1nonc1C(=NO)Nc1ccc(F)c(Cl)c1)N1CCOCC1] | 398.1 | Ex. 34 | B | Free Base | N-({4-[(E/Z)-[(3-chloro-4-fluoro-phenyl)amino](hydroxy-imino)methyl]-1,2,5-oxadiazol-3-yl}-methyl)morpholine-4-carboxamide |
| 123 | 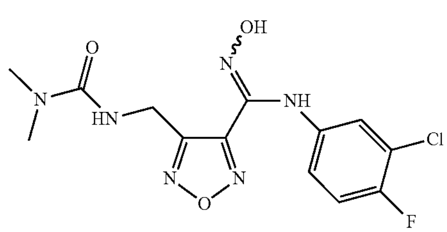 | 356.1 | Ex. 34 | B | Free Base | N-(3-chloro-4-fluoro-phenyl)-4-({[(dimeth-ylamino)carbonyl]amino]-methyl)-N'-hydroxy-1,2,5-oxa-diazole-3-carboximidamide |

TABLE 2-continued

| Ex. No. | Structure | MS (M + 1) | Prep. Ex. | Pur. Meth. | Salt | Name |
|---|---|---|---|---|---|---|
| 124 | 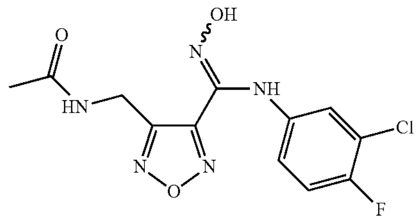 [SMILES: CC(=O)NCc1nonc1C(=NO)Nc1ccc(F)c(Cl)c1] | 327.1 | Ex. 33 | B | Free Base | N-({4-[(E/Z)-[(3-chloro-4-fluoro-phenyl)amino](hydroxy-imino)methyl]-1,2,5-oxadiazol-3-yl}-methyl)acetamide |
| 125 | 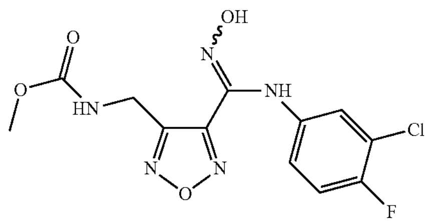 [SMILES: COC(=O)NCc1nonc1C(=NO)Nc1ccc(F)c(Cl)c1] | 343.0 | Ex. 36 | B | Free Base | methyl ({4-[(E/Z)-[(3-chloro-4-fluoro-phenyl)amino](hydroxy-imino)methyl]-1,2,5-oxadiazol-3-yl]-methyl)carbamate |
| 126 | 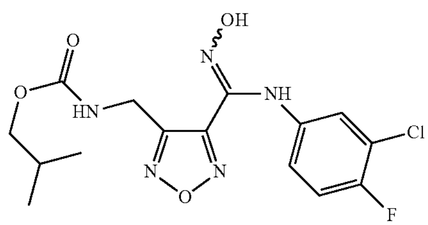 [SMILES: CC(C)COC(=O)NCc1nonc1C(=NO)Nc1ccc(F)c(Cl)c1] | 385.1 | Ex. 36 | B | Free Base | isobutyl ({4-[(E/Z)-[(3-chloro-4-fluoro-phenyl)amino](hydroxy-imino)methyl]-1,2,5-oxadiazol-3-yl}-methyl)carbamate |
| 127 | 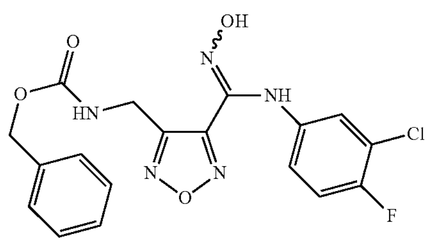 [SMILES: O=C(NCc1nonc1C(=NO)Nc1ccc(F)c(Cl)c1)OCc1ccccc1] | 419.1 | Ex. 36 | B | Free Base | benzyl ({4-[(E/Z)-[(3-chloro-4-fluoro-phenyl)amino](hydroxy-imino)methyl]-1,2,5-oxadiazol-3-yl}-methyl)carbamate |
| 128 | 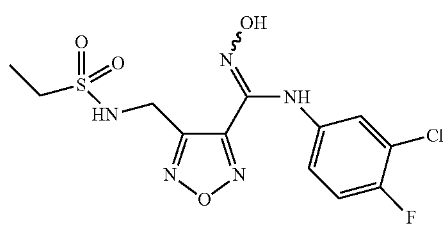 [SMILES: CCS(=O)(=O)NCc1nonc1C(=NO)Nc1ccc(F)c(Cl)c1] | 377.0 | Ex. 35 | B | Free Base | N-(3-chloro-4-fluoro-phenyl)-4-{[(ethyl-sulfonyl)amino]methyl}-N'-hydroxy-1,2,5-oxadiazole-3-carboximidamide |
| 129 | 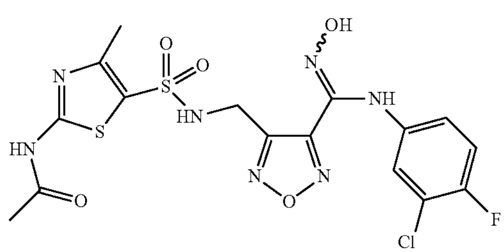 [SMILES: CC(=O)Nc1nc(C)c(S(=O)(=O)NCc2nonc2C(=NO)Nc2ccc(F)c(Cl)c2)s1] | 503.0 | Ex. 35 | B | Free Base | N-(5-{[({4-[(E/Z)-[(3-chloro-4-fluoro-phenyl)amino](hydroxy-imino)methyl-oxadiazol-3-yl}-methyl)amino]sulfonyl}-4-methyl-1,3-thiazol-2-yl)acetamide |

TABLE 2-continued

| Ex. No. | Structure | MS (M + 1) | Prep. Ex. | Pur. Meth. | Salt | Name |
|---|---|---|---|---|---|---|
| 130 | 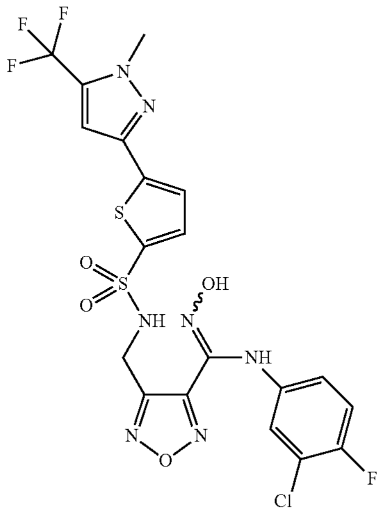 [SMILES: Cn1nc(-c2ccc(S(=O)(=O)NCc3nonc3C(=NO)Nc3ccc(F)c(Cl)c3)s2)cc1C(F)(F)F] | 579.0 | Ex. 35 | B | Free Base | N-(3-chloro-4-fluoro-phenyl)-N'-hydroxy-4-{[({5-[1-methyl-5-(tri-fluoromethyl)-1H-pyrazol-3-yl]-2-thienyl}sulfonyl)-amino]methyl}-1,2,5-oxadiazole-3-carboximidamide |
| 131 | 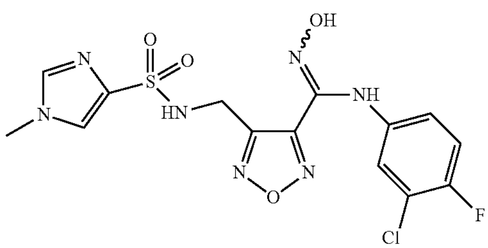 [SMILES: Cn1cnc(S(=O)(=O)NCc2nonc2C(=NO)Nc2ccc(F)c(Cl)c2)c1] | 429.0 | Ex. 35 | B | Free Base | N-(3-chloro-4-fluoro-phenyl)-N'-hydroxy-4-({[(1-methyl-1H-imidazol-4-yl)-sulfonyl]amino}-methyl)-1,2,5-oxadiazole-3-carboximidamide |
| 132 | 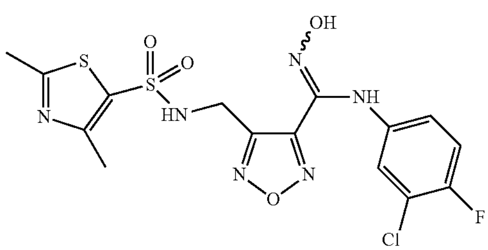 [SMILES: Cc1nc(C)c(S(=O)(=O)NCc2nonc2C(=NO)Nc2ccc(F)c(Cl)c2)s1] | 460.0 | Ex. 35 | B | Free Base | N-(3-chloro-4-fluoro-phenyl)-4-({[(2,4-dimethyl-1,3-thiazol-5-yl)sulfonyl]-amino}methyl)-N'-hydroxy-1,2,5-oxadiazole-3-carboximidamide |
| 133 | 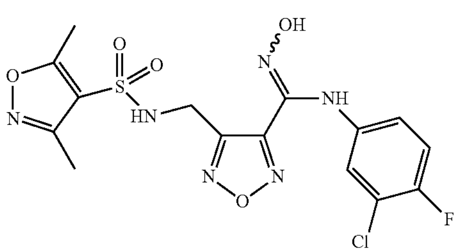 [SMILES: Cc1noc(C)c1S(=O)(=O)NCc1nonc1C(=NO)Nc1ccc(F)c(Cl)c1] | 444.0 | Ex. 35 | B | Free Base | N-(3-chloro-4-fluoro-phenyl)-4-({[(3,5-dimethylisoxazol-4-yl)sulfonyl]amino}-methyl)-N'-hydroxy-1,2,5-oxadiazole-3-carboximidamide |
| 134 | 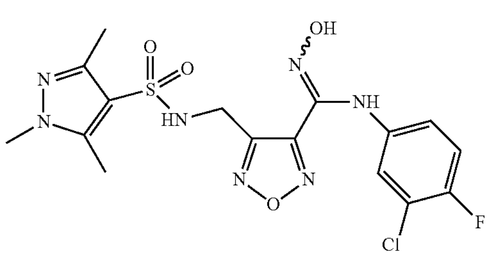 [SMILES: Cc1nn(C)c(C)c1S(=O)(=O)NCc1nonc1C(=NO)Nc1ccc(F)c(Cl)c1] | 457.1 | Ex. 35 | B | Free Base | N-(3-chloro-4-fluoro-phenyl)-N'-hydroxy-4-({[(1,3,5-trimethyl-1H-pyrazol-4-yl)-sulfonyl]amino}methyl)-1,2,5-oxadiazole-3-carboximidamide |

TABLE 2-continued

| Ex. No. | Structure | MS (M + 1) | Prep. Ex. | Pur. Meth. | Salt | Name |
|---|---|---|---|---|---|---|
| 135 | 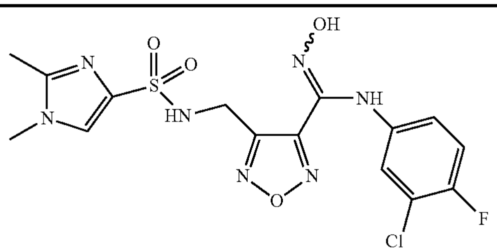 | 443.1 | Ex. 35 | B | Free Base | N-(3-chloro-4-fluoro-phenyl)-4-({[(1,2-di-methyl-1H-imidazol-4-yl)sulfonyl]amino}-methyl)-N'-hydroxy-1,2,5-oxadiazole-3-carboximidamide |
| 136 | 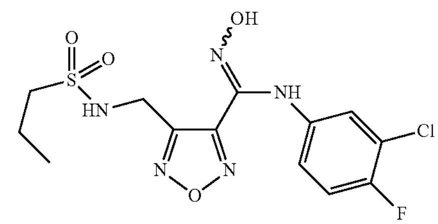 [SMILES: CCCS(=O)(=O)NCc1nonc1C(=NO)Nc1ccc(F)c(Cl)c1] | 391.1 | Ex. 35 | B | Free Base | N-(3-chloro-4-fluoro-phenyl)-N'-hydroxy-4-{[(propylsulfonyl)-amino]methyl}-1,2,5-oxadiazole-3-carboximidamide |
| 137 | 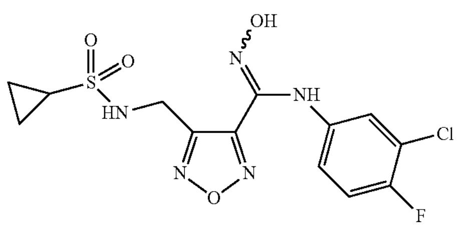 [SMILES: O=S(=O)(NCc1nonc1C(=NO)Nc1ccc(F)c(Cl)c1)C1CC1] | 389.0 | Ex. 35 | B | Free Base | N-(3-chloro-4-fluoro-phenyl)-4-{[(cyclo-propylsulfonyl)amino]-methyl}-N'-hydroxy-1,2,5-oxadiazole-3-carboximidamide |
| 138 | 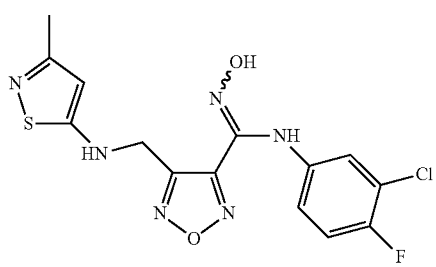 [SMILES: Cc1cc(NCc2nonc2C(=NO)Nc2ccc(F)c(Cl)c2)sn1] | 382.0 | Ex. 4 | B | Free Base | N-(3-chloro-4-fluoro-phenyl)-N'-hydroxy-4-{[(3-methylisothiazol-5-yl)amino]methyl}-1,2,5-oxadiazole-3-carboximidamide |

Example 139

Ethyl 3-(4-(N-(3-chloro-4-fluorophenyl)-N'-hydrox-yearbamimidoyl)-1,2,5-oxadiazol-3-yl)propanoate

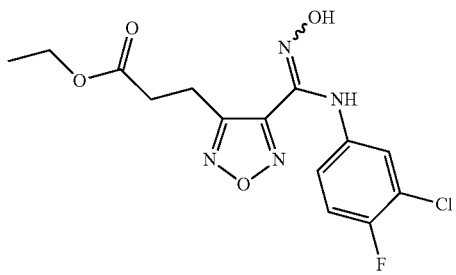 [SMILES: CCOC(=O)CCc1nonc1C(=NO)Nc1ccc(F)c(Cl)c1]

Step 1: N-(3-Chloro-4-fluorophenyl)-4-formyl-1,2,5-oxadiazole-3-carboxamide

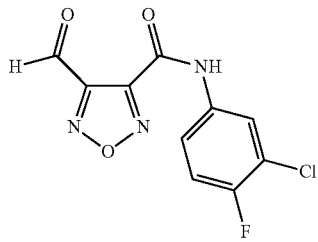 [SMILES: O=Cc1nonc1C(=O)Nc1ccc(F)c(Cl)c1]

A solution of N-(3-chloro-4-fluorophenyl)-4-(hydroxym-ethyl)-1,2,5-oxadiazole-3-carboxamide (8.50 g, 31.3 mmol) and Dess-Martin periodinane (14.6 g, 34.4 mmol) in DCM (400 mL) was stirred at 25° C. for 3 h. The reaction was diluted with saturated sodium bicarbonate solution and extracted with ethyl acetate three times, dried with sodium sulfate, filtered, and concentrated in vacuo. The crude residue was purified by flash column chromatography to yield the desired product (7.50 g, 89%). LCMS for $C_{10}H_6ClFN_3O_3$ (M+H)$^+$: m/z=270.0.

Step 2: Ethyl (2E)-3-(4-[(3-chloro-4-fluorophenyl) amino]carbonyl-1,2,5-oxadiazol-3-yl)acrylate

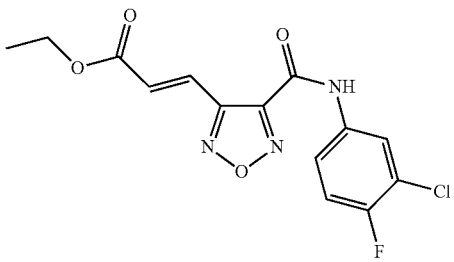 [SMILES: CCOC(=O)/C=C/c1nonc1C(=O)Nc1ccc(F)c(Cl)c1]

To a solution of (carbethoxymethyl)triphenylphosphonium bromide (3.14 g, 7.32 mmol) in toluene (37 mL) was added sodium tert-butoxide (723 mg, 7.52 mmol) at rt under a nitrogen atmosphere. After stirring for 30 min, a solution of N-(3-chloro-4-fluorophenyl)-4-formyl-1,2,5-oxadiazole-3-carboxamide (811 mg, 3.01 mmol) in THF (10 mL) was cannulated into reaction flask. The resulting solution was heated at 80° C. for 3 h, then cooled to rt overnight. The reaction was quenched with a 1 N HCl solution, the aqueous solution was then extracted with ethyl acetate. The combined organic solutions were washed with brine, dried over $Na_2SO_4$, filtered and concentrated under reduced pressure. The residue was purified with flash chromatography (30% ethyl acetate/hexane) to give the desired product as a white solid. $^1$H NMR (400 MHz, CD$_3$OD): δ 7.92 (m, 2 H), 7.65 (m, 1 H), 7.26 (m, 1H), 7.01 (m, 1 H), 4.27 (m, 2 H), 1.33 (m, 3 H); LCMS for $C_{14}H_{12}ClFN_3O_4$(M+H)$^+$: m/z=340.

Step 3: Ethyl 3-(4-[(3-chloro-4-fluorophenyl)amino] carbonyl-1,2,5-oxadiazol-3-yl)propanoate

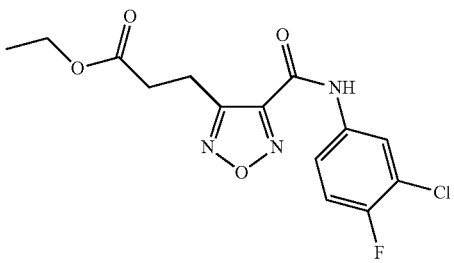 [SMILES: CCOC(=O)CCc1nonc1C(=O)Nc1ccc(F)c(Cl)c1]

To a solution of ethyl (2E)-3-(4-[(3-chloro-4-fluorophenyl)amino]carbonyl-1,2,5-oxadiazol-3-yl)acrylate (0.86 g, 0.0025 mol) in ethyl acetate (10 mL, 0.1 mol) was added palladium (600 mg, 0.006 mol). The mixture was stirred at rt under an atmosphere of hydrogen for 2 h. The reaction solution was filtered through a pad of celite. The filtrate was concentrated and purified by flash chromatography (40% ethyl acetate/hexane) to give the desired product as a white solid (609 mg, 70%). LCMS for $C_{14}H_{14}ClFN_3O_4$(M+H)$^+$: m/z=342.1.

Step 4: Ethyl 3-4-[(Z)-[(3-chloro-4-fluorophenyl) amino] (hydroxyimino)methyl]-1,2,5-oxadiazol-3-ylpropanoate Ethyl 3-(4-[(3-chloro-4-fluorophenypamino]carbonyl-1,2,5-oxadiazol-3-yl)-propanoate (27 mg, 0.079 mmol) was suspended in benzene (1 mL) under a nitrogen atmosphere, and phosphorus pentachloride (18.0 mg, 0.086 mmol) was added and the solution was heated to reflux for 2.5 h. The solvent was removed in vacuo. The residue was dissolved in EtOH (1.0 mL) and hydroxylamine (100 μL, 2 mmol) (50% solution in water) was added to the reaction. After stirring 1 h, the solution was diluted with MeOH and purified with preparative LCMS to give the desired product (8.5 mg, 30%). $^1$H NMR (400 MHz, CD$_3$OD): δ 7.03 (t, J=8.9 Hz, 1 H), 6.95 (dd, J=6.4, 2,7 Hz, 1 H), 6.71 (m, 1 H), 4.12 (q, J=7.2 Hz, 2 H), 3.11 (t, J=7.2 Hz, 2 H), 2.80 (t, J=7.2 Hz, 2 H), 1.23 (t, J=7.2 Hz, 3 H); LCMS for $C_{14}H_{15}ClFN_4O_4$(M+H)$^+$: m/z=357.1.

Example 140

N-(3-Chloro-4-fluorophenyl)-N'-hydroxy-4-(3-morpholin-4-ylpropyl)-1,2,5-oxadiazole-3-carboximidamide

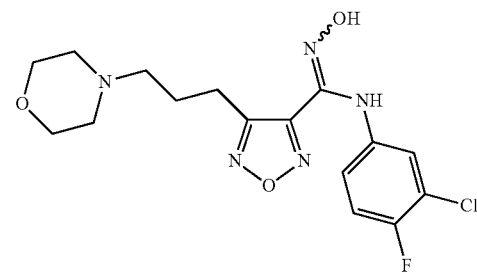 [SMILES: ON=C(Nc1ccc(F)c(Cl)c1)c1nonc1CCCN1CCOCC1]

Step 1: N-(3-Chloro-4-fluorophenyl)-4-(3-hydroxypropyl)-1,2,5-oxadiazole-3-carboxamide

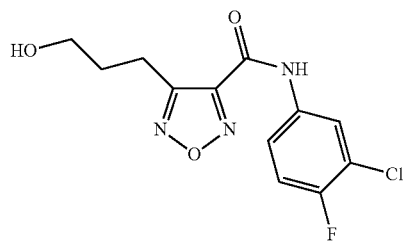 [SMILES: O=C(Nc1ccc(F)c(Cl)c1)c1nonc1CCCO]

To a solution of ethyl 3-(4-[(3-chloro-4-fluorophenyl) amino]carbonyl-1,2,5-oxadiazol-3-yl)propanoate (97.5 mg, 0.285 mmol) in THF (1.2 mL) was added lithium tetrahydroborate (14.3 mg, 0.656 mmol) at 0° C. under an atmosphere of nitrogen. The reaction solution was allowed to warm to rt for 2 h. The reaction was quenched with MeOH and concentrated. The residue was purified by flash chromatography (60% ethyl acetate/hexane) to give product. LCMS for $C_{12}H_{12}ClFN_3O_3(M+H)^+$: m/z=300.1.

Step 2: 3-(4-[3-Chloro-4-fluorophenyl)amino]carbonyl-1,2,5-oxadiazol-3-yl)propyl methanesulfonate

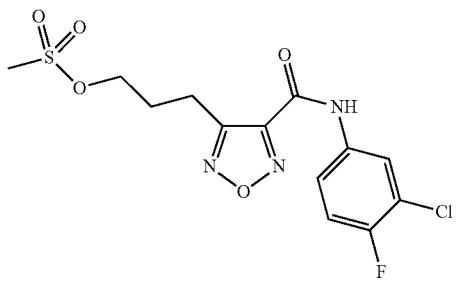 [SMILES: CS(=O)(=O)OCCCc1nonc1C(=O)Nc1ccc(F)c(Cl)c1]

N-(3-Chloro-4-fluorophenyl)-4-(3-hydroxypropyl)-1,2,5-oxadiazole-3-carboxamide (60 mg, 0.20 mmol) was dissolved in anhydrous DCM (2 mL), followed by addition of TEA (57 μL, 0.41 mmol). The reaction was stirred and cooled to 0° C., and then methanesulfonyl chloride (29 μL, 0.37 mmol) was added dropwise. The reaction was quenched with water and diluted with DCM. The organic solution was separated, dried over $Na_2SO_4$, filtered, concentrated and purified by silica gel chromatography (25%-70% EtOAc/hexane) to give the desired product (19 mg). LCMS for $C_{13}H_{14}ClFN_3O_5S(M+H)^+$: m/z=378.

Step 3: N-(3-Chloro-4-fluorophenyl)-4-(3-morpholin-4-ylpropyl)-1,2,5-oxadiazole-3-carboxamide

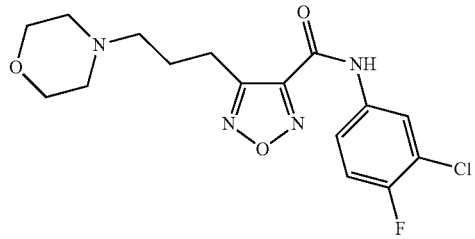 [SMILES: O=C(Nc1ccc(F)c(Cl)c1)c1nonc1CCCN1CCOCC1]

3-(4-[(3-Chloro-4-fluorophenyl)amino]carbonyl-1,2,5-oxadiazol-3-yl)propylmethanesulfonate (19 mg, 0.051 mmol) was dissolved in anhydrous ACN (100 μL) followed by addition of DIPEA (44 μL, 0.26 mmol) and morpholine (6.7 μL, 76.8 μmol). The reaction was stirred and heated at 70° C. for 3 h. The reaction was concentrated and purified with silica gel chromatography (60-100% ethyl acetate/hex) to give the desired product (10 mg, 54%). LCMS for $C_{16}H_{19}ClFN_4O_3(M+H)^+$: m/z=369.1.

Step 4: N-(3-Chloro-4-fluorophenyl)-N'-hydroxy-4-(3-morpholin-4-ylpropyl)-1,2,5-oxadiazole-3-carboximidamide N-(3-Chloro-4-fluorophenyl)-4-(3-morpholin-4-ylpropyl)-1,2,5-oxadiazole-3-carboxamide (10.0 mg, 27.1 μmol) was suspended in benzene (0.4 mL) under a nitrogen atmosphere and phosphorus pentachloride (6.2 mg, 29.8 μmol) was added and the solution was heated at reflux for 2.5 h. The reaction was then stripped to dryness in vacuo. The reaction was dissolved in EtOH (0.3 mL) and hydroxylamine (40 μL, 0.7 mmol) (50% solution in water) was added to the reaction. After stirring for 1 h, the reaction solution was diluted with MeOH and purified with preparative LCMS to give product (5.2 mg, 50%). LCMS for $C_{16}H_{20}ClFN_5O_3(M+H)^+$: m/z=384.1.

Example 141

5-[(5-Amino-1H-tetrazol-1-yl)methyl]-N-(3-chloro-4-fluorophenyl)-N'-hydroxy-1,2,3-thiadiazole-4-carboximidamide

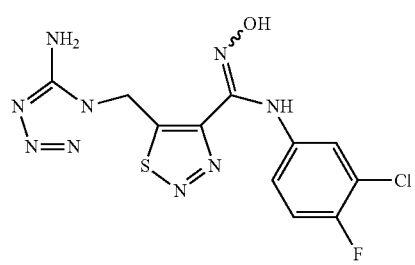 [SMILES: N=N/N=C(/N)NCc1snnc1C(=NO)Nc1ccc(F)c(Cl)c1]

Step A: Methyl 2-diazo-4-methoxy-3-oxobutanoate

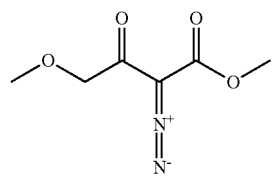

Methyl 4-methoxy-3-oxobutanoate (4.28 g, 0.029 mol) was dissolved in ether (20 mL). The solution was cooled in an ice bath. To the solution was added p-toluenesulfonyl azide (5.78 g, 0.029 mol) followed by N-ethylethanamine (2.0 mL, 0.019 mol). The solution was stirred at 0° C. for 15 minutes, then at rt for 30 minutes. Upon evaporation, the tosyl amide bi-product solidified. This was filtered off and the filtrate was purified by flash chromatography to give the desired product (4.5 g, 89%) as a light oil. $^1$H NMR (400 MHz, $CDCl_3$): δ 4.55 (s, 2H), 3.83 (s, 3H), 3.45 (s, 3H). MF $C_6H_8N_2O_4$. LCMS calculated for $C_6H_9N_2O_4(M+H)^+$: m/z=173.0.

Step B: Methyl 5-(methoxymethyl)-1,2,3-thiadiazole-4-carboxylate

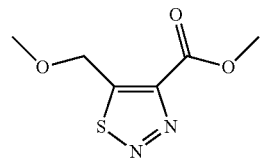

Methyl 2-diazo-4-methoxy-3-oxobutanoate (4.5 g, 0.026 mol) was cooled in an ice bath and ammonium sulfide (8.0 g, 0.12 mol) (40-48%) was added drop-wise over 2 minutes. White precipitate formed. The slurry was stirred for 30 minutes, and then purified by flash chromatography to give the desired product (4.2 g, 85%) as a light oil, that crystallized readily upon standing. $^1$H NMR (400 MHz, CD$_3$OD): δ 5.02 (s, 2H), 3.98 (s, 3H), 3.57 (s, 3H). MF=C$_6$H$_8$N$_2$O$_3$S; LCMS calculated for C$_6$H$_9$N$_2$O$_3$S (M+H)$^+$: m/z=189.0.

Step C: Methyl 5-formyl-1,2,3-thiadiazole-4-carboxylate

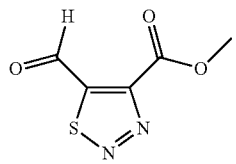

Methyl 5-(methoxymethyl)-1,2,3-thiadiazole-4-carboxylate (4.18 g, 0.022 mol) was dissolved in carbon tetrachloride (60 mL). To the solution was added bromine (4.18 g, 0.026 mol) and the solution was refluxed upon irradiation with long wavelength UV light (100 watts) for 3 h. The volatiles were evaporated in vacuo and the crude material purified by flash chromatography to give the desired product (2.70 g, 71%) as a viscous oil. $^1$H NMR (400 MHz, CDCl$_3$): δ 10.67 (s, 1H), 4.15 (s, 3H). MF=C$_5$H$_4$N$_2$O$_3$S; LCMS calculated for C$_5$H$_5$N$_2$O$_3$S (M+H)$^+$: m/z=173.0.

Step D: Methyl 5-(hydroxymethyl)-1,2,3-thiadiazole-4-carboxylate

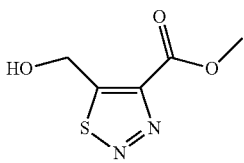

Methyl 5-formyl-1,2,3-thiadiazole-4-carboxylate (460.0 mg, 0.0026 mol) was dissolved in ethanol (40 mL) and sodium tetrahydroborate (50 mg, 0.0013 mol) was added at 0° C. The orange solution was allowed to warm to room temp and was stirred for 30 minutes. The reaction was quenched with acetic acid and then purified by preparative LCMS to give the desired product (340 mg, 73%). MF=C$_5$H$_6$N$_2$O$_3$S; LCMS calculated for C$_5$H$_7$N$_2$O$_3$S (M+H)$^+$: m/z=175.1.

Step E: Methyl 5-[(triisopropylsilyl)oxy]methyl-1,2,3-thiadiazole-4-carboxylate

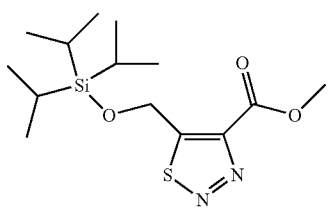 [SMILES: COC(=O)c1nnsc1CO[Si](C(C)C)(C(C)C)C(C)C]

To a solution of methyl 5-(hydroxymethyl)-1,2,3-thiadiazole-4-carboxylate (1.22 g, 0.007 mol) in DCM (20 mL) at 0° C. was added 2,6-lutidine (2.0 mL, 0.018 mol) followed by triisopropylsilyl triflate (2.4 mL, 0.0091 mol). The solution was stirred at 0° C. for 5 minutes. The reaction was then concentrated and purified by flash chromatography to give the desired product (2.0 g, 87%). $^1$H NMR (400 MHz, CDCl$_3$): δ; MF=C$_{14}$H$_{26}$N$_2$O$_3$SSi; LCMS calculated for C$_{14}$H$_{27}$N$_2$O$_3$SSi (M+H)$^+$: m/z 331.1.

Step F: N-(3-chloro-4-fluorophenyl)-5-[(triisopropylsilyl)oxy]methyl-1,2,3-thiadiazole-4-carboxamide

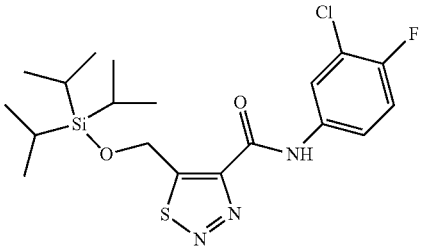 [SMILES: CC(C)[Si](OCc1snnc1C(=O)Nc1ccc(F)c(Cl)c1)(C(C)C)C(C)C]

To a cooled solution (0° C.) of methyl 5-[(triisopropylsilyl)oxy]methyl-1,2,3-thiadiazole-4-carboxylate (2.2 g, 0.0066 mol) and 3-chloro-4-fluoroaniline (1.5 g, 0.010 mol) in DCM (20 mL, 0.4 mol) was added 2.0 M of trimethylaluminum in hexane (12 mL) under nitrogen and stirred for 15 minutes. The volatiles were removed in vacuo and the crude was purified by flash chromatography to give the desired product (2.3 g, 78%). MF=C$_{19}$H$_{27}$ClFN$_3$O$_2$SSi; LCMS calculated for C$_{19}$H$_{28}$ClFN$_3$O$_2$SSi (M+H)$^+$: m/z=444.1.

Step G: N-(3-chloro-4-fluorophenyl)-5-[(triisopropylsilyl)oxy]methyl-1,2,3-thiadiazole-4-carbothioamide

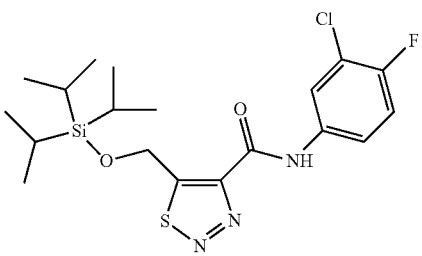 [SMILES: CC(C)[Si](OCc1snnc1C(=O)Nc1ccc(F)c(Cl)c1)(C(C)C)C(C)C]

A solution of N-(3-chloro-4-fluorophenyl)-5-[(triisopropylsilyl)oxy]methyl-1,2,3-thiadiazole-4-carboxamide (2.3 g, 0.0052 mol) in anhydrous THF (10 mL) was distributed equally into 2 microwave vials. 2,4-bis(4-methoxyphenyl)-2,4-dithioxo-1,3,2,4-dithiadiphosphetane (4.2 g, 0.010 mol) (Lawesson's reagent) was added to each vial. The reactions were each heated at 160° C. in a microwave for 15 minutes. The solutions were combined, concentrated and purified by flash chromatography to give the desired product (1.80 g, 76%). MF=C$_{19}$H$_{27}$ClFN$_3$OS$_2$Si; LCMS calculated for C$_{19}$H$_{28}$ClFN$_3$OS$_2$Si (M+H)$^+$: m/z=460.1.

Step H: Methyl N-(3-chloro-4-fluorophenyl)-5-[(triisopropylsilyl)oxy]methyl-1,2,3-thiadiazole-4-carbimidothioate

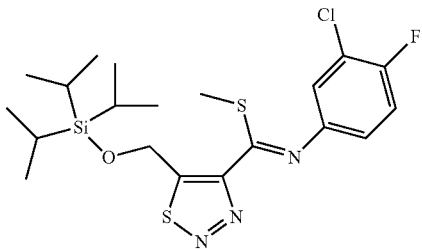 [SMILES: CS/C(=N\c1ccc(F)c(Cl)c1)c1nnsc1CO[Si](C(C)C)(C(C)C)C(C)C]

To a solution of N-(3-chloro-4-fluorophenyl)-5-[(triisopropylsilyl)oxy]methyl-1,2,3-thia-diazole-4-carbothioamide (0.18 g, 0.00039 mol) in anhydrous DCM (3 mL, 0.04 mol) under $N_2$ was added DIPEA (82 μL, 0.00047 mol) followed by methyl trifluoromethanesulfonate (47 μL, 0.00043 mol). The reaction was stirred for 5 minutes and then concentrated in vacuo. The crude material was used in the next step. The product amount was estimated (185 mg, 100%). MF=$C_{20}H_{29}ClFN_3OS_2Si$; LCMS calculated for $C_{20}H_{30}ClFN_3OS_2Si$ (M+H)$^+$: m/z=474.1.

Step I: N-(3-chloro-4-fluorophenyl)-N'-hydroxy-5-[(triisopropylsilyl)oxy]methyl-1,2,3-thiadiazole-4-carboximidamide

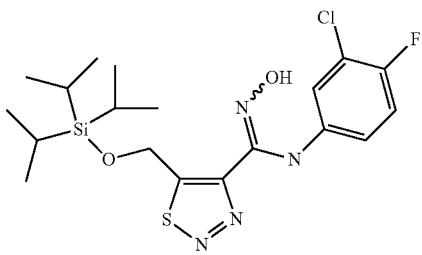 [SMILES: CC(C)[Si](OCc1snnc1C(=NO)Nc1ccc(F)c(Cl)c1)(C(C)C)C(C)C]

Methyl N-(3-chloro-4-fluorophenyl)-5-[(triisopropylsilyl)oxy]methyl-1,2,3-thiadiazole-4-carbimidothioate (90 mg, 0.0002 mol) was dissolved in EtOH (2 mL) followed by addition of hydroxylamine (116 μL, 0.00190 mol) (50% by wt, 99.9% in water solution). The reaction was stirred at 60° C. for 4 h and overnight at room temperature. The reaction was evaporated and purified by flash chromatography to give the desired product (85 mg, 98%). $^1$H NMR (400 MHz, CDCl$_3$): δ 7.32 (s, 1H), 7.25 (s, 1H), 6.90 (m, 2H), 6.62 (m, 2H), 5.17 (s, 2H), 1.05 (m, 21H). MF=$C_{19}H_{28}ClFN_4O_2SSi$; LCMS calculated for $C_{19}H_{29}ClFN_4O_2SSi$ (M+H)$^+$: m/z=459.2.

Step J: 4-(3-Chloro-4-fluorophenyl)-3-(5-[(triisopropylsilyl)oxy]methyl-1,2,3-thiadiazol-4-yl)-1,2,4-oxadiazol-5(4H)-one

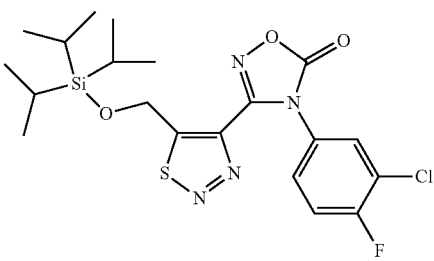 [SMILES: CC(C)[Si](OCc1snnc1-c1noc(=O)n1-c1ccc(F)c(Cl)c1)(C(C)C)C(C)C]

Into a round bottom flask was added N-(3-chloro-4-fluorophenyl)-N'-hydroxy-5-[(triisopropylsilyl)oxy]methyl-1,2,3-thiadiazole-4-carboximidamide (85.0 mg, 0.185 mmol), anhydrous THF (1.1 mL), and N,N-carbonyldiimidazole (55 mg, 0.34 mmol). The reaction was heated to 70° C. for 2.5 h. The reaction was concentrated in vacuo and the crude purified by flash chromatography to give the desired product (89 mg, 99%). MF=$C_{20}H_{26}ClFN_4O_3SSi$; LCMS calculated for $C_{20}H_{27}ClFN_4O_3S$ Si (M+H)$^+$: m/z=485.2.

Step K: 4-(3-Chloro-4-fluorophenyl)-3-[5-(hydroxymethyl)-1,2,3-thiadiazol-4-yl]-1,2,4-oxadiazol-5(4H)-one

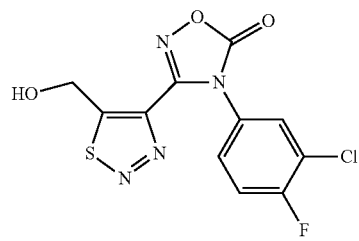 [SMILES: O=c1onc(-c2nnsc2CO)n1-c1ccc(F)c(Cl)c1]

Into a round bottom flask was added 4-(3-chloro-4-fluorophenyl)-3-(5-[(triisopropylsilyl)-oxy]methyl-1,2,3-thiadiazol-4-yl)-1,2,4-oxadiazol-5(4H)-one (89 mg, 0.18 mmol), anhydrous MeOH (1.5 mL), and hydrogen chloride in 1,4-dioxane (1.5 mL, 4.0 M). The reaction was heated to 70° C. for 2.5 h. The reaction was concentrated in vacuo and the crude purified by flash chromatography to give the desired product (52 mg, 86%). MF=$C_{11}H_6ClFN_4O_3S$; LCMS calculated for $C_{11}H_7ClFN_4O_3S$ (M+H)$^+$: m/z=329.0.

Step L: 4-[4-(3-Chloro-4-fluorophenyl)-5-oxo-4,5-dihydro-1,2,4-oxadiazol-3-yl]-1,2,3-thiadiazol-5-ylmethyl methanesulfonate

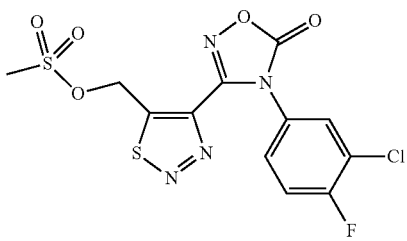 [SMILES: CS(=O)(=O)OCc1snnc1-c1noc(=O)n1-c1ccc(F)c(Cl)c1]

4-(3-Chloro-4-fluorophenyl)-3-[5-(hydroxymethyl)-1,2,3-thiadiazol-4-yl]-1,2,4-oxadiazol-5(4H)-one was dissolved in anhydrous DCM (2 mL) followed by addition of TEA (26 μL, 0.19 mmol). The reaction was stirred at 0° C. for 15 minutes. Methanesulfonyl chloride (13 μL, 0.17 mmol) was added drop-wise and stirred for 15 minutes at 0° C. The reaction was concentrated in vacuo and the crude purified by flash chromatography to give the desired product (42 mg, 65%). $^1$H NMR (400 MHz, CDCl$_3$): δ 7.50 (m, 1H), 7.25 (m, 2H), 5.83 (s, 2H), 3.20 (s, 3H). MF $C_{12}H_8ClFN_4O_5S_2$; LCMS calculated for $C_{12}H_9ClFN_4O_5S_2$(M+H)$^+$: m/z=406.9.

Step M: 3-5-[(5-Amino-1H-tetrazol-1-yl)methyl]-1,
2,3-thiadiazol-4-yl-4-(3-chloro-4-fluorophenyl)-1,2,
4-oxadiazol-5(4H)-one trifluoroacetate

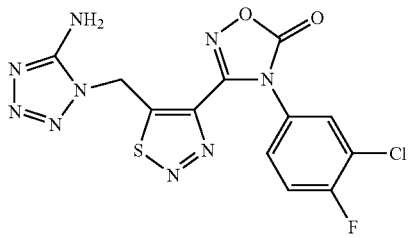 [SMILES: Nc1nnnn1Cc1snnc1-c1noc(=O)n1-c1ccc(F)c(Cl)c1]

4-[4-(3-Chloro-4-fluorophenyl)-5-oxo-4,5-dihydro-1,2,4-oxadiazol-3-yl]-1,2,3-thiadiazol-5-ylmethyl methanesulfonate (42 mg, 0.10 mmol) was dissolved in anhydrous ACN (100 μL) followed by addition of DIPEA (90 μL, 0.52 mmol) and 1H-tetrazol-5-amine (13 mg, 0.15 mmol). The reaction was stirred and heated at 40° C. for 2 hrs. The reaction was diluted with MeOH and purified by preparative HPLC to yield 2 isomers, the desired product is peak 1 (15 mg, 37%). $^1$H NMR (400 MHz, d$_6$-DMSO): δ☐ 8.0 (m, 1H), 7.67 (m, 2H), 6.98 (s, 2H), 5.80 (s, 2H). MF=$C_{12}H_7ClFN_9O_2S$; LCMS calculated for $C_{12}H_8ClFN_9O_2S$ (M+H)$^+$: m/z=396.0.

Step N: 5-[(5-Amino-1H-tetrazol-1-yl)methyl]-N-(3-chloro-4-fluorophenyl)-N'-hydroxy-1,2,3-thiadiazole-4-carboximidamide trifluoroacetate

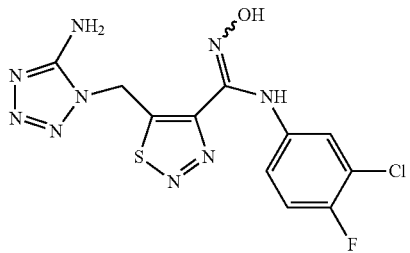 [SMILES: Nc1nnnn1Cc1snnc1C(=NO)Nc1ccc(F)c(Cl)c1]

To a solution of 3-5-[(5-amino-1H-tetrazol-1-yl)methyl]-1,2,3-thiadiazol-4-yl-4-(3-chloro-4-fluorophenyl)-1,2,4-oxadiazol-5(4H)-one in EtOH (400 μL, 0.006 mol) was added a solution of sodium hydroxide in water (76 μL, 2.0 M). After stirring for 2 h, the reaction was quenched with acetic acid and diluted with MeOH and purified by preparative LCMS to give the desired product as white powder, (9.9 mg, 71%). $^1$H NMR (400 MHz, d$_6$-DMSO): δ☐ 11.29 (s, 1H), 9.18 (s, 1H), 7.09 (m, 3H), 6.86 (m, 1H), 6.60 (m, 1H), 5.92 (s, 1H). MF=$C_{11}H_9ClFN_9OS$; LCMS calculated for $C_{11}H_{10}ClFN_9OS$ (M+H)$^+$: m/z=370.0.

Example 142

N-(3-Chloro-4-fluorophenyl)-N'-hydroxy-5-(hydroxymethyl)-1,2,3-thiadiazole-4-carboximidamide

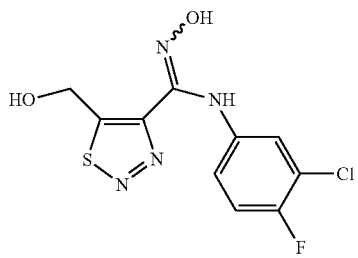 [SMILES: OCc1snnc1C(=NO)Nc1ccc(F)c(Cl)c1]

N-(3-Chloro-4-fluorophenyl)-N'-hydroxy-5-[(triisopropylsilyl)oxy]methyl-1,2,3-thiadiazole-4-carboximidamide (10.0 mg, 0.0218 mmol) was stirred in MeOH (500 μL) and hydrogen chloride in 1,4-dioxane (500 μL, 4.0 M) was added. The mixture was stirred for 30 min at rt. Purification by preparative LCMS gave the desired product (2.8 mg, 42%). $^1$H NMR (400 MHz, d$_6$-DMSO): δ☐ 11.00 (s, 1H), 8.99 (s, 1H), 7.09 (m, 1H), 6.82 (m, 1H), 6.53 (m, 1H), 5.92 (s, 1H), 4.95 (s, 1H). MF=$C_{10}H_8ClFN_4O_2S$; LCMS calculated for $C_{10}H_9ClFN_4O_2S$ (M+H)$^+$: m/z=303.0.

Example 143

4-[(Aminosulfonyl)amino]methyl-N-(3-chloro-4-fluorophenyl)-N'-hydroxy-1,2,5-oxadiazole-3-carboximidamide trifluoroacetate

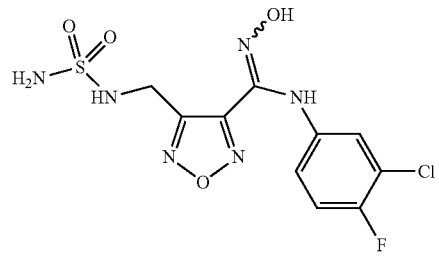 [SMILES: NS(=O)(=O)NCc1nonc1C(=NO)Nc1ccc(F)c(Cl)c1]

3-[4-(Aminomethyl)-1,2,5-oxadiazol-3-yl]-4-(3-chloro-4-fluorophenyl)-1,2,4-oxadiazol-5(4H)-one trifluoroacetate (30 mg, 0.07 mmol) and sulfamide (20 mg, 0.2 mmol) was dissolved in pyridine (1.0 mL) and heated at 120° C. for 3 min in a microwave. A solution of sodium hydroxide in water (0.5 mL, 1 N) was added and the solution was stirred for 30 minutes. Acidification with acetic acid and purification by preparative LCMS gave the desired product (17 mg, 50%). MF=$C_{10}H_{10}ClFN_6O_4S$; LCMS calculated for $C_{10}H_{11}ClFN_6O_4S$ (M+H)$^+$: m/z=364.9. $^1$H NMR (400 MHz, CD$_3$OD): δ 7.02 (m, 2H), 6.76 (m, 1H), 4.50 (s, 2H).

Example 144

N-(3-Chloro-4-fluorophenyl)-4-([[(E/Z)-(cyanoimino)(methylamino)methyl]-aminomethyl)-N'-hydroxy-1,2,5-oxadiazole-3-carboximidamide

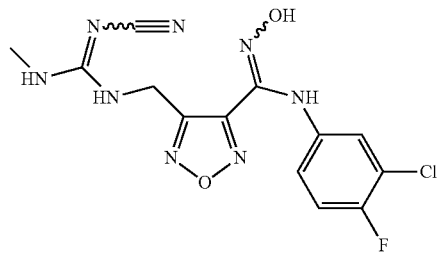 [SMILES: CNC(=NC#N)NCc1nonc1C(=NO)Nc1ccc(F)c(Cl)c1]

3-[4-(Aminomethyl)-1,2,5-oxadiazol-3-yl]-4-(3-chloro-4-fluorophenyl)-1,2,4-oxadiazol-5(4H)-one trifluoroacetate (50 mg, 0.1 mmol) was dissolved in THF (3.0 mL). Diphenyl cyanocarbonimidate (33.6 mg, 0.141 mmol) and TEA (49 μL, 0.35 mmol) were added. The reaction was stirred at room temperature for 2 h. A solution of methylamine in THF (0.6 mL, 2.0 M) was then added and the mixture stirred for 2 h at rt. 1.0 M of sodium hydroxide in water (1.7 mL) was added and the mixture stirred for 1 h at rt. Acidification with acetic acid and purification by preparative LCMS at pH 10 gave the desired product as a white powder, (27 mg, 63%). MF=$C_{13}H_{12}ClFN_8O_2$; LCMS calculated for $C_{13}H_{13}ClFN_8O_2$(M+H)$^+$: m/z=367.0. $^1$H NMR (400 MHz, CD$_3$OD): δ 7.01 (m, 2H), 6.75 (m, 1H), 4.66 (s, 2H), 2.83 (s, 3H).

Example 145

N-(3-Chloro-4-fluorophenyl)-N'-hydroxy-4-([(methylamino)sulfonyl]amino-methyl)-1,2,5-oxadiazole-3-carboximidamide trifluoroacetate

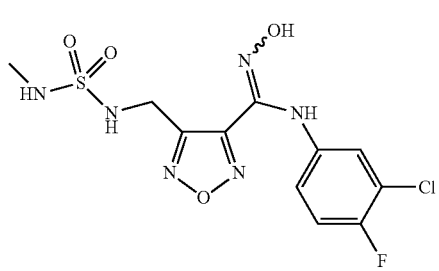 [SMILES: CNS(=O)(=O)NCc1nonc1C(=NO)Nc1ccc(F)c(Cl)c1]

Sulfamide (32 mg, 0.33 mmol) and methylamine (15 μL, 0.33 mmol) were dissolved in pyridine (1.0 mL). The solution was heated to 120° C. for 5 minutes in a microwave. 3-[4-(aminomethyl)-1,2,5-oxadiazol-3-yl]-4-(3-chloro-4-fluorophenyl)-1,2,4-oxadiazol-5(4H)-one trifluoroacetate (32 mg, 0.075 mmol) was than added and the solution was heated to 120° C. for 3 minutes. A solution of sodium hydroxide in water (1 mL, 1 N) was added and the solution stirred at room temperature for 30 minutes. Acidification with acetic acid and purification by preparative LCMS gave the desired product (2.3 mg, 7%). MF=$C_{11}H_{12}ClFN_6O_4S$; LCMS calculated for $C_{11}H_{13}ClFN_6O_4S$ (M+H)$^+$: m/z=378.9.

Example 146

4-[(Aminocarbonyl)amino]methyl-N-(3-chloro-4-fluorophenyl)-N'-hydroxy-1,2,5-oxadiazole-3-carboximidamide trifluoroacetate

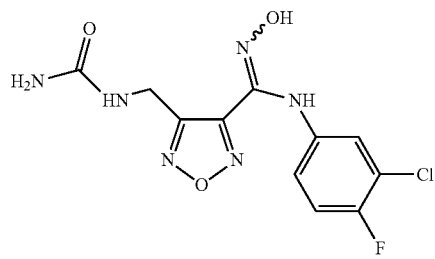 [SMILES: NC(=O)NCc1nonc1C(=NO)Nc1ccc(F)c(Cl)c1]

4-([(tert-Butylamino)carbonyl]aminomethyl)-N-(3-chloro-4-fluorophenyl)-N'-hydroxy-1,2,5-oxadiazole-3-carboximidamide trifluoroacetate (10 mg, 0.02 mmol) was stirred in TFA (2.0 mL) for 2 hrs. The reaction was warmed gently with heat gun. Evaporation and purification by preparative LCMS gave the desired product (8 mg, 70%). MF=$C_{11}H_{13}ClFN_6O_3$; LCMS calculated for $C_{11}H_{11}ClFN_6O_3$(M+H)$^+$: m/z=329.0. $^1$H NMR (400 MHz, CD$_3$OD): δ 7.01 (m, 2H), 6.85 (m, 1H), 4.59 (s, 2H).

Example 147

4-([(Tert-butylamino)carbonyl]aminomethyl)-N-(3-chloro-4-fluorophenyl)-N'-hydroxy-1,2,5-oxadiazole-3-carboximidamide trifluoroacetate

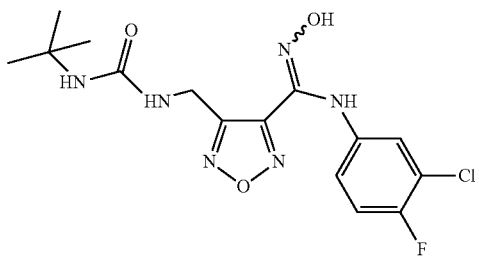 [SMILES: CC(C)(C)NC(=O)NCc1nonc1C(=NO)Nc1ccc(F)c(Cl)c1]

3-[4-(Aminomethyl)-1,2,5-oxadiazol-3-yl]-4-(3-chloro-4-fluorophenyl)-1,2,4-oxadiazol-5(4H)-one trifluoroacetate (15 mg, 0.035 mmol) and TEA (15 pt, 0.10 mmol) were dissolved in DCM (0.5 mL) and then 2-isocyanato-2-methylpropane (24 μL, 0.21 mmol) was added. The reaction was stirred for 16 h at room temperature. A solution of sodium hydroxide in water (0.50 mL, 1.0; N) was added and the mixture stirred at room temperature for 2 h. Acidification with acetic acid and purification by preparative LCMS gave the desired product (12 mg, 68%). MF=$C_{15}H_{18}ClFN_6O_3$; LCMS calculated for $C_{15}H_{19}ClFN_6O_3$ (M+H)$^+$: m/z=385.0.

Example 148

N-(3-Chloro-4-fluorophenyl)-N'-hydroxy-4-([(3-morpholin-4-ylpropyl)sulfonyl]-aminomethyl)-1,2,5-oxadiazole-3-carboximidamide trifluoroacetate

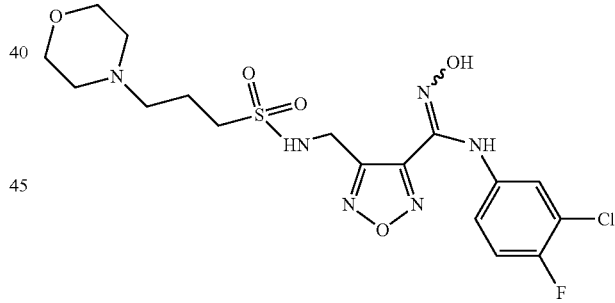

Step A: 3-Chloro-N-({4-[4-(3-chloro-4-fluorophenyl)-5-oxo-4,5-dihydro-1,2,4-oxadiazol-3-yl]-1,2,5-oxadiazol-3-yl}methyl)propane-1-sulfonamide

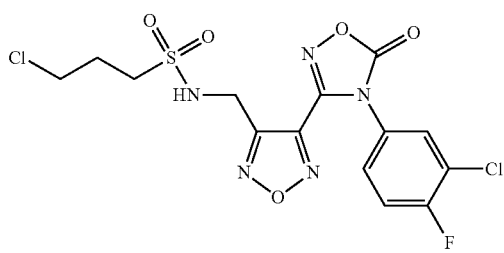 [SMILES: O=c1onc(-c2nonc2CNS(=O)(=O)CCCCl)n1-c1ccc(F)c(Cl)c1]

To a solution of 3-[4-(aminomethyl)-1,2,5-oxadiazol-3-yl]-4-(3-chloro-4-fluorophenyl)-1,2,4-oxadiazol-5(4H)-one (100 mg, 0.32 mol) in DCM (2 mL) under an atmosphere of nitrogen was added DIPEA (168 µL, 0.96 mmol), and 3-chloropropane-1-sulfonyl chloride (117 µL, 0.66 mmol). The reaction was stirred at 25° C. for 5 min. The reaction was quenched with MeOH and purified by preparative HPLC to yield the desired product (38 mg, 20%). $^1$H NMR (400 MHz, CDCl$_3$): δ 7.5 (m, 1H), 7.3 (m, 2H), 4.8 (d, 2H), 3.7 (t, 2H), 3.25 (t, 2H), 2.3 (m, 2H). MF=C$_{14}$H$_{12}$Cl$_2$FN$_5$O$_5$S; LCMS calculated for C$_{14}$H$_{13}$Cl$_2$FN$_5$O$_5$S (M+H)$^+$: m/z=452.2

Step B: N-(3-Chloro-4-fluorophenyl)-N'-hydroxy-4-([(3-morpholin-4-ylpropyl)sulfonyl]aminomethyl)-1,2,5-oxadiazole-3-carboximidamide trifluoroacetate A solution of 3-chloro-N-(4-[4-(3-chloro-4-fluorophenyl)-5-oxo-4,5-dihydro-1,2,4-oxadiazol-3-yl]-1,2,5-oxadiazol-3-ylmethyl)propane-1-sulfonamide (8.20 mg, 0.018 mmol) and morpholine (500 µL, 5.7 mmol) was stirred at 25° C. overnight. The reaction mixture was purified on preparative LCMS using pH 2 buffer. The solvents were evaporated in vacuo and the product was treated with a solution of sodium hydroxide in water (500 µL, 1 N) and ethanol (500 µL) at 25° C. for 20 min. The reaction was neutralized with acetic acid and purified on preparative LCMS using pH 2 buffer to give the desired product (2 mg, 23.1%). MF=C$_{17}$H$_{22}$ClFN$_6$O$_5$S; LCMS calculated for C$_{17}$H$_{23}$ClFN$_6$O$_5$S (M+H)$^+$: m/z=477.1

Example 149

N-(3-Chloro-4-fluorophenyl)-N'-hydroxy-4-[(piperidin-4-ylsulfonyl)amino]-methyl-1,2,5-oxadiazole-3-carboximidamide trifluoroacetate

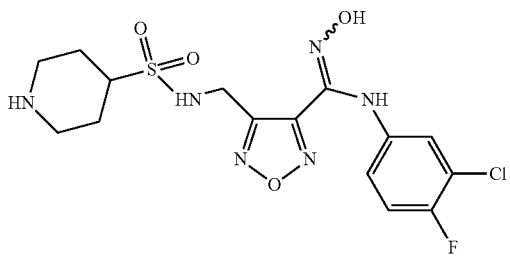 [SMILES: O=S(=O)(NCc1nonc1C(=NO)Nc1ccc(F)c(Cl)c1)C1CCNCC1]

Step A: N-(4-[4-(3-Chloro-4-fluorophenyl)-5-oxo-4,5-dihydro-1,2,4-oxadiazol-3-yl]-1,2,5-oxadiazol-3-ylmethyl)piperidine-4-sulfonamide trifluoroacetate

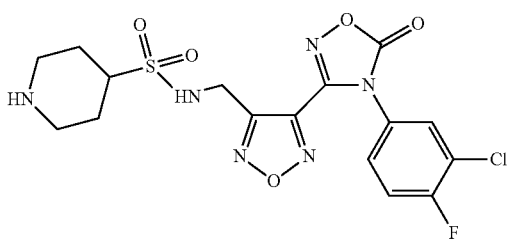 [SMILES: O=c1onc(-c2nonc2CNS(=O)(=O)C2CCNCC2)n1-c1ccc(F)c(Cl)c1]

A solution of 3-[4-(aminomethyl)-1,2,5-oxadiazol-3-yl]-4-(3-chloro-4-fluorophenyl)-1,2,4-oxadiazol-5(4h)-one (100 mg, 0.32 mmol), DIPEA (170 pt, 0.96 mmol), benzyl 4-(chloro-sulfonyl)piperidine-1-carboxylate (310 mg, 0.96 mmol) in DCM (2 mL) was stirred at 25° C. for 15 min. The crude was quenched with MeOH and purified by preparative LCMS using pH 2 buffer. The pure Cbz protected product was treated with a solution of hydrogen bromide in acetic acid (2.0 mL, 4 N) for 20 minutes. The reaction was quenched with MeOH and purified on LCMS using pH 2 buffer to yield the desired product (38 mg, 20%). MF=C$_{16}$H$_{16}$ClFN$_6$O$_5$S; LCMS calculated for C$_{16}$H$_{17}$ClFN$_6$O$_5$S (M+H)$^+$: m/z=459.0.

Step B: N-(3-Chloro-4-fluorophenyl)-N'-hydroxy-4-[(piperidin-4-ylsulfonyl)amino]methyl-1,2,5-oxadiazole-3-carboximidamide trifluoroacetate To a solution of N-(4-[4-(3-chloro-4-fluorophenyl)-5-oxo-4,5-dihydro-1,2,4-oxadiazol-3-yl]-1,2,5-oxadiazol-3-ylmethyl)piperidine-4-sulfonamide (7 mg, 0.015 mmol) in EtOH (500 µL), a solution of sodium hydroxide in water (500 µL, 1 N) was added and was stirred at 25° C. for 20 min. The reaction was neutralized with acetic acid and diluted with MeOH and purified on preparative LCMS using pH 2 buffer to yield the desired product (2.8 mg, 42%). MF=C$_{15}$H$_{19}$ClFN$_6$O$_4$S; LCMS calculated for C$_{15}$H$_{19}$ClFN$_6$O$_4$S (M+H)$^+$: m/z=433.1.

Example 150

4-[([1-(Aminosulfonyl)piperidin-4-yl]sulfonylamino)methyl]-N-(3-chloro-4-fluorophenyl)-N'-hydroxy-1,2,5-oxadiazole-3-carboximidamide trifluoroacetate

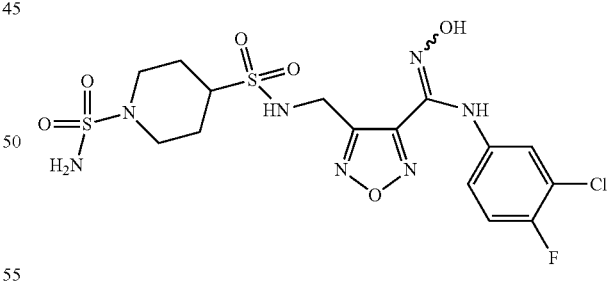

A solution of N-(4-[4-(3-chloro-4-fluorophenyl)-5-oxo-4,5-dihydro-1,2,4-oxadiazol-3-yl]-1,2,5-oxadiazol-3-ylmethyl)piperidine-4-sulfonamide (15 mg, 0.033 mmol) and sulfamide (9.4 mg, 0.098 mmol) in pyridine (1 mL) was heated at 130° C. for 3 min in a microwave. A solution of sodium hydroxide in water (0.5 mL, 1 N) was added and stirred for 20 minutes. The reaction mixture was acidified with acetic acid and purified by preparative LCMS to yield the desired product (8.2 mg, 49%). MF=C$_{15}$K$_9$ClFN$_7$O$_6$S$_2$; LCMS calculated for C$_{15}$H$_{20}$ClFN$_7$O$_6$S$_2$(M+H)$^+$: m/z=512.1

Example 151

4-([(1-Acetylpiperidin-4-yl)sulfonyl]aminomethyl)-N-(3-chloro-4-fluorophenyl)-N'-hydroxy-1,2,5-oxadiazole-3-carboximidamide trifluoroacetate

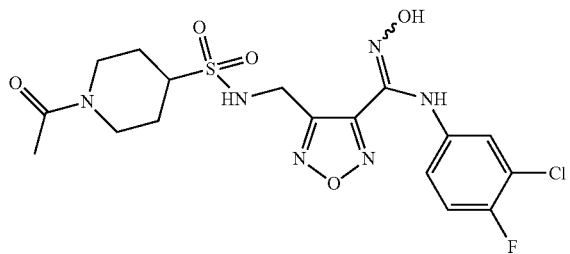 [SMILES: CC(=O)N1CCC(S(=O)(=O)NCc2nonc2C(=NO)Nc2ccc(F)c(Cl)c2)CC1]

A solution of N-(4-[4-(3-chloro-4-fluorophenyl)-5-oxo-4,5-dihydro-1,2,4-oxadiazol-3-yl]-1,2,5-oxadiazol-3-ylmethyl)piperidine-4-sulfonamide (23 mg, 0.050 mmol) and acetic anhydride (500 μL, 5.30 mmol) in pyridine (1 mL) was stirred at 25° C. for 30 min. A solution of sodium hydroxide in water (0.5 mL, 1 N) was added and stirred for another 30 min. Acidification with acetic acid and purification by preparative LCMS gave the desired product (23 mg, 96%). MF=$C_{17}H_{20}ClFN_6O_5S$; LCMS calculated for $C_{17}H_{21}ClFN_6O_5S$ (M+H)$^+$: m/z=475.1

Example 152

N-(3-Chloro-4-fluorophenyl)-N'-hydroxy-4-[5-(morpholin-4-ylmethyl)-2H-tetrazol-2-yl]methyl-1,2,5-oxadiazole-3-carboximidamide trifluoroacetate

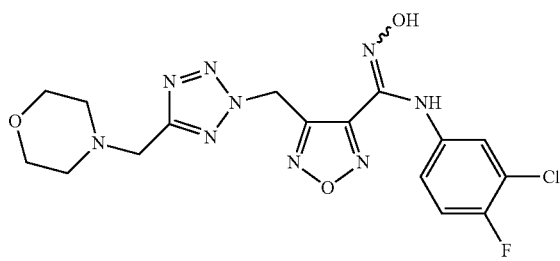 [SMILES: ON=C(Nc1ccc(F)c(Cl)c1)c1nonc1Cn1nnc(CN2CCOCC2)n1]

and

Example 153

N-(3-Chloro-4-fluorophenyl)-N'-hydroxy-4-[5-(morpholin-4-ylmethyl)-1H-tetrazol-1-yl]methyl-1,2,5-oxadiazole-3-carboximidamide trifluoroacetate

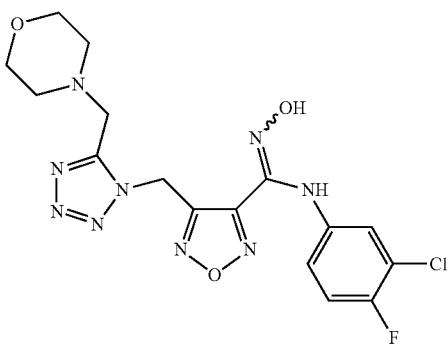 [SMILES: ON=C(Nc1ccc(F)c(Cl)c1)c1nonc1Cn1nnnc1CN1CCOCC1]

Step A: 4-(1H-tetrazol-5-ylmethyl)morpholine

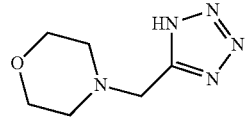 [SMILES: C1CN(Cc2nnn[nH]2)CCO1]

A solution of 5-(chloromethyl)-1H-tetrazole (260 mg, 2.2 mmol) in morpholine (1.5 mL, 17.2 mmol) was stirred at 25° C. for 20 minutes. The crude reaction mixture was purified by preparative LCMS using pH 2 buffer to yield the desired product (300 mg, 82%). MF=$C_6H_{11}N_5O$; LCMS calculated for $C_6H_{12}N_5O$ (M+H)$^+$: m/z=170.1.

Step B: N-(3-chloro-4-fluorophenyl)-N'-hydroxy-4-[5-(morpholin-4-ylmethyl)-2H-tetrazol-2-yl]-methyl-1,2,5-oxadiazole-3-carboximidamide trifluoroacetate and N-(3-Chloro-4-fluorophenyl)-N'-hydroxy-4-[5-morpholin-4-ylmethyl)-1H-tetrazol-1-yl]methyl-1,2,5-oxadiazole-3-carboximidamide trifluoroacetate 4-[4-(3-Chloro-4-fluorophenyl)-5-oxo-4,5-dihydro-1,2,4-oxadiazol-3-yl]-1,2,5-oxadiazol-3-ylmethyl methanesulfonate (81 mg, 0.21 mmol) was dissolved in anhydrous ACN (500 μL) followed by addition of DIPEA (0.18 mL, 1.0 mmol) and 4-(1H-tetrazol-5-ylmethyl)morpholine (110 mg, 0.62 mmol). The reaction mixture was stirred and heated at 45° C. for 1 hour. The reaction was then diluted with MeOH and purified by preparative LCMS to yield two isomers. The purified isomers were concentrated to dryness, redissolved in EtOH (1.0 mL) and a solution of sodium hydroxide in water (0.5 mL, 1 N) was added. The reactions were stirred for 20 minutes. Reactions were quenched with acetic acid, diluted with MeOH and purified by preparative LCMS to yield the two isomers (2.2 mg, 2.4%) and (3.2 mg, 3.5%).

Example 152

$^1$H NMR (400 MHz, DMSO-d$_6$): δ 11.5 (s, 1H), 9.0 (s, 1H), 7.2 (t, 1H), 7.0 (d, 1H), 6.75 (d, 1H), 6.4 (s, 2H), 3.6 (bs, 8H). MF=$C_{16}H_{17}ClFN_9O_3$; LCMS calculated for $C_{16}H_{18}ClFN_9O_3$ (M+H)$^+$: m/z=438.1

Example 153

$^1$H NMR (400 MHz, DMSO-d$_6$): δ 11.5 (1H, s), 9.0 (1H, s), 7.2 (1H, t), 7.0 (1H, d), 6.8 (1H, d), 6.15 (2H, s), 3.6 (8H, bs). MF=$C_{16}H_{17}ClFN_9O_3$; LCMS calculated for $C_{16}H_{18}ClFN_9O_3$ (M+H)$^+$: m/z=438.1

Example 154

4-[(5-Amino-1,3,4-thiadiazol-2-yl)thio]methyl-N-(3-chloro-4-fluorophenyl)-N'-hydroxy-1,2,5-oxadiazole-3-carboximidamide trifluoroacetate

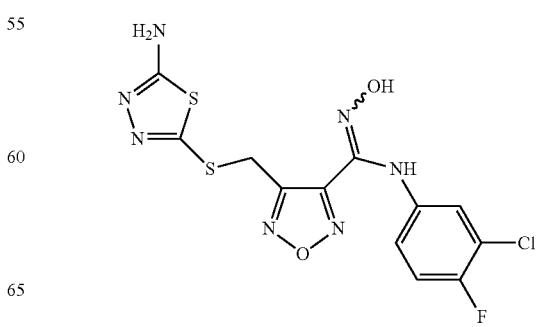

4-[4-(3-Chloro-4-fluorophenyl)-5-oxo-4,5-dihydro-1,2,4-oxadiazol-3-yl]-1,2,5-oxadiazol-3-ylmethyl methanesulfonate (23 mg, 0.059 mmol) was dissolved in anhydrous ACN (1.0 mL) followed by addition of DIPEA (51 μL, 0.29 mmol) and 5-amino-1,3,4-thiadiazole-2-thiol (24 mg, 0.18 mmol). The reaction was stirred and heated at 45° C. for 16 h. The reaction mixture was diluted with MeOH and purified by preparative LCMS. The purified product was evaporated to dryness, redissolved in EtOH (0.5 mL) and a solution of sodium hydroxide in water (0.5 mL, 1 N) was added. The reaction was stirred for 20 minutes and quenched with acetic acid, diluted with MeOH and purified by preparative LCMS using pH 2 buffer to yield the desired product (7.1 mg, 23%). $^1$H NMR (400 MHz, DMSO-$d_6$): δ 11.7 (s, 1H), 9.1 (s, 1H), 7.2 (t, 1H), 7.0 (1H, d), 6.75 (1H, m), 4.6 (s, 2H). MF=$C_{12}H_9ClFN_7O_2S_2$; LCMS calculated for $C_{12}H_{10}ClFN_7O_2S_2$(M+H)$^+$: m/z=402.1

Example 155

4-[(5-Amino-4H-1,2,4-triazol-3-yl)thio]methyl-N-(3-chloro-4-fluorophenyl)-N'-hydroxy-1,2,5-oxadiazole-3-carboximidamide trifluoroacetate

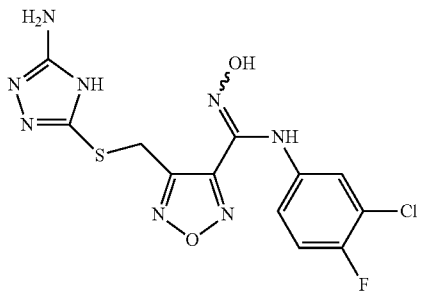 [SMILES: Nc1nnc(SCc2nonc2C(=NO)Nc2ccc(F)c(Cl)c2)[nH]1]

4-[4-(3-Chloro-4-fluorophenyl)-5-oxo-4,5-dihydro-1,2,4-oxadiazol-3-yl]-1,2,5-oxadiazol-3-ylmethyl methanesulfonate (23 mg, 0.059 mmol) was dissolved in anhydrous ACN (1.0 mL) followed by addition of DIPEA (51 μL, 0.29 mmol) and 5-amino-4H-1,2,4-triazole-3-thiol (21 mg, 0.18 mmol). The reaction mixture was stirred and heated at 45° C. for 16 h. The reaction was diluted with MeOH and purified by preparative LCMS. The purified product was evaporated to dryness, redissolved in EtOH(1 mL) and a solution of sodium hydroxide in water (0.5 mL, 1 N) was added and stirred for 20 minutes. The reaction was quenched with acetic acid, diluted with MeOH and purified by preparative LCMS using pH 2 buffer to yield the desired product (15 mg, 52%). $^1$H NMR (400 MHz, $d_6$-DMSO): δ 11.7 (s, 1H), 9.1 (s, 1H), 7.2 (t, 1H), 7.0 (d, 1H), 6.75 (m, 1H), 4.6 (s, 2H). MF=$C_{12}H_9ClFN_8O_2S$; LCMS calculated for $C_{12}H_{10}ClFN_8O_2S$ (M+H)$^+$: m/z=385.1.

Example 156

4-[(5-Amino-4H-1,2,4-triazol-3-yl)sulfonyl]methyl-N-(3-chloro-4-fluorophenyl)-N'-hydroxy-1,2,5-oxadiazole-3-carboximidamide trifluoroacetate

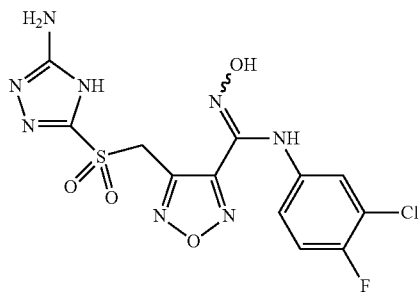 [SMILES: Nc1nnc(S(=O)(=O)Cc2nonc2C(=NO)Nc2ccc(F)c(Cl)c2)[nH]1]

A solution of 4-[(5-amino-4h-1,2,4-triazol-3-yl)thio]methyl-N-(3-chloro-4-fluorophenyl)-N'-hydroxy-1,2,5-oxadiazole-3-carboximidamide trifluoroacetate (11 mg, 0.023 mmol), m-chloroperbenzoic acid (10 mg, 0.046 mmol) and 1,4-dioxane (0.5 mL) was stirred at 25° C. for 1 hr. The reaction was diluted with MeOH and purified on preparative LCMS using pH 2 buffer to yield the desired product (5.8 mg, 48%). MF=$C_{12}H_9ClFN_8O_4S$; LCMS calculated for $C_{12}H_{10}ClFN_8O_4S$ (M+H)$^+$: m/z=417.1

Example 157

N-(3-Chloro-4-fluorophenyl)-4-[((E/Z)-(cyanoimino)[(4-methoxybenzyl)amino]-methylamino)methyl]-N'-hydroxy-1,2,5-oxadiazole-3-carboximidamide trifluoroacetate

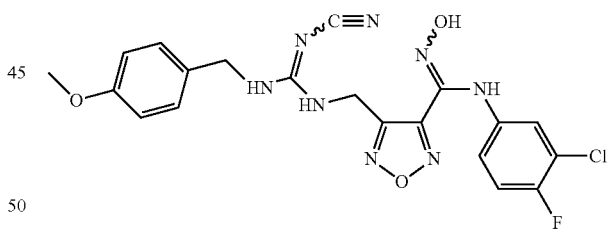

Into the reaction was dissolved 3-[4-(aminomethyl)-1,2,5-oxadiazol-3-yl]-4-(3-chloro-4-fluorophenyl)-1,2,4-oxadiazol-5(4H)-one trifluoroacetate (30 mg, 0.07 mmol) in THF (0.74 mL). Diphenyl cyanocarbonimidate (20 mg, 0.08 mmol) and TEA (29 μL, 0.21 mmol) were added and the reaction was stirred at room temperature for 2 hr. A solution of sodium hydroxide in water (0.5 mL, 1 N) was added and the mixture was stirred at room temperature for 30 minutes. Acidification with acetic acid and purification by preparative LCMS gave the desired product (40 mg, 97%). MF=$C_{22}H_{19}ClF_4N_8O_5$; LCMS calculated for $C_{22}H_{20}ClF_4N_8O_5$ (M+H)$^+$: m/z=473.1. $^1$H NMR (400 MHz, $CD_3OD$): δ 7.2 (m, 2H), 7.03 (m, 1H), 6.95 (m, 1H), 6.8 (m, 2H), 6.74 (m, 1H), 4.68 (s, 2H), 4.38 (s, 2H), 3.75 (s, 3H).

Example 158

4-[({(E/Z)-[(Aminocarbonyl)imino][(4-methoxybenzyl)amino]methyl}amino)-methyl]-N-(3-chloro-4-fluorophenyl)-N'-hydroxy-1,2,5-oxadiazole-3-carboximidamide trifluoroacetate

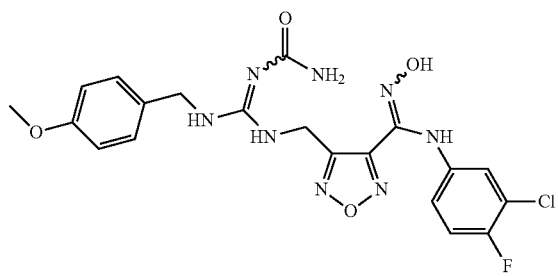 [SMILES: COc1ccc(CNC(=NC(N)=O)NCc2nonc2C(=NO)Nc2ccc(F)c(Cl)c2)cc1]

N-(3-Chloro-4-fluorophenyl)-4-[((E/Z)-(cyanoimino)[(4-methoxybenzyl)amino]methyl-amino)methyl]-N'-hydroxy-1,2,5-oxadiazole-3-carboximidamide trifluoroacetate (20 mg, 0.04 mmol) was dissolved in TFA (1.0 mL) and stirred for 1 hour at rt. Purification by preparative LCMS gave the desired product (12 mg, 50%).

MF=$C_{22}H_{21}ClF_4N_8O_6$; LCMS calculated for $C_{22}H_{22}ClF_4N_8O_6$ (M+H)$^+$: m/z=491.0. $^1$H NMR (400 MHz, $CD_3OD$): δ☐ 7.24 (m, 2H), 7.03 (m, 1H), 7.00 (m, 1H), 6.95 (m, 2H), 6.80 (m, 1H), 4.93 (s, 2H), 4.52 (s, 2H), 3.79 (s, 3H).

Example 159

4-({[(E/Z)-Amino(nitroimino)methyl]amino}methyl)-N-(3-chloro-4-fluoro-phenyl)-N'-hydroxy-1,2,5-oxadiazole-3-carboximidamide trifluoroacetate

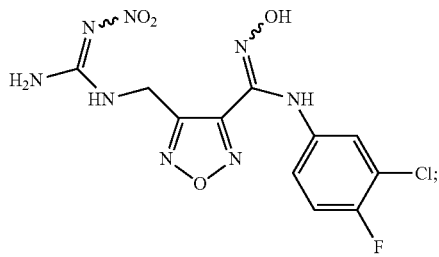 [SMILES: NC(=N[N+](=O)[O-])NCc1nonc1C(=NO)Nc1ccc(F)c(Cl)c1]

and

Example 160

4-({[Amino(imino)methyl]amino}methyl)-N-(3-chloro-4-fluorophenyl)-N'-hydroxy-1,2,5-oxadiazole-3-carboximidamide

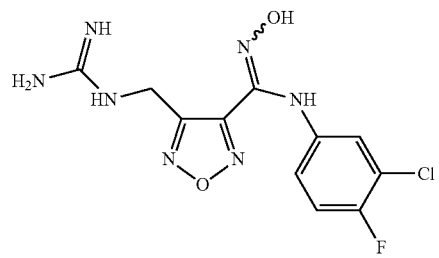 [SMILES: N=C(N)NCc1nonc1C(=NO)Nc1ccc(F)c(Cl)c1]

3-[4-(Aminomethyl)-1,2,5-oxadiazol-3-yl]-4-(3-chloro-4-fluorophenyl)-1,2,4-oxadiazol-5(4H)-one trifluoroacetate (30 mg, 0.07 mmol) and nitroguanidine (50 mg, 0.5 mmol) were dissolved in pyridine (1.0 mL). The reaction mixture was heated in a microwave at 170° C. for 30 minutes. The pyridine was evaporated and a solution of sodium hydroxide in water (0.5 mL, 1 N) was added. The mixture was stirred at room temperature for 30 minutes. Acidification with acetic acid and purification by preparative LCMS gave the desired nitroguanyl product (3.2 mg, 9%) and the guanyl product (4.7 mg, contaminated with pyridine). The guanyl material was treated with saturated aqueous sodium bicarbonate solution (1.0 mL) and extracted with ethyl acetate (3×3 mL). The combined extracts were dried with sodium sulfate, filtered and concentrated to give the desired guanyl free base (2.3 mg, 10%). MF=$C_{11}H_{10}ClFN_8O_4$; LCMS calculated for $C_{11}H_{11}ClFN_8O_4$ (M+H)$^+$: m/z=373.0. $^1$H NMR (400 MHz, $CD_3OD$): δ☐ 7.03 (m, 2H), 6.80 (m, 1H), 4.77 (s, 2H). MF=$C_{11}H_{11}ClFN_7O_2$; LCMS calculated for $C_{11}H_{12}ClFN_7O_2$ (M+H)$^+$: m/z=328.0. $^1$H NMR (400 MHz, $CD_3OD$): δ☐ 7.04 (m, 1H), 7.00 (m, 1H), 6.80 (m, 1H), 4.77 (s, 2H).

Example 161

N-(3-Chloro-4-fluorophenyl)-N'-hydroxy-4-(4H-1,2,4-triazol-4-ylmethyl)-1,2,5-oxadiazole-3-carboximidamide trifluoroacetate

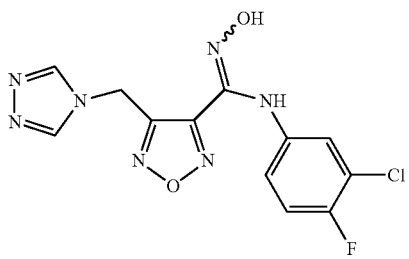 [SMILES: ON=C(Nc1ccc(F)c(Cl)c1)c1nonc1Cn1cnnc1]

A solution of 3-[4-(aminomethyl)-1,2,5-oxadiazol-3-yl]-4-(3-chloro-4-fluorophenyl)-1,2,4-oxadiazol-5(4h)-one trifluoroacetate (14.0 mg, 32.0 mmol), N'-[(1e)-(dimethylamino)methylene]-N,N-dimethylhydrazonoformamide (6.80 mg, 48.0 mmol), and p-toluenesulfonic acid (550 mg, 3.2 mmol) in DMF (1 mL) was heated at 170° C. for 15 min in the microwave. A solution of sodium hydroxide in water (0.5 mL, 1 N) was added and the mixture was stirred for 30 minutes at room temperature. Acidification with acetic acid and purification by preparative LCMS gave the desired product (1.3 mg, 9%). MF=$C_{12}H_9ClFN_7O_2$; LCMS calculated for $C_{12}H_{10}ClFN_7O_2$ (M+H)$^+$: m/z=337.9.

Example 162

4-[2-(5-Amino-1H-tetrazol-1-yl)ethyl]-N-(3-chloro-4-fluorophenyl)-N'-hydroxy-1,2,5-oxadiazole-3-carboximidamide

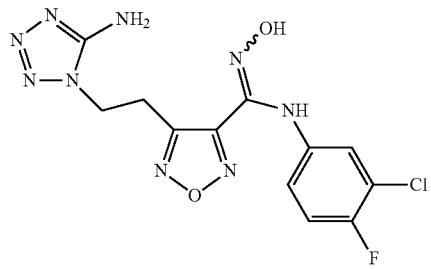 [SMILES: Nc1nnnn1CCc1nonc1C(=NO)Nc1ccc(F)c(Cl)c1]

Step A: N-(3-Chloro-4-fluorophenyl)-4-[(E)-2-methoxyvinyl]-1,2,5-oxadiazole-3-carboxamide N-(3-chloro-4-fluorophenyl)-4-[(Z)-2-methoxyvinyl]-1,2,5-oxadiazole-3-carboxamide

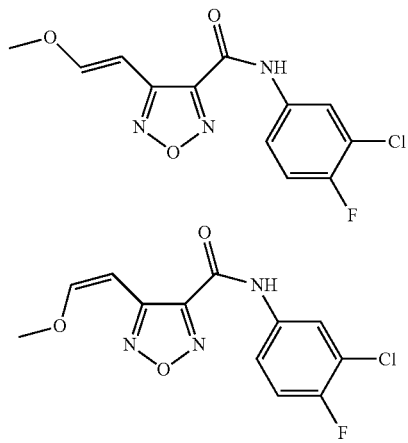

To a solution of (methoxymethyl)(triphenyl)phosphonium chloride (23.0 g, 66.0 mmol) in toluene (183 mL) was added sodium tert-butoxide (6.60 g, 0.066 mol) at rt under an atmosphere of nitrogen. After stirring for 30 min, a solution of N-(3-chloro-4-fluorophenyl)-4-formyl-1,2,5-oxadiazole-3-carboxamide (7.6 g, 28 mmol) in THF (18 mL) was cannulated into reaction flask. The resulting solution was stirred at rt for 1 h. The reaction was quenched with 1 N HCl and diluted with ethyl acetate and the aqueous layer was extracted with ethyl acetate once. The combined organic solutions were washed with brine, dried over $Na_2SO_4$, filtered and concentrated. The residue was purified with silica gel chromatography (20% ethyl acetate/Hex) to give product (2.0 g 24%, E isomer, 2.6 g, 31%, Z isomer) as white solids. Z isomer: $^1$H NMR (400 MHz, $CDCl_3$): δ☐ 8.54 (s, 1 H) 7.87 (dd, J=6.4, 2.7 Hz, 1 H), 7.42 (m, 1 H), 7.16 (t, J=8.5 Hz, 1 H), 6.66 (d, J=6.6 Hz, 1 H), 6.03 (d, J=6.6 Hz, 1 H), 3.97 (s, 3 H). MF=$C_{12}H_{10}ClFN_3O_3$; LCMS for $C_{12}H_{10}ClFN_3O_3(M+H)^+$: m/z=298.0.

Step B: N-(3-Chloro-4-fluorophenyl)-4-(2-methoxyethyl)-1,2,5-oxadiazole-3-carboxamide

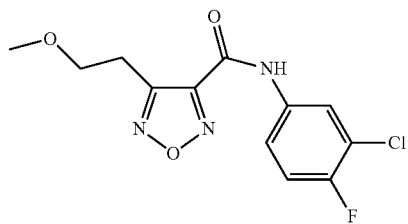 [SMILES: COCCc1nonc1C(=O)Nc1ccc(F)c(Cl)c1]

N-(3-Chloro-4-fluorophenyl)-4-[(E,Z)-2-methoxyvinyl]-1,2,5-oxadiazole-3-carboxamide (4.6 g, 15 mmol) was dissolved in and ethyl acetate (77 mL) and 10% palladium on carbon (0.8 g) was added to reaction flask. The mixture was reacted under a 55 psi hydrogen atmosphere for 4 h. The solution was filtered through a pad of celite. The filtrate was concentrated and purified by silica gel chromatography (20% ethyl acetate/hex) to give the desired product as a white solid (2.5 g, 54%). MF=$C_{12}H_{11}ClFN_3O_3$; LCMS calculated for $C_{12}H_{12}ClFN_3O_3(M+H)^+$: m/z=300.1.

Step C: N-(3-Chloro-4-fluorophenyl)-N'-hydroxy-4-(2-methoxyethyl)-1,2,5-oxadiazole-3-carboximidamide

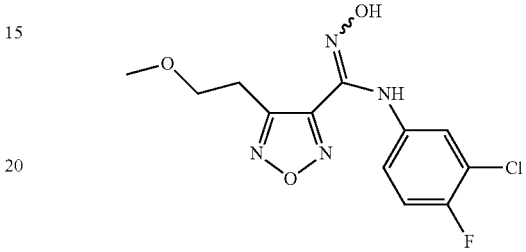

N-(3-Chloro-4-fluorophenyl)-4-(2-methoxyethyl)-1,2,5-oxadiazole-3-carboxamide (2.5 g, 8.3 mmol) was suspended in benzene (40 mL), pyridine (2.7 mL) and phosphorus pentachloride (3.5 g, 17 mmol) was added to the solution. The mixture was heated at 60° C. for 2.5 h. The reaction was then concentrated to dryness in vacuo. The crude was dissolved in EtOH (50 mL) and cooled to 0° C. and 50% hydroxylamine in water (10 mL) was added to the reaction flask until the pH reached 8. The reaction solution was concentrated, diluted with ethyl acetate and the aqueous layer was extracted with ethyl acetate once. The combined organic solutions were concentrated in vacuo and purified by silica gel chromatography (20%-50% ethyl acetate/hex) to give the desired product (2.5 g, 95%) as a yellow solid. MF=$C_{12}H_{12}ClFN_4O_3$; LCMS calculated for $C_{12}H_{13}ClFN_4O_3(M+H)^+$: m/z=315.1.

Step D: 4-(3-Chloro-4-fluorophenyl)-3-[4-(2-methoxyethyl)-1,2,5-oxadiazol-3-yl]-1,2,4-oxadiazol-5(4H)-one

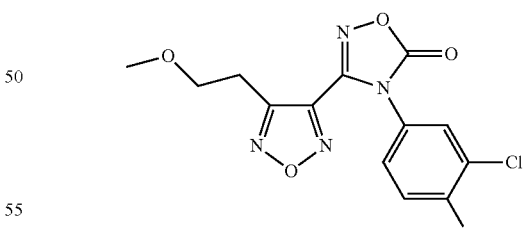

N-(3-Chloro-4-fluorophenyl)-N-hydroxy-4-(2-methoxyethyl)-1,2,5-oxadiazole-3-carboximidamide (2.5 g, 7.9 mmol) was dissolved in THF (44 mL) followed by addition of N,N-carbonyl-diimidazole (1.5 g, 9.5 mmol). The reaction was heated to 70° C. for 1.5 h. The reaction solution was concentrated and purified by silica gel chromatography (20% ethyl acetate/hexane) to give the desired product (2.7 g, 99%). MF=$C_{13}H_{10}ClFN_4O_4$; LCMS calculated for $C_{13}H_{11}ClFN_4O_4(M+H)^+$: m/z=341.0.

Step E: 4-(3-Chloro-4-fluorophenyl)-3-[4-(2-hydroxyethyl)-1,2,5-oxadiazol-3-yl]-1,2,4-oxadiazol-5 (4H)-one

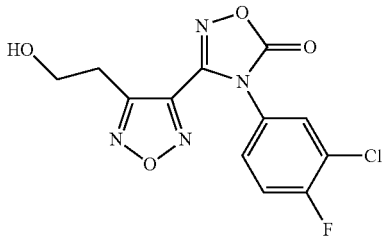 [SMILES: O=c1onc(-c2nonc2CCO)n1-c1ccc(F)c(Cl)c1]

To a solution of 4-(3-chloro-4-fluorophenyl)-3-[4-(2-methoxyethyl)-1,2,5-oxadiazol-3-yl]-1,2,4-oxadiazol-5(41-1)-one (2.55 g, 0.00748 mol) in DCM (24 mL) was added 1.0 M of boron tribromide in DCM (22.4 mL) under an atmosphere of nitrogen at −78° C. The reaction solution was allowed to warm to rt over 2.5 h. The reaction was quenched with saturated NaHCO₃ at 0° C. and diluted with ethyl acetate. The aqueous layer was extracted with ethyl acetate once, the combined organic solutions were dried over Na₂SO₄, filtered and concentrated in vacuo. The crude product was purified by silica gel chromatography (60% ethyl acetate/hexane) to give the desired product as an off white solid (2.3 g, 96%). MF=$C_{12}H_8ClFN_4O_4$; LCMS calculated for $C_{12}H_9ClFN_4O_4$(M+H)⁺: m/z 327.0.

Step F: 2-4-[4-(3-Chloro-4-fluorophenyl)-5-oxo-4,5-dihydro-1,2,4-oxadiazol-3-yl]-1,2,5-oxadiazol-3-ylethyl methanesulfonate

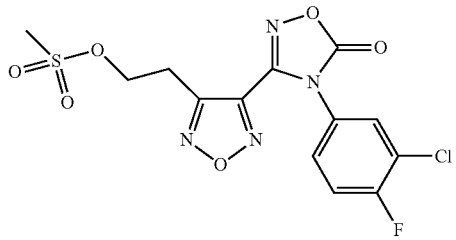 [SMILES: CS(=O)(=O)OCCc1nonc1-c1noc(=O)n1-c1ccc(F)c(Cl)c1]

To a solution of 4-(3-chloro-4-fluorophenyl)-3-[4-(2-hydroxyethyl)-1,2,5-oxadiazol-3-yl]-1,2,4-oxadiazol-5(4H)-one (2.50 g, 7.65 mmol) in DCM (34 mL) was added TEA (2.1 mL, 15 mmol) and methanesulfonyl chloride (0.83 mL, 10.7 mmol) at rt. After stirring for 30 min, the reaction was quenched with a 0.1 N HCl solution and diluted with ethyl acetate. The organic layer was dried over Na₂SO₄, filtered, concentrated. The residue was purified by silica gel column (20-70% ethyl acetate/hexane) to give the desired product as a white solid (2.74 g, 88%); MF=$C_{13}H_{10}ClFN_4O_6S$; LCMS calculated for $C_{13}H_{11}ClFN_4O_6S$(M+H)⁺: m/z=405.0.

Step G: 4-[2-(5-Amino-1H-tetrazol-1-yl)ethyl]-N-(3-chloro-4-fluorophenyl)-N'-hydroxy-1,2,5-oxadiazole-3-carboximidamide 2-4-[4-(3-Chloro-4-fluorophenyl)-5-oxo-4,5-dihydro-1,2,4-oxadiazol-3-yl]-1,2,5-oxadiazol-3-ylethyl methanesulfonate (16.0 mg, 0.039 mmol) was dissolved in anhydrous ACN (0.6 mL), followed by addition of DIPEA (27.5 µL, 0.158 mmol) and 1H-tetrazol-5-amine (4.0 mg, 0.047 mmol). The mixture was heated at 50° C. for 4 h. The reaction solution was then diluted with MeOH and purified by preparative HPLC to yield two isomers. The first eluting peak (isomer 1) was dissolved in MeOH (0.5 mL) and 2.0 N of sodium hydroxide in water (0.079 mL) was added. After stirring for 0.5 h, reaction solution was diluted with MeOH and few drops of acetic acid and purified by preparative LCMS to give the desired product as a white powder (2.1 mg, 14%). MF=$C_{12}H_{11}ClFN_9O_2$; LCMS calculated for $C_{12}H_{11}ClFN_9O_2$; $O_2$ (M+H)⁺: m/z=368.1. ¹H NMR (400 MHz, DMSO-d₆): δ 11.60 (s, 1 H), 8.99 (s, 1 H), 7.17 (t, J=9.0 Hz, 1 H), 7.00 (dd, J=6.4, 2.7 Hz, 1 H), 6.79 (s, 2 H), 6.72 (m 1 H), 4.55 (t, J=7.0 Hz, 2 H), 3.41 (t, J=7.0 Hz, 2 H);

Example 163

4-[2-(5-Amino-2H-tetrazol-2-yl)ethyl]-N-(3-chloro-4-fluorophenyl)-N'-hydroxy-1,2,5-oxadiazole-3-carboximidamide

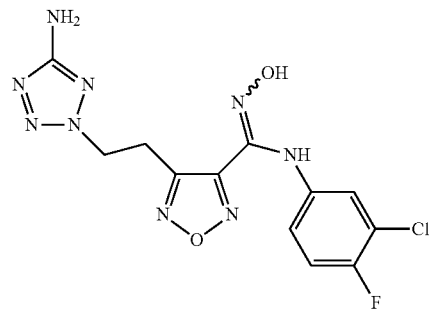 [SMILES: Nc1nnn(CCc2nonc2C(=NO)Nc2ccc(F)c(Cl)c2)n1]

2-4-[4-(3-Chloro-4-fluorophenyl)-5-oxo-4,5-dihydro-1,2,4-oxadiazol-3-yl]-1,2,5-oxadiazol-3-ylethyl methanesulfonate (16.0 mg, 0.039 mmol) was dissolved in anhydrous ACN (0.6 mL), followed by addition of DIPEA (27.5 µL, 0.158 mmol) and 1H-tetrazol-5-amine (4.0 mg, 0.047 mmol). The solution was heated at 50° C. for 4 h. The reaction solution was then diluted with MeOH and purified by preparative HPLC to yield two isomers. The first eluting peak (isomer 1) was dissolved in MeOH (0.5 mL) and 2.0 N of sodium hydroxide in water (0.079 mL) was added. After stirring for 0.5 h, reaction solution was diluted with MeOH and few drops of acetic acid and purified by preparative LCMS to give the desired product as a white powder (3.8 mg, 26%). MF=$C_{12}H_{11}ClFN_9O_2$; LCMS calculated for $C_{12}H_{12}ClFN_9O_2$(M+H)⁺: m/z=368.1.

Example 164

N-(3-Chloro-4-fluorophenyl)-N-hydroxy-4-[2-(1H-imidazol-1-yl)ethyl]-1,2,5-oxadiazole-3-carboximidamide

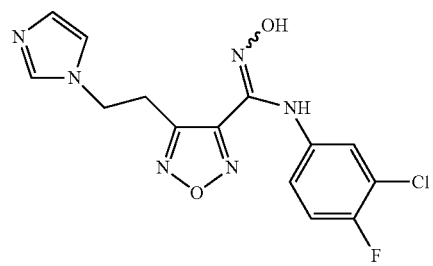 [SMILES: ON=C(Nc1ccc(F)c(Cl)c1)c1nonc1CCn1ccnc1]

2-4-[4-(3-Chloro-4-fluorophenyl)-5-oxo-4,5-dihydro-1,2,4-oxadiazol-3-yl]-1,2,5-oxadiazol-3-ylethyl methanesulfonate (9.0 mg, 0.022 mmol) was dissolved in anhydrous ACN (0.5 mL), followed by addition of DIPEA (15.5 µL, 0.0889 mmol), and imidazole (3.0 mg, 0.044 mmol). The reaction solution was heated at 60° C. for 12 h. The reaction solution was then treated with 2.0 M of sodium hydroxide in water (0.20 mL). After stirring for 0.5 h, to the solution was added a few drops of acetic acid and diluted with MeOH and purified by preparative LCMS to give the desired product (3.5 mg, 45%). MF=$C_{14}H_{12}ClFN_6O_2$; LCMS for $C_{14}H_{13}ClFN_6O_2$ (M+H)$^+$: m/z=351.1.

Example 165

N-(3-Chloro-4-fluorophenyl)-N'-hydroxy-4-(2-morpholin-4-ylethyl)-1,2,5-oxadiazole-3-carboximidamide

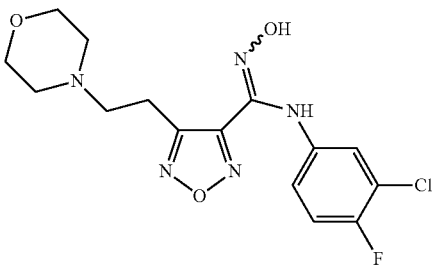 [SMILES: ON=C(Nc1ccc(F)c(Cl)c1)c1nonc1CCN1CCOCC1]

This compound was prepared according to the procedure of Example 164, using 2-4-[4-(3-chloro-4-fluorophenyl)-5-oxo-4,5-dihydro-1,2,4-oxadiazol-3-yl]-1,2,5-oxadiazol-3-ylethyl methanesulfonate and morpholine as the starting materials. MF=$C_{15}H_{17}ClFN_5O_3$; LCMS for $C_{15}H_{18}ClFN_5O_3$ (M+H)$^+$: m/z=370.1.

Example 166

N-(3-Chloro-4-fluorophenyl)-N'-hydroxy-4-[2-(4-methylpiperazin-1-yl)ethyl]-1,2,5-oxadiazole-3-carboximidamide

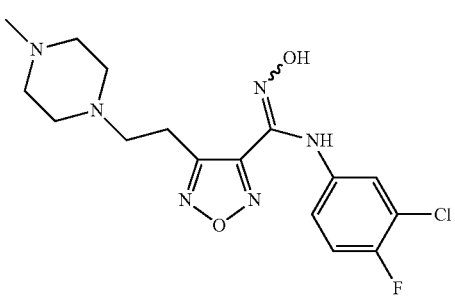 [SMILES: CN1CCN(CCc2nonc2C(=NO)Nc2ccc(F)c(Cl)c2)CC1]

This compound was prepared according to the procedure of Example 164, using 2-4-[4-(3-chloro-4-fluorophenyl)-5-oxo-4,5-dihydro-1,2,4-oxadiazol-3-yl]-1,2,5-oxadiazol-3-ylethyl methane-sulfonate and 1-methylpiperazine as the starting materials. MF=$C_{16}H_{20}ClFN_6O_2$; LCMS for $C_{16}H_{21}ClFN_6O_2$ (M+H)$^+$: m/z=383.1.

Example 167

N-(3-Chloro-4-fluorophenyl)-N'-hydroxy-4-[2-(4H-1,2,4-triazol-4-yl)ethyl]-1,2,5-oxadiazole-3-carboximidamide

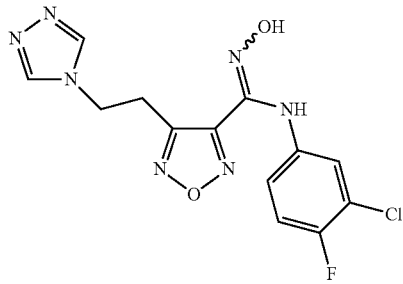 [SMILES: ON=C(Nc1ccc(F)c(Cl)c1)c1nonc1CCn1cnnc1]

This compound was prepared according to the procedure of Example 164, using 2-4-[4-(3-chloro-4-fluorophenyl)-5-oxo-4,5-dihydro-1,2,4-oxadiazol-3-yl]-1,2,5-oxadiazol-3-ylethyl methane-sulfonate and 1H-1,2,4-triazole as the starting materials. MF=$C_{13}H_{11}ClFN_7O_2$; LCMS for $C_{13}H_{12}ClFN_7O_2$ (M+H)$^+$: m/z=352.1. $^1$H NMR (400 MHz, DMSO-$d_6$): δ 11.60 (s, 1 H), 10.53 (s, 0.1 H), 9.14 (s, 0.1 H), 8.99 (s, 1 H), 8.58 (s, 2H), 8.52 (s, 0.2 H), 7.98 (m, 0.1 H), 7.35 (m, 0.2 H), 7.10 (t, J=9.0 Hz, 1 H), 6.98 (dd, J=6.5, 2.8 Hz, 1 H), 6.68 (m, 1 H), 4.49 (t, J=7.1 Hz, 2 H), 3.41 (t, J=7.1 Hz, 2 H) 3.34 (t, J=6.8 Hz, 0.4 H);

Example 168

N-(3-Chloro-4-fluorophenyl)-N-hydroxy-4-[2-(1H-1,2,4-triazol-1-yl)ethyl]-1,2,5-oxadiazole-3-carboximidamide

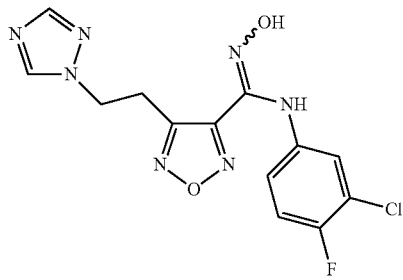 [SMILES: ON=C(Nc1ccc(F)c(Cl)c1)c1nonc1CCn1cncn1]

This compound was prepared according to the procedure of Example 164, using 2-4-[4-(3-chloro-4-fluorophenyl)-5-oxo-4,5-dihydro-1,2,4-oxadiazol-3-yl]-1,2,5-oxadiazol-3-ylethyl methane-sulfonate and 1H-1,2,4-triazole as the starting materials. MF=$C_{13}H_{11}ClFN_7O_2$; LCMS for $C_{13}H_{12}ClFN_7O_2$ (M+H)$^+$: m/z=352.1.

Example 169

N-(3-Chloro-4-fluorophenyl)-N'-hydroxy-4-[2-(1H-tetrazol-1-yl)ethyl]-1,2,5-oxa-diazole-3-carboximidamide

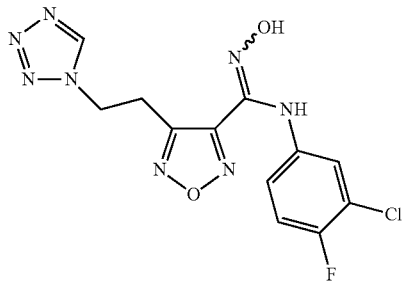 [SMILES: ON=C(Nc1ccc(F)c(Cl)c1)c1nonc1CCn1cnnn1]

This compound was prepared according to the procedure of Example 164, using 2-4-[4-(3-chloro-4-fluorophenyl)-5-oxo-4,5-dihydro-1,2,4-oxadiazol-3-yl]-1,2,5-oxadiazol-3-ylethyl methane-sulfonate and 1H-tetrazole as the starting materials. MF=$C_{12}H_{10}ClFN_8O_2$; LCMS for $C_{12}H_{11}ClF_8O_2$ (M+H)$^+$: m/z=353.1. $^1$H NMR (400 MHz, DMSO-d$_6$): δ 11.61 (s, 1 H), 9.43 (s, 1 H), 9.39 (s, 0.1 H), 9.11 (s, 0.1 H), 8.99 (s, 1 H), 7.34 (m, 0.2 H), 7.17 (t, J=9.0 Hz, 1 H), 7.00 (dd, J=6.4 Hz, 2.7 Hz, 1 H), 6.72 (m, 1 H), 4.93 (t, J=6.8 Hz, 2 H), 3.56 (t, J=6.8 Hz, 2 H);

Example 170

N-(3-Chloro-4-fluorophenyl)-N-hydroxy-4-[2-(2H-tetrazol-2-yl)ethyl]-1,2,5-oxadiazole-3-carboximidamide

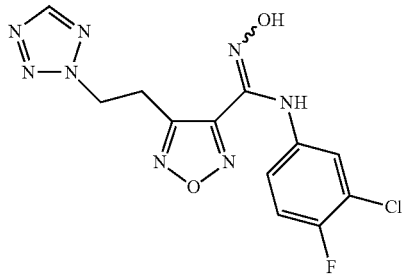 [SMILES: ON=C(Nc1ccc(F)c(Cl)c1)c1nonc1CCn1ncnn1]

This compound was prepared according to the procedure of Example 164, using 2-4-[4-(3-chloro-4-fluorophenyl)-5-oxo-4,5-dihydro-1,2,4-oxadiazol-3-yl]-1,2,5-oxadiazol-3-ylethyl methane-sulfonate and 1H-tetrazole as the starting materials. MF=$C_{12}H_{10}ClFN_8O_2$; LCMS for $C_{12}H_{11}ClFN_8O_2$ (M+H)$^+$: m/z=353.1.

Example 171

N-(3-Chloro-4-fluorophenyl)-N'-hydroxy-4-vinyl-1,2,5-oxadiazole-3-carboximidamide

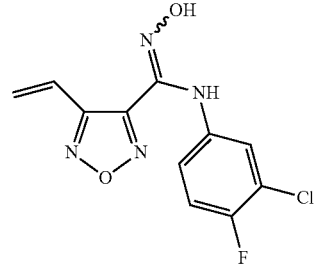 [SMILES: C=Cc1nonc1C(=NO)Nc1ccc(F)c(Cl)c1]

This compound was prepared according to the procedure of Example 164, using 2-4-[4-(3-chloro-4-fluorophenyl)-5-oxo-4,5-dihydro-1,2,4-oxadiazol-3-yl]-1,2,5-oxadiazol-3-ylethyl methane-sulfonate and DIPEA as the starting materials. MF=$C_{11}H_8ClFN_4O_2$; LCMS for $C_{11}H_9ClFN_4O_2$ (M+H)$^+$: m/z=283.0.

Example 172

N-(3-Chloro-4-fluorophenyl)-4-[2-(dimethylamino)ethyl]-N'-hydroxy-1,2,5-oxa-diazole-3-carboximidamide

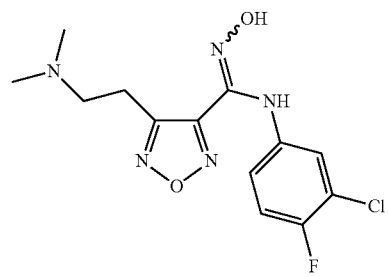 [SMILES: CN(C)CCc1nonc1C(=NO)Nc1ccc(F)c(Cl)c1]

This compound was prepared according to the procedure of Example 164, using 2-4-[4-(3-chloro-4-fluorophenyl)-5-oxo-4,5-dihydro-1,2,4-oxadiazol-3-yl]-1,2,5-oxadiazol-3-ylethyl methane-sulfonate and dimethylamine as the starting materials. MF=$C_{13}H_5ClFN_5O_2$; LCMS for $C_{13}H_{16}ClFN_5O_2$ (M+H)$^+$: m/z=3281

Example 173

N-(3-Chloro-4-fluorophenyl)-N-hydroxy-4-(2-thiomorpholin-4-ylethyl)-1,2,5-oxadiazole-3-carboximidamide

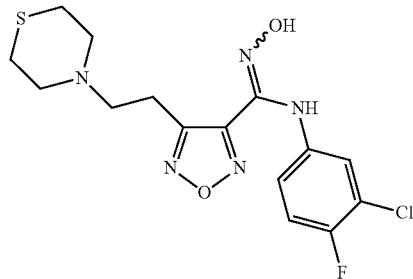 [SMILES: ON=C(Nc1ccc(F)c(Cl)c1)c1nonc1CCN1CCSCC1]

This compound was prepared according to the procedure of Example 164, using 2-4-[4-(3-chloro-4-fluorophenyl)-5-oxo-4,5-dihydro-1,2,4-oxadiazol-3-yl]-1,2,5-oxadiazol-3-ylethyl methane-sulfonate and thiomorpholine as the starting materials. MF=$C_{15}H_{17}ClFN_5O_2S$; LCMS for $C_{15}H_{18}ClFN_5O_2S$ (M+H)$^+$: m/z=386.1.

Example 174

N-(3-Chloro-4-fluorophenyl)-N'-hydroxy-4-(2-pyrrolidin-1-ylethyl)-1,2,5-oxadiazole-3-carboximidamide

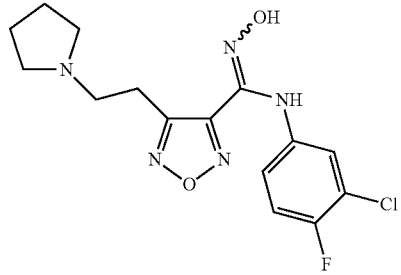 [SMILES: ON=C(Nc1ccc(F)c(Cl)c1)c1nonc1CCN1CCCC1]

This compound was prepared according to the procedure of Example 164, using 2-4-[4-(3-chloro-4-fluorophenyl)-5-oxo-4,5-dihydro-1,2,4-oxadiazol-3-yl]-1,2,5-oxadiazol-3-ylethyl methane-sulfonate and pyrrolidine as the starting materials. MF=$C_{15}H_{17}ClFN_5O_2$; LCMS for $C_{15}H_{18}ClFN_5O_2$ (M+H)$^+$: m/z=354.1.

Example 175

N-(3-Chloro-4-fluorophenyl)-1\-hydroxy-4-{2-[isopropyl(methyl)amino]ethyl}1,2,5-oxadiazole-3-carboximidamide

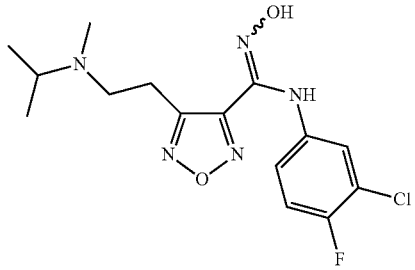 [SMILES: CC(C)N(C)CCc1nonc1C(=NO)Nc1ccc(F)c(Cl)c1]

This compound was prepared according to the procedure of Example 164, using 2-4-[4-(3-chloro-4-fluorophenyl)-5-oxo-4,5-dihydro-1,2,4-oxadiazol-3-yl]-1,2,5-oxadiazol-3-ylethyl methane-sulfonate and N-methyl-2-propanamine as the starting materials. MF=$C_{15}H_{19}ClFN_5O_2$; LCMS for $C_{15}H_{20}ClFN_5O_2$(M+H)$^+$: m/z=356.1.

Example 176

N-(3-Chloro-4-fluorophenyl)-N-hydroxy-4-2-[(methylsulfonyl)amino]ethyl-1,2,5-oxadiazole-3-carboximidamide

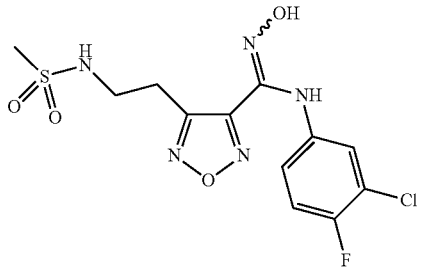 [SMILES: CS(=O)(=O)NCCc1nonc1C(=NO)Nc1ccc(F)c(Cl)c1]

Step A: 3-[4-(2-azidoethyl)-1,2,5-oxadiazol-3-yl]-4-(3-chloro-4-fluorophenyl)-1,2,4-oxadiazol-5 (4H)-one

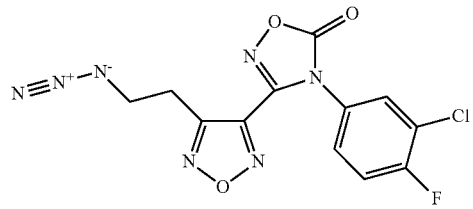 [SMILES: N#[N+][N-]CCc1nonc1-c1noc(=O)n1-c1ccc(F)c(Cl)c1]

2-4-[4-(3-Chloro-4-fluorophenyl)-5-oxo-4,5-dihydro-1,2,4-oxadiazol-3-yl]-1,2,5-oxadiazol-3-ylethyl methane-sulfonate (370 mg, 0.91 mmol) was dissolved in DMF (5 mL) followed by addition of sodium azide (120 mg, 1.80 mmol). The reaction mixture was heated at 60° C. for 2 h. The reaction solution was then cooled to rt and diluted with water and ethyl acetate and the aqueous layer was extracted with ethyl acetate once. The combined organic solutions were dried over $Na_2SO_4$, filtered and concentrated. The residue was purified by silica gel chromatography (30% ethyl acetate/hex) to give the desired product as a white solid (231 mg, 72%). MF=$C_{12}H_7ClFN_7O_3$; LCMS calculated for $C_{12}H_8ClFN_7O_3$ (M+H)$^+$: m/z=352.0.

Step B: 3-[4-(2-aminoethyl)-1,2,5-oxadiazol-3-yl]-4-(3-chloro-4-fluorophenyl)-1,2,4-oxadiazol-5 (4H)-one trifluoroacetate

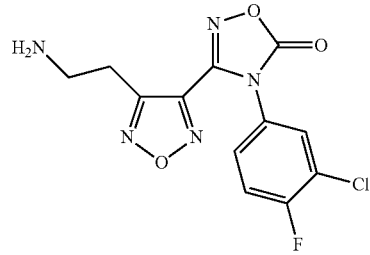 [SMILES: NCCc1nonc1-c1noc(=O)n1-c1ccc(F)c(Cl)c1]

3-[4-(2-Azidoethyl)-1,2,5-oxadiazol-3-yl]-4-(3-chloro-4-fluorophenyl)-1,2,4-oxadiazol-5(4H)-one (230 mg, 0.65 mmol) was dissolved in THF (4.0 mL) and water (4.0 mL). The reaction solution was cooled to 0° C., followed by addition triphenylphosphine (0.34 g, 1.3 mmol). After stirring at 0° C. for 30 min, solvent was removed in vacuo and the residue was dissolved in MeOH. The compound was purified by preparative LCMS to give the desired product as a white solid (121 mg, 56.8%). MF=$C_{12}H_9ClFN_5O_3$; LCMS calculated for $C_{12}H_{10}ClFN_5O_3$(M+H)$^+$: m/z=326.0.

Step C: N-(3-chloro-4-fluorophenyl)-N'-hydroxy-4-2-[(methylsulfonyl)amino]ethyl-1,2,5-oxadiazole-3-carboximidamide To a solution of 3-[4-(2-amino ethyl)-1,2,5-oxadiazol-3-yl]-4-(3-chloro-4-fluorophenyl)-1,2,4-oxadiazol-5(4H)-one trifluoroacetate (16.0 mg, 0.037 mmol) in DCM (1.0 mL) was added TEA (15 µL, 0.11 mmol) and methanesulfonyl chloride (4.2 µL, 0.055 mmol). The resulting mixture was stirred at rt for 1 h and then the solvent was removed under reduced pressure. The residue was dissolve in MeOH (1 mL) and 2.0 M sodium hydroxide in water (0.10 mL) was added. After stirring for 4 h, the reaction solution was diluted with MeOH and a few drop of acetic acid and then purified by preparative LCMS to give the desired product as a white solid (14.1 mg, 78.3%). MF=$C_{12}H_{13}ClFN_5O_4S$; LCMS calculated $C_{12}H_{14}ClFN_5O_4S$ (M+H)$^+$: m/z=377.0.

Example 177

N-(3-Chloro-4-fluorophenyl)-N'-hydroxy-4-(2-(sulfamoylamino)ethyl)-1,2,5-oxadiazole-3-carboximidamide

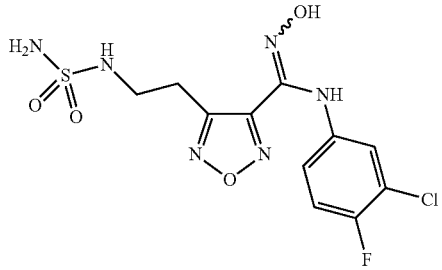 [SMILES: NS(=O)(=O)NCCc1nonc1C(=NO)Nc1ccc(F)c(Cl)c1]

A solution of 3-[4-(2-aminoethyl)-1,2,5-oxadiazol-3-yl]-4-(3-chloro-4-fluorophenyl)-1,2,4-oxadiazol-5(4h)-one trifluoroacetate (23.0 mg, 53.0 mmol), sulfamide (15.0 mg, 160 mmol) and pyridine (1.0 mL) was heated at 120° C. for 3 min in a microwave. To the reaction solution was added 0.5 mL 1 N NaOH and stirred for 30 min. The reaction solution was then acidified with acetic acid and purified by preparative LCMS to give the desired product (12 mg, 46%). MF=$C_{11}H_{12}ClFN_6O_4S$; LCMS calculated for $C_{11}H_{13}ClFN_6O_4S$ (M+H)$^+$: m/z=379.0. $^1$H NMR (400 MHz, DMSO-$d_6$): d 11.52 (s, 1 H), 10.45 (s, 0.1 H), 9.05 (s, 0.1 H), 8.98 (s, 1 H), 7.95 (m, 0.1 H), 7.32 (m, 0.2 H), 7.15 (t, J=9.0 Hz, 1 H), 7.00 (dd, J=6.5 Hz, 2.7 Hz, 1 H), 6.76 (t, J=5.9 Hz, 1 H), 6.65 (m, 1 H), 6.59 (s, 2H), 3.29 (m, 2 H), 3.07 (t, J=7.2 Hz, 2 H);

Example 178

Ethyl 3-(4-(N-(3-chloro-4-fluorophenyl)-N'-hydroxycarbamimidoyl)-1,2,5-oxadiazol-3-yl)propanoate

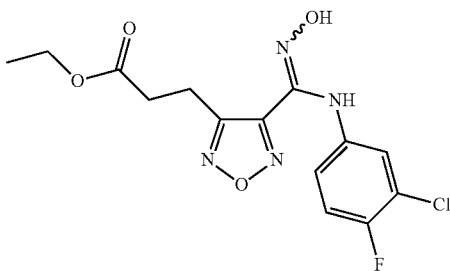 [SMILES: CCOC(=O)CCc1nonc1C(=NO)Nc1ccc(F)c(Cl)c1]

Step 1: N-(3-Chloro-4-fluorophenyl)-4-formyl-1,2,5-oxadiazole-3-carboxamide

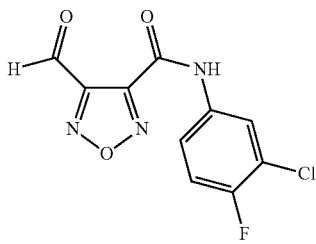 [SMILES: O=Cc1nonc1C(=O)Nc1ccc(F)c(Cl)c1]

A solution of N-(3-chloro-4-fluorophenyl)-4-(hydroxymethyl)-1,2,5-oxadiazole-3-carbo x-amide (8.50 g, 31.3 mmol), Dess-Martin periodinane (14.6 g, 34.4 mmol) and DCM (400 mL) was stirred at 25° C. for 3 h. The reaction was diluted with a saturated sodium bicarbonate solution and extracted with ethyl acetate three times, dried with sodium sulfate, filtered, and concentrated in vacuo. The crude residue was purified by flash column chromatography to yield the desired product (7.50 g, 89%). LCMS for $C_{10}H_6ClFN_3O_3$ (M+H)$^+$: m/z=270.0.

Step 2: Ethyl (2E)-3-(4-[(3-chloro-4-fluorophenyl)amino]carbonyl-1,2,5-oxadiazol-3-yl)acrylate

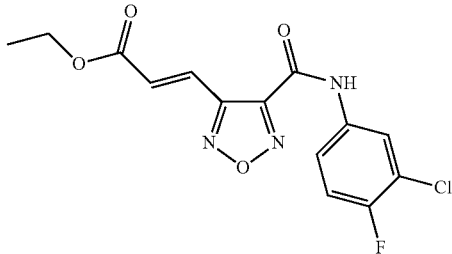 [SMILES: CCOC(=O)/C=C/c1nonc1C(=O)Nc1ccc(F)c(Cl)c1]

To a solution of (carbethoxymethyl)triphenylphosphonium bromide (3.14 g, 7.32 mmol) in toluene (37 mL) was added sodium tert-butoxide (723 mg, 7.52 mmol) at rt under a nitrogen atmosphere. After stirring for 30 min, a solution of N-(3-chloro-4-fluorophenyl)-4-formyl-1,2,5-oxadiazole-3-carboxamide (811 mg, 3.01 mmol) in THF (10 mL) was cannulated into reaction flask. The resulting solution was heated at 80° C. for 3 h, then cooled to rt overnight. The reaction was quenched with a 1 N HCl solution, the aqueous solution was extracted with ethyl acetate. The combined organic solutions were washed with brine, dried over $Na_2SO_4$, filtered and concentrate under reduced pressure. The residue was purified with flash chromatography (30% ethyl acetate/hexane) to give the desired product as a white solid (0.91 g, 89%). $^1$H NMR (400 MHz, CD$_3$OD): δ 7.92 (m, 2 H), 7.65 (m, 1 H), 7.26 (m, 1H), 7.01 (m, 1 H), 4.27 (m, 2 H), 1.33 (m, 3 H); LCMS for $C_{14}H_{12}ClFN_3O_4$(M+H)$^+$: m/z=340.

Step 3: Ethyl 3-(4-[(3-chloro-4-fluorophenyl)amino]carbonyl-1,2,5-oxadiazol-3-yl)propanoate

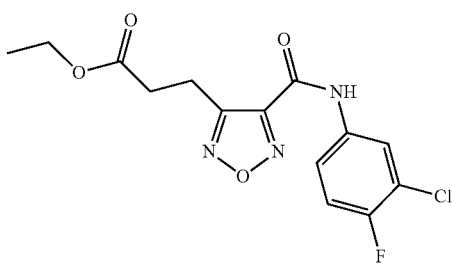 [SMILES: CCOC(=O)CCc1nonc1C(=O)Nc1ccc(F)c(Cl)c1]

To a solution of ethyl (2E)-3-(4-[(3-chloro-4-fluorophenyl)amino]carbonyl-1,2,5-oxadiazol-3-yl)acrylate (0.86 g, 0.0025 mol) in ethyl acetate (10 mL, 0.1 mol) was added palladium (600 mg, 0.006 mol). The mixture was stirred at room temperature under an atmosphere of hydrogen for 2 h. The reaction solution was filtered through a pad of celite. The filtrate was concentrated and purified by flash chromatography (40% ethyl acetate/hexane) to give the desired product as a white solid (609 mg, 70%). LCMS for $C_{14}H_{14}ClFN_3O_4$(M+H)$^+$: m/z-=342.1.

Step 4: Ethyl 3-(4-(N-(3-chloro-4-fluorophenyl)-N'-hydroxycarbamimidoyl)-1,2,5-oxadiazol-3-yl)propanoate Ethyl 3-(4-[(3-chloro-4-fluorophenyl)amino]carbonyl-1,2,5-oxadiazol-3-yl)propanoate (27 mg, 0.079 mmol) was suspended in benzene (1 mL) under an atmosphere of nitrogen and phosphorus pentachloride (18.0 mg, 0.086 mmol) was added. The solution was heated to reflux for 2.5 h. The solvent was removed in vacuo. The residue was dissolved in EtOH (1.0 mL) and hydroxylamine (100 µL, 2 mmol) (50% solution in water) was added to the reaction. After stirring 1 h, the solution was diluted with MeOH and purified by preparative LCMS to give the desired product (8.5 mg, 30%). $^1$H NMR (400 MHz, CD$_3$OD): δ 7.03 (t, J=8.9 Hz, 1 H), 6.95 (dd, J=6.4, 2.7 Hz, 1 H), 6.71 (m, 1 H), 4.12 (q, J=7.2 Hz, 2 H), 3.11 (t, J=7.2 Hz, 2 H), 2.80 (t, J=7.2 Hz, 2 H), 1.23 (t, J=7.2 Hz, 3 H); LCMS for $C_{14}H_{15}ClFN_4O_1$(M+H)$^+$: m/z=357.1.

Example 179

N-(3-Chloro-4-fluorophenyl)-N'-hydroxy-4-(3-morpholin-4-ylpropyl)-1,2,5-oxadiazole-3-carboximidamide

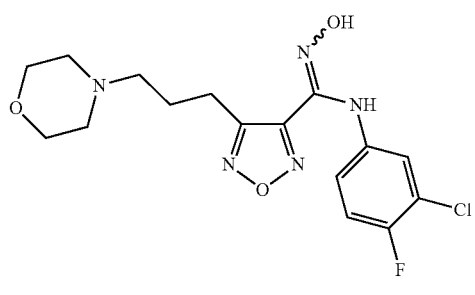 [SMILES: ON=C(Nc1ccc(F)c(Cl)c1)c1nonc1CCCN1CCOCC1]

Step 1: N-(3-Chloro-4-fluorophenyl)-4-(3-hydroxypropyl)-1,2,5-oxadiazole-3-carboxamide

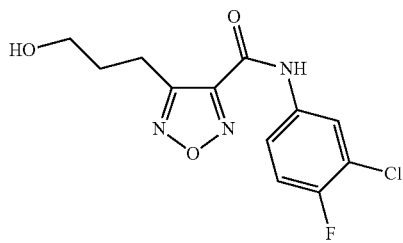 [SMILES: O=C(Nc1ccc(F)c(Cl)c1)c1nonc1CCCO]

To a solution of ethyl 3-(4-[(3-chloro-4-fluorophenyl)amino]carbonyl-1,2,5-oxadiazol-3-yl)propanoate (97.5 mg, 0.285 mmol) in THF (1.2 mL) was added lithium tetrahydroborate (14.3 mg, 0.656 mmol) at 0° C. under an atmosphere of nitrogen. The reaction solution was allowed to warm to rt for 2 h. The reaction was quenched with MeOH and concentrated. The residue was purified by flash chromatography (60% ethyl acetate/hexane) to give the desired product (70 mg, 80%). LCMS for $C_{12}H_{12}ClFN_3O_3$(M+H)$^+$: m/z=300.1.

Step 2: 3-(4-[(3-Chloro-4-fluorophenyl)amino]carbonyl-1,2,5-oxadiazol-3-yl)propyl methane-sulfonate

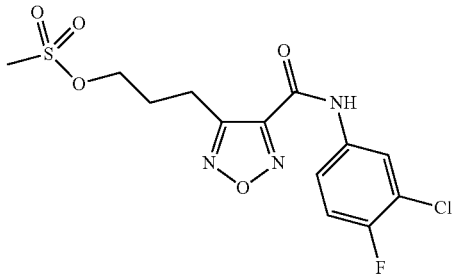 [SMILES: CS(=O)(=O)OCCCc1nonc1C(=O)Nc1ccc(F)c(Cl)c1]

N-(3-Chloro-4-fluorophenyl)-4-(3-hydroxypropyl)-1,2,5-oxadiazole-3-carboxamide (60 mg, 0.20 mmol) was dissolved in anhydrous DCM (2 mL), followed by addition of TEA (57 µL, 0.41 mmol). The reaction was stirred and cooled to 0° C., and methanesulfonyl chloride (29 µL, 0.37 mmol) was added drop-wise. The reaction was quenched with water and diluted with DCM. The organic layer was separated, dried over Na$_2$SO$_4$, filtered, concentrated and purified by silica gel chromatography (25%-75% EtOAc/hexane) to give the desired product (60 mg, 80%). LCMS for $C_{13}H_{14}ClFN_3O_5S$ (M+H)$^+$: m/z=378.

Step 3: N-(3-Chloro-4-fluorophenyl)-4-(3-morpholin-4-ylpropyl)-1,2,5-oxadiazole-3-carboxamide

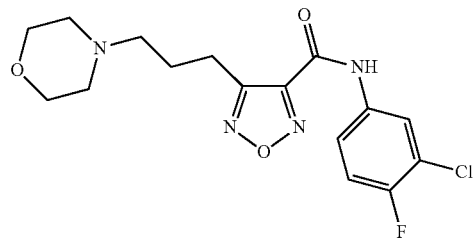 [SMILES: O=C(Nc1ccc(F)c(Cl)c1)c1nonc1CCCN1CCOCC1]

3-(4-[(3-Chloro-4-fluorophenyl)amino]carbonyl-1,2,5-oxadiazol-3-yl)propyl methane-sulfonate (19 mg, 0.051 mmol) was dissolved in anhydrous ACN (100 µL) followed by the addition of DIPEA (44 µL, 0.26 mmol) and morpholine (6.7 µL, 76.8 µmol). The reaction were stirred and heated at 70° C. for 3 h. The reaction was concentrated and purified by silica gel chromatography (60-100% ethyl acetate/hexanes) to give the desired product (10.2 mg, 54%). LCMS for $C_{16}H_{19}ClFN_4O_3$ (M+H)$^+$ m/z=369.1.

Step 4: N-(3-Chloro-4-fluorophenyl)-N'-hydroxy-4-(3-morpholin-4-ylpropyl)-1,2,5-oxadiazole-3-carboximidamide N-(3-Chloro-4-fluorophenyl)-4-(3-morpholin-4-ylpropyl)-1,2,5-oxadiazole-3-carboxamide (10.0 mg, 27 µmol) was suspended in benzene (0.4 mL) under an atmosphere of nitrogen and phosphorus pentachloride (6.2 mg, 29.8 µmol) was added. The solution was heated at reflux for 2.5 h. The volatiles were evaporated in vacuo. The reaction was dissolved in EtOH (0.3 mL) and hydroxylamine (40 µL, 0.7 mmol) (50% solution in water) was added to the reaction. After stirring for 1 h, the reaction solution was diluted with MeOH and purified by preparative LCMS to give the desired product (5.2 mg, 50%). LCMS for $C_{16}H_{20}ClFN_5O_3(M+H)^+$: m/z=384.1.

Example 180

4-{3-[(Aminosulfonyl)amino]propyl}-N-(3-chloro-4-fluorophenyl)-N'-hydroxy-1,2,5-oxadiazole-3-carboximidamide

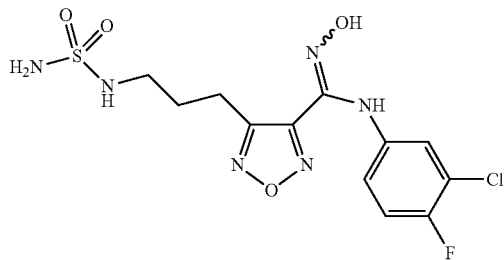 [SMILES: NS(=O)(=O)NCCCc1nonc1C(=NO)Nc1ccc(F)c(Cl)c1]

3-[4-(3-Aminopropyl)-1,2,5-oxadiazol-3-yl]-4-(3-chloro-4-fluorophenyl)-1,2,4-oxadiazol-5(4H)-one trifluoroacetate (7.8 mg, 0.017 mmol) and sulfamide (9.4 mg, 0.98 mol) was dissolved in pyridine (1.0 mL). The solution was heated at 120° C. for 3 minutes in a microwave. A solution of sodium hydroxide in water (0.5 mL, 1.0; N) was added and the mixture stirred at room temperature for 16 hrs. Acidification with acetic acid and purification by preparative LCMS gave the desired product (5.7 mg, 84%). $^1$H NMR (400 MHz, CD$_3$OD): δ 7.02 (t, 1H), 6.95 (m, 1H), 6.7 (m, 1H), 3.1 (m, 2H), 2.9 (m, 2H), 2.0 (m, 2H). MF=$C_{12}H_{14}ClFN_6O_4S$. LCMS calculated for $C_{12}H_{15}ClFN_6O_4S$ (M+H)$^+$: m/z=393.0.

Step 1: 3-[4-(3-Azidopropyl)-1,2,5-oxadiazol-3-yl]-4-(3-chloro-4-fluorophenyl)-1,2,4-oxadiazol-5(4H)-one

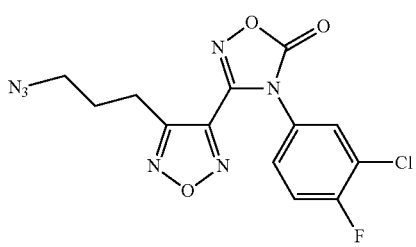 [SMILES: [N-]=[N+]=NCCCc1nonc1-c1noc(=O)n1-c1ccc(F)c(Cl)c1]

3-4-[4-(3-Chloro-4-fluorophenyl)-5-oxo-4,5-dihydro-1,2,4-oxadiazol-3-yl]-1,2,5-oxadiazol-3-ylpropyl methanesulfonate (0.25 g, 0.60 mmol) was dissolved in anhydrous DMF (3.0 mL). Sodium azide (97 mg, 1.5 mmol) was added and the reaction was stirred at 65° C. for 1 h. The reaction mixture was quenched with water and extracted with EtOAc. EtOAc extracts were washed with water and brine, dried over Na$_2$SO$_4$, filtered and volatiles evaporated. Crude material was used in the next step without further purification (200 mg, 92%). MF=$C_{13}H_9ClFN_7O_3$; LCMS calculated for $C_{13}H_{10}ClFN_7O_3(M+H)^+$: m/z=366.0.

Step 2: 3-[4-(3-Aminopropyl)-1,2,5-oxadiazol-3-yl]-4-(3-chloro-4-fluorophenyl)-1,2,4-oxadiazol-5(4H)-one trifluoroacetate

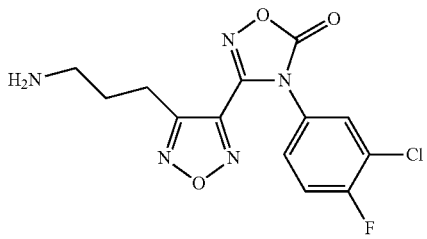 [SMILES: NCCCc1nonc1-c1noc(=O)n1-c1ccc(F)c(Cl)c1]

3-[4-(3-Azidopropyl)-1,2,5-oxadiazol-3-yl]-4-(3-chloro-4-fluorophenyl)-1,2,4-oxadiazol-5(4H)-one (200 mg, 0.5 mmol) was dissolved in anhydrous THF (3 mL) and water (3 mL). The reaction was cooled to 0° C. followed by addition of triphenylphosphine (430 mg, 1.6 mmol). The reaction was stirred at 0° C. for 30 minutes and then the volatiles evaporated in vacuo. The residue was azeotroped with toluene, dissolved in MeOH and purified by preparative LCMS using pH 2 buffer to give the desired product (45.3 mg, 20%). MF=$C_{13}H_{10}ClFN_5O_3$; LCMS calculated for $C_{13}H_{11}ClFN_5O_3(M+H)^+$: m/z=340.0.

Example 181

N-(3-Chloro-4-fluorophenyl)-4-(3-{[(E/Z)-(cyanoimino)(methyl-amino)methyl]amino}propyl)-N'-hydroxy-1,2,5-oxadiazole-3-carboximidamide trifluoroacetate

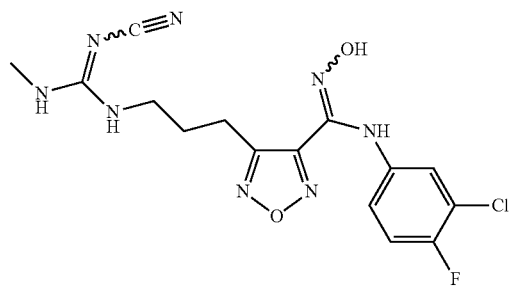 [SMILES: CNC(=NC#N)NCCCc1nonc1C(=NO)Nc1ccc(F)c(Cl)c1]

3-[4-(3-Aminopropyl)-1,2,5-oxadiazol-3-yl]-4-(3-chloro-4-fluorophenyl)-1,2,4-oxadiazol-5(4H)-one trifluoroacetate (11.0 mg, 0.0251 mmol) was dissolved in THF (0.32 mL). Diphenyl cyanocarbonimidate (8.73 mg, 0.0366 mmol) and TEA (13 µL, 0.092 mmol) were added and the reaction stirred at room temperature for two hrs. A solution of methylamine in THF (46 µL, 2.0; N) was added and the reaction was stirred at room temperature for two hrs. A solution of sodium hydroxide in water (0.5 mL, 1.0; N) was added and the mixture stirred at room temperature for 16 hrs. Acidification with acetic acid and purification by preparative LCMS gave the desired product (5.6 mg, 44%). MF=$C_{15}H_{15}ClFN_8O_2$; LCMS calculated for $C_{15}H_{16}ClFN_8O_2(M+H)^+$: m/z=395.0.

Example 182

N-(3-Chloro-4-fluorophenyl)-N'-hydroxy-4-[3-(4H-1,2,4-triazol-4-yl)propyl]-1,2,5-oxadiazole-3-carboximidamide trifluoroacetate

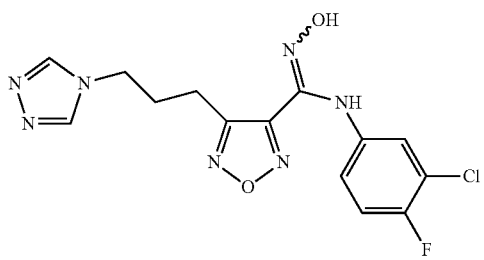 [SMILES: ON=C(Nc1ccc(F)c(Cl)c1)c1nonc1CCCn1cnnc1]

To a microwave tube was added 3-[4-(3-aminopropyl)-1,2,5-oxadiazol-3-yl]-4-(3-chloro-4-fluorophenyl)-1,2,4-oxadiazol-5(4H)-one trifluoroacetate (26.3 mg, 0.0580 mmol), N-[(1E)-(dimethylamino)methylene]-N,N-dimethylhydrazonoformamide (9.1 mg, 0.064 mmol), p-toluene-sulfonic acid monohydrate (1 mg, 0.006 mmol) and toluene (0.5 mL). The reaction was heated in a microwave at 170° C. for 30 minutes. Solvent was removed in vacuo and the residue was purified by preparative LCMS. A solution of sodium hydroxide in water (0.5 mL, 1.0; N) was added and the mixture stirred at room temperature for 16 hrs. Acidification with acetic acid and purification by preparative LCMS gave the desired product give product (13 g, 48%). $^1$HNMR (400 MHz, CD$_3$OD): δ 9.0 (s, 2H), 7.02 (m, 1H), 6.9 (m, 1H), 6.7 (m, 1H), 4.3 (m, 2H), 2.95 (m, 2H), 2.4 (m, 2H). MF=C$_{14}$H$_{12}$ClFN$_7$O$_2$; LCMS calculated for C$_{14}$H$_{13}$ClFN$_7$O$_2$(M+H)$^+$: m/z=366.0.

Data for additional example compounds of the invention are provided in Table 3, below.

TABLE 3

| Ex. No. | Structure | MS (M + 1) | Prep. Ex. | Pur. Meth. | Salt | Name |
|---|---|---|---|---|---|---|
| 183 | 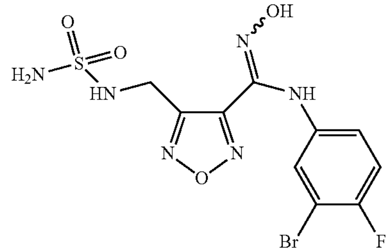 [SMILES: NS(=O)(=O)NCc1nonc1C(=NO)Nc1ccc(F)c(Br)c1] | 408.0 | 143 | A | Free Base | 4-{[(aminosulfonyl)-amino]methyl}-N-(3-bromo-4-fluoro-phenyl)-N'-hydroxy-1,2,5-oxadiazole-3-carboximidamide |
| 184 | 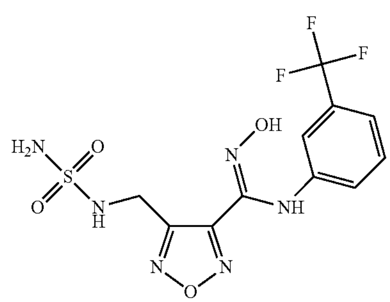 [SMILES: NS(=O)(=O)NCc1nonc1/C(=N/O)Nc1cccc(C(F)(F)F)c1] | 381.0 | 143 | A | Free Base | 4-{[(aminosulfonyl)-amino]methyl}-N'-hydroxy-N-[3-(tri-fluoromethyl)phenyl]-1,2,5-oxadiazole-3-carboximidamide |
| 185 | 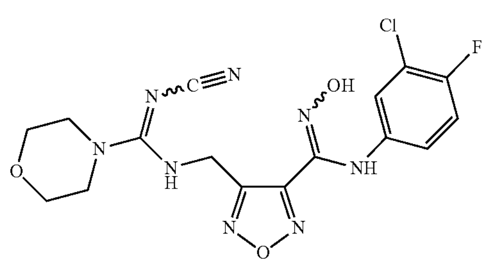 [SMILES: N#CN=C(NCc1nonc1C(=NO)Nc1ccc(F)c(Cl)c1)N1CCOCC1] | 423.0 | 144 | B | Free Base | N-({4-[(E/Z)-[(3-chloro-4-fluoro-phenyl)amino](hydroxy-imino)methyl]-1,2,5-oxadiazol-3-yl}-methyl)-N'-cyano-morpholine-4-carboximidamide |
| 186 | 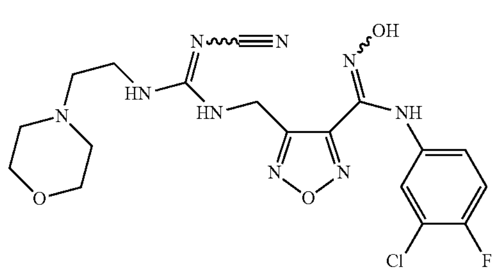 [SMILES: N#CN=C(NCCN1CCOCC1)NCc1nonc1C(=NO)Nc1ccc(F)c(Cl)c1] | 466.0 | 144 | B | Free Base | N-(3-chloro-4-fluoro-phenyl)-4-[({(E/Z)-(cyanoimino)[(2-morpholin-4-ylethyl)-amino]methyl}amino)methyl]-N'-hydroxy-1,2,5-oxadiazole-3-carboximidamide |

TABLE 3-continued

| Ex. No. | Structure | MS (M + 1) | Prep. Ex. | Pur. Meth. | Salt | Name |
|---|---|---|---|---|---|---|
| 187 | 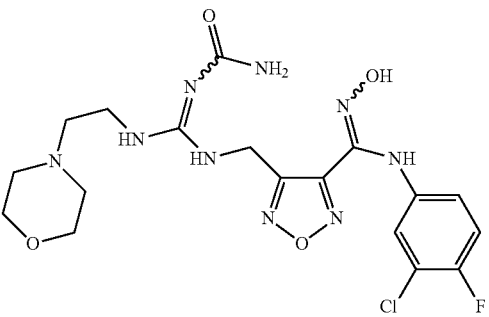 [SMILES: NC(=O)N=C(NCCN1CCOCC1)NCc1nonc1C(=NO)Nc1ccc(F)c(Cl)c1] | 484.1 | 144 | B | Free Base | 4-[({(E/Z)-[(amino-carbonyl)imino][(2-morpholin-4-ylethyl)-amino]methyl}amino)methyl]-N-(3-chloro-4-fluorophenyl)-N'-hydroxy-1,2,5-oxadiazole-3-carboximidamide |
| 188 | 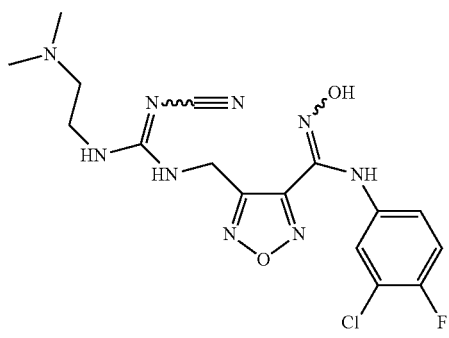 [SMILES: CN(C)CCNC(=NC#N)NCc1nonc1C(=NO)Nc1ccc(F)c(Cl)c1] | 424.0 | 144 | B | Free Base | N-(3-chloro-4-fluoro-phenyl)-4-{[((E/Z)-(cyanoimino){[2-(dimethylamino)ethyl]amino}methyl)amino]methyl}-N'-hydroxy-1,2,5-oxadiazole-3-carboximidamide |
| 189 | 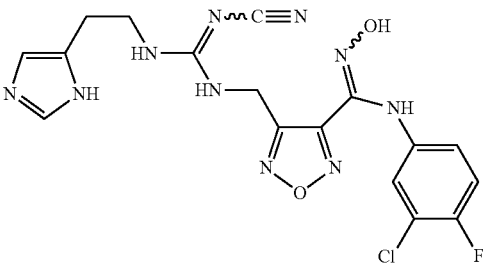 [SMILES: N#CN=C(NCCc1cnc[nH]1)NCc1nonc1C(=NO)Nc1ccc(F)c(Cl)c1] | 447.1 | 144 | B | Free Base | N-(3-chloro-4-fluoro-phenyl)-4-{[((E/Z)-(cyanoimino){[2-(1H-imidazol-5-yl)ethyl]-amino}methyl)amino]methyl}-N'-hydroxy-1,2,5-oxadiazole-3-carboximidamide |
| 190 | 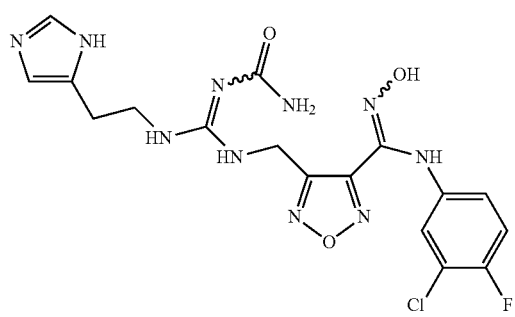 [SMILES: NC(=O)N=C(NCCc1cnc[nH]1)NCc1nonc1C(=NO)Nc1ccc(F)c(Cl)c1] | 465.1 | 144 | B | Free Base | 4-{[((E/Z)-[(amino-carbonyl)imino]{[2-(1H-imidazol-5-yl)-ethyl]amino}methyl)amino]methyl}-N-(3-chloro-4-fluoro-phenyl)-N'-hydroxy-1,2,5-oxadiazole-3-carboximidamide |
| 191 | 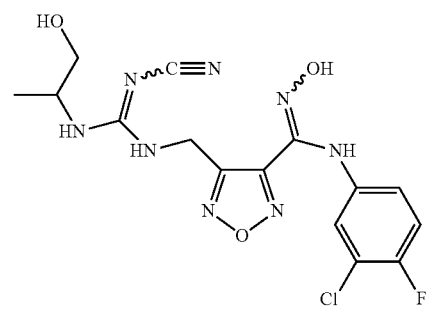 [SMILES: CC(CO)NC(=NC#N)NCc1nonc1C(=NO)Nc1ccc(F)c(Cl)c1] | 411.0 | 144 | B | Free Base | N-(3-chloro-4-fluoro-phenyl)-4-[({(E/Z)-(cyanoimino)[(2-hydroxy-1-methyl-ethyl)amino]methyl}amino)methyl]-N'-hydroxy-1,2,5-oxadiazole-3-carboximidamide |

TABLE 3-continued

| Ex. No. | Structure | MS (M + 1) | Prep. Ex. | Pur. Meth. | Salt | Name |
|---|---|---|---|---|---|---|
| 192 | 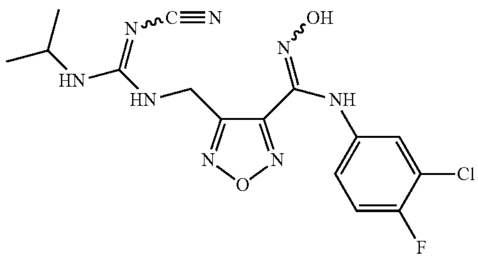 [SMILES: CC(C)NC(=NC#N)NCc1nonc1C(=NO)Nc1ccc(F)c(Cl)c1] | 395.1 | 144 | A | TFA | N-(3-chloro-4-fluoro-phenyl)-4-({[(E/Z)-(cyanoimino)(isopropylamino)methyl]-amino}methyl)-N'-hydroxy-1,2,5-oxadiazole-3-carboximidamide trifluoroacetate |
| 193 | 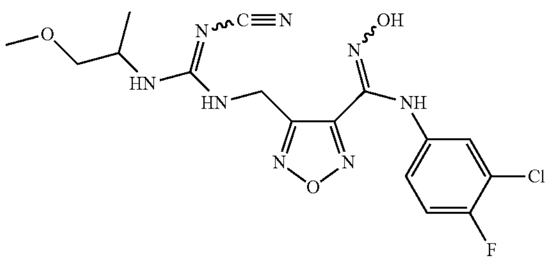 [SMILES: COCC(C)NC(=NC#N)NCc1nonc1C(=NO)Nc1ccc(F)c(Cl)c1] | 425.1 | 144 | A | TFA | N-(3-chloro-4-fluoro-phenyl)-4-[({(E/Z)-(cyanoimino)[(2-methoxy-1-methyl-ethyl)amino]methyl}amino)methyl]-N'-hydroxy-1,2,5-oxadiazole-3-carboximidamide trifluoroacetate |
| 194 | 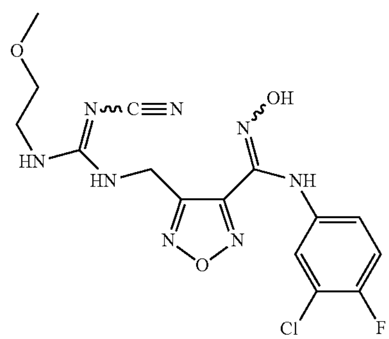 [SMILES: COCCNC(=NC#N)NCc1nonc1C(=NO)Nc1ccc(F)c(Cl)c1] | 411.0 | 144 | A | TFA | N-(3-chloro-4-fluoro-phenyl)-4-[({(E/Z)-(cyanoimino)[(2-methoxyethyl)amino]methyl}amino)methyl]-N'-hydroxy-1,2,5-oxadiazole-3-carboximidamide trifluoroacetate |
| 195 | 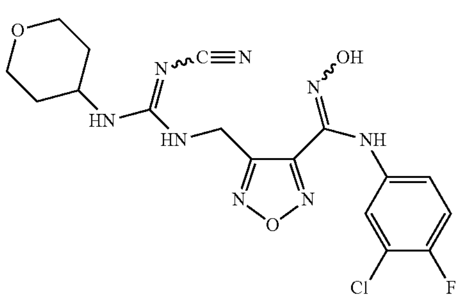 [SMILES: N#CN=C(NCc1nonc1C(=NO)Nc1ccc(F)c(Cl)c1)NC1CCOCC1] | 437.0 | 144 | A | TFA | N-(3-chloro-4-fluoro-phenyl)-4-({[(E/Z)-(cyanoimino)(tetrahydro-2H-pyran-4-ylamino)methyl]amino}methyl)-N'-hydroxy-1,2,5-oxadiazole-3-carboximidamide trifluoroacetate |
| 196 | 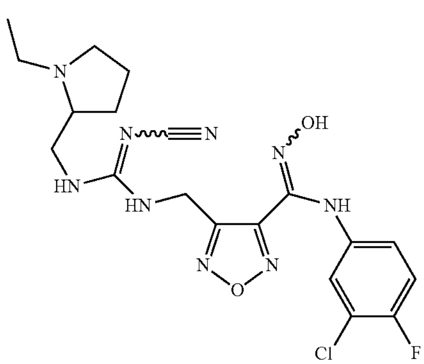 [SMILES: CCN1CCCC1CNC(=NC#N)NCc1nonc1C(=NO)Nc1ccc(F)c(Cl)c1] | 464.1 | 144 | A | 2 TFA | N-(3-chloro-4-fluoro-phenyl)-4-{[((E/Z)-(cyanoimino){[(1-ethylpyrrolidin-2-yl)methyl]amino}methyl)amino]methyl}-N'-hydroxy-1,2,5-oxadiazole-3-carboximidamide bis(trifluoroacetate) |

TABLE 3-continued

| Ex. No. | Structure | MS (M + 1) | Prep. Ex. | Pur. Meth. | Salt | Name |
|---|---|---|---|---|---|---|
| 197 | 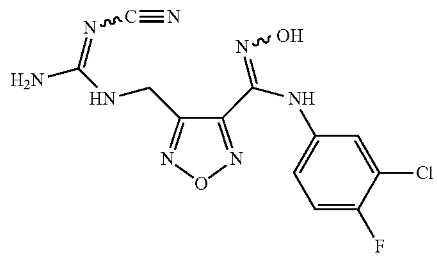 [SMILES: N#CN=C(N)NCc1nonc1C(=NO)Nc1ccc(F)c(Cl)c1] | 353.0 | 144 | A | TFA | 4-({[(E/Z)-amino-(cyanoimino)methyl]amino}methyl)-N-(3-chloro-4-fluoro-phenyl)-N'-hydroxy-1,2,5-oxadiazole-3-carboximidamide trifluoroacetate |
| 198 | 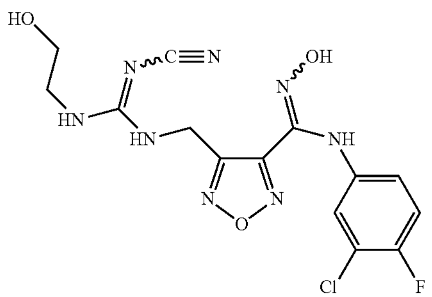 [SMILES: N#CN=C(NCCO)NCc1nonc1C(=NO)Nc1ccc(F)c(Cl)c1] | 397.1 | 144 | A | TFA | N-(3-chloro-4-fluoro-phenyl)-4-[({(E/Z)-(cyanoimino)[(2-hydroxyethyl)amino]methyl}amino)-methyl]-N'-hydroxy-1,2,5-oxadiazole-3-carboximidamide trifluoroacetate |
| 199 | 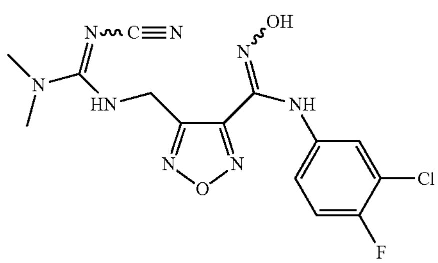 [SMILES: CN(C)C(=NC#N)NCc1nonc1C(=NO)Nc1ccc(F)c(Cl)c1] | 381.0 | 144 | B | Free Base | N-(3-chloro-4-fluoro-phenyl)-4-({[(E/Z)-(cyanoimino)(di-methylamino)methyl]-amino}methyl)-N'-hydroxy-1,2,5-oxadiazole-3-carboximidamide |
| 200 | 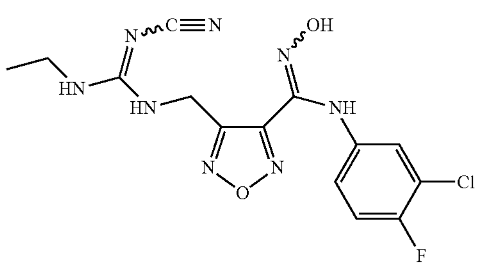 [SMILES: CCNC(=NC#N)NCc1nonc1C(=NO)Nc1ccc(F)c(Cl)c1] | 381.0 | 144 | B | Free Base | N-(3-chloro-4-fluoro-phenyl)-4-({[(E/Z)-(cyanoimino)(ethyl-amino)methyl]amino}methyl)-N'-hydroxy-1,2,5-oxadiazole-3-carboximidamide |
| 201 | 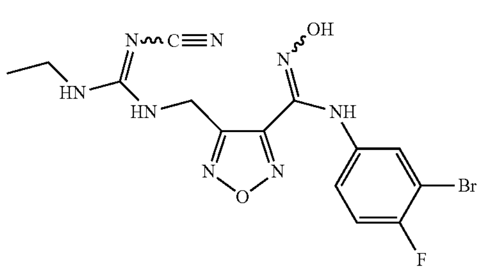 [SMILES: CCNC(=NC#N)NCc1nonc1C(=NO)Nc1ccc(F)c(Br)c1] | 424.0 | 144 | B | Free Base | N-(3-bromo-4-fluoro-phenyl)-4-({[(E/Z)-(cyanoimino)(ethyl-amino)methyl]amino}methyl)-N'-hydroxy-1,2,5-oxadiazole-3-carboximidamide |

TABLE 3-continued

| Ex. No. | Structure | MS (M + 1) | Prep. Ex. | Pur. Meth. | Salt | Name |
|---|---|---|---|---|---|---|
| 202 | 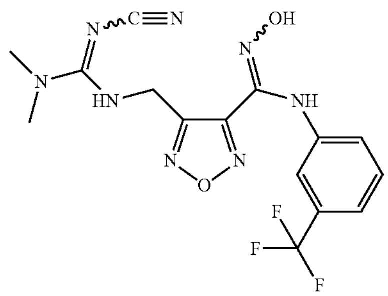 [SMILES: CN(C)C(=NC#N)NCc1nonc1C(=NO)Nc1cccc(C(F)(F)F)c1] | 397.1 | 144 | B | Free Base | 4-({[(E/Z)-(cyano-imino)(dimethyl-amino)methyl]amino}methyl)-N'-hydroxy-N-[3-(trifluoro-methyl)phenyl]-1,2,5-oxadiazole-3-carboximidamide |
| 203 | 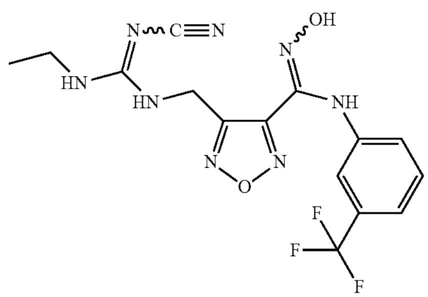 [SMILES: CCNC(=NC#N)NCc1nonc1C(=NO)Nc1cccc(C(F)(F)F)c1] | 397.1 | 144 | B | Free Base | 4-({[(E/Z)-(cyano-imino)(ethylamino)-methyl]amino}-methyl)-N'-hydroxy-N-[3-(trifluoro-methyl)phenyl]-1,2,5-oxadiazole-3-carboximidamide |
| 204 | 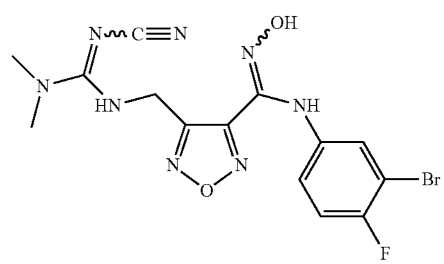 [SMILES: CN(C)C(=NC#N)NCc1nonc1C(=NO)Nc1ccc(F)c(Br)c1] | 424.0 | 144 | B | Free Base | N-(3-bromo-4-fluoro-phenyl)-4-({[(E/Z)-(cyanoimino)(di-methylamino)methyl]amino}methyl)-N'-hydroxy-1,2,5-oxadiazole-3-carboximidamide |
| 205 | 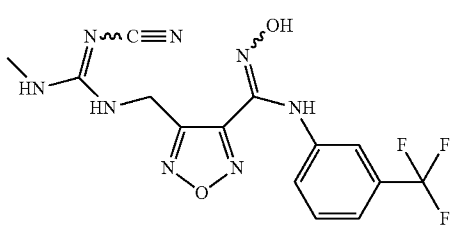 [SMILES: CNC(=NC#N)NCc1nonc1C(=NO)Nc1cccc(C(F)(F)F)c1] | 383.0 | 144 | A | TFA | 4-({[(E/Z)-(cyano-imino)(methylamino)methyl]amino}-methyl)-N'-hydroxy-N-[3-(trifluoro-methyl)phenyl]-1,2,5-oxadiazole-3-carboximidamide trifluoroacetate |
| 206 | 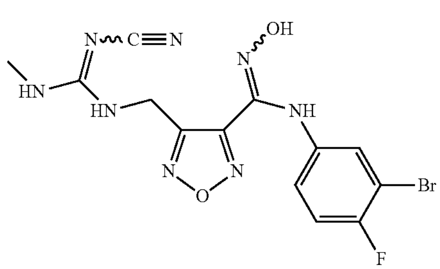 [SMILES: CNC(=NC#N)NCc1nonc1C(=NO)Nc1ccc(F)c(Br)c1] | 410.0 | 144 | B | Free Base | N-(3-bromo-4-fluoro-phenyl)-4-({[(E/Z)-(cyanoimino)(methyl-amino)methyl]amino}methyl)-N'-hydroxy-1,2,5-oxadiazole-3-carboximidamide |

TABLE 3-continued

| Ex. No. | Structure | MS (M + 1) | Prep. Ex. | Pur. Meth. | Salt | Name |
|---|---|---|---|---|---|---|
| 207 | 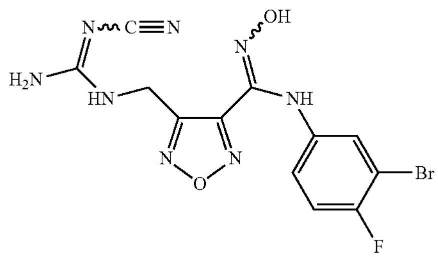 [SMILES: N#CN=C(N)NCc1nonc1C(=NO)Nc1ccc(F)c(Br)c1] | 396.0 | 144 | B | Free Base | 4-({[(E/Z)-amino-(cyanoimino)methyl]-amino}methyl)-N-(3-bromo-4-fluoro-phenyl)-N'-hydroxy-1,2,5-oxadiazole-3-carboximidamide |
| 208 | 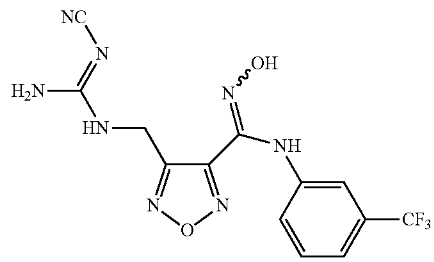 [SMILES: N#C/N=C(\N)NCc1nonc1C(=NO)Nc1cccc(C(F)(F)F)c1] | 369.0 | 144 | B | Free Base | 4-({[(E/Z)-amino-(cyanoimino)methyl]-amino}methyl)-N'-hydroxy-N-[3-(tri-fluoromethyl)phenyl]-1,2,5-oxadiazole-3-carboximidamide |
| 209 | 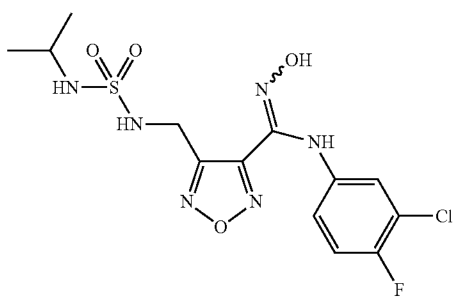 [SMILES: CC(C)NS(=O)(=O)NCc1nonc1C(=NO)Nc1ccc(F)c(Cl)c1] | 407.0 | 145 | A | Free Base | N-(3-chloro-4-fluoro-phenyl)-N'-hydroxy-4-({[(isopropylamino)sulfonyl]amino}methyl)-1,2,5-oxadiazole-3-carboximidamide |
| 210 | 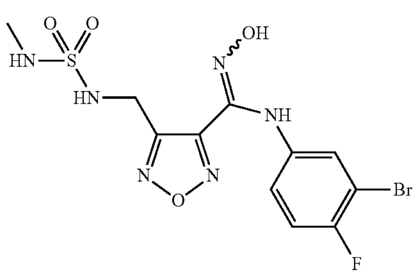 [SMILES: CNS(=O)(=O)NCc1nonc1C(=NO)Nc1ccc(F)c(Br)c1] | 422.0 | 145 | A | Free Base | N-(3-bromo-4-fluoro-phenyl)-N'-hydroxy-4-({[(methylamino)sulfonyl]amino}methyl)-1,2,5-oxadiazole-3-carboximidamide |
| 211 | 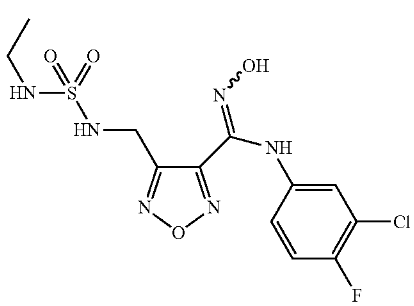 [SMILES: CCNS(=O)(=O)NCc1nonc1C(=NO)Nc1ccc(F)c(Cl)c1] | 392.9 | 145 | A | Free Base | N-(3-chloro-4-fluoro-phenyl)-4-({[(ethyl-amino)sulfonyl]amino}methyl)-N'-hydroxy-1,2,5-oxadiazole-3-carboximidamide |

TABLE 3-continued

| Ex. No. | Structure | MS (M + 1) | Prep. Ex. | Pur. Meth. | Salt | Name |
|---|---|---|---|---|---|---|
| 212 | 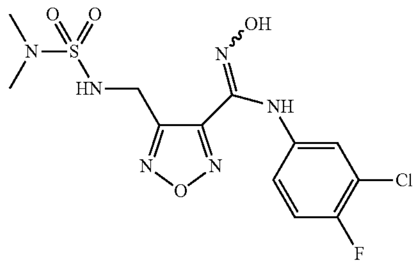 [SMILES: CN(C)S(=O)(=O)NCc1nonc1C(=NO)Nc1ccc(F)c(Cl)c1] | 393.0 | 145 | B | Free Base | N-(3-chloro-4-fluoro-phenyl)-4-({[(di-methylamino)sulfonyl]amino}methyl)-N'-hydroxy-1,2,5-oxadiazole-3-carboximidamide |
| 213 | 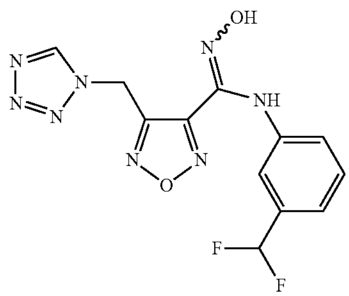 [SMILES: ON=C(Nc1cccc(C(F)F)c1)c1nonc1Cn1cnnn1] | 337.0 | 39 | A | Free Base | N-[3-(difluoro-methyl)phenyl]-N'-hydroxy-4-(1H-tetrazol-1-ylmethyl)-1,2,5-oxadiazole-3-carboximidamide |
| 214 | 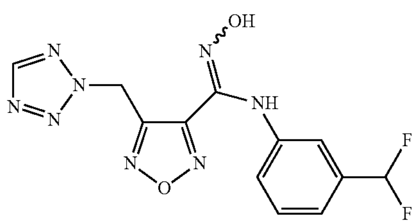 [SMILES: ON=C(Nc1cccc(C(F)F)c1)c1nonc1Cn1ncnn1] | 337.0 | 40 | A | Free Base | N-[3-(difluoro-methyl)phenyl]-N'-hydroxy-4-(2H-tetrazol-2-ylmethyl)-1,2,5-oxadiazole-3-carboximidamide |
| 215 | 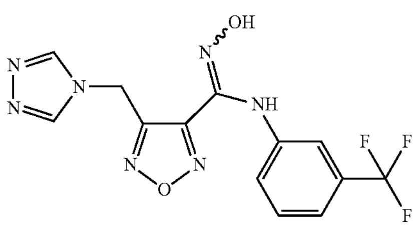 [SMILES: ON=C(Nc1cccc(C(F)(F)F)c1)c1nonc1Cn1cnnc1] | 354.0 | 161 | A | Free Base | N'-hydroxy-4-(4H-1,2,4-triazol-4-yl-methyl)-N-[3-(tri-fluoromethyl)phenyl]-1,2,5-oxadiazole-3-carboximidamide |
| 216 | 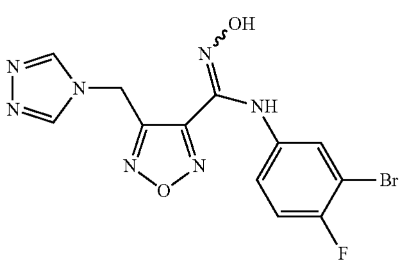 [SMILES: ON=C(Nc1ccc(F)c(Br)c1)c1nonc1Cn1cnnc1] | 381.0 | 161 | A | Free Base | N-(3-bromo-4-fluoro-phenyl)-N'-hydroxy-4-(4H-1,2,4-triazol-4-yl-methyl)-1,2,5-oxadiazole-3-carboximidamide |
| 217 | 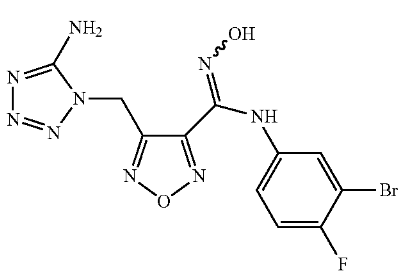 [SMILES: Nc1nnnn1Cc1nonc1C(=NO)Nc1ccc(F)c(Br)c1] | 397.0 | 39 | A | Free Base | 4-[(5-amino-1H-tetrazol-1-yl)methyl]-N-(3-bromo-4-fluoro-phenyl)-N'-hydroxy-1,2,5-oxadiazole-3-carboximidamide |

TABLE 3-continued

| Ex. No. | Structure | MS (M + 1) | Prep. Ex. | Pur. Meth. | Salt | Name |
|---|---|---|---|---|---|---|
| 218 | 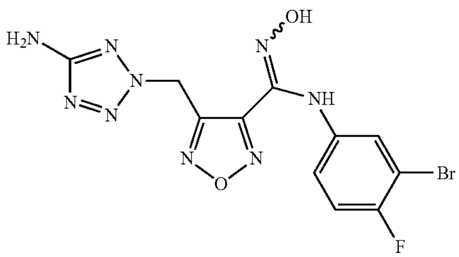 [SMILES: Nc1nnn(Cc2nonc2C(=NO)Nc2ccc(F)c(Br)c2)n1] | 397.0 | 40 | A | Free Base | 4-[(5-amino-2H-tetrazol-2-yl)methyl]-N-(3-bromo-4-fluorophenyl)-N'-hydroxy-1,2,5-oxadiazole-3-carboximidamide |
| 219 | 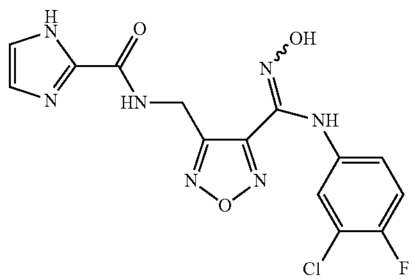 [SMILES: O=C(NCc1nonc1C(=NO)Nc1ccc(F)c(Cl)c1)c1ncc[nH]1] | 380.0 | 33 | A | TFA | N-({4-[(Z)-[(3-chloro-4-fluorophenyl)amino](hydroxyimino)methyl]-1,2,5-oxadiazol-3-yl}methyl)-1H-imidazole-2-carboxamide trifluoroacetate |
| 220 | 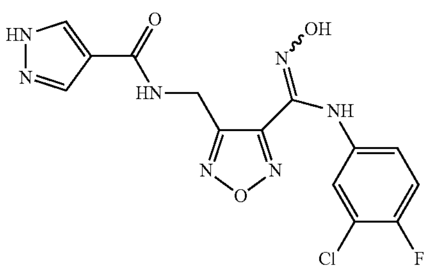 [SMILES: O=C(NCc1nonc1C(=NO)Nc1ccc(F)c(Cl)c1)c1cn[nH]c1] | 380.0 | 33 | A | TFA | N-({4-[(Z)-[(3-chloro-4-fluorophenyl)amino](hydroxyimino)methyl]-1,2,5-oxadiazol-3-yl}methyl)-1H-pyrazole-4-carboxamide trifluoroacetate |
| 221 | 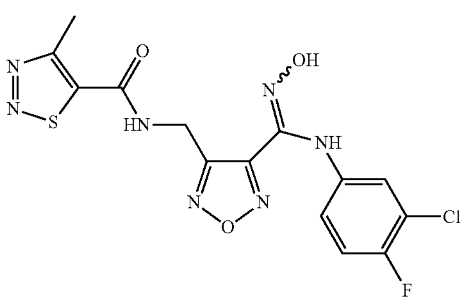 [SMILES: Cc1nnsc1C(=O)NCc1nonc1C(=NO)Nc1ccc(F)c(Cl)c1] | 412.0 | 33 | A | Free Base | N-({4-[(Z)-[(3-chloro-4-fluorophenyl)amino](hydroxyimino)methyl]-1,2,5-oxadiazol-3-yl}methyl)-4-methyl-1,2,3-thiadiazole-5-carboxamide |
| 222 | 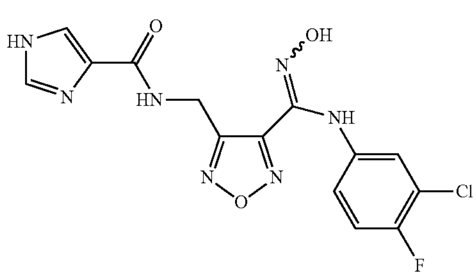 [SMILES: O=C(NCc1nonc1C(=NO)Nc1ccc(F)c(Cl)c1)c1c[nH]cn1] | 380.0 | 33 | A | TFA | N-({4-[(Z)-[(3-chloro-4-fluorophenyl)amino](hydroxyimino)methyl]-1,2,5-oxadiazol-3-yl}methyl)-1H-imidazole-4-carboxamide trifluoroacetate |

TABLE 3-continued

| Ex. No. | Structure | MS (M + 1) | Prep. Ex. | Pur. Meth. | Salt | Name |
|---|---|---|---|---|---|---|
| 223 | 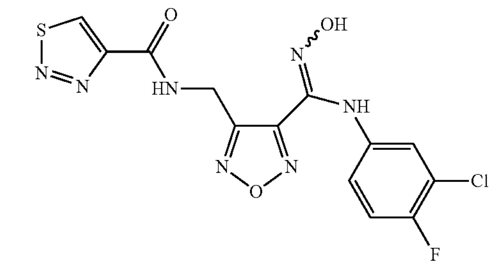 [SMILES: O=C(NCc1nonc1C(=NO)Nc1ccc(F)c(Cl)c1)c1csnn1] | 398.0 | 33 | A | Free Base | N-({4-[(Z)-[3-chloro-4-fluorophenyl)-amino](hydroxyimino)methyl]-1,2,5-oxadiazol-3-yl}-methyl)-1,2,3-thiadiazole-4-carboxamide |
| 224 | 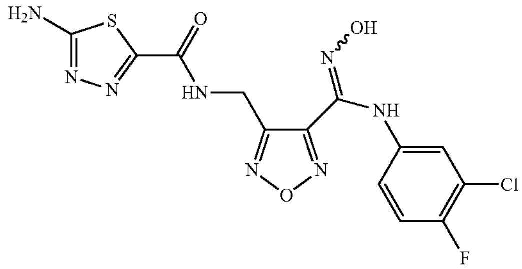 [SMILES: Nc1nnc(C(=O)NCc2nonc2C(=NO)Nc2ccc(F)c(Cl)c2)s1] | 413.0 | 33 | A | Free Base | 5-amino-N-({4-[(Z)-[(3-chloro-4-fluorophenyl)amino]-(hydroxyimino)-methyl]-1,2,5-oxadiazol-3-yl}-methyl)-1,3,4-thiadiazole-2-carboxamide |
| 225 | 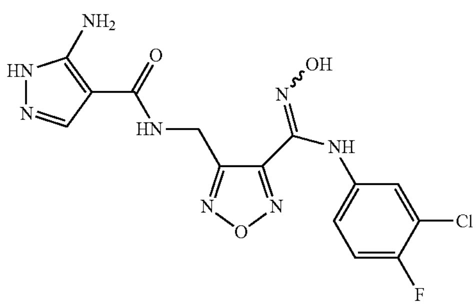 [SMILES: Nc1[nH]ncc1C(=O)NCc1nonc1C(=NO)Nc1ccc(F)c(Cl)c1] | 395.0 | 33 | A | Free Base | 5-amino-N-({4-[(Z)-[(3-chloro-4-fluorophenyl)amino](hydroxyimino)methyl]-1,2,5-oxadiazol-3-yl}-methyl)-1H-pyrazole-4-carboxamide |
| 226 | 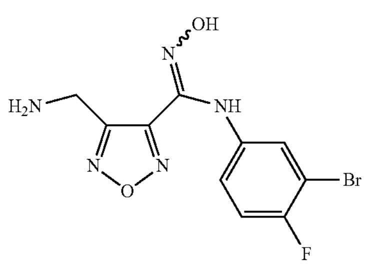 [SMILES: NCc1nonc1C(=NO)Nc1ccc(F)c(Br)c1] | 329.0 | Ex. 33 (step B) | A | TFA | 4-(aminomethyl)-N-(3-bromo-4-fluorophenyl)-N'-hydroxy-1,2,5-oxadiazole-3-carboximidamide trifluoroacetate |
| 227 | 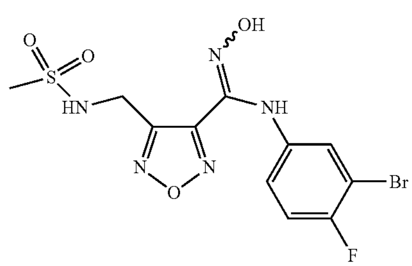 [SMILES: CS(=O)(=O)NCc1nonc1C(=NO)Nc1ccc(F)c(Br)c1] | 407.0 | 35 | B | Free Base | N-(3-bromo-4-fluorophenyl)-N'-hydroxy-4-{[(methylsulfonyl)amino]methyl}-1,2,5-oxadiazole-3-carboximidamide |
| 228 | 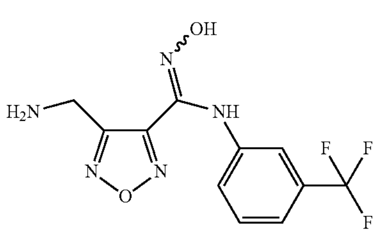 [SMILES: NCc1nonc1C(=NO)Nc1cccc(C(F)(F)F)c1] | 302.0 | Ex. 33 (step B) | A | TFA | 4-(aminomethyl)-N'-hydroxy-N-[3-(trifluoromethyl)phenyl]-1,2,5-oxadiazole-3-carboximidamide trifluoroacetate |

TABLE 3-continued

| Ex. No. | Structure | MS (M + 1) | Prep. Ex. | Pur. Meth. | Salt | Name |
| --- | --- | --- | --- | --- | --- | --- |
| 229 | 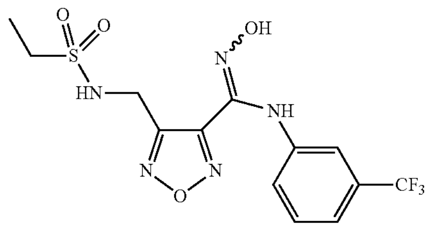 [SMILES: CCS(=O)(=O)NCc1nonc1C(=NO)Nc1cccc(C(F)(F)F)c1] | 380.0 | 35 | B | Free Base | N'-hydroxy-4-{[(methylsulfonyl)-amino]methyl}-N-[3-(trifluoromethyl)-phenyl]-1,2,5-oxadiazole-3-carboximidamide |
| 230 | 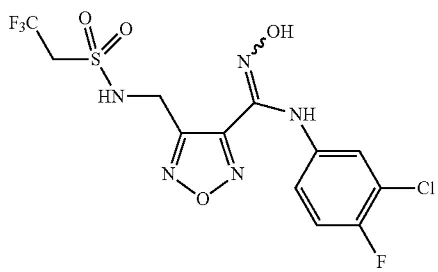 [SMILES: O=S(=O)(CC(F)(F)F)NCc1nonc1C(=NO)Nc1ccc(F)c(Cl)c1] | 432.0 | 35 | B | Free Base | N-(3-chloro-4-fluoro-phenyl)-N'-hydroxy-4-({[(2,2,2-trifluoro-ethyl)sulfonyl]amino}methyl)-1,2,5-oxadiazole-3-carboximidamide |
| 231 | 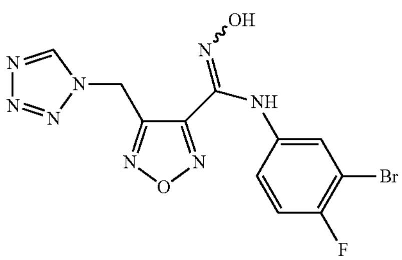 [SMILES: ON=C(Nc1ccc(F)c(Br)c1)c1nonc1Cn1cnnn1] | 382.0 | 39 | A | Free Base | N-(3-bromo-4-fluoro-phenyl)-N'-hydroxy-4-(1H-tetrazol-1-yl-methyl)-1,2,5-oxadiazole-3-carboximidamide |
| 232 | 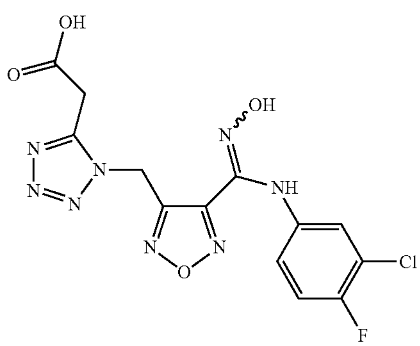 [SMILES: O=C(O)Cc1nnnn1Cc1nonc1C(=NO)Nc1ccc(F)c(Cl)c1] | 379.0 | 39 | A | Free Base | [1-({4-[(Z)-[(3-chloro-4-fluorophenyl)-amino](hydroxy-imino)methyl]-1,2,5-oxadiazol-3-yl}-methyl)-1H-tetrazol-5-yl]acetic acid |
| 233 | 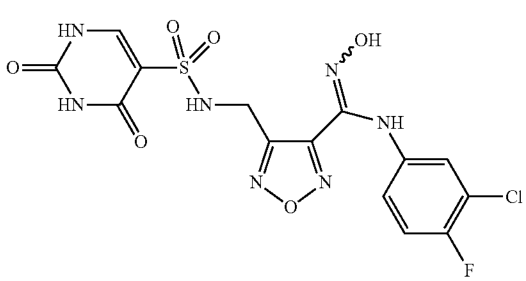 [SMILES: O=c1[nH]cc(S(=O)(=O)NCc2nonc2C(=NO)Nc2ccc(F)c(Cl)c2)c(=O)[nH]1] | 460.0 | 35 | B | Free Base | N-(3-chloro-4-fluoro-phenyl)-4-({[(2,4-dioxo-1,2,3,4-tetra-hydropyrimidin-5-yl)-sulfonyl]amino}-methyl)-N'-hydroxy-1,2,5-oxadiazole-3-carboximidamide |

TABLE 3-continued

| Ex. No. | Structure | MS (M + 1) | Prep. Ex. | Pur. Meth. | Salt | Name |
|---|---|---|---|---|---|---|
| 234 | 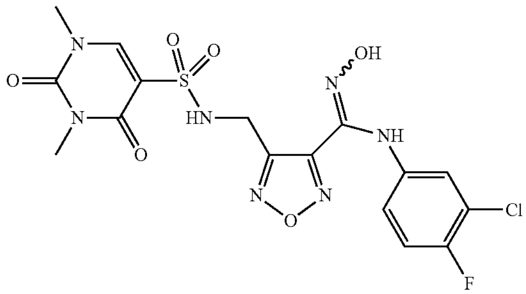 [SMILES: Cn1cc(S(=O)(=O)NCc2nonc2C(=NO)Nc2ccc(F)c(Cl)c2)c(=O)n(C)c1=O] | 488.0 | 35 | B | Free Base | N-(3-chloro-4-fluoro-phenyl)-4-({[(1,3-dimethyl-2,4-dioxo-1,2,3,4-tetrahydro-pyrimidin-5-yl)sulfonyl]amino}methyl)-N'-hydroxy-1,2,5-oxadiazole-3-carboximidamide |
| 235 | 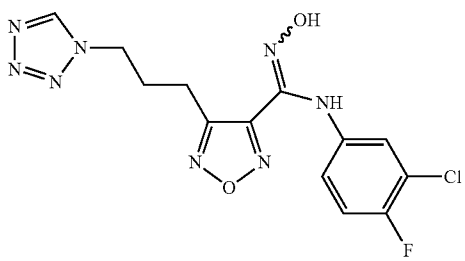 [SMILES: ON=C(Nc1ccc(F)c(Cl)c1)c1nonc1CCCn1cnnn1] | 367.0 | 39 | A | Free Base | N-(3-chloro-4-fluoro-phenyl)-N'-hydroxy-4-[3-(1H-tetrazol-1-yl)-propyl]-1,2,5-oxadiazole-3-carboximidamide |
| 236 | 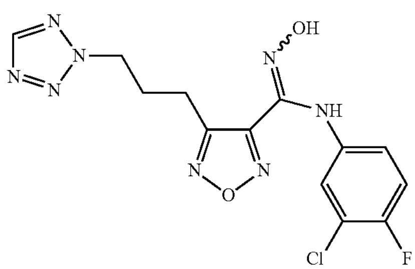 [SMILES: ON=C(Nc1ccc(F)c(Cl)c1)c1nonc1CCCn1ncnn1] | 367.0 | 40 | A | Free Base | N-(3-chloro-4-fluoro-phenyl)-N'-hydroxy-4-[3-(2H-tetrazol-2-yl)-propyl]-1,2,5-oxadiazole-3-carboximidamide |
| 237 | 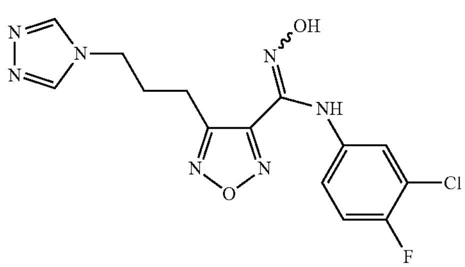 [SMILES: ON=C(Nc1ccc(F)c(Cl)c1)c1nonc1CCCn1cnnc1] | 366.0 | 39 | A | Free Base | N-(3-chloro-4-fluoro-phenyl)-N'-hydroxy-4-[3-(4H-1,2,4-triazol-4-yl)propyl]-1,2,5-oxadiazole-3-carboximidamide |
| 238 | 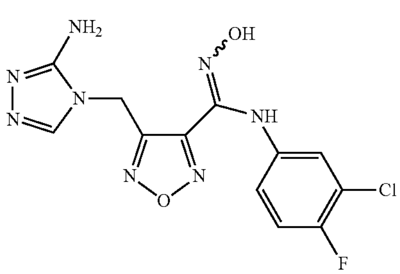 | 353.0 | 39 | A | Free Base | 4-[(3-amino-4H-1,2,4-triazol-4-yl)methyl]-N-(3-chloro-4-fluoro-phenyl]-N'-hydroxy-1,2,5-oxadiazole-3-carboximidamide |

TABLE 3-continued

| Ex. No. | Structure | MS (M + 1) | Prep. Ex. | Pur. Meth. | Salt | Name |
|---|---|---|---|---|---|---|
| 239 | 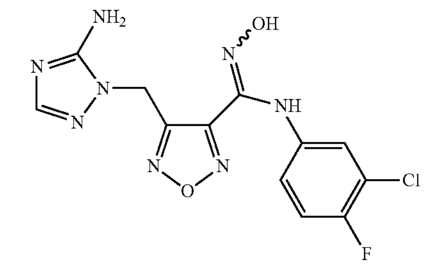 [SMILES: Nc1ncnn1Cc1nonc1C(=NO)Nc1ccc(F)c(Cl)c1] | 353.0 | 39 | A | Free Base | 4-[(5-amino-1H-1,2,4-triazol-1-yl)methyl]-N-(3-chloro-4-fluorophenyl)-N'-hydroxy-1,2,5-oxadiazole-3-carboximidamide |
| 240 | 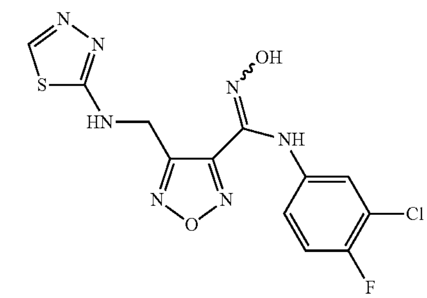 [SMILES: ON=C(Nc1ccc(F)c(Cl)c1)c1nonc1CNc1nncs1] | 370.0 | 4 | A | TFA | N-(3-chloro-4-fluorophenyl)-N'-hydroxy-4-[(1,3,4-thiadiazol-2-ylamino)methyl]-1,2,5-oxadiazole-3-carboximidamide trifluoroacetate |
| 241 | 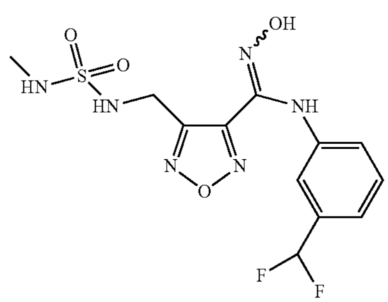 [SMILES: CNS(=O)(=O)NCc1nonc1C(=NO)Nc1cccc(C(F)F)c1] | 377.0 | 145 | B | Free Base | N-[3-(difluoromethyl)phenyl]-N'-hydroxy-4-({[(methylamino)sulfonyl]amino}methyl)-1,2,5-oxadiazole-3-carboximidamide |
| 242 | 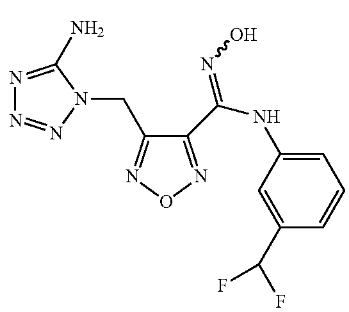 [SMILES: Nc1nnnn1Cc1nonc1C(=NO)Nc1cccc(C(F)F)c1] | 352.0 | 39 | B | Free Base | 4-[(5-amino-1H-tetrazol-1-yl)methyl]-N-[3-(difluoromethyl)phenyl]-N'-hydroxy-1,2,5-oxadiazole-3-carboximidamide |
| 243 | 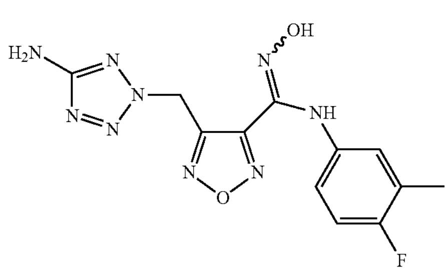 [SMILES: Cc1cc(NC(=NO)c2nonc2Cn2nnc(N)n2)ccc1F] | 334.0 | 40 | B | Free Base | 4-[(5-amino-2H-tetrazol-2-yl)methyl]-N-(4-fluoro-3-methylphenyl)-N'-hydroxy-1,2,5-oxadiazole-3-carboximidamide |

TABLE 3-continued

| Ex. No. | Structure | MS (M + 1) | Prep. Ex. | Pur. Meth. | Salt | Name |
|---|---|---|---|---|---|---|
| 244 | 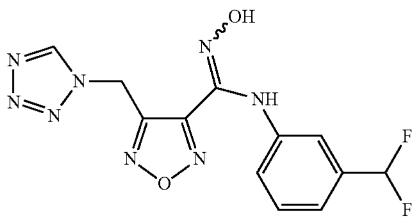 [SMILES: ON=C(Nc1cccc(C(F)F)c1)c1nonc1Cn1cnnn1] | 337.0 | 39 | A | Free Base | N-[3-(difluoromethyl)phenyl]-N'-hydroxy-4-(1H-tetrazol-1-ylmethyl)-1,2,5-oxadiazole-3-carboximidamide |
| 245 | 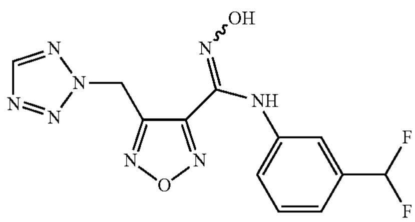 [SMILES: ON=C(Nc1cccc(C(F)F)c1)c1nonc1Cn1ncnn1] | 337.0 | 40 | A | Free Base | N-[3-(difluoromethyl)phenyl]-N'-hydroxy-4-(2H-tetrazol-2-ylmethyl)-1,2,5-oxadiazole-3-carboximidamide |
| 246 | 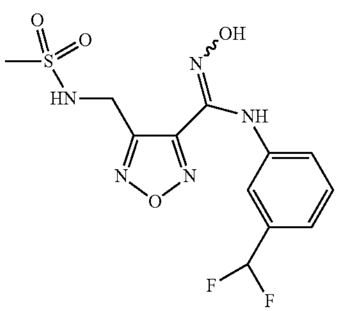 [SMILES: CS(=O)(=O)NCc1nonc1C(=NO)Nc1cccc(C(F)F)c1] | 362.0 | 35 | B | Free Base | N-[3-(difluoromethyl)phenyl]-N'-hydroxy-4-{[(methylsulfonyl)amino]methyl}-1,2,5-oxadiazole-3-carboximidamide |
| 247 | 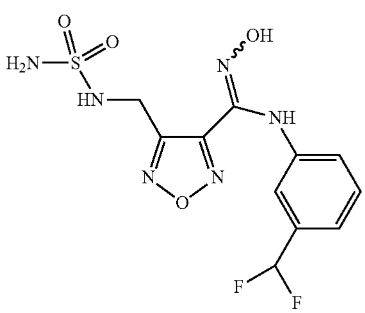 [SMILES: NS(=O)(=O)NCc1nonc1C(=NO)Nc1cccc(C(F)F)c1] | 363.0 | 143 | B | Free Base | 4-{[(aminosulfonyl)amino]methyl}-N-[3-(difluoromethyl)phenyl]-N'-hydroxy-1,2,5-oxadiazole-3-carboximidamide |
| 248 | 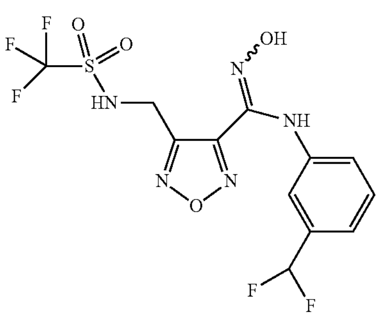 [SMILES: O=S(=O)(NCc1nonc1C(=NO)Nc1cccc(C(F)F)c1)C(F)(F)F] | 416.0 | 35 | B | Free Base | N-[3-(difluoromethyl)phenyl]-N'-hydroxy-4-({[(trifluoromethyl)sulfonyl]amino}methyl)-1,2,5-oxadiazole-3-carboximidamide |

TABLE 3-continued

| Ex. No. | Structure | MS (M + 1) | Prep. Ex. | Pur. Meth. | Salt | Name |
|---|---|---|---|---|---|---|
| 249 | 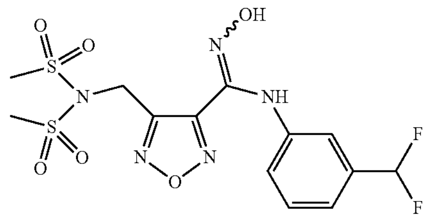 [SMILES: CS(=O)(=O)N(Cc1nonc1C(=NO)Nc1cccc(C(F)F)c1)S(C)(=O)=O] | 440.0 | 35 | B | Free Base | 4-{[bis(methyl-sulfonyl)amino]methyl}-N-[3-(difluoro-methyl)phenyl]-N'-hydroxy-1,2,5-oxadiazole-3-carboximidamide |
| 250 | 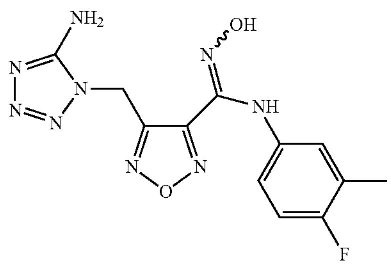 [SMILES: Cc1cc(NC(=NO)c2nonc2Cn2nnnc2N)ccc1F] | 334.0 | 39 | B | Free Base | 4-[(5-amino-1H-tetrazol-1-yl)methyl]-N-(4-fluoro-3-methyl-phenyl)-N'-hydroxy-1,2,5-oxadiazole-3-carboximidamide |
| 251 | 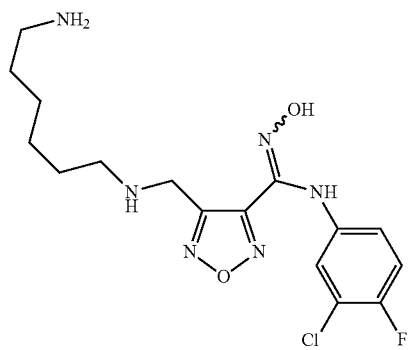 [SMILES: NCCCCCCNCc1nonc1C(=NO)Nc1ccc(F)c(Cl)c1] | 385.0 | 3 | B | Free Base | 4-{[(6-aminohexyl)-amino]methyl}-N-(3-chloro-4-fluoro-phenyl)-N'-hydroxy-1,2,5-oxadiazole-3-carboximidamide |
| 252 | 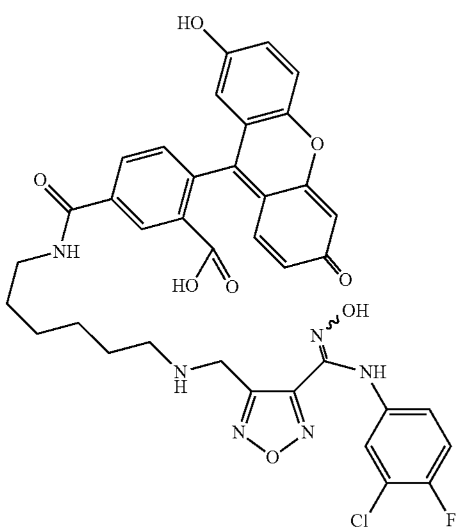 [SMILES: O=C(NCCCCCCNCc1nonc1C(=NO)Nc1ccc(F)c(Cl)c1)c1ccc(-c2c3ccc(=O)cc-3oc3ccc(O)cc23)c(C(=O)O)c1] | 744.0 | 3 | B | Free Base | 5-[({6-[({4-[(Z)-[(3-chloro-4-fluoro-phenyl)amino](hydroxy-imino)methyl]-1,2,5-oxadiazol-3-yl}-methyl)amino]hexyl}-amino)carbonyl]-2-(7-hydroxy-3-oxo-3H-xanthen-9-yl)benzoic acid |

TABLE 3-continued

| Ex. No. | Structure | MS (M + 1) | Prep. Ex. | Pur. Meth. | Salt | Name |
|---|---|---|---|---|---|---|
| 253 | 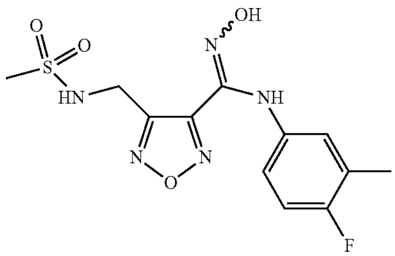 | 344.0 | 35 | B | Free Base | N-(4-fluoro-3-methyl-phenyl)-N'-hydroxy-4-{[(methylsulfonyl)-amino]methyl}-1,2,5-oxadiazole-3-carboximidamide |
| 254 | 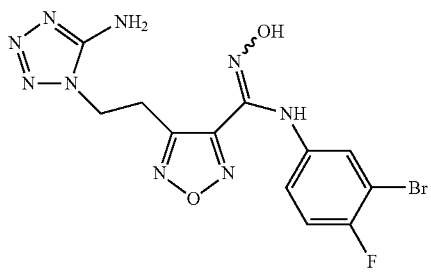 [SMILES: Nc1nnnn1CCc1nonc1C(=NO)Nc1ccc(F)c(Br)c1] | 412, 414 | 162 | A | Free Base | 4-[2-(5-amino-1H-tetrazol-1-yl)ethyl]-N-(3-bromo-4-fluoro-phenyl)-N'-hydroxy-1,2,5-oxadiazole-3-carboximidamide |
| 255 | 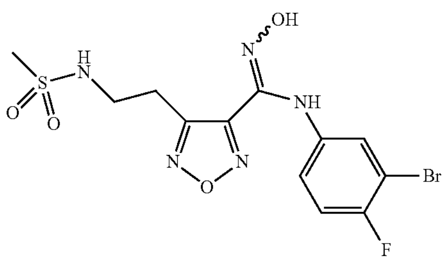 [SMILES: CS(=O)(=O)NCCc1nonc1C(=NO)Nc1ccc(F)c(Br)c1] | 422, 424 | 176 | A | Free Base | N-(3-bromo-4-fluoro-phenyl)-N'-hydroxy-4-{2-[(methylsulfonyl)-amino]ethyl}-1,2,5-oxadiazole-3-carboximidamide |
| 256 | 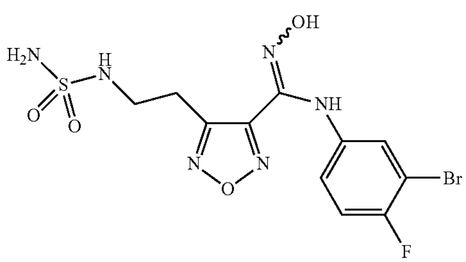 [SMILES: NS(=O)(=O)NCCc1nonc1C(=NO)Nc1ccc(F)c(Br)c1] | 423, 425 | 177 | A | Free Base | 4-{2-[(aminosulfonyl)amino]ethyl}-N-(3-bromo-4-fluoro-phenyl)-N'-hydroxy-1,2,5-oxadiazole-3-carboximidamide |

Example A

Human Indoleamine 2,3-Dioxygenasae (IDO) Enzyme Assay

Human indoleamine 2,3-dioxygenasae (IDO) with an N-terminal His tag was expressed in *E. coli* and purified to homogeneity. IDO catalyzes the oxidative cleavage of the pyrrole ring of the indole nucleus of tryptophan to yield N'-formylkynurenine. The assays were performed at room temperature as described in the literature using 95 nM IDO and 2 mM D-Trp in the presence of 20 mM ascorbate, 5 μM methylene blue and 0.2 mg/mL catalase in 50 mM potassium phosphate buffer (pH 6.5). The initial reaction rates were recorded by continuously following the absorbance increase at 321 nm due to the formation of N'-formylkynurenine. See: Sono, M., Taniguchi, T., Watanabe, Y., and Hayaishi, O. (1980) *J. Biol. Chem.* 255, 1339-1345 Compounds of the invention having an $IC_{50}$ less than about 100 μM were considered active.

Example B

Determination of Inhibitor Activity in HeLa Cell-Based Indoleamine 2,3-Dioxygenase (IDO)/Kynurenine Assay HeLa cells (#CCL-2) were obtained from the American Type Tissue Culture Collection (ATCC, Manassas, Va.) and routinely maintained in minimum essential medium (eagle) with 2 mM L-glutamine and Earle's BSS adjusted to contain 1.5 g/L sodium bicarbonate, 0.1 mM non-essential amino acids, 1 mM sodium pyruvate and 10% fetal bovine serum (all from Invitrogen). Cells were kept at 37° C. in a humidified incubator supplied with 5% $CO_2$. The assay was performed as follows: HeLa cells were seeded in a 96 well culture plate at a density of $5 \times 10^3$ per well and grown overnight. On the next day, IFN-γ (50 ng/mL final concentration) and serial dilutions of compounds (in total volume of 200 μL culture medium) were added into cells. After 48 hours of incubation, 140 μL of the supernatant per well was transferred to a new 96 well plate. 10 μL of 6.1; N trichloroacetic acid (#T0699, Sigma) was mixed into each well and incubated at 50° C. for 30 min to hydrolyze N-formylkynurenine produced by indoleamine 2,3-dioxygenase to kynurenine. The reaction mixture was then centrifuged for 10 min at 2500 rpm to remove sediments. 100 μL, of the supernatant per well was transferred to another 96 well plate and mixed with 100 μL of 2% (w/v) p-dimethyl-aminobenzaldehyde (#15647-7, Sigma-Aldrich) in acetic acid. The yellow color derived from Kynurenine was measured at 480 nm using a SPECTRAmax 250 microplate reader (Molecular Devices). L-kynurenine (#K8625, Sigma) was used as standard. The standards (240, 120, 60, 30, 15, 7.5, 3.75, 1.87 μM) were prepared in 100 μL culture media and mixed with equal volume of 2% (w/v) p-dimethylaminoben-zaldehyde. The percent inhibition at individual concentrations was determined and the average values of duplicates were obtained. The data was analyzed by using nonlinear regression to generate $IC_{50}$ values (Prism Graphpad). See: Takikawa O, et al. (1988). Mechanism of interferon-gamma action. Characterization of indoleamine 2,3-dioxygenase in cultured human cells induced by interferon-gamma and evaluation of the enzyme-mediated tryptophan degradation in its anticellular activity. *J. Biol. Chem.* 263(4):2041-8. Compounds of the invention having an $IC_{50}$ less than about 100 μM were considered active.

Example C

Determination of Effect of IDO Inhibitors on T Cell Proliferation that is Suppressed by IDO-Expressing Dendritic Cells Monocytes were collected from human peripheral mono-nuclear cells by leukophoresis. Monocytes were then seeded at a density of $1 \times 10^6$ cells/well in a 96 well plate, using RPMI 1640 medium supplemented with 10% fetal bovine serum and 2 in M L-glutamine (all from Invitrogen). Adherent cells were retained on the plate after overnight culture at 37° C. Adherent monocytes were then stimulated for 5-7 days with 100 ng/ml GM-CSF (#300-03, PeproTech) and 250 ng/ml IL-4 (#200-04, PeproTech), followed by activation with 5 μg/mL LPS from *Salmonella typhimurium* (#437650, Sigma) and 50 ng/mL IFN-γ (#285-IF, R&D Systems) for additional 2 days to induce dendritic cell maturation.

After dendritic cell activation, the medium was replaced with completed RPMI 1640 supplemented with 100-200 U/mL IL-2 (#CYT-209, ProSpec-Tany TechnoGene) and 100 ng/mL anti-CD3 antibody (#555336, PharMingen), T cells ($2-3 \times 10^5$ cells/well), and serial dilutions of IDO compounds. After incubation for 2 more days, T cell proliferation was measured by BrdU incorporation assay, using a colorimetric Cell Proliferation ELISA kit per manufacturer's instruction (#1647229, Roche Molecular Biochemicals). Cells were continuously cultured for 16-18 hrs in presence of 10 μM BrdU labeling solution. Then, the labeling medium was removed, and 200 μL FixDenat per well was added to the cells and incubated for 30 minutes at room temperature. The FixDenat solution was removed and 100 μL/well anti-BrdU-POD antibody conjugate working solution was added. The reaction was carried out for 90 minutes at room temperature. The antibody conjugate was then removed, and cells were rinsed three times with 200 μL/well washing solution. Finally, 100 μL/well of substrate solution was added and the results were obtained using a microplate reader (Spectra Max PLUS, Molecular Devices) during color development. Multiple readings at various time points were obtained to ensure the data was within the linear range. The data was routinely obtained from replicated experiments, and appropriate controls were included. See: Terness P, et al. (2002). Inhibition of allogeneic T cell proliferation by indoleamine 2,3-dioxyge-nase-expressing dendritic cells: mediation of suppression by tryptophan metabolites. *J. Exp. Med.* 196(4):447-57; and Hwu P, et al. (2000). Indoleamine 2,3-dioxygenase production by human dendritic cells results in the inhibition of T cell proliferation. *J. Immunol.* 164(7):3596-9. Compounds of the invention having an $IC_{50}$ less than about 100 μM were considered active.

Example D

In Vivo Testing of IDO Inhibitors for Antitumor Activity

In vivo anti-tumor efficacy can be tested using modified tumor allograft/xenograft protocols. For instance, it has been described in the literature that IDO inhibition can syngerize with cytotoxic chemotherapy in immune-competent mice (Muller, A. J., et al). This synergy was shown to be dependent on T-cells by comparison of the synergistic effects of an investigational IDO inhibitor in murine tumor xenograft models (e.g. B16 and related variants, CT-26, LLC) grown in immune competent syngenic mice to that observed in syn-genic mice treated with neutralizing anti-CD4 antibodies, or the same tumors grown in immune-compromised mice (e.g. nu/nu).

The concept of differential anti-tumor effects in immune-competent versus immune-compromised mice may also permit testing of investigational IDO inhibitors as single agents. For instance, LLC tumors grow well in their syngeneic host strain, C57Bl/6. However, if these mice are treated with the IDO inhibitor 1-MT (versus placebo) the formation of tumors is markedly delayed, implying that IDO inhibition was growth inhibitory (Friberg, M., et al). Following this logic, one can examine the efficacy of IDO inhibition in the LLC xenograft tumor model grown in C57Bl/6 immune competent mice and compare that to the effects of IDO inhibitors on LLC tumor growth in nude or SCID mice (or C57Bl/6 mice treated with antibodies that neutralize T-cell activity). As the effects of relieving the tumor-mediated immune suppressive activity of IDO will likely differ depending on the immunogenic potential of different tumor models, genetic modifications can be made to the tumor cells to increase their immunogenic potential. For instance, expression of GM-CSF in B16.F10 cells increases their immunogenic potential (Dranoff, G., et al). As such, in some tumor models (e.g. B16.F10) one can generate [poly]clones that express immune stimulatory proteins such as GM-CSF and test the growth inhibitory effects of IDO inhibitors against tumors established from these tumor cells in both immune-competent and compromised mice.

A third avenue for assessing the efficacy of IDO inhibitors in vivo employs 'pre-immunization' murine tumor allograft/xenograft models. In these models, immune-competent mice are sensitized to a specific tumor antigen or antigens to mimic a therapeutic anti-tumor vaccination. This primes the mice for an anti-tumor response mediated by the immune system when mice are subsequently challenged with murine tumor cell lines (possessing similar tumor antigens to those used for immunization) in xenograft experiments. Expression of IDO has been shown to blunt the anti-tumor response and allow xenografts to grow more rapidly. Importantly, the growth of tumors in this model is inhibited by the IDO inhibitor 1-MT (Uyttenhove, C., et al). This model is particularly attractive as IDO activity is permissive for P815 tumor growth and specific inhibition of IDO should therefore growth inhibitory.

Lastly, therapeutic immunization may be used to evaluate the impact of IDO inhibitors in vivo. For example, it has been demonstrated using B 16-BL6 cells that one can challenge Blk/6 mice with an intravenous injection of tumor cells followed by treatment with a well characterized immunogenic peptide (e.g. TRP-2) expressed by the tumor cells (Ji, et al., *J. Immunol*, 2005, 175:1456-63). Importantly, immune system modifiers, such as anti-CTL-4 antibody, can improve responses to such therapeutic immunizations. The impact of IDO inhibitors may be evaluated in a similar manner tumor peptide immunization with or without IDO inhibitor. Efficacy is assess by animal survival (time to morbidity) or by the measurement of tumor metastases to the lungs and/or other organs at defined timepoints.

In any/all of the above mentioned models, it may also be possible to directly and/or indirectly measure the number and/or activity of tumor reactive immune cells. Methods for measuring the number and/or activity of tumor reactive immune cells are well established and can be performed using techniques familiar to those schooled in the art (Current Protocols in Immunology, vol 4, Coligan, J. E., et al; *Immunotherapy of Cancer*, Human Press, 2006, Disis, M. L. and references therein). Conceptually, a reduction in the immune suppressive effects of IDO may result in increased numbers or reactivity of tumor specific immune cells. Further, IDO inhibition may further increase the number or reactivity of tumor reactive immune cells when combined with other therapeutics, for example chemotherapeutics and/or immune modulators (e.g. anti-CTLA4 antibody).

All allograft/xenograft experiments can be performed using standard tumor techniques (reviewed by Corbett, et al). The cloning and introduction of genes (e.g. IDO, GM-CSF) into tumor cell lines, can be performed using techniques familiar to those schooled in the art (reviewed in Sambrook, J, et al). See: Corbett, T., Polin, L., et al. In vivo methods for screening and preclinical testing. Cancer Drug Discovery and Development: Anticancer Drug Development Guide: Preclinical Screening, Clinical Trials, and Approval, $2n^d$ Ed. Teicher, B. A. and Andrews, P. A., Gumana Press Inc., Totowa, N. J., 2004; Dranoff, G., Jaffee, E., et al. Vaccination with irradiated tumor cells engineered to secrete murine granulocyte-macrophage colony-stimulating factor stimulates potent, specific, and long-lasting anti-tumor immunity. *Proc. Natl. Acad. Sci, USA,* 90:3539-3543, 1993; Friberg, M., Jennings, R., et al. Indoleamine 2,3-dioxygenase contributes to tumor cell evasion of T cell-mediated rejection. *Int. J. Cancer:* 101:151-155, 2002; Muller, A. J., DuHadaway, J. B., et al. Inhibition of indoleamine 2,3-dioxygenase, an immunoregulatory target of the cancer suppression gene Bin1, potentiates cancer chemotherapy. *Nat. Med.* 11:312-319, 2005; Sambrook, J, Russel, D. Molecular Cloning: A laboratory Manual ($3^{rd}$ edition). Cold Spring Harbor Laboratory Press. Cold Spring Harbor, N.Y., USA. 2001; and Uyttenhove, C., Pilotte, L., et al. Evidence for a tumoral immune resistance mechanism based on tryptophan degradation by indoleamine 2,3-dioxygenase. *Nat. Med.* 9:1269-1274, 2003.

Example E

In Vivo Testing of IDO Inhibitors in Human Immunodeficiency Virus-1 (HIV-1) Encephalitis Model 1. Cell Isolation and Viral Infection Monocytes and PBL can be obtained by countercurrent centrifugal elutriation of leukopheresis packs from HIV-1, 2 and hepatitis B seronegative donors. Monocytes are cultivated in suspension culture using Teflon flasks in Dulbecco's Modified Eagle's Medium (DMEM, Sigma-Aldrich) supplemented with 10% heat-inactivated pooled human serum, 1% glutamine, 50 µg/mL gentamicin, 10 µg/mL ciprofloxacin (Sigma), and 1000 U/mL highly purified recombinant human macrophage colony stimulating factor. After seven days in culture, MDM are infected with HIV-$1_{ADA}$ at multiplicity of infection of 0.01.

2. Hu-PBL-NOD/SCID HIVE Mice

Four-wk old male NOD/C.B-17 SCID mice can be purchased (Jackson Laboratory). Animals are maintained in sterile microisolator cages under pathogen-free conditions. All animals are injected intraperitoneally with rat anti-CD122 (0.25 mg/mouse) three days before PBL transplantation and twice with rabbit asialo-GM1 antibodies (0.2 mg/mouse) (Wako) one day before and three days after PBL injection ($20 \times 10^6$ cells/mouse). HIV-$1_{ADA}$-infected MDM ($3 \times 10^5$ cells in 10 µL) are injected intracranially (i.c.) eight days following PBL reconstitution generating hu-PBL-NOD/SCID HIVE mice. Immediately following i.c. injection of HIV-1 infected MDM the hu-PBL-NOD/SCID HIVE mice are subcutaneously (s.c) implanted with control (vehicle) or compound pellets (14 or 28 day slow release, Innovative Research). Initial experiments are designed to confirm the induction of virus-specific CTL in the hu PBL-NOD/SCID HIVE animals treated with IDO compounds. This is confirmed by tetramer staining and neuropathologic analyses of MDM elimination from the brain tissue. Then, the experiment is designed to analyze human lymphocyte reconstitution, humoral immune responses, and neuropathological alterations. In these experiments, animals are bled on day 7 and sacrificed at 14 and 21 days after i.c. injection of human MDM. Blood collected in EDTA-containing tubes is used for flow cytometry and plasma is used for detection of HIV-1 p24 using ELISA (Beckman Coulter™). HIV-1-specific antibodies are detected by Western blot tests according to the manufacturer instructions (Cambridge Biotech HIV-1 Western blot kit, Calypte Biomedical). Similar amount of virus-specific antibodies are detected in control and compound-treated animals. A total of three independent experiments can be performed using three different human leukocyte donors.

3. FACScan of Peripheral Blood and Spleen in Hu PBL-NOD/SCID HIVE Mice

Two-color FACS analysis can be performed on peripheral blood at wk 1-3 and splenocytes at wk 2 and 3 after i.c. injection of human MDM. Cells are incubated with fluorochrome-conjugated monoclonal Abs (mAbs) to human CD4, CD8, CD56, CD3, IFN-γ (eBioscience) for 30 min at 4° C. To evaluate the cellular immune response, IFN-γ intracellular staining is performed in combination with anti-human CD8 and FITC-conjugated anti-mouse CD45 to exclude murine cells. To determine the Ag-specific CTL, allophycocyanin-conjugated tetramer staining for HIV-$1^{gag}$ (p17 (aa77-85) SLYNTVATL, SL-9) and HIV-$1^{pol}$ [(aa476-485) ILKEPVHGV, IL-9] is performed on phytohemaglutinin/interleukin-2 (PHA/IL-2)-stimulated splenocytes. Cells are stained following the recommendation of the NIH/National Institute of Allergy and Infections Disease, National Tetramer Core Facilities. Data were analyzed with a FACS Calibur™ using CellQuest software (Becton Dickinson Immunocytometry System).

4. Histopathology and Image Analyses

Brain tissue is collected at days 14 and 21 after i.c. injection of MDM, fixed in 4% phosphate-buffered paraformaldehyde and embedded in paraffin or frozen at 80° C. for later use. Coronal sections from the embedded blocks are cut in order to identify the injection site. For each mouse, 30-100 (5-μm-thick) serial sections are cut from the human MDM injection site and 3-7 slides (10 sections apart) are analyzed. Brain sections are deparaffinized with xylene and hydrated in gradient alcohols. Immunohistochemical staining follows a basic indirect protocol, using antigen retrieval by heating to 95° C. in 0.01 mol/L citrate buffer for 30 min for antigen retrieval. To identify human cells in mouse brains, mAb to vimentin (1:50, clone 3B4, Dako Corporation), which identifies all human leukocytes is used. Human MDM and CD8$^+$ lymphocytes are detected with CD68 (1:50 dilution, clone KP 1) and CD8 (1:50 dilution, clone 144B) antibodies, respectively. Virus-infected cells are labeled with mAb to HIV-1 p24 (1:10, clone Kal-1, all from Dako). Reactive murine microglial cells are detected with Iba-1 antibody (1:500, Wako). Expression of human IDO (huIDO) is visualized with Abs obtained from the Department of Cell Pharmacology, Central Research Institute, Graduate School of Medicine, Hokkaido University, Sapporo, Japan. Primary antibodies are detected with the appropriate biotinylated secondary antibodies and visualized with avidin-biotin complexes (Vectastain Elite ABC kit, Vector Laboratories) and horseradish peroxidase (HRP) coupled dextran polymer (EnVision, Dako Corporation). Immunostained sections are counterstained with Mayer's hematoxylin. Sections from which primary antibody is deleted or irrelevant IgG isotype is incorporated served as controls. Two independent observers in a blinded fashion count the numbers of CD8$^+$lymphocytes, CD68$^+$MDM and HIV-1 p24$^+$cells in each section from each mouse. Light microscopic examination is performed with a Nikon Eclipse 800 microscope (Nikon Instruments Inc). Semi-quantitative analysis for Iba1 (percentage of area occupied by immunostaining) is carried out by computer-assisted image analysis (Image-Pro®Plus, Media Cybernetics) as previously described.

5. Statistic Analysis

Data can be analyzed using Prism (Graph Pad) with Student t-test for comparisons and ANOVA. P-values <0.05 were considered significant.

6. Reference

Poluektova L Y, Munn D H, Persidsky Y, and Gendelman H E (2002). Generation of cytotoxic T cells against virus-infected human brain macrophages in a murine model of HIV-1 encephalitis. J. Immunol. 168(8):3941-9.

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:

1. A method of inhibiting immunosuppression or treating a cancer selected from melanoma, ovarian cancer, and breast cancer, in a patient comprising administering to said patient an effective amount of a compound of Formula Ia:

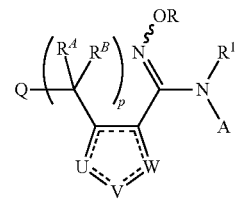

or a pharmaceutically acceptable salt thereof, wherein:

U is N;

V is O;

W is N, wherein the five-membered ring containing U, V, and W is an aromatic heterocycle;

A is aryl, or heteroaryl, each optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ cyanoalkyl, $Cy^1$, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^i)NR^cR^d$, $NR^cC(=NR^i)NR^cR^d$, $P(R^f)_2$, $P(OR^e)_2$, $P(O)R^eR^f$, $P(O)OR^eOR^f$, $S(O)R^b$, $S(O)NR^cR^d$, $S(O)_2R^b$, $NR^cS(O)_2R^b$, and $S(O)_2NR^cR^d$, wherein said $C_{1-6}$ alkyl, $C_{2-6}$ alkenyl, and $C_{2-6}$ alkynyl is optionally substituted with 1, 2, or 3 substitutents independently selected from $Cy^1$, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^i)NR^cR^d$, $NR^cC(=NR^i)NR^cR^d$, $P(R^f)_2$, $P(OR^e)_2$, $P(O)R^eR^f$, $P(O)OR^eOR^f$, $S(O)R^b$, $S(O)NR^cR^d$, $S(O)_2R^b$, $NR^cS(O)_2R^b$, and $S(O)_2NR^cR^d$;

R is H;

$R^A$ and $R^B$ are each H;

Q is $OR^Q$, $OC(O)R^Q$, $OC(O)NR^4R^Q$, $NR^4R^Q$, $NR^4C(O)R^Q$, $NR^4C(O)NR^4R^Q$, $NR^4C(O)OR^Q$, $NR^4S(O)R^Q$, $NR^4S(O)_2R^Q$, $NR^4C(=NR^i)NR^4R^Q$, $SR^Q$, $S(O)R^Q$, $S(O)NR^4R^Q$, $S(O)_2R^Q$, $S(O)_2NR^4R^Q$, $C(O)R^Q$, $C(O)OR^Q$, $C(O)NR^4R^Q$, halo, cyano, azido, or nitro;

$R^Q$ is H, $C_{1-6}$ alkyl, $C_{2-6}$ alkenyl, $C_{2-6}$ alkynyl, $C_{1-6}$ haloalkyl, aryl, cycloalkyl, heteroaryl, heterocycloalkyl, arylalkyl, cycloalkylalkyl, heteroarylalkyl, or heterocycloalkylalkyl, wherein said $C_{1-6}$ alkyl, $C_{2-6}$ alkenyl, $C_{2-6}$ alkynyl, aryl, cycloalkyl, heteroaryl, heterocycloalkyl, arylalkyl, cycloalkylalkyl, heteroarylalkyl, or heterocycloalkylalkyl is optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ cyanoalkyl, halosulfanyl, Cy, —($C_{1-4}$ alkyl)-Cy, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $C(=NR^i)NR^{c2}R^{d2}$, $NR^{c2}C(=NR^i)NR^{c2}R^{d2}$, $P(R^{f2})_2$, $P(OR^{e2})_2$, $P(O)R^{e2}R^{f2}$, $P(O)OR^{e2}OR^{f2}$, $S(O)R^{b2}$, $S(O)NR^{c2}R^{d2}$, $S(O)_2R^{b2}$, $NR^{c2}S(O)_2R^{b2}$, and $S(O)_2NR^{c2}R^{d2}$;

or $R^4$ and $R^Q$ together with the N atom to which they are attached form a 4-20 membered heterocycloalkyl group or 5-20 membered heteroaryl group, each optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ cyanoalkyl, halosulfanyl, Cy, —($C_{1-4}$ alkyl)-Cy, CN, $NO_2$, $OR^{a2}$, —($C_{1-4}$ alkyl)-$OR^{a2}$, $SR^{a2}$, —($C_{1-4}$ alkyl)-$SR^{a2}$, $C(O)R^{b2}$, —($C_{1-4}$ alkyl)-$C(O)R^{b2}$, $C(O)NR^{c2}R^{d2}$, —($C_{1-4}$ alkyl)-$C(O)NR^{c2}R^{d2}$, $C(O)OR^{a2}$, —($C_{1-4}$ alkyl)-$C(O)$ $OR^{a2}$, $OC(O)R^{b2}$, $-(C_{1-4}$ alkyl)-$OC(O)R^{b2}$, $OC(O)NR^{c2}R^{d2}$, $-(C_{1-4}$ alkyl)-$OC(O)NR^{c2}R^{d2}$, $NR^{c2}R^{d2}$, $-(C_{1-4}$ alkyl)-$NR^{c2}R^{d2}$, $NR^{c2}C(O)R^{b2}$, $-(C_{1-4}$ alkyl)-$NR^{c2}C(O)R^{b2}$, $NR^{c2}C(O)NR^{c2}R^{d2}$, $-(C_{1-4}$ alkyl)-$NR^{c2}C(O)NR^{c2}R^{d2}$, $NR^{c2}C(O)OR^{a2}$, $-(C_{1-4}$ alkyl)-$NR^{c2}C(O)OR^{a2}$, $C(=NR^i)NR^{c2}R^{d2}$, $NR^{c2}C(=NR^i)NR^{c2}R^{d2}$, $P(R^{f2})_2$, $P(OR^{e2})_2$, $P(O)R^{e2}R^{f2}$, $P(O)OR^{e2}OR^{f2}$, $S(O)R^{b2}$, $-(C_{1-4}$ alkyl)-$S(O)R^{b2}$, $S(O)NR^{c2}R^{d2}$, $-(C_{1-4}$ alkyl)-$S(O)NR^{c2}R^{d2}$, $S(O)_2R^{b2}$, $-(C_{1-4}$ alkyl)-$S(O)_2R^{b2}$, $NR^{c2}S(O)_2R^{b2}$, $-(C_{1-4}$ alkyl)-$NR^{c2}S(O)_2R^{b2}$, $S(O)_2NR^{c2}R^{d2}$, and $-(C_{1-4}$ alkyl)-$S(O)_2NR^{c2}R^{d2}$;

Cy, $Cy^1$, and $Cy^2$ are independently selected from aryl, heteroaryl, cycloalkyl, and heterocycloalkyl, each optionally substituted by 1, 2, 3, 4 or 5 substituents independently selected from halo, $C_{1-4}$ alkyl, $C_{2-4}$ alkenyl, $C_{2-4}$ alkynyl, $C_{1-4}$ haloalkyl, halosulfanyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $C(=NR^i)NR^{c3}R^{d3}$, $NR^{c3}C(=NR^i)NR^{c3}R^{d3}$, $P(R^{f3})_2$, $P(OR^{e3})_2$, $P(O)R^{e3}R^{f3}$, $P(O)OR^{e3}OR^{f3}$, $S(O)R^{b3}$, $S(O)NR^{c3}R^{d3}$, $S(O)_2R^{b3}$, and $S(O)_2NR^{c3}R^{d3}$;

$R^1$ is H or $C_{1-4}$ alkyl;

$R^4$ is H, $C_{1-4}$ alkyl, $C_{2-4}$ alkenyl, $C_{2-4}$ alkynyl, $C(O)-R^{4a}$, $SO_2-R^{4a}$, aryl, cycloalkyl, heteroaryl, heterocycloalkyl, arylalkyl, cycloalkylalkyl, heteroarylalkyl, or heterocycloalkylalkyl, wherein said $C_{1-4}$ alkyl, $C_{2-4}$ alkenyl, $C_{2-4}$ alkynyl, aryl, cycloalkyl, heteroaryl, heterocycloalkyl, arylalkyl, cycloalkylalkyl, heteroarylalkyl, or heterocycloalkylalkyl is optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ cyanoalkyl, aryl, heteroaryl, cycloalkyl, heterocycloalkyl, halosulfanyl, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)NR^{c4}R^{d4}$, $NR^{c4}C(O)OR^{a4}$, $C(=NR^i)NR^{c4}R^{d4}$, $NR^{c4}C(=NR^i)NR^{c4}R^{d4}$, $P(R^{f4})_2$, $P(OR^{e4})_2$, $P(O)R^{e4}R^{f4}$, $P(O)OR^{e4}OR^{f4}$, $S(O)R^{b4}$, $S(O)NR^{c4}R^{d4}$, $S(O)_2R^{b4}$, $NR^{c4}S(O)_2R^{b4}$, and $S(O)_2NR^{c4}R^{d4}$;

$R^{4a}$ is H, $C_{1-4}$ alkyl, $C_{2-4}$ alkenyl, $C_{2-4}$ alkynyl, aryl, cycloalkyl, heteroaryl, heterocycloalkyl, arylalkyl, cycloalkylalkyl, heteroarylalkyl, or heterocycloalkylalkyl;

$R^a$, $R^{a3}$, $R^{a4}$, and $R^{a5}$ are independently selected from H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein said $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or heterocycloalkylalkyl is optionally substituted with OH, amino, halo, $C_{1-6}$ alkyl, aryl, arylalkyl, heteroaryl, heteroarylalkyl, cycloalkyl, or heterocycloalkyl;

$R^b$, $R^{b3}$, $R^{b4}$, and $R^{b5}$ are independently selected from H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein said $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with OH, amino, halo, $C_{1-6}$ alkyl, $C_{1-6}$ haloalkyl, aryl, arylalkyl, heteroaryl, heteroarylalkyl, cycloalkyl, or heterocycloalkyl;

$R^{a2}$ is H, $C_{1-6}$ alkyl, $C_{1-6}$ haloalkyl, $C_{2-6}$ alkenyl, $C_{2-6}$ alkynyl, $Cy^2$, or $Cy^2$-($C_{1-6}$ alkyl)-, wherein said $C_{1-6}$ alkyl, $C_{1-6}$ haloalkyl, $C_{2-6}$ alkenyl, or $C_{2-6}$ alkynyl, is optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ cyanoalkyl, halosulfanyl, $Cy^2$, CN, $NO_2$, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^i)NR^{c5}R^{d5}$, $NR^{c5}C(=NR^i)NR^{c5}R^{d5}$, $P(R^{f5})_2$, $P(OR^{e5})_2$, $P(O)R^{e5}R^{f5}$, $P(O)OR^{e5}OR^{f5}$, $S(O)R^{b5}$, $S(O)NR^{c5}R^{d5}$, $R^{b2}$, $S(O)_2R^{b5}$, $NR^{c5}S(O)_2R^{b5}$, and $S(O)_2NR^{c5}R^{d5}$;

$R^{b2}$ is H, $C_{1-6}$ alkyl, $C_{1-6}$ haloalkyl, $C_{2-6}$ alkenyl, $C_{2-6}$ alkynyl, aryl, $Cy^2$, or $Cy^2$-($C_{1-6}$ alkyl)-, wherein said $C_{1-6}$ alkyl, $C_{1-6}$ haloalkyl, $C_{2-6}$ alkenyl, $C_{2-6}$ alkynyl, or aryl is optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ cyanoalkyl, halosulfanyl, $Cy^2$, CN, $NO_2$, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{cc5}R^{d5}$, $NR^{c5}C(O)OR^{a5}$, $C(=NR^i)NR^{c5}R^{d5}$, $NR^{c5}C(=NR^i)NR^{c5}R^{d5}$, $P(R^{f5})_2$, $P(OR^{e5})_2$, $P(O)R^{e5}R^{f5}$, $P(O)OR^{e5}OR^{f5}$, $S(O)R^{b5}$, $S(O)NR^{c5}R^{d5}$, $S(O)_2R^{b5}$, $NR^{c5}S(O)_2R^{b5}$, and $S(O)_2NR^{c5}R^{d5}$;

$R^c$ and $R^d$ are independently selected from H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl, and heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl, or heterocycloalkylalkyl is optionally substituted with OH, amino, halo, $C_{1-6}$ alkyl, $C_{1-6}$ haloalkyl, aryl, arylalkyl, heteroaryl, heteroarylalkyl, cycloalkyl, or heterocycloalkyl;

or $R^c$ and $R^d$ together with the N atom to which they are attached form a 4-, 5-, 6- or 7-membered heterocycloalkyl group;

$R^{c2}$ and $R^{d2}$ are independently selected from H, $C_{1-10}$ alkyl, $C_{1-6}$ haloalkyl, $C_{2-6}$ alkenyl, $C_{2-6}$ alkynyl, $Cy^2$ and $Cy^2$-($C_{1-6}$ alkyl)-, wherein said $C_{1-10}$ alkyl, $C_{1-6}$ haloalkyl, $C_{2-6}$ alkenyl, and $C_{2-6}$ alkynyl, is optionally substituted with 1, 2, or 3, substituents independently selected from halo, $C_{1-4}$ alkyl, $C_{2-4}$ alkenyl, $C_{2-4}$ alkynyl, $C_{1-4}$ haloalkyl, halosulfanyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $C(=NR^i)NR^{c3}R^{d3}$, $NR^{c3}C(=NR^i)NR^{c3}R^{d3}$, $P(R^{f3})_2$, $P(OR^{e3})_2$, $P(O)R^{e3}R^{f3}$, $P(O)OR^{e3}OR^{f3}$, $S(O)R^{b3}$, $S(O)NR^{c3}R^{d3}$, $S(O)_2R^{b3}$, and $S(O)_2NR^{c3}R^{d3}$;

or $R^{c2}$ and $R^{d2}$ together with the N atom to which they are attached form a 4-, 5-, 6- or 7-membered heterocycloalkyl group optionally substituted with 1, 2, or 3, substitutents independently selected from $Cy^2$, $Cy^2$-($C_{1-6}$ alkyl)-, halo, $C_{1-4}$ alkyl, $C_{2-4}$ alkenyl, $C_{2-4}$ alkynyl, $C_{1-4}$ haloalkyl, halosulfanyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $C(=NR^i)NR^{c3}R^{d3}$, $NR^{c3}C(=NR^i)NR^{c3}R^{d3}$, $P(R^{f3})_2$, $P(OR^{e3})_2$, $P(O)R^{e3}R^{f3}$, $P(O)OR^{e3}OR^{f3}$, $S(O)R^{b3}$, $S(O)NR^{c3}R^{d3}$, $S(O)_2R^{b3}$, and $S(O)_2NR^{c3}R^{d3}$;

$R^{c3}$ and $R^{d3}$ are independently selected from H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl, and heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl, or heterocycloalkylalkyl is optionally substituted with OH, amino, halo, $C_{1-6}$ alkyl, $C_{1-6}$ haloalkyl, aryl, arylalkyl, heteroaryl, heteroarylalkyl, cycloalkyl, or heterocycloalkyl;

or $R^{c3}$ and $R^{d3}$ together with the N atom to which they are attached form a 4-, 5-, 6- or 7-membered heterocycloalkyl group;

$R^{c4}$ and $R^{d4}$ are independently selected from H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl, and heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl, and heterocycloalkylalkyl is optionally substituted with OH, amino, halo, $C_{1-6}$ alkyl, $C_{1-6}$ haloalkyl, aryl, arylalkyl, heteroaryl, heteroarylalkyl, cycloalkyl, or heterocycloalkyl;

or $R^{c4}$ and $R^{d4}$ together with the N atom to which they are attached form a 4-, 5-, 6- or 7-membered heterocycloalkyl group;

$R^{c5}$ and $R^{d5}$ are independently selected from H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl, and heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl, or heterocycloalkylalkyl is optionally substituted with OH, amino, halo, $C_{1-6}$ alkyl, $C_{1-6}$ haloalkyl, aryl, arylalkyl, heteroaryl, heteroarylalkyl, cycloalkyl, or heterocycloalkyl;

or $R^{c5}$ and $R^{d5}$ together with the N atom to which they are attached form a 4-, 5-, 6- or 7-membered heterocycloalkyl group;

$R^{e}$, $R^{e2}$, $R^{e3}$, $R^{e4}$, and $R^{e5}$ are independently selected from H, $C_{1-6}$ alkyl, $C_{1-6}$ haloalkyl, $C_{2-6}$ alkenyl, $(C_{1-6}$ alkoxy)-$C_{1-6}$ alkyl, $C_{2-6}$ alkynyl, aryl, cycloalkyl, heteroaryl, heterocycloalkyl, arylalkyl, cycloalkylalkyl, heteroarylalkyl, and heterocycloalkylalkyl;

$R^{f}$, $R^{f2}$, $R^{f3}$, $R^{f4}$, and $R^{f5}$ are independently selected from H, $C_{1-6}$ alkyl, $C_{1-6}$ haloalkyl, $C_{2-6}$ alkenyl, $C_{2-6}$ alkynyl, aryl, cycloalkyl, heteroaryl, and heterocycloalkyl;

$R^{i}$ is H, CN, $C(O)NH_2$, or $NO_2$; and p is 1, 2, 3, 4, 5.

2. The method of claim 1, wherein A is phenyl optionally substituted by 1, 2, 3, 4, or 5 substituents selected from halo, $C_{1-6}$ alkyl, $C_{1-6}$ haloalkyl, $C_{1-6}$ hydroxyalkyl, $C_{1-6}$ cyanoalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $S(O)R^b$, $S(O)NR^cR^d$, $S(O)_2R^b$, $NR^cS(O)_2R^b$, and $S(O)_2NR^cR^d$.

3. The method of claim 1, wherein A is phenyl optionally substituted by 1, 2, 3, 4, or 5 substituents selected from halo, $C_{1-6}$ alkyl, and $C_{1-6}$ haloalkyl.

4. The method of claim 1, wherein Q is $OR^Q$.

5. The method of claim 1, wherein Q is $NR^4R^Q$.

6. The method of claim 1, wherein $R^Q$ is $C_{1-6}$ alkyl optionally substituted by 1, 2, 3, 4, or 5 substituents selected from halo, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ cyanoalkyl, Cy, —($C_{1-4}$ alkyl)-Cy, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $C(=NR^i)NR^{c2}R^{d2}$, $NR^{c2}C(=NR^i)NR^{c2}R^{d2}$, $P(R^{f2})_2$, $P(OR^{e2})_2$, $P(O)R^{e2}R^{f2}$, $P(O)OR^{e2}OR^{f2}$, $S(O)R^{b2}$, $S(O)NR^{c2}R^{d2}$, $S(O)_2R^{b2}$, $NR^{c2}S(O)_2R^{b2}$, and $S(O)_2NR^{c2}R^{d2}$.

7. The method of claim 1, wherein $R^Q$ is aryl, heteroaryl, arylalkyl, or heteroarylalkyl, each optionally substituted by 1, 2, 3, 4, or 5 substituents selected from halo, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ cyanoalkyl, Cy, —($C_{1-4}$ alkyl)-Cy, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $C(=NR^i)NR^{c2}R^{d2}$, $NR^{c2}C(=NR^i)NR^{c2}R^{d2}$, $P(R^{f2})_2$, $P(OR^{e2})_2$, $P(O)R^{e2}R^{f2}$, $P(O)OR^{e2}OR^{f2}$, $S(O)R^{b2}$, $S(O)NR^{c2}R^{d2}$, $S(O)_2R^{b2}$, $NR^{c2}S(O)_2R^{b2}$, and $S(O)_2NR^{c2}R^{d2}$.

8. The method of claim 1, wherein $R^4$ is H.

9. The method of claim 1, wherein $R^1$ is H.

10. The method of claim 1, wherein the compound is a compound having Formula II:

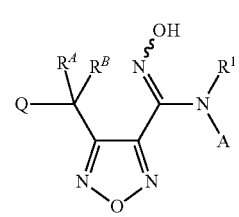

II or pharmaceutically acceptable salt thereof.

11. The method of claim 1, wherein the compound is selected from:

N-(3-chloro-4-fluoro-phenyl)-N'-hydroxy-4-hydroxymethyl-furazan-3-carboxamidine;

N-(3-chloro-4-fluorophenyl)-N'-hydroxy-4-(phenoxymethyl)-1,2,5-oxadiazole-3-carboximidamide;

4-[(E/Z)-[(3-chloro-4-fluorophenyl)amino](hydroxyimino)methyl]-1,2,5-oxadiazol-3-ylmethyl phenylcarbamate;

4-[(benzylamino)methyl]-N-(3-chloro-4-fluorophenyl)-N-hydroxy-1,2,5-oxadiazole-3-carboximidamide;

N-(3-chloro-4-fluorophenyl)-4-[(2-chlorophenoxy)methyl]-N'-hydroxy-1,2,5-oxadiazole-3-carboximidamide;

N-(3-chloro-4-fluorophenyl)-4-[(3-chlorophenoxy)methyl]-N'-hydroxy-1,2,5-oxadiazole-3-carboximidamide;

N-(3-chloro-4-fluorophenyl)-4-[(4-chlorophenoxy)methyl]-N'-hydroxy-1,2,5-oxadiazole-3-carboximidamide;

N-(3-chloro-4-fluorophenyl)-N'-hydroxy-4-[(2-methoxyphenoxy)methyl]-1,2,5-oxadiazole-3-carboximidamide;

N-(3-chloro-4-fluorophenyl)-N'-hydroxy-4-[(3-methoxyphenoxy)methyl]-1,2,5-oxadiazole-3-carboximidamide;

N-(3-chloro-4-fluorophenyl)-N'-hydroxy-4-[(4-methoxyphenoxy)methyl]-1,2,5-oxadiazole-3-carboximidamide;

N-(3-chloro-4-fluorophenyl)-4-[(3-cyanophenoxy)methyl]-N'-hydroxy-1,2,5-oxadiazole-3-carboximidamide;

N-(3-chloro-4-fluorophenyl)-4-[(4-chloro-2-methoxyphenoxy)methyl]-N'-hydroxy-1,2,5-oxadiazole-3-carboximidamide;

N-(3-chloro-4-fluorophenyl)-4-[(3,4-dimethoxyphenoxy)methyl]-N'-hydroxy-1,2,5-oxadiazole-3-carboximidamide;

{4-[(E/Z)-[(3-chloro-4-fluorophenyl)amino](hydroxyimino)methyl]-1,2,5-oxadiazol-3-yl}methyl phenylcarbamate;

{4-[(E/Z)-[(3-chloro-4-fluorophenyl)amino](hydroxyimino)methyl]-1,2,5-oxadiazol-3-yl}methyl isopropylcarbamate;

N-(3-chloro-4-fluorophenyl)-N'-hydroxy-4-(piperidin-1-ylmethyl)-1,2,5-oxadiazole-3-carboximidamide;

N-(3-chloro-4-fluorophenyl)-4-[(dimethylamino)methyl]-N'-hydroxy-1,2,5-oxadiazole-3-carboximidamide;

N-(3-chloro-4-fluorophenyl)-N'-hydroxy-4-[(4-phenylpiperazin-1-yl)methyl]-1,2,5-oxadiazole-3-carboximidamide;

N-(3-chloro-4-fluorophenyl)-N-hydroxy-4-[(isoxazol-3-ylamino)methyl]-1,2,5-oxadiazole-3-carboximidamide;

4-{[(1-benzylpiperidin-4-yl)amino]methyl}-N-(3-chloro-4-fluorophenyl)-N'-hydroxy-1,2,5-oxadiazole-3-carboximidamide;

N-(3-chloro-4-fluorophenyl)-N'-hydroxy-4-{[4-(2-methoxyphenyl)piperazin-1-yl]methyl}-1,2,5-oxadiazole-3-carboximidamide;

N-(3-chloro-4-fluorophenyl)-N'-hydroxy-4-{[(pyridin-2-ylmethyl)amino]methyl}-1,2,5-oxadiazole-3-carboximidamide;

N-(3-chloro-4-fluorophenyl)-N'-hydroxy-4-{[(2-phenylethyl)amino]methyl}-1,2,5-oxadiazole-3-carboximidamide;

N-(3-chloro-4-fluorophenyl)-N'-hydroxy-4-{[(3-phenylpropyl)amino]methyl}-1,2,5-oxadiazole-3-carboximidamide;

N-(3-chloro-4-fluorophenyl)-N'-hydroxy-4-({[(1R)-1-phenylethyl]amino}methyl)-1,2,5-oxadiazole-3-carboximidamide;

4-{[(2-chlorobenzyl)amino]methyl}-N-(3-chloro-4-fluorophenyl)-N'-hydroxy-1,2,5-oxadiazole-3-carboximidamide;

N-(3-chloro-4-fluorophenyl)-N'-hydroxy-4-{[(4-phenylbutyl)amino]methyl}-1,2,5-oxadiazole-3-carboximidamide;

N-(3-chloro-4-fluorophenyl)-4-(3,4-dihydroisoquinolin-2(1H)-ylmethyl)-N'-hydroxy-1,2,5-oxadiazole-3-carboximidamide;

N-(3-chloro-4-fluorophenyl)-4-(2,3-dihydro-1H-indol-1-ylmethyl)-N'-hydroxy-1,2,5-oxadiazole-3-carboximidamide;

N-(3-chloro-4-fluorophenyl)-N'-hydroxy-4-(morpholin-4-ylmethyl)-1,2,5-oxadiazole-3-carboximidamide;

3-(4-[(2-morpholin-4-ylethyl)amino]methyl-1,2,5-oxadiazol-3-yl)-4-[3-(trifluoromethyl)phenyl]-1,2,4-oxadiazol-5(4H)-one;

N-(3-chloro-4-fluorophenyl)-N'-hydroxy-4-[(methylsulfonyl)(2-morpholin-4-ylethyl)amino]-methyl-1,2,5-oxadiazole-3-carboximidamide;

N-{4-[N-(3-chloro-4-fluoro-phenyl)-N'-hydroxy-carbamimidoyl]-furazan-3-ylmethyl}-benzamide;

N-(3-chloro-4-fluoro-phenyl)-N'-hydroxy-4-[(3-phenyl-ureido)-methyl]-furazan-3-carboxamidine;

4-(benzenesulfonylamino-methyl)-N-(3-chloro-4-fluorophenyl)-N'-hydroxy-furazan-3-carboxamidine;

benzyl({4-[(E/Z)-[(3-chloro-4-fluorophenyl)amino](hydroxyimino)methyl]-1,2,5-oxadiazol-3-yl}methyl)carbamate;

N-(3-cyanophenyl)-N'-hydroxy-4-methyl-1,2,5-oxadiazole-3-carboximidamide;

4-[(5-amino-1H-tetrazol-1-yl)methyl]-N-(3-chloro-4-fluorophenyl)-N'-hydroxy-1,2,5-oxadiazole-3-carboximidamide;

4-[(5-amino-2H-tetrazol-2-yl)methyl]-N-(3-chloro-4-fluorophenyl)-N'-hydroxy-1,2,5-oxadiazole-3-carboximidamide;

N-(3-chloro-4-fluorophenyl)-N'-hydroxy-4-[(1H-tetrazol-5-ylamino)methyl]-1,2,5-oxadiazole-3-carboximidamide;

N-(3-chloro-4-fluorophenyl)-N'-hydroxy-4-({[3-(1H-imidazol-1-yl)propyl]amino}methyl)-1,2,5-oxadiazole-3-carboximidamide;

N-(3-chloro-4-fluorophenyl)-N'-hydroxy-4-{[(2-morpholin-4-ylethyl)amino]methyl}-1,2,5-oxadiazole-3-carboximidamide;

{4-[({4-[(E/Z)-[(3-chloro-4-fluorophenyl)amino](hydroxyimino)methyl]-1,2,5-oxadiazol-3-yl}-methyl)amino]phenyl}acetic acid;

N-(3-chloro-4-fluorophenyl)-N'-hydroxy-4-[(4-hydroxypiperidin-1-yl)methyl]-1,2,5-oxadiazole-3-carboximidamide;

N-(3-chloro-4-fluorophenyl)-N'-hydroxy-4-{[4-(2-hydroxyethyl)piperazin-1-yl]methyl}-1,2,5-oxadiazole-3-carboximidamide;

N-(3-chloro-4-fluorophenyl)-N'-hydroxy-4-({[(1R)-2-hydroxy-1-phenylethyl]amino}methyl)-1,2,5-oxadiazole-3-carboximidamide;

N-(3-chloro-4-fluorophenyl)-N'-hydroxy-4-{[(2-hydroxyethyl)amino]methyl}-1,2,5-oxadiazole-3-carboximidamide;

N-(3-chloro-4-fluorophenyl)-N'-hydroxy-4-{[(2-pyridin-4-ylethyl)amino]methyl}-1,2,5-oxadiazole-3-carboximidamide;

N-(3-chloro-4-fluorophenyl)-N'-hydroxy-4-{[(tetrahydrofuran-2-ylmethyl)amino]methyl}-1,2,5-oxadiazole-3-carboximidamide;

N-(3-chloro-4-fluorophenyl)-N'-hydroxy-4-{[(1,3-thiazol-2-ylmethyl)amino]methyl}-1,2,5-oxadiazole-3-carboximidamide;

4-({[4-(aminosulfonyl)benzyl]amino}methyl)-N-(3-chloro-4-fluorophenyl)-N'-hydroxy-1,2,5-oxadiazole-3-carboximidamide;

{4-[(E/Z)-[(3-chloro-4-fluorophenyl)amino](hydroxyimino)methyl]-1,2,5-oxadiazol-3-yl}methyl dimethylcarbamate;

4-{[4-(aminosulfonyl)phenoxy]methyl}-N-(3-chloro-4-fluorophenyl)-N'-hydroxy-1,2,5-oxadiazole-3-carboximidamide;

N-(3-chloro-4-fluorophenyl)-N'-hydroxy-4-{[4-(methylsulfonyl)phenoxy]methyl}-1,2,5-oxadiazole-3-carboximidamide;

N-(3-chloro-4-fluorophenyl)-N'-hydroxy-4(1H-imidazol-1-ylmethyl)-1,2,5-oxadiazole-3-carboximidamide;

N-(3-chloro-4-fluorophenyl)-N'-hydroxy-4(1H-1,2,4-triazol-1-ylmethyl)-1,2,5-oxadiazole-3-carboximidamide;

4-[({2-[4-(aminosulfonyl)phenyl]ethyl}amino)methyl]-N-(3-chloro-4-fluorophenyl)-N'-hydroxy-1,2,5-oxadiazole-3-carboximidamide;

N-(3-chloro-4-fluorophenyl)-N'-hydroxy-4-(2H-tetrazol-2-ylmethyl)-1,2,5-oxadiazole-3-carboximidamide;

N-(3-chloro-4-fluorophenyl)-N'-hydroxy-4(1H-tetrazol-1-ylmethyl)-1,2,5-oxadiazole-3-carboximidamide;

{4-[(E/Z)-[(3-chloro-4-fluorophenyl)amino](hydroxyimino)methyl]-1,2,5-oxadiazol-3-yl}methyl morpholine-4-carboxylate;

2-[4-({4-[(E/Z)-[(3-chloro-4-fluorophenyl)amino](hydroxyimino)methyl]-1,2,5-oxadiazol-3-yl}-methoxy)phenyl]acetamide;

4-(aminomethyl)-N-(3-chloro-4-fluorophenyl)-N'-hydroxy-1,2,5-oxadiazole-3-carboximidamide;

4-[(5-amino-1H-tetrazol-1-yl)methyl]-N-[3-(trifluoromethyl)phenyl]-N'-hydroxy-1,2,5-oxadiazole-3-carboximidamide;

4-[(5-benzyl-1H-tetrazol-1-yl)methyl]-N-(3-chloro-4-fluorophenyl)-N'-hydroxy-1,2,5-oxadiazole-3-carboximidamide;

4-[(5-benzyl-2H-tetrazol-2-yl)methyl]-N-(3-chloro-4-fluorophenyl)-N'-hydroxy-1,2,5-oxadiazole-3-carboximidamide;

[2-({4-[(E/Z)-[(3-chloro-4-fluorophenyl)amino](hydroxyimino)methyl]-1,2,5-oxadiazol-3-yl}-methyl)-2H-tetrazol-5-yl]acetic acid;

N-(3-chloro-4-fluorophenyl)-4-(cyanomethyl)-N'-hydroxy-1,2,5-oxadiazole-3-carboximidamide;

N-(3-chloro-4-fluorophenyl)-N'-hydroxy-4-[(2-oxo-1,3-oxazolidin-3-yl)methyl]-1,2,5-oxadiazole-3-carboximidamide;

N-(3-chloro-4-fluorophenyl)-4-({[2-(dimethylamino)ethyl]amino}methyl)-N'-hydroxy-1,2,5-oxadiazole-3-carboximidamide;

N-(3-chloro-4-fluorophenyl)-N'-hydroxy-4-{[(3-morpholin-4-ylpropyl)amino]methyl}-1,2,5-oxadiazole-3-carboximidamide;

N-(3-chloro-4-fluorophenyl)-N'-hydroxy-4-[(5-pyridin-4-yl-2H-tetrazol-2-yl)methyl]-1,2,5-oxadiazole-3-carboximidamide;

4-({[4-(aminosulfonyl)benzyl]amino}methyl)-N-[3-(trifluoromethyl)phenyl]-N'-hydroxy-1,2,5-oxadiazole-3-carboximidamide;

N-[3-(trifluoromethyl)phenyl]-N'-hydroxy-4-(1H-tetrazol-1-ylmethyl)-1,2,5-oxadiazole-3-carboximidamide;

N-[3-(trifluoromethyl)phenyl]-N'-hydroxy-4-(2H-tetrazol-2-ylmethyl)-1,2,5-oxadiazole-3-carboximidamide;

N-[3-(trifluoromethyl)phenyl]-N'-hydroxy-4-{[(2-morpholin-4-ylethyl)amino]methyl}-1,2,5-oxadiazole-3-carboximidamide;

N-(3-chloro-4-fluorophenyl)-N'-hydroxy-4-{[(pyridin-3-ylmethyl)amino]methyl}-1,2,5-oxadiazole-3-carboximidamide;

N-(3-chloro-4-fluorophenyl)-N'-hydroxy-4-{[(2-pyrrolidin-1-ylethyl)amino]methyl}-1,2,5-oxadiazole-3-carboximidamide;

N-(3-chloro-4-fluorophenyl)-N'-hydroxy-4-({[2-(1H-imidazol-4-yl)ethyl]amino}methyl)-1,2,5-oxadiazole-3-carboximidamide;

N-(3-chloro-4-fluorophenyl)-N'-hydroxy-4-({[2-(2-oxopyrrolidin-1-yl)ethyl]amino}methyl)-1,2,5-oxadiazole-3-carboximidamide;

N-(3-choro-4-fluorophenyl)-N'-hydroxy-4-[(5-methyl-1H-tetrazol-1-yl)methyl]-1,2,5-oxadiazole-3-carboximidamide;

N-(3-chloro-4-fluorophenyl)-N'-hydroxy-4-[(5-methyl-2H-tetrazol-2-yl)methyl]-1,2,5-oxadiazole-3-carboximidamide;

N-({4-[(E/Z)-[(3-chloro-4-fluorophenyl)amino](hydroxyimino)methyl]-1,2,5-oxadiazol-3-yl}-methyl)-N-(2-morpholin-4-ylethyl)acetamide;

N-(3-chloro-4-fluorophenyl)-N'-hydroxy-4-{[5-(methylthio)-2H-tetrazol-2-yl]methyl}-1,2,5-oxadiazole-3-carboximidamide;

N-(3-chloro-4-fluorophenyl)-N'-hydroxy-4-{[5-(methylthio)-1H-tetrazol-1-yl]methyl}-1,2,5-oxadiazole-3-carboximidamide;

N-(3-chloro-4-fluorophenyl)-N'-hydroxy-4-[(5-phenyl-1H-tetrazol-1-yl)methyl]-1,2,5-oxadiazole-3-carboximidamide;

N-(3-chloro-4-fluorophenyl)-N'-hydroxy-4-[(5-phenyl-2H-tetrazol-2-yl)methyl]-1,2,5-oxadiazole-3-carboximidamide;

N-(3-chloro-4-fluorophenyl)-N'-hydroxy-4-({5-[3-(trifluoromethoxy)phenyl]-2H-tetrazol-2-yl}-methyl)-1,2,5-oxadiazole-3-carboximidamide;

N-(3-chloro-4-fluorophenyl)-N'-hydroxy-4-[(5-pyridin-3-yl-2H-tetrazol-2-yl)methyl]-1,2,5-oxadiazole-3-carboximidamide;

N-(3-chloro-4-fluorophenyl)-N'-hydroxy-4-[(5-pyrrolidin-1-yl-2H-tetrazol-2-yl)methyl]-1,2,5-oxadiazole-3-carboximidamide;

N-(3-chloro-4-fluorophenyl)-N'-hydroxy-4-({5-[3-(trifluoromethoxy)phenyl]-1H-tetrazol-1-yl}-methyl)-1,2,5-oxadiazole-3-carboximidamide;

N-(3-chloro-4-fluorophenyl)-N'-hydroxy-4-[(5-pyridin-2-yl-1H-tetrazol-1-yl)methyl]-1,2,5-oxadiazole-3-carboximidamide;

N-(3-chloro-4-fluorophenyl)-N'-hydroxy-4-[(5-pyrrolidin-1-yl-1H-tetrazol-1-yl)methyl]-1,2,5-oxadiazole-3-carboximidamide;

N-(3-chloro-4-fluorophenyl)-4-{[5-(4-fluorophenyl)-1H-tetrazol-1-yl]methyl}-N'-hydroxy-1,2,5-oxadiazole-3-carboximidamide;

N-(3-chloro-4-fluorophenyl)-4-({5-[2-(dimethylamino)ethyl]-1H-tetrazol-1-yl}methyl)-N'-hydroxy-1,2,5-oxadiazole-3-carboximidamide N-(3-chloro-4-fluorophenyl)-4-{[5-(4-fluorophenyl)-2H-tetrazol-2-yl]methyl}-N'-hydroxy-1,2,5-oxadiazole-3-carboximidamide;

N-(3-chloro-4-fluorophenyl)-4-({5-[2-(4-chlorophenoxy)ethyl]-2H-tetrazol-2-yl}methyl)-N'-hydroxy-1,2,5-oxadiazole-3-carboximidamide;

N-(3-chloro-4-fluorophenyl)-N'-hydroxy-4-({5-[5-(trifluoromethyl)pyridin-2-yl]-2H-tetrazol-2-yl}methyl)-1,2,5-oxadiazole-3-carboximidamide;

N-(3-chloro-4-fluorophenyl)-4-({5-[2-(4-chlorophenoxy)ethyl]-1H-tetrazol-1-yl}methyl)-N'-hydroxy-1,2,5-oxadiazole-3-carboximidamide;

N-(3-chloro-4-fluorophenyl)-4-[({2-[(2R,6S)-2,6-dimethylmorpholin-4-yl]ethyl}amino)methyl]-N'-hydroxy-1,2,5-oxadiazole-3-carboximidamide;

N-(3-chloro-4-fluorophenyl)-N'-hydroxy-4-({[2-(2-methylpiperidin-l-yOethyl]amino}methyl)-1,2,5-oxadiazole-3-carboximidamide;

N-(3-chloro-4-fluorophenyl)-4-{[(1,1-dimethyl-2-morpholin-4-ylethyl)amino]methyl}-N'-hydroxy-1,2,5-oxadiazole-3-carboximidamide;

N-(3-chloro-4-fluorophenyl)-N'-hydroxy-4-{[(2-piperazin-l-ylethyl)amino]methyl}-1,2,5-oxadiazole-3-carboximidamide;

N-(3-chloro-4-fluorophenyl)-4-({[(1-ethylpyrrolidin-2-yl)methyl]amino}methyl)-N'-hydroxy-1,2,5-oxadiazole-3-carboximidamide;

N-(3-chloro-4-fluorophenyl)-4-({[2-(dimethylamino)propyl]amino}methyl)-N'-hydroxy-1,2,5-oxadiazole-3-carboximidamide;

N-(3-chloro-4-fluorophenyl)-N'-hydroxy-4-{[(2-methyl-2-morpholin-4-ylpropyl)amino]methyl}-1,2,5-oxadiazole-3-carboximidamide;
N-(3-chloro-4-fluorophenyl)-N'-hydroxy-4-{[(2-methyl-2-piperidin-1-ylpropyl)amino]methyl}-1,2,5-oxadiazole-3-carboximidamide;
N-(3-chloro-4-fluorophenyl)-N'-hydroxy-4-{[(piperidin-2-ylmethyl)amino]methyl}-1,2,5-oxadiazole-3-carboximidamide;
N-(3-chloro-4-fluorophenyl)-4-({[2-(1,1-dioxidothiomorpholin-4-yl(ethyl]-amino}-methyl)-N'-hydroxy-1,2,5-oxadiazole-3-carboximidamide;
N-(3-chloro-4-fluorophenyl)-N'-hydroxy-4-[(piperidin-3-ylamino)methyl]-1,2,5-oxadiazole-3-carboximidamide;
N-(3-chloro-4-fluorophenyl)-N'-hydroxy-4-{[(pyrrolidin-3-ylmethyl)amino]methyl}-1,2,5-oxadiazole-3-carboximidamide;
N-({4-[(E/Z)-[(3-chloro-4-fluorophenyl)amino](hydroxyimino)methyl]-1,2,5-oxadiazol-3-yl}-methyl)-2-methylpropanamide;
N-({4-[(E/Z)-[(3-chloro-4-fluorophenyl)amino](hydroxyimino)methyl]-1,2,5-oxadiazol-3-yl}-methyl)-2,2-dimethylpropanamide;
N-({4-[(E/Z)-[(3-chloro-4-fluorophenyl)amino](hydroxyimino)methyl]-1,2,5-oxadiazol-3-yl}-methyl)-2-phenylacetamide;
N-({4-[(E/Z)-[(3-chloro-4-fluorophenyl)amino](hydroxyimino)methyl]-1,2,5-oxadiazol-3-yl}-methyl)-3-phenylpropanamide;
N-({4-[(E/Z)-[(3-chloro-4-fluorophenyl)amino](hydroxyimino)methyl]-1,2,5-oxadiazol-3-yl}-methyl)-1,3-thiazole-5-carboxamide;
N-({4-[(E/Z)-[(3-chloro-4-fluorophenyl)amino](hydroxyimino)methyl]-1,2,5-oxadiazol-3-yl}-methyl)cyclopentanecarboxamide;
N-(3-chloro-4-fluorophenyl)-N'-hydroxy-4-{[(methylsulfonyl)amino]methyl}-1,2,5-oxadiazole-3-carboximidamide;
4-({[(benzylamino)carbonyl]amino}methyl)-N-(3-chloro-4-fluorophenyl)-N'-hydroxy-1,2,5-oxadiazole-3-carboximidamide;
N-(3-chloro-4-fluorophenyl)-N'-hydroxy-4-[({[(2-phenylethyl)-amino]carbonyl}-amino)methyl]-1,2,5-oxadiazole-3-carboximidamide;
N-(3-chloro-4-fluorophenyl)-N'-hydroxy-4-({[(isopropylamino)-carbonyl]amino}-methyl)-1,2,5-oxadiazole-3-carboximidamide;
N-({4-[(E/Z)-[(3-chloro-4-fluorophenyl)amino](hydroxyimino)methyl]-1,2,5-oxadiazol-3-yl}-methyl)morpholine-4-carboxamide;
N-(3-chloro-4-fluorophenyl)-4-({[(dimethylamino)carbonyl]amino}methyl)-N'-hydroxy-1,2,5-oxadiazole-3-carboximidamide;
N-({4-[(E/Z)-[(3-chloro-4-fluorophenyl)amino](hydroxyimino)methyl]-1,2,5-oxadiazol-3-yl}methyl)acetamide;
methyl ({4-[(E/Z)-[(3-chloro-4-fluorophenyl)amino](hydroxyimino)methyl]-1,2,5-oxadiazol-3-yl}methyl)carbamate;
isobutyl({4-[(E/Z)-[(3-chloro-4-fluorophenyl)amino](hydroxyimino)methyl]-1,2,5-oxadiazol-3-yl}methyl)carbamate;
benzyl({4-[(E/Z)-[(3-chloro-4-fluorophenyl)amino](hydroxyimino)methyl]-1,2,5-oxadiazol-3-yl}methyl)carbamate;
N-(3-chloro-4-fluorophenyl)-4-{[(ethylsulfonyl)amino]methyl}-N'-hydroxy-1,2,5-oxadiazole-3-carboximidamide;
N-(5-{[({4-[(E/Z)-[(3-chloro-4-fluorophenyl)amino](hydroxyimino)methyl]-1,2,5-oxadiazol-3-yl}methyl)amino]sulfonyl}-4-methyl-1,3-thiazol-2-yl)acetamide;
N-(3-chloro-4-fluorophenyl)-N'-hydroxy-4-{[({5-[1-methyl-5-(trifluoromethyl)-1H-pyrazol-3-yl]-2-thienyl}sulfonyl)amino]methyl}-1,2,5-oxadiazole-3-carboximidamide;
N-(3-chloro-4-fluorophenyl)-N'-hydroxy-4-({[(1-methyl-1H-imidazol-4-yl)sulfonyl]amino}-methyl)-1,2,5-oxadiazole-3-carboximidamide;
N-(3-chloro-4-fluorophenyl)-4-({[(2,4-dimethyl-1,3-thiazol-5-yl)sulfonyl]amino}methyl)-N'-hydroxy-1,2,5-oxadiazole-3-carboximidamide;
N-(3-chloro-4-fluorophenyl)-4-({[(3,5-dimethylisoxazol-4-yl)sulfonyl]amino}methyl)-N'-hydroxy-1,2,5-oxadiazole-3-carboximidamide;
N-(3-chloro-4-fluorophenyl)-N'-hydroxy-4-({[(1,3,5-trimethyl-1H-pyrazol-4-yl)sulfonyl]amino}-methyl)-1,2,5-oxadiazole-3-carboximidamide;
N-(3-chloro-4-fluorophenyl)-4-({[(1,2-dimethyl-1H-imidazol-4-yl)sulfonyl]amino}methyl)-N'-hydroxy-1,2,5-oxadiazole-3-carboximidamide;
N-(3-chloro-4-fluorophenyl)-N'-hydroxy-4-{[(propylsulfonyl)amino]methyl}-1,2,5-oxadiazole-3-carboximidamide;
N-(3-chloro-4-fluorophenyl)-4-{[(cyclopropylsulfonyl)amino]methyl}-N'-hydroxy-1,2,5-oxadiazole-3-carboximidamide;
N-(3-chloro-4-fluorophenyl)-N'-hydroxy-4-{[(3-methylisothiazol-5-yl)amino]methyl}-1,2,5-oxadiazole-3-carboximidamide;
ethyl 3-4-[(Z)-[(3-chloro-4-fluorophenyl)amino](hydroxyimino)methyl]-1,2,5-oxadiazol-3-ylpropanoate;
N-(3-chloro-4-fluorophenyl)-N'-hydroxy-4-(3-morpholin-4-ylpropyl)-1,2,5-oxadiazole-3-carboximidamide;
4-[(aminosulfonyl)amino]methyl-N-(3-chloro-4-fluorophenyl)-N'-hydroxy-1,2,5-oxadiazole-3-carboximidamide;
N-(3-chloro-4-fluorophenyl)-4-([(E/Z)-(cyanoimino)(methylamino)methyl]aminomethyl)-N'-hydroxy-1,2,5-oxadiazole-3-carboximidamide;
N-(3-chloro-4-fluorophenyl)-N'-hydroxy-4-([(methylamino)-sulfonyl]aminomethyl)-1,2,5-oxadiazole-3-carboximidamide;
4-[(aminocarbonyl)amino]methyl-N-(3-chloro-4-fluorophenyl)-N'-hydroxy-1,2,5-oxadiazole-3-carboximidamide;
4-([(tert-butylamino)carbonyl]aminomethyl)-N-(3-chloro-4-fluorophenyl)-N'-hydroxy-1,2,5-oxadiazole-3-carboximidamide;
N-(3-chloro-4-fluorophenyl)-N'-hydroxy-4-([(3-morpholin-4-ylpropyl)sulfonyl]aminomethyl)-1,2,5-oxadiazole-3-carboximidamide trifluoroacetate;
N-(3-chloro-4-fluorophenyl)-N'-hydroxy-4-[(piperidin-4-ylsulfonyl)amino]methyl-1,2,5-oxadiazole-3-carboximidamide trifluoroacetate;
4-[([1-(aminosulfonyl)piperidin-4-yl]sulfonylamino)methyl]-N-(3-chloro-4-fluorophenyl)-N'-hydroxy-1,2,5-oxadiazole-3-carboximidamide;
4-([(1-acetylpiperidin-4-yl)sulfonyl]aminomethyl)-N-(3-chloro-4-fluorophenyl)-N'-hydroxy-1,2,5-oxadiazole-3-carboximidamide;

N-(3-chloro-4-fluorophenyl)-N'-hydroxy-4-[5-(morpholin-4-ylmethyl)-2H-tetrazol-2-yl]methyl-1,2,5-oxadiazole-3-carboximidamide trifluoroacetate;

N-(3-chloro-4-fluorophenyl)-N'-hydroxy-4-[5-(morpholin-4-ylmethyl)-1H-tetrazol-1-yl]methyl-1,2,5-oxadiazole-3-carboximidamide trifluoroacetate;

4-[(5-amino-1,3,4-thiadiazol-2-yl)thio]methyl-N-(3-chloro-4-fluorophenyl)-N'-hydroxy-1,2,5-oxadiazole-3-carboximidamide;

4-[(5-amino-4H-1,2,4-triazol-3-yl)thio]methyl-N-(3-chloro-4-fluorophenyl)-N'-hydroxy-1,2,5-oxadiazole-3-carboximidamide;

4-[(5-amino-4H-1,2,4-triazol-3-yl)sulfonyl]methyl-N-(3-chloro-4-fluorophenyl)-N'-hydroxy-1,2,5-oxadiazole-3-carboximidamide;

N-(3-chloro-4-fluorophenyl)-4-[({(E/Z)-(cyanoimino)[(4-methoxybenzyl)amino]methyl}amino)-methyl]-N-hydroxy-1,2,5-oxadiazole-3-carboximidamide trifluoroacetate;

4-[({(E/Z)-[(aminocarbonyl)imino][(4-methoxybenzyl)amino]methyl}amino)methyl]-N-(3-chloro-4-fluorophenyl)-N-hydroxy-1,2,5-oxadiazole-3-carboximidamide;

4-({[(E/Z)-amino(nitroimino)methyl]amino}methyl)-N-(3-chloro-4-fluorophenyl)-N-hydroxy-1,2,5-oxadiazole-3-carboximidamide trifluoroacetate;

4-({[amino(imino)methyl]amino}methyl)-N-(3-chloro-4-fluorophenyl)-N'-hydroxy-1,2,5-oxadiazole-3-carboximidamide;

N-(3-chloro-4-fluorophenyl)-N'-hydroxy-4-(4H-1,2,4-triazol-4-ylmethyl)-1,2,5-oxadiazole-3-carboximidamide;

4-[2-(5-amino-1H-tetrazol-1-yl)ethyl]-N-(3-chloro-4-fluorophenyl)-N'-hydroxy-1,2,5-oxadiazole-3-carboximidamide;

4-[2-(5-amino-2H-tetrazol-2-yl)ethyl]-N-(3-chloro-4-fluorophenyl)-N'-hydroxy-1,2,5-oxadiazole-3-carboximidamide;

N-(3-chloro-4-fluorophenyl)-N'-hydroxy-4-[2-(1H-imidazol-1-yl)ethyl]-1,2,5-oxadiazole-3-carboximidamide trifluoroacetate;

N-(3-chloro-4-fluorophenyl)-N'-hydroxy-4-(2-morpholin-4-ylethyl)-1,2,5-oxadiazole-3-carboximidamide trifluoroacetate;

N-(3-chloro-4-fluorophenyl)-N'-hydroxy-4-[2-(4-methylpiperazin-1-yl)ethyl]-1,2,5-oxadiazole-3-carboximidamide bis(trifluoroacetate);

N-(3-chloro-4-fluorophenyl)-N'-hydroxy-4-[2-(4H-1,2,4-triazol-4-yl)ethyl]-1,2,5-oxadiazole-3-carboximidamide;

N-(3-chloro-4-fluorophenyl)-N'-hydroxy-4-[2-(1H-1,2,4-triazol-1-yl)ethyl]-1,2,5-oxadiazole-3-carboximidamide;

N-(3-chloro-4-fluorophenyl)-N'-hydroxy-4-[2-(1H-tetrazol-1-yl(ethyl]-1,2,5-oxadiazole-3-carboximidamide;

N-(3-chloro-4-fluorophenyl)-N'-hydroxy-4-[2-(2H-tetrazol-2-yl(ethyl]-1,2,5-oxadiazole-3-carboximidamide;

N-(3-chloro-4-fluorophenyl)-4-[2-(dimethylamino)ethyl]-N'-hydroxy-1,2,5-oxadiazole-3-carboximidamide trifluoroacetate;

N-(3-chloro-4-fluorophenyl)-N'-hydroxy-4-(2-thiomorpholin-4-ylethyl)-1,2,5-oxadiazole-3-carboximidamide trifluoroacetate;

N-(3-chloro-4-fluorophenyl)-N'-hydroxy-4-(2-pyrrolidin-1-ylethyl)-1,2,5-oxadiazole-3-carboximidamide trifluoroacetate;

N-(3-chloro-4-fluorophenyl)-N'-hydroxy-4-{2-[isopropyl(methyl)amino]ethyl}-1,2,5-oxadiazole-3-carboximidamide trifluoroacetate;

N-(3-chloro-4-fluorophenyl)-N'-hydroxy-4-{2-[(methylsulfonyl)amino]ethyl}-1,2,5-oxadiazole-3-carboximidamide;

4-{2-[(aminosulfonyl)amino]ethyl}-N-(3-chloro-4-fluorophenyl)-N'-hydroxy-1,2,5-oxadiazole-3-carboximidamide;

4-{[(aminosulfonyl)amino]methyl}-N-(3-bromo-4-fluorophenyl)-N-hydroxy-1,2,5-oxadiazole-3-carboximidamide;

4-{[(aminosulfonyl)amino]methyl}-N-hydroxy-N-[3-(trifluoromethyl)phenyl]-1,2,5-oxadiazole-3-carboximidamide;

N-({4-[(E/Z)-[(3-chloro-4-fluorophenyl)amino](hydroxyimino)methyl]-1,2,5-oxadiazol-3-yl}-methyl)-N'-cyanomorpholine-4-carboximidamide;

N-(3-chloro-4-fluorophenyl)-4-[({(E/Z)-(cyanoimino)[(2-morpholin-4-ylethyl)amino]methyl}-amino)methyl]-N'-hydroxy-1,2,5-oxadiazole-3-carboximidamide;

4-[({(E/Z)-[(aminocarbonyl)imino][(2-morpholin-4-ylethyl)amino]methyl}amino)methyl]-N-(3-chloro-4-fluorophenyl)-N'-hydroxy-1,2,5-oxadiazole-3-carboximidamide;

N-(3-chloro-4-fluorophenyl)-4-{[((E/Z)-(cyanoimino){[2-(dimethylamino)ethyl]amino}methyl)-amino]methyl}-N-hydroxy-1,2,5-oxadiazole-3-carboximidamide;

N-(3-chloro-4-fluorophenyl)-4-{[((E/Z)-(cyanoimino){[2-(1H-imidazol-5-yl)ethyl]amino}-methyl)amino]methyl}-N-hydroxy-1,2,5-oxadiazole-3-carboximidamide;

4-{[((E/Z)-[(aminocarbonyl)imino]{[2-(1H-imidazol-5-yl)ethyl]amino}methyl)amino]methyl}-N-(3-chloro-4-fluorophenyl)-N'-hydroxy-1,2,5-oxadiazole-3-carboximidamide;

N-(3-chloro-4-fluorophenyl)-4-[({(E/Z)-(cyanoimino)[(2-hydroxy-1-methylethyl)amino]methyl}-amino)methyl]-N-hydroxy-1,2,5-oxadiazole-3-carboximidamide;

N-(3-chloro-4-fluorophenyl)-4-({[(E/Z)-(cyanoimino)(isopropylamino)methyl]amino}methyl)-N'-hydroxy-1,2,5-oxadiazole-3-carboximidamide trifluoroacetate;

N-(3-chloro-4-fluorophenyl)-4-[({(E/Z)-(cyanoimino)[(2-methoxy-1-methylethyl)amino]-methyl}amino)methyl]-N'-hydroxy-1,2,5-oxadiazole-3-carboximidamide trifluoroacetate;

N-(3-chloro-4-fluorophenyl)-4-[({(E/Z)-(cyanoimino)[(2-methoxyl(ethyl)amino]methyl}amino)-methyl]-N'-hydroxy-1,2,5-oxadiazole-3-carboximidamide trifluoroacetate;

N-(3-chloro-4-fluorophenyl)-4-({[(E/Z)-(cyanoimino)(tetrahydro-2H-pyran-4-ylamino)methyl]-amino}methyl)-N'-hydroxy-1,2,5-oxadiazole-3-carboximidamide trifluoroacetate;

N-(3-chloro-4-fluorophenyl)-4-{[((E/Z)-(cyanoimino){[(1-ethylpyrrolidin-2-yl)methyl]amino}-methyl)amino]methyl}-N'-hydroxy-1,2,5-oxadiazole-3-carboximidamide bis(trifluoroacetate);

4-({[(E/Z)-amino(cyanoimino)methyl]amino}methyl)-N-(3-chloro-4-fluorophenyl)-N'-hydroxy-1,2,5-oxadiazole-3-carboximidamide trifluoroacetate;

N-(3-chloro-4-fluorophenyl)-4-[({(E/Z)-(cyanoimino)[(2-hydroxyl(ethyl)amino]methyl}amino)-methyl]-N'-hydroxy-1,2,5-oxadiazole-3-carboximidamide trifluoroacetate;

N-(3-chloro-4-fluorophenyl)-4-({[(E/Z)-(cyanoimino)(dimethylamino)methyl]amino}methyl)-N'-hydroxy-1,2,5-oxadiazole-3-carboximidamide;

N-(3-chloro-4-fluorophenyl)-4-({[(E/Z)-(cyanoimino)(ethylamino)methyl]amino}methyl)-N'-hydroxy-1,2,5-oxadiazole-3-carboximidamide;

N-(3-bromo-4-fluorophenyl)-4-({[(E/Z)-(cyanoimino)(ethylamino)methyl]amino}methyl)-N'-hydroxy-1,2,5-oxadiazole-3-carboximidamide;

4-({[(E/Z)-(cyanoimino)(dimethylamino)methyl]amino}methyl)-N'-hydroxy-N-[3-(trifluoro-methyl)phenyl]-1,2,5-oxadiazole-3-carboximidamide;

4-({[(E/Z)-(cyanoimino)(ethylamino)methyl]amino}methyl)-N'-hydroxy-N-[3-(trifluoromethyl)phenyl]-1,2,5-oxadiazole-3-carboximidamide;

N-(3-bromo-4-fluorophenyl)-4-({[(E/Z)-(cyanoimino)(dimethylamino)methyl]amino}methyl)-N'-hydroxy-1,2,5-oxadiazole-3-carboximidamide;

4-({[(E/Z)-(cyanoimino)(methylamino)methyl]amino}methyl)-N'-hydroxy-N-[3-(trifluoro-methyl)phenyl]-1,2,5-oxadiazole-3-carboximidamide trifluoroacetate;

N-(3-bromo-4-fluorophenyl)-4-({[(E/Z)-(cyanoimino)(methylamino)methyl]amino}methyl)-N'-hydroxy-1,2,5-oxadiazole-3-carboximidamide;

4-({[(E/Z)-amino(cyanoimino)methyl]amino}methyl)-N-(3-bromo-4-fluorophenyl)-N'-hydroxy-1,2,5-oxadiazole-3-carboximidamide;

4-({[(E/Z)-amino(cyanoimino)methyl]amino}methyl)-N'-hydroxy-N-[3-(trifluoromethyl)phenyl]-1,2,5-oxadiazole-3-carboximidamide;

N-(3-chloro-4-fluorophenyl)-N'-hydroxy-4-({[(isopropylamino)sulfonyl]amino}methyl)-1,2,5-oxadiazole-3-carboximidamide;

N-(3-bromo-4-fluorophenyl)-N'-hydroxy-4-({[(methylamino)sulfonyl]amino}methyl)-1,2,5-oxadiazole-3-carboximidamide;

N-(3-chloro-4-fluorophenyl)-4-({[(ethylamino)sulfonyl]amino}methyl)-N'-hydroxy-1,2,5-oxadiazole-3-carboximidamide;

N-(3-chloro-4-fluorophenyl)-4-({[(dimethylamino)sulfonyl]amino}methyl)-N'-hydroxy-1,2,5-oxadiazole-3-carboximidamide;

N-[3-(difluoromethyl)phenyl]-N'-hydroxy-4-(1H-tetrazol-1-ylmethyl)-1,2,5-oxadiazole-3-carboximidamide;

N-[3-(difluoromethyl)phenyl]-N'-hydroxy-4-(2H-tetrazol-2-ylmethyl)-1,2,5-oxadiazole-3-carboximidamide;

N-hydroxy-4-(4H-1,2,4-triazol-4-ylmethyl)-N-[3-(trifluoromethyl)phenyl]-1,2,5-oxadiazole-3-carboximidamide;

N-(3-bromo-4-fluorophenyl)-N'-hydroxy-4-(4H-1,2,4-triazol-4-ylmethyl)-1,2,5-oxadiazole-3-carboximidamide;

4-[(5-amino-1H-tetrazol-1-yl)methyl]-N-(3-bromo-4-fluorophenyl)-N'-hydroxy-1,2,5-oxadiazole-3-carboximidamide;

4-[(5-amino-2H-tetrazol-2-yl)methyl]-N-(3-bromo-4-fluorophenyl)-N'-hydroxy-1,2,5-oxadiazole-3-carboximidamide;

N-({4-[(Z)-[(3-chloro-4-fluorophenyl)amino](hydroxyimino)methyl]-1,2,5-oxadiazol-3-yl}-methyl)-1H-imidazole-2-carboxamide trifluoroacetate;

N-({4-[(Z)-[(3-chloro-4-fluorophenyl)amino](hydroxyimino)methyl]-1,2,5-oxadiazol-3-yl}-methyl)-1H-pyrazole-4-carboxamide trifluoroacetate;

N-({4-[(Z)-[(3-chloro-4-fluorophenyl)amino](hydroxyimino)methyl]-1,2,5-oxadiazol-3-yl}-methyl)-4-methyl-1,2,3-thiadiazole-5-carboxamide;

N-({4-[(Z)-[(3-chloro-4-fluorophenyl)amino](hydroxyimino)methyl]-1,2,5-oxadiazol-3-yl}-methyl)-1H-imidazole-4-carboxamide trifluoroacetate;

N-({4-[(Z)-[(3-chloro-4-fluorophenyl)amino](hydroxyimino)methyl]-1,2,5-oxadiazol-3-yl}-methyl)-1,2,3-thiadiazole-4-carboxamide;

5-amino-N-({4-[(Z)-[(3-chloro-4-fluorophenyl)amino](hydroxyimino)methyl]-1,2,5-oxadiazol-3-yl}methyl)-1,3,4-thiadiazole-2-carboxamide;

5-amino-N-({4-[(Z)-[(3-chloro-4-fluorophenyl)amino](hydroxyimino)methyl]-1,2,5-oxadiazol-3-yl}methyl)-1H-pyrazole-4-carboxamide;

4-(aminomethyl)-N-(3-bromo-4-fluorophenyl)-N'-hydroxy-1,2,5-oxadiazole-3-carboximidamide trifluoroacetate;

N-(3-bromo-4-fluorophenyl)-N'-hydroxy-4-{[(methylsulfonyl)amino]methyl}-1,2,5-oxadiazole-3-carboximidamide;

4-(aminomethyl)-N'-hydroxy-N-[3-(trifluoromethyl)phenyl]-1,2,5-oxadiazole-3-carboximidamide trifluoroacetate;

N-hydroxy-4-{[(methylsulfonyl)amino]methyl}-N-[3-(trifluoromethyl)phenyl]-1,2,5-oxadiazole-3-carboximidamide;

N-(3-chloro-4-fluorophenyl)-N'-hydroxy-4-({[(2,2,2-trifluoroethyl)sulfonyl]amino}methyl)-1,2,5-oxadiazole-3-carboximidamide;

N-(3-bromo-4-fluorophenyl)-N'-hydroxy-4-(1H-tetrazol-1-ylmethyl)-1,2,5-oxadiazole-3-carboximidamide;

[1-({4-[(Z)-[(3-chloro-4-fluorophenyl)amino](hydroxyimino)methyl]-1,2,5-oxadiazol-3-yl}-methyl)-1H-tetrazol-5-yl]acetic acid;

N-(3-chloro-4-fluorophenyl)-4-({[(2,4-dioxo-1,2,3,4-tetrahydropyrimidin-5-yl)sulfonyl]amino}-methyl)-N'-hydroxy-1,2,5-oxadiazole-3-carboximidamide;

N-(3-chloro-4-fluorophenyl)-4-({[(1,3-dimethyl-2,4-dioxo-1,2,3,4-tetrahydropyrimidin-5-yl)-sulfonyl]amino}methyl)-N'-hydroxy-1,2,5-oxadiazole-3-carboximidamide;

N-(3-chloro-4-fluorophenyl)-N'-hydroxy-4-[3-(1H-tetrazol-1-yl)propyl]-1,2,5-oxadiazole-3-carboximidamide;

N-(3-chloro-4-fluorophenyl)-N'-hydroxy-4-[3-(2H-tetrazol-2-yl)propyl]-1,2,5-oxadiazole-3-carboximidamide;

N-(3-chloro-4-fluorophenyl)-N'-hydroxy-4-[3-(4H-1,2,4-triazol-4-yl)propyl]-1,2,5-oxadiazole-3-carboximidamide;

4-{3-[(aminosulfonyl)amino]propyl}-N-(3-chloro-4-fluorophenyl)-N'-hydroxy-1,2,5-oxadiazole-3-carboximidamide;

N-(3-chloro-4-fluorophenyl)-4-(3-{[(E/Z)-(cyanoimino)(methylamino)methyl]amino}propyl)-N'-hydroxy-1,2,5-oxadiazole-3-carboximidamide trifluoroacetate;

4-[(3-amino-4H-1,2,4-triazol-4-yl)methyl]-N-(3-chloro-4-fluorophenyl)-N'-hydroxy-1,2,5-oxadiazole-3-carboximidamide;

4-[(5-amino-1H-1,2,4-triazol-1-yl)methyl]-N-(3-chloro-4-fluorophenyl)-N'-hydroxy-1,2,5-oxadiazole-3-carboximidamide;

N-(3-chloro-4-fluorophenyl)-N'-hydroxy-4-[(1,3,4-thiadiazol-2-ylamino)methyl]-1,2,5-oxadiazole-3-carboximidamide trifluoroacetate;

N-[3-(difluoromethyl)phenyl]-N-hydroxy-4-({[(methylamino)sulfonyl]amino}methyl)-1,2,5-oxadiazole-3-carboximidamide;

4-[(5-amino-1H-tetrazol-1-yl)methyl]-N'-[3-(difluoromethyl)phenyl]-N'-hydroxy-1,2,5-oxadiazole-3-carboximidamide;

4-[(5-amino-2H-tetrazol-2-yl)methyl]-N-(4-fluoro-3-methylphenyl)-N'-hydroxy-1,2,5-oxadiazole-3-carboximidamide;

N-[3-(difluoromethyl)phenyl]-N-hydroxy-4-(1H-tetrazol-1-ylmethyl)-1,2,5-oxadiazole-3-carboximidamide;

N-[3-(difluoromethyl)phenyl]-N'-hydroxy-4-(2H-tetrazol-2-ylmethyl)-1,2,5-oxadiazole-3-carboximidamide;

N-[3-(difluoromethyl)phenyl]-N'-hydroxy-4-{[(methylsulfonyl)amino]methyl}-1,2,5-oxadiazole-3-carboximidamide;

4-{[(aminosulfonyl)amino]methyl}-N-[3-(difluoromethyl)phenyl]-N'-hydroxy-1,2,5-oxadiazole-3-carboximidamide;

N-[3-(difluoromethyl)phenyl]-N'-hydroxy-4-({[(trifluoromethyl)sulfonyl]amino}methyl)-1,2,5-oxadiazole-3-carboximidamide;

4-{[bis(methylsulfonyl)amino]methyl}-N-[3-(difluoromethyl)phenyl]-N'-hydroxy-1,2,5-oxadiazole-3-carboximidamide;

4-[(5-amino-1H-tetrazol-1-yl)methyl]-N-(4-fluoro-3-methylphenyl)-N'-hydroxy-1,2,5-oxadiazole-3-carboximidamide;

4-{[(6-aminohexyl)amino]methyl}-N-(3-chloro-4-fluorophenyl)-N'-hydroxy-1,2,5-oxadiazole-3-carboximidamide;

N-(4-fluoro-3-methylphenyl)-N'-hydroxy-4-{[(methylsulfonyl)amino]methyl}-1,2,5-oxadiazole-3-carboximidamide;

4-[2-(5-amino-1H-tetrazol-1-yl)ethyl]-N-(3-bromo-4-fluorophenyl)-N'-hydroxy-1,2,5-oxadiazole-3-carboximidamide;

N-(3-bromo-4-fluorophenyl)-N'-hydroxy-4-{2-[(methylsulfonyl)amino]ethyl}-1,2,5-oxadiazole-3-carboximidamide;

4-{2-[(aminosulfonyl)amino]ethyl}-N-(3-bromo-4-fluorophenyl)-N'-hydroxy-1,2,5-oxadiazole-3-carboximidamide; and pharmaceutically acceptable salts thereof.

12. The method of claim 1 further comprising administering an anti-viral agent, a chemotherapeutic, an immunosuppressant, radiation, an anti-tumor vaccine, an anti-viral vaccine, cytokine therapy, a tyrosine kinase inhibitor, an anti-CTLA-4 antibody, or an anti-PD-1 antibody.

13. The method of claim 1, wherein the cancer is melanoma.

14. The method of claim 13 further comprising administering a chemotherapeutic, radiation, an anti-tumor vaccine, or cytokine therapy.

15. The method of claim 1, wherein the cancer is breast cancer.

16. The method of claim 1, wherein the cancer is ovarian cancer.

17. The method of claim 1, wherein the method is a method of inhibiting immunosuppression.

* * * * *

UNITED STATES PATENT AND TRADEMARK OFFICE
CERTIFICATE OF CORRECTION

PATENT NO. : 8,951,536 B2
APPLICATION NO. : 13/780510
DATED : February 10, 2015
INVENTOR(S) : Andrew P. Combs et al.

It is certified that error appears in the above-identified patent and that said Letters Patent is hereby corrected as shown below:

On the Title Page under item (56), Other Publications

Page 2, Col. 2, Line 63, delete "antihypertenstive" and insert -- antihypertensive --.

Page 3, Col. 1, Line 52, delete "Gumana Press Inc.," and insert -- Humana Press Inc., --.

Page 3, Col. 1, Line 58, delete ""Compaunds" and insert -- "Compounds --.

Page 3, Col. 1, Line 64, delete ""Compaunds" and insert -- "Compounds --.

Page 3, Col. 2, Line 7, delete "dihydrosoxazole" and insert -- dihydroisoxazole --.

Page 5, Col. 2, Line 5, delete "2-pheny1" and insert -- 2-phenyl --.

Page 5, Col. 2, Line 14, delete "Cycloaddtion" and insert -- cycloaddition --.

Page 6, Col. 1, Line 15, delete "chloroximinofurazan"" and insert -- chloroiminofurazan" --.

Page 6, Col. 1, Line 34, delete "Allogenieic" and insert -- Allogeneic --.

Page 7, Col. 2, Line 44, delete "Cytokin" and insert -- Cytokine --.

In the Claims

Col. 170, Line 27, Claim 1, delete "substitutents" and insert -- substituents --.

Col. 172, Line 23, Claim 1, delete "$NR^{cc5}R^{d5}$," and insert -- $NR^{c5}R^{d5}$, --.

Col. 172, Line 45, Claim 1, delete "substitutents" and insert -- substituents --.

Col. 172, Line 56, Claim 1, delete "substitutents" and insert -- substituents --.

Col. 174, Line 43, Claim 11, delete "N-hydroxy" and insert -- N'-hydroxy --.

Col. 175, Line 18, Claim 11, delete "N-hydroxy" and insert -- N'-hydroxy --.

Col. 176, Lines 13-14, Claim 11, delete "(1 H" and insert -- (1H --.

Col. 178, Line 37, Claim 11, delete "carboximidamide" and insert -- carboximidamide; --.

Col. 178, Line 54, Claim 11, delete "yOethyl]" and insert -- yl)ethyl] --.

Col. 179, Line 48, Claim 11, delete "carb onyl]" and insert -- carbonyl] --.

Signed and Sealed this
First Day of March, 2016

Michelle K. Lee
*Director of the United States Patent and Trademark Office*

CERTIFICATE OF CORRECTION (continued)

U.S. Pat. No. 8,951,536 B2

Col. 179, Line 62, Claim 11, delete "isobutyl({" and insert -- isobutyl ({ --.

Col. 179, Line 65, Claim 11, delete "benzyl({" and insert -- benzyl ({ --.

Col. 181, Line 18, Claim 11, delete "N-hydroxy" and insert -- N'-hydroxy --.

Col. 181, Line 23, Claim 11, delete "N-hydroxy" and insert -- N'-hydroxy --.

Col. 181, Line 26, Claim 11, delete "N-hydroxy" and insert -- N'-hydroxy --.

Col. 181, Line 56, Claim 11, delete "yl(ethyl]" and insert -- yl)ethyl] --.

Col. 181, Line 58, Claim 11, delete "yl(ethyl]" and insert -- yl)ethyl] --.

Col. 182, Line 12, Claim 11, delete "N-hydroxy" and insert -- N'-hydroxy --.

Col. 182, Line 14, Claim 11, delete "N-hydroxy" and insert -- N'-hydroxy --.

Col. 182, Line 29, Claim 11, delete "{[2- (dimethylamino)" and insert -- {[2-(dimethylamino) --.

Col. 182, Line 30, Claim 11, delete "N-hydroxy" and insert -- N'-hydroxy --.

Col. 182, Line 35, Claim 11, delete "N-hydroxy" and insert -- N'-hydroxy --.

Col. 182, Line 43, Claim 11, delete "N-hydroxy" and insert -- N'-hydroxy --.

Col. 182, Line 48, Claim 11, delete "fluorophenyl) -4" and insert -- fluorophenyl)-4 --.

Col. 182, Line 54, Claim 11, delete "methoxyl(ethyl)amino]" and insert -- methoxyethyl)amino] --.

Col. 183, Line 53, Claim 11, delete "N-hydroxy" and insert -- N'-hydroxy --.

Col. 184, Line 28, Claim 11, delete "N-hydroxy" and insert -- N'-hydroxy --.

Col. 184, Line 39, Claim 11, delete "1,2,3 ,4" and insert -- 1,2,3,4 --.

Col. 184, Line 54, Claim 11, delete "N-hydroxy" and insert -- N'-hydroxy --.

Col. 184, Line 56, Claim 11, delete "fluorophenyl) -4" and insert -- fluorophenyl)-4 --.

Col. 185, Line 1, Claim 11, delete "N-hydroxy" and insert -- N'-hydroxy --.

Col. 185, Line 4, Claim 11, delete "-N'-[3" and insert -- -N-[3 --.

Col. 185, Line 9, Claim 11, delete "N-hydroxy" and insert -- N'-hydroxy --.